(12) United States Patent
Liu et al.

(10) Patent No.: US 10,273,242 B2
(45) Date of Patent: Apr. 30, 2019

(54) COMPOUND INHIBITING ACTIVITIES OF BTK AND/OR JAK3 KINASES

(71) Applicant: BEIJING HANMI PHARMACEUTICAL CO., LTD., Beijing (CN)

(72) Inventors: Jinming Liu, Beijing (CN); Mi Young Cha, Beijing (CN); Gong Li, Beijing (CN); Zhanmei Li, Beijing (CN); Hongjuan Qiu, Beijing (CN); Maengsup Kim, Beijing (CN)

(73) Assignee: BEIJING HANMI PHARMACEUTICAL CO., LTD., Beijing (CN)

( * ) Notice: Subject to any disclaimer, the term of this patent is extended or adjusted under 35 U.S.C. 154(b) by 0 days.

(21) Appl. No.: 15/799,315

(22) Filed: Oct. 31, 2017

(65) Prior Publication Data

US 2018/0051036 A1 Feb. 22, 2018

Related U.S. Application Data

(62) Division of application No. 15/022,248, filed as application No. PCT/CN2014/086820 on Sep. 18, 2014, now Pat. No. 9,840,517.

(30) Foreign Application Priority Data

Sep. 18, 2013 (CN) ............ 2013 1 0429844
Sep. 18, 2013 (CN) ............ 2013 1 0430071
Sep. 18, 2013 (CN) ............ 2013 1 0430761

(51) Int. Cl.
| | |
|---|---|
| *A61K 31/519* | (2006.01) |
| *C07D 495/04* | (2006.01) |
| *A61K 31/53* | (2006.01) |
| *A61K 31/5377* | (2006.01) |
| *C07D 487/04* | (2006.01) |
| *C07D 491/048* | (2006.01) |
| *A61K 45/06* | (2006.01) |
| *C07D 519/00* | (2006.01) |

(52) U.S. Cl.
CPC .......... *C07D 495/04* (2013.01); *A61K 31/519* (2013.01); *A61K 31/53* (2013.01); *A61K 31/5377* (2013.01); *A61K 45/06* (2013.01); *C07D 487/04* (2013.01); *C07D 491/048* (2013.01); *C07D 519/00* (2013.01)

(58) Field of Classification Search
CPC .. A61K 31/519; C07D 487/04; C07D 493/04; C07D 495/04
USPC ............. 514/260.1, 265.1; 544/278, 280
See application file for complete search history.

(56) References Cited

U.S. PATENT DOCUMENTS

2016/0229865 A1 8/2016 Liu et al.

FOREIGN PATENT DOCUMENTS

| | | |
|---|---|---|
| AU | 2014323777 A1 | 4/2016 |
| EP | 3 048 105 A1 | 7/2016 |
| JP | 2008/13527 | 1/2008 |
| JP | 2010-509348 | 3/2010 |
| JP | 2011-518219 | 6/2011 |
| JP | 2011-526299 | 10/2011 |
| JP | 2012-526113 | 10/2012 |
| KR | 20110025224 A | 3/2011 |
| KR | 20120047208 A | 5/2012 |
| RU | 2 528 340 C2 | 11/2011 |
| WO | WO 00/49018 A1 | 8/2000 |
| WO | WO 2010/111406 | 9/2010 |
| WO | WO 2010/129053 A2 | 11/2010 |
| WO | WO 2011/079231 A1 | 6/2011 |
| WO | WO 2011/162515 | 12/2011 |
| WO | WO 2011/162515 A2 | 12/2011 |
| WO | WO 2012/048222 | 4/2012 |
| WO | WO 2013/042006 A1 | 3/2013 |
| WO | WO 2014/140989 A2 | 9/2014 |
| WO | WO 2015/039612 A1 | 3/2015 |
| WO | WO 2015/075598 A1 | 5/2015 |
| WO | WO 2015/083028 A1 | 6/2015 |

OTHER PUBLICATIONS

Zhou, W. et al., "Discovery of selective irreversible inhibitors for EGFR-T790M", Bioorganic & Medicinal Chemistry Letters, (2011), vol. 21, pp. 638-643.
Extended European Search Report dated Apr. 13, 2017 issued in Corresponding European Patent Application No. 14846251.8.
Canadian Office Action dated Feb. 10, 2017 issued in corresponding Canadian Patent Application No. 2,924,362.
International Search Report dated Dec. 24, 2014 received in International Application No. PCT/CN2014/086820.

*Primary Examiner* — Jeffrey H Murray
(74) *Attorney, Agent, or Firm* — Scully Scott Murphy & Presser

(57) ABSTRACT

The present invention relates to a compound inhibiting the activities of Bruton's tyrosine kinase (BTK) and/or Janus kinase 3 (JAK3), a pharmaceutical composition of the compound, pharmaceutical applications of same, a method for using the compound in inhibiting the activities of BTK and/or JAK3, and a method for using the compound in treatment and/or prevention of BTK- and/or JAK3-mediated diseases or disorders in mammals (especially human). The compound is as represented by structural formula (I).

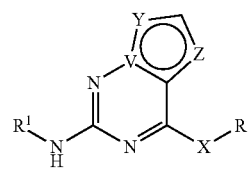

9 Claims, 2 Drawing Sheets

COMPOUND INHIBITING ACTIVITIES OF BTK AND/OR JAK3 KINASES

TECHNICAL FIELD

The present invention relates to a compound for inhibiting activities of BTK (Bruton's tyrosine kinase) and/or JAK3 (Janus kinase 3) kinases, a pharmaceutical composition thereof, the use thereof in the manufacture of a medicament, a method of using the compound in inhibiting BTK and/or JAK3 activities and a method of using the compound in the treatment and/or prevention of BTK- and/or JAK3-mediated diseases or disorders in mammals, especially in humans.

BACKGROUND ART

Protein kinase is one of the largest families in human enzymes, and more than 500 kinds of protein kinases have been identified in the human body to date. These protein kinases modulate the activities of particular proteins by transferring phosphate groups to the proteins, and then control complex signaling pathways. Aberrant activities of protein kinases are correlated with many diseases including cancers, autoimmune disorders, and so on. Because of the essential role of protein kinases in signaling pathways and the correlation between the kinase activities and many diseases, kinase inhibitors have now become a hot topic for the research and discovery of new chemical entities.

BTK (Bruton's tyrosine kinase) is a non-receptor tyrosine kinase of TEC family BTK is an essential media of B cell receptor (BCR) signaling pathway and it is a key modulator of early B cell development, and activation, signaling and survival of mature B cells. Thus, BTK inhibitors can be used for treating diseases associated with aberrant activation of B cells, for example, autoimmune diseases including rheumatoid arthritis and systemic lupus erythematosus, etc. The efficacy for treating autoimmune diseases by BTK inhibitors has been preliminary demonstrated in the preclinical animal models (Honigberg, L. A. et al, *Proceedings of the National Academy of Sciences of the United States of America*, 2010, 107, 13075-13080). Besides B cells, there are experimental evidences showing that BTK also takes part in the signal pathways of monocytes, macrophages, neutrophils and mast cells. BTK inhibitors can depress FcγR-induced release of cytokines including TNFa, IL-1β and IL-6, from monocytes and macrophages, and can also reduce the FcγR-induced degranulation of mast cells (Chang B. Y. et al, *Arthritis Research & Therapy*, 2011, 13, R115).

The B cell receptor (BCR)-mediated signaling pathway is vital to the survival of many lymphomas. As a key kinase in the BCR pathway, BTK is therefore a potential therapeutic target of lymphomas. In clinical trials, BTK inhibitors show significant effects in the treatment of chronic lymphocytic leukemia (CLL). BTK inhibitors also exhibit significant effects on other lymphomas such as diffused large B-cell lymphoma and mantle cell lymphoma, etc. (Buggy, J. J. et al, *International Reviews of Immunology*, 2012, 31, 119-132).

Janus kinases are essential tyrosine kinases for modulating the cellular function of lymphatic and hematopoietic cells. Janus kinases include four known members, which are JAK1, JAK2, JAK3 and TYK2, respectively, and wherein JAK3 (Janus tyrosine kinase 3) is mainly expressed in lymphocytes and natural killer cells. JAK3 is constitutively bound to the common γc chain, which is a common receptor subunit for IL-2, IL-4, IL-7, IL-9, IL-15 and IL-21 (Ghoreschi K. et al, *Immunological Reviews*, 2009, 228, 273-87). These cytokines, mediated through JAK3, are essential for the proliferation, differentiation and functions of lymphocytes. The function loss of the JAK3 kinase will result in the immunodeficiency of both human and mice. Because of the essential role of JAK3 kinase in the immune system, JAK3 kinase is a very attractive target for the treatment of immune-associated diseases, for example, autoimmune diseases like rheumatoid arthritis or allograft rejection in the patients with organ transplantation. Selective JAK3 inhibitors show significant efficacy in the clinical trials of rheumatoid arthritis.

In addition to the individual efficacy of BTK inhibitors and JAK3 inhibitors, simultaneously inhibiting both BTK pathway and JAK3 pathway will potentially have synergetic effects in clinical application. For example, via experiments, Cetkovic-Cvrlje M et al prove that the combination of using BTK and JAK3 inhibitors may improve the survival rates of animals in Graft-Versus-Host Disease (GVHD) models (Cetkovic-Cvrlje M. et al, *British Journal of Haematology*, 2004, 126, 821-827).

Therefore, it is necessary to develop novel compounds aiming at BTK and/or JAK3 pathways, wherein the novel compounds show good efficacy and can be orally available, which also exhibit pharmacokinetic properties favorable to the therapeutic applications and show sufficiently low toxic and side effects in vivo.

SUMMARY OF THE INVENTION

According to one aspect of the present invention, the present invention provides a compound represented by formula I (hereinafter sometimes referred to as a compound of formula I):

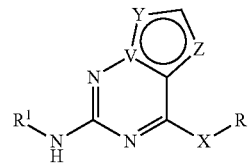

wherein:
R is selected from $C_{3-8}$ cycloalkyl substituted by —$NR^2W$; a 4- to 10-membered saturated N-heterocyclyl group which contains only one nitrogen atom on its ring and the nitrogen atom is substituted by W; or $C_{1-4}$ alkyl substituted by a 4- to 10-membered saturated N-heterocyclyl group which contains only one nitrogen atoms on its ring and the nitrogen atom is substituted by W;

W is selected from

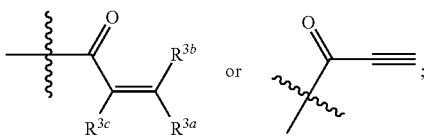

V is selected from C or N;
X is selected from O, S, or $NR^4$;
Y is selected from CH, O, or S;
Z is selected from CH, O, S, or $NR^5$;
$R^1$ is $C_{6-12}$ aryl or 5- to 12-membered heteroaryl, optionally substituted by one or more $R^6$;

R² is selected from hydrogen or $C_{1-8}$ aliphatic;

$R^{3a}$, $R^{3b}$, and $R^{3c}$ are independently selected from the group consisting of hydrogen, halogen, and di($C_{1-8}$ aliphatic)aminomethyl;

R⁴ is selected from hydrogen or $C_{1-8}$ aliphatic;

R⁵ is selected from hydrogen or $C_{1-8}$ aliphatic;

each R⁶ is independently selected from the group consisting of halogen, nitro, cyano, heterocyclyl, $C_{6-12}$ aryl, 5- to 12-membered heteroaryl, $C_{1-8}$ aliphatic, $C_{1-8}$ halo aliphatic, heterocyclyl $C_{1-8}$ aliphatic, hydroxy $C_{1-8}$ aliphatic, $C_{1-8}$ aliphaticoxy $C_{1-8}$ aliphatic, $C_{1-8}$ aliphaticcarbonyloxy $C_{1-8}$ aliphatic, amino $C_{1-8}$ aliphatic, carboxy $C_{1-8}$ aliphatic, $C_{1-8}$ aliphaticamino $C_{1-8}$ aliphatic, di($C_{1-8}$ aliphatic)amino $C_{1-8}$ aliphatic, $C_{1-8}$ aliphaticacylamino $C_{1-8}$ aliphatic, $C_{1-8}$ aliphaticcarbonyl $C_{1-8}$ aliphatic, $C_{1-8}$ aliphaticoxycarbonyl $C_{1-8}$ aliphatic, aminoacyl $C_{1-8}$ aliphatic, $C_{1-8}$ aliphaticaminoacyl $C_{1-8}$ aliphatic, di($C_{1-8}$ aliphatic)aminoacyl $C_{1-8}$ aliphatic, $C_{1-8}$ aliphaticsulfonyl $C_{1-8}$ aliphatic, $C_{1-8}$ aliphaticsulfinyl $C_{1-8}$ aliphatic, $C_{1-8}$ aliphatic sulfonylamino, $C_{1-8}$ aliphaticsulfonylamino $C_{1-8}$ aliphatic, sulfamoyl $C_{1-8}$ aliphatic, $C_{1-8}$ aliphaticaminosulfonyl $C_{1-8}$ aliphatic, di($C_{1-8}$ aliphatic)aminosulfonyl $C_{1-8}$ aliphatic, di($C_{1-8}$ aliphatic)phosphonyl $C_{1-8}$ aliphatic, hydroxy, $C_{1-8}$ aliphaticoxy, heterocyclyloxy, heterocyclyl $C_{1-8}$ aliphaticoxy, hydroxy $C_{1-8}$ aliphaticoxy, $C_{1-8}$ aliphaticoxy $C_{1-8}$ aliphaticoxy, amino $C_{1-8}$ aliphaticoxy, $C_{1-8}$ aliphaticamino $C_{1-8}$ aliphaticoxy, di($C_{1-8}$ aliphatic)amino $C_{1-8}$ aliphaticoxy, $C_{1-8}$ aliphaticacylamino $C_{1-8}$ aliphaticoxy, $C_{1-8}$ aliphaticcarbonyl $C_{1-8}$ aliphaticoxy, aminoacyl $C_{1-8}$ aliphaticoxy, $C_{1-8}$ aliphaticaminoacyl $C_{1-8}$ aliphaticoxy, di($C_{1-8}$ aliphatic)aminoacyl $C_{1-8}$ aliphaticoxy, amino, $C_{1-8}$ aliphaticamino, di($C_{1-8}$ aliphatic)amino, heterocyclylamino, heterocyclyl $C_{1-8}$ aliphaticamino, hydroxy $C_{1-8}$ aliphaticamino, $C_{1-8}$ aliphaticoxy $C_{1-8}$ aliphaticamino, amino $C_{1-8}$ aliphaticamino, $C_{1-8}$ aliphaticamino $C_{1-8}$ aliphaticamino, di($C_{1-8}$ aliphatic)amino $C_{1-8}$ aliphaticamino, $C_{1-8}$ aliphaticacylamino $C_{1-8}$ aliphaticamino, $C_{1-8}$ aliphaticcarbonyl $C_{1-8}$ aliphaticamino, aminoacyl $C_{1-8}$ aliphaticamino, $C_{1-8}$ aliphaticaminoacyl $C_{1-8}$ aliphaticamino, di($C_{1-8}$ aliphatic)aminoacyl $C_{1-8}$ aliphaticamino, $C_{1-8}$ aliphaticacylamino, heterocyclyl $C_{1-8}$ aliphaticacylamino, heterocyclylacylamino, hydroxy $C_{1-8}$ aliphaticacylamino, $C_{1-8}$ aliphaticoxy $C_{1-8}$ aliphaticacylamino, amino $C_{1-8}$ aliphaticacylamino, $C_{1-8}$ aliphaticamino $C_{1-8}$ aliphaticacylamino, di($C_{1-8}$ aliphatic)amino $C_{1-8}$ aliphaticacylamino, $C_{1-8}$ aliphaticcarbonyl, heterocyclylcarbonyl, heterocyclyl $C_{1-8}$ aliphaticcarbonyl, $C_{1-8}$ aliphaticoxycarbonyl, heterocyclyl $C_{1-8}$ aliphaticoxycarbonyl, di($C_{1-8}$ aliphatic)amino $C_{1-8}$ aliphaticoxycarbonyl, aminoacyl, $C_{1-8}$ aliphaticaminoacyl, di($C_{1-8}$ aliphatic)aminoacyl, heterocyclyl $C_{1-8}$ aliphaticaminoacyl, heterocyclylaminoacyl, hydroxy $C_{1-8}$ aliphaticaminoacyl, $C_{1-8}$ aliphaticoxy $C_{1-8}$ aliphaticaminoacyl, amino $C_{1-8}$ aliphaticaminoacyl, $C_{1-8}$ aliphaticamino $C_{1-8}$ aliphaticaminoacyl, di($C_{1-8}$ aliphatic)amino $C_{1-8}$ aliphaticaminoacyl, $C_{1-8}$ aliphaticsulfhydryl, heterocyclylsulfhydryl, heterocyclyl $C_{1-8}$ aliphaticsulfhydryl, $C_{1-8}$ aliphaticsulfonyl, $C_{1-8}$ aliphaticsulfinyl, heterocyclylsulfonyl, heterocyclylsulfinyl, heterocyclyl $C_{1-8}$ aliphaticsulfonyl, heterocyclyl $C_{1-8}$ aliphaticsulfinyl, sulfamoyl, $C_{1-8}$ aliphaticaminosulfonyl, di($C_{1-8}$ aliphatic)aminosulfonyl, heterocyclyl $C_{1-8}$ aliphaticaminosulfonyl, heterocyclylaminosulfonyl, di($C_{1-8}$ aliphatic) amino $C_{1-8}$ aliphaticaminosulfonyl, aminosulfinyl, $C_{1-8}$ aliphaticaminosulfinyl, di($C_{1-8}$ aliphatic)aminosulfinyl, heterocyclylaminosulfinyl and di($C_{1-8}$ aliphatic)phosphonyl, wherein:

heterocyclyl, as an independent group or a part of other group(s), represents a saturated or partially unsaturated 3- to 12-membered heterocyclyl group containing one or more heteroatoms selected from the group consisting of N, O, and S; optionally, each heterocyclyl is independently substituted by one or more substituents selected from the group consisting of halogen, $C_{1-8}$ aliphatic, hydroxy $C_{1-8}$ aliphatic, $C_{1-8}$ aliphaticoxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, heterocyclyl $C_{1-8}$ aliphatic, heterocyclyl, 5- to 12-membered heteroaryl, hydroxy, $C_{1-8}$ aliphaticoxy, amino, $C_{1-8}$ aliphaticamino, di($C_{1-8}$ aliphatic)amino, $C_{1-8}$ aliphaticcarbonyl, heterocyclylcarbonyl, heterocyclyl $C_{1-8}$ aliphaticcarbonyl, hydroxy $C_{1-8}$ aliphaticcarbonyl, $C_{1-8}$ aliphaticoxy $C_{1-8}$ aliphaticcarbonyl, di($C_{1-8}$ aliphatic)amino $C_{1-8}$ aliphaticcarbonyl, $C_{1-8}$ aliphaticoxycarbonyl, aminoacyl, $C_{1-8}$ aliphaticaminoacyl, di($C_{1-8}$ aliphatic)aminoacyl, $C_{1-8}$ aliphaticsulfonyl, $C_{1-8}$ aliphaticsulfinyl, heterocyclylsulfonyl, heterocyclylsulfinyl, heterocyclyl $C_{1-8}$ aliphaticsulfonyl, heterocyclyl $C_{1-8}$ aliphaticsulfinyl, sulfamoyl, $C_{1-8}$ aliphaticaminosulfonyl, and di($C_{1-8}$ aliphatic)aminosulfonyl; and optionally, $C_{6-12}$ aryl and 5- to 12-membered heteroaryl are independently substituted by one or more substituents selected from the group consisting of halogen, $C_{1-8}$ aliphatic, hydroxy, $C_{1-8}$ aliphaticoxy, amino, $C_{1-8}$ aliphaticamino and di($C_{1-8}$ aliphatic)amino, wherein $C_{1-8}$ aliphatic, at each occurrence, is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl, or a stereoisomer, a tautomer, a solvate, or a pharmaceutically acceptable salt thereof.

In some embodiments, the present invention provides a compound represented by formula Ia (hereinafter sometimes referred to as a compound of formula Ia):

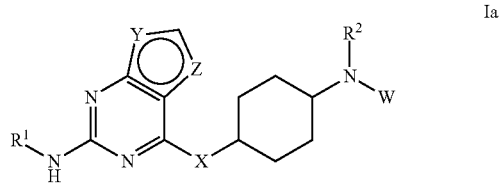

Ia wherein, X, Y, Z, W, R¹, and R² are all defined as in formula I, or a stereoisomer, a tautomer, a solvate, or a pharmaceutically acceptable salt thereof.

In some embodiments, the present invention provides a compound represented by formula Ib (hereinafter sometimes referred to as a compound of formula Ib):

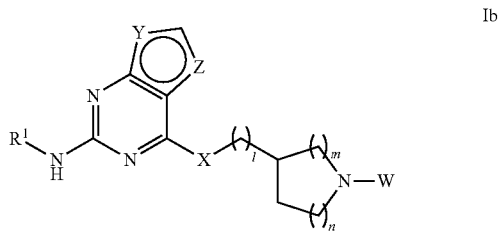

Ib wherein:

X, Y, Z, W, and R¹ are all defined as in formula I;

l is selected from 0, 1, 2, 3, or 4, wherein when l is 0,

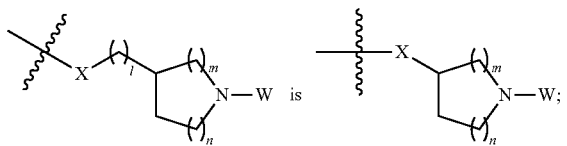

m is selected from 0, 1, 2, 3, or 4; wherein when m is 0,

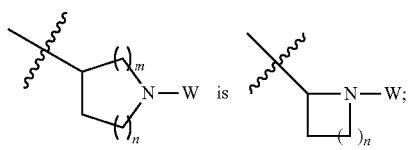

and
n is selected from 0, 1, 2, 3; wherein when n is 0,

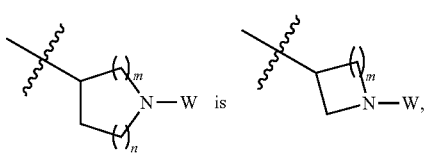

or a stereoisomer, a tautomer, a solvate, or a pharmaceutically acceptable salt thereof.

In some embodiments, the present invention provides a compound represented by formula Ic (hereinafter sometimes referred to as a compound of formula Ic):

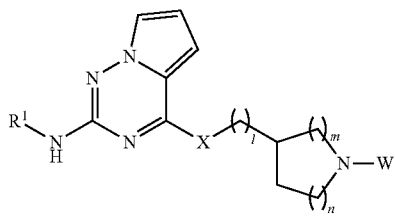

Ic wherein:
X, W, and $R^1$ are all defined as in formula I;
l is selected from 0, 1, 2, 3, or 4; wherein when l is 0,

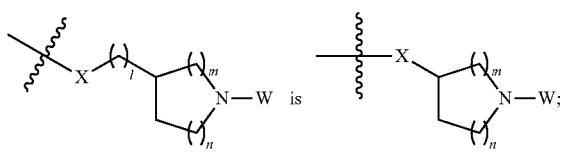

m is selected from 0, 1, 2, 3, or 4; wherein when m is 0,

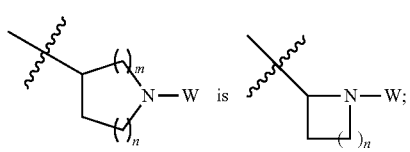

and
n is selected from 0, 1, 2, or 3; wherein when n is 0,

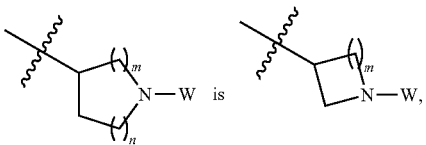

or a stereoisomer, a tautomer, a solvate, or a pharmaceutically acceptable salt thereof.

Another aspect of the present invention relates to a pharmaceutical composition comprising one or more compounds of formula I (especially compounds of formulae Ia, Ib and Ic) of the present invention, or a stereoisomer, a tautomer, a solvate, or a pharmaceutically acceptable salt thereof, and pharmaceutically acceptable excipients.

The pharmaceutical composition of the present invention further comprises one or more agents selected from the group consisting of immunosuppressants, corticosteroids, nonsteroidal anti-inflammatory drugs, Cox-2 specific inhibitors, TNF-α binding proteins, interferons and interleukins.

Another aspect of the present invention relates to use of the compound of formula I, especially the compounds of formulae Ia, Ib and Ic, of the present invention, or a stereoisomer, a tautomer, a solvate, or a pharmaceutically acceptable salt thereof, in the manufacture of a medicament for inhibiting BTK and/or JAK3 activities.

Another aspect of the present invention relates to use of the compound of formula I, especially the compounds of formulae Ia, Ib and Ic, of the present invention, or a stereoisomer, a tautomer, a solvate, or a pharmaceutically acceptable salt thereof, in the manufacture of a medicament for the prevention or treatment of BTK- and/or JAK3-mediated diseases.

Another aspect of the present invention relates to use of the pharmaceutical composition of the present invention comprising one or more compounds of formula I, especially compounds of formulae Ia, Ib and Ic, of the present invention, or a stereoisomer, a tautomer, a solvate, or a pharmaceutically acceptable salt thereof, and pharmaceutically acceptable excipients in the manufacture of a medicament for inhibiting BTK and/or JAK3 activities. In some embodiments, the pharmaceutical composition further comprises, in addition to the above-mentioned compounds, one or more agents selected from the group consisting of immunosuppressants, corticosteroids, nonsteroidal anti-inflammatory drugs, Cox-2 specific inhibitors, TNF-α binding proteins, interferons and interleukins.

Another aspect of the present invention relates to use of the pharmaceutical composition of the present invention comprising one or more compounds of formula I, especially compounds of formulae Ia, Ib and Ic, of the present invention, or stereoisomers, tautomers, solvates, or pharmaceutically acceptable salts thereof, and pharmaceutically acceptable excipients in the manufacture of a medicament for the prevention or treatment of BTK- and/or JAK3-mediated diseases. In some embodiments, the pharmaceutical composition further comprises, in addition to the above-mentioned compounds, one or more agents selected from the group consisting of immunosuppressants, corticosteroids, nonsteroidal anti-inflammatory drugs, Cox-2 specific inhibitors, TNF-α binding proteins, interferons and interleukins.

Another aspect of the present invention relates to a compound of formula I, especially compounds of formulae Ia, Ib and Ic, of the present invention, or a stereoisomer, a tautomer, a solvate, or a pharmaceutically acceptable salt thereof, for inhibiting BTK and/or JAK3 activities.

Another aspect of the present invention relates to a compound of formula I, especially compounds of formulae Ia, Ib and Ic, of the present invention, or a stereoisomer, a tautomer, a solvate, or a pharmaceutically acceptable salt thereof, for the prevention or treatment of BTK- and/or JAK3-mediated diseases.

Another aspect of the present invention relates to a pharmaceutical composition comprising a compound of formula I, especially compounds of formulae Ia, Ib and Ic, of the present invention, or a stereoisomer, a tautomer, a solvate, or a pharmaceutically acceptable salt thereof, for inhibiting BTK and/or JAK3 activities.

Another aspect of the present invention relates to a pharmaceutical composition comprising a compound of formula I, especially compounds of formulae Ia, Ib and Ic, of the present invention, or a stereoisomer, a tautomer, a solvate, or a pharmaceutically acceptable salt thereof, for the prevention or treatment of BTK- and/or JAK3-mediated diseases.

Another aspect of the present invention relates to a method of inhibiting BTK and/or JAK3 activities in a biological system comprising bringing the biological system into contact with a compound of formula I, especially compounds of formulae Ia, Ib and Ic, of the present invention, or a stereoisomer, a tautomer, a solvate, or a pharmaceutically acceptable salt thereof, or with a pharmaceutical composition comprising a compound of formula I, especially compounds of formulae Ia, Ib and Ic, of the present invention, or a stereoisomer, a tautomer, a solvate, or a pharmaceutically acceptable salt thereof.

Another aspect of the present invention relates to a method of preventing or treating BTK- and/or JAK3-mediated diseases comprising administering to a mammal (especially a human) in need thereof a therapeutically effective amount of a compound of formula I, especially compounds of formulae Ia, Ib and Ic, of the present invention, or a stereoisomer, a tautomer, a solvate, or a pharmaceutically acceptable salt thereof, or of a pharmaceutical composition comprising a compound of formula I, especially compounds of formulae Ia, Ib and Ic, of the present invention, or a stereoisomer, a tautomer, a solvate, or a pharmaceutically acceptable salt thereof.

Another aspect of the present invention relates to use of a compound of formula I, especially compounds of formulae Ia, Ib and Ic, of the present invention, or a stereoisomer, a tautomer, a solvate, or a pharmaceutically acceptable salt thereof, in combination with one or more active agents selected from the group consisting of immunosuppressants, corticosteroids, nonsteroidal anti-inflammatory drugs, Cox-2 specific inhibitors, TNF-α binding proteins, interferons and interleukins in the manufacture of a medicament for treating BTK- and/or JAK3-mediated diseases.

In the present application, the BTK- and/or JAK3-mediated diseases are selected from the group consisting of autoimmune diseases, inflammatory diseases, heteroimmune conditions or diseases, thromboembolic diseases and cancers.

DETAILED DESCRIPTION OF THE EMBODIMENTS

Figure 1:
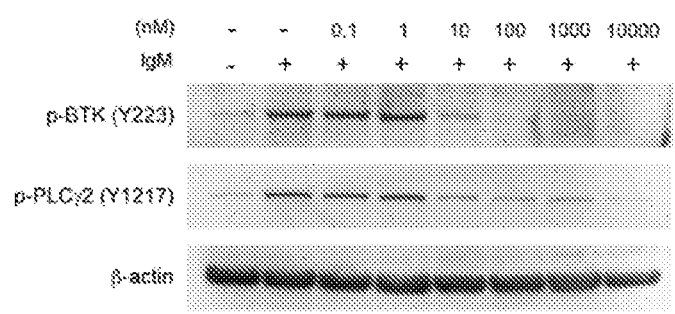
FIG. 1 shows the inhibiting effect of compound 132 on the BTK pathway in Ramos cells.

Unless otherwise indicated, scientific and technical terms used herein have the same meanings as those commonly understood by an ordinary skilled person in the art.

It should be understood that the above-outlined contents and the following detailed description are exemplary only for illustration purposes without limiting the subject matter of the present invention in any way.

All literatures or sections of literatures including but not limited to, patents, patent applications, articles, books, manuals and theses as cited in the present application are incorporated herein by reference in its entirety.

The total number of carbon atoms present in a chemical group as defined herein is represented by a shorthand notation before the group. For example, $C_{1-8}$ aliphatic refers to an aliphatic group as defined hereinafter having 1 to 8 carbon atoms in total; $C_{1-8}$ alkyl refers to an alkyl group as defined hereinafter having 1 to 8 carbon atoms in total; $C_{3-8}$ cycloalkyl refers to a cycloalkyl group as defined hereinafter having 3 to 8 carbon atoms in total; $C_{6-12}$ aryl refers to an aryl group as defined hereinafter having 6 to 12 carbon atoms in total. Carbon atoms that may exist in the substituents of the chemical group are not included in the total number of carbon atoms in the shorthand notation.

Unless otherwise indicated in this specification, all combined groups according to the present invention (i.e., groups comprised of two or more groups) are attached to the rest of the molecule in such a way that the lastly described group acts as the point of attachment. By way of example, "heterocyclyl aliphatic" means that the heterocyclyl group is attached to the rest of the molecule via the aliphatic group; "aliphaticoxy" means that the aliphatic group is attached to the rest of the molecule via an oxy group; etc.

In addition to the above-mentioned, as used in the specification and claims, unless otherwise indicated, the following terms have the meanings as set forth below:

"Amino" refers to the —$NH_2$ group.
"Cyano" refers to the —CN group.
"Hydroxy" refers to the —OH group.
"Nitro" refers to the —$NO_2$ group.
"Oxo" refers to the =O substituent.
"Carbonyl" or "acyl" refers to the —C(=O)— group.
"Sulfhydryl" refers to the —S group.
"Sulfonyl" refers to the —S(=O)$_2$— group.
"Sulfinyl" refers to the —S(=O)— group.
"Phosphonyl" refers to the —P(=O)(OH)$_2$ group.
"Aminoacyl" refers to the —C(=O)—$NH_2$ group.
"Sulfamoyl" refers to the —S(=O)$_2$—$NH_2$ group.
"Aminosulfinyl" refers to the —S(=O)—$NH_2$ group.

In the present application, the term "halogen" refers to fluorine, chlorine, bromine or iodine, preferably fluorine or chlorine.

In the present application, as an independent group or a part of other group(s), the term "aliphatic" or "aliphatic group" refers to a saturated or unsaturated group having the fundamental properties of an aliphatic compound, consisting solely of carbon atoms and hydrogen atoms, and which is attached to the rest of the molecules by a single bond. An aliphatic group includes straight or branched alkyl, alkenyl, alkynyl, cycloalkyl and cycloalkenyl groups, wherein alkyl, alkenyl, alkynyl, cycloalkyl and cycloalkenyl are as defined hereinafter. In the present application, aliphatic refers to alkyl, alkenyl, alkynyl, cycloalkyl and/or cycloalkenyl, preferably refers to alkyl and/or cycloalkyl. All hydrogen atoms on an aliphatic group are optionally replaced with any suitable groups, for example, halogen, hydroxy, amino, mono-substituted amino, di-substituted amino, alkoxy, heterocyclyl, and the like.

In the present application, as an independent group or a part of other group(s), the term "alkyl" or "alkyl group" refers to a straight or branched group consisting solely of carbon and hydrogen atoms, containing no unsaturated bond, and which is attached to the rest of the molecule by a single bond. An alkyl group may comprise, for example, from 1 to 18, preferably 1 to 12, more preferably 1 to 8 carbon atoms. Examples of alkyl include, but are not limited to, methyl, ethyl, propyl, isopropyl, n-butyl, isobutyl, t-butyl, n-pentyl, 2-pentyl, hexyl, heptyl, 2-methylhexyl, 3-methylhexyl, octyl, nonyl, decyl and the like, preferably methyl, ethyl, propyl, isopropyl, and n-butyl, more preferably methyl, ethyl, propyl and isopropyl. All hydrogen atoms on an alkyl group are optionally replaced with any suitable groups, for example, halogen, hydroxy, amino, mono-substituted amino, di-substituted amino, alkoxy, heterocyclyl, and the like.

In the present application, as an independent group or a part of other group(s), the term "alkenyl" or "alkenyl group" refers to a straight or branched hydrocarbon chain group, consisting solely of carbon and hydrogen atoms, containing at least one double bond, having for example from 2 to 18, preferably 2 to 10, more preferably 2 to 8 carbon atoms, and which is attached to the rest of the molecule by a single bond, which includes but is not limited to, ethenyl, propenyl, allyl, but-1-enyl, but-2-enyl, pent-1-enyl, pent-2-enyl, pent-1,4-dienyl and the like, preferably ethenyl and propenyl. All hydrogen atoms on an alkenyl group may optionally be replaced with any suitable groups, for example, halogen, hydroxy, amino, mono-substituted amino, di-substituted amino, alkoxy, heterocyclyl, and the like.

In the present application, as an independent group or a part of other group(s), the term "alkynyl" or "alkynyl group" refers to a straight or branched hydrocarbon chain group consisting solely of carbon and hydrogen atoms, containing at least one triple bond and optionally containing one or more double bonds, having for example from 2 to 18, preferably 2 to 10, more preferably 2 to 8 carbon atoms, and which is attached to the rest of the molecule by a single bond. Examples of alkynyl include, but are not limited to, ethynyl, prop-1-ynyl, pent-1-en-4-ynyl, and the like. All hydrogen atoms on an alkynyl group are optionally replaced with any suitable groups, for example, halogen, hydroxy, amino, alkoxy, heterocyclyl, and the like.

In the present application, as an independent group or a part of other group(s), the term "cycloalkyl" or "cycloalkyl group" refers to a stable saturated non-aromatic monocyclic or polycyclic hydrocarbon group consisting solely of carbon and hydrogen atoms, which may include fused or bridged cyclic systems, having for example from 3 to 15, preferably 3 to 10, more preferably 3 to 8 carbon atoms, and which is attached to the rest of the molecule by a single bond via any suitable carbon atom on the ring. A cycloalkyl group includes, but is not limited to, cyclopropyl, cyclobutyl, cyclopentyl, cyclohexyl, cycloheptyl, cyclooctyl, bicyclo[2.2.1]heptyl, 7,7-dimethyl-bicyclo[2.2.1]heptyl, bicyclo[2.2.2]octyl, bicyclo[3.1.1]heptyl, bicyclo[3.2.1]octyl, adamantyl, and the like, preferably cyclobutyl, cyclopentyl, and cyclohexyl groups. All hydrogen atoms on a cycloalkyl group may optionally replaced with any suitable groups, for example, halogen, hydroxy, amino, mono-substituted amino, di-substituted amino, alkyl, alkoxy, heterocyclyl, and the like.

In the present application, as an independent group or a part of other group(s), the term "cycloalkenyl" refers to a stable non-aromatic monocyclic or polycyclic hydrocarbon group consisting solely of carbon and hydrogen atoms, and containing at least one double bond, which may include fused or bridged cyclic systems with for example, from 3 to 15, preferably 3 to 10, more preferably 3 to 8 carbon atoms, and which is attached to the rest of the molecule by a single bond via any suitable carbon atom on the ring. Examples of cycloalkenyl include, but are not limited to, cyclobutenyl, cyclopentenyl, cyclohexenyl, 1,3-cyclohexadiene, 1,4-cyclohexadiene, 1H-indenyl, 2,3-dihydro-indenyl, 1,2,3,4-tetrahydro-naphthyl, 5,6,7,8-tetrahydro-naphthyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, bicyclo[2.2.1]heptenyl, bicyclo[2.2.2]octyl, bicyclo[2.2.2]octenyl, bicyclo[3.2.1]octenyl, octahydro-4,7-methylene-1H-indenyl, octahydro-2,5-methylene-pentadienyl, and the like. All hydrogen atoms on a cycloalkenyl group are optionally replaced with any suitable groups, for example, halogen, hydroxy, amino, mono-substituted amino, di-substituted amino, alkyl, alkoxy, heterocyclyl, and the like.

In the present application, the term "halo aliphatic" refers to an aliphatic group, as defined above, which is substituted by one or more halogen atoms. Examples of halo aliphatic include, but are not limited to, fluoromethyl, difluoromethyl, trifluoromethyl, fluoroethyl, 1,1-difluoroethyl, chloromethyl, chloroethyl, dichloromethyl, 1,2-dichloroethyl, fluoroethenyl, fluorocyclopentyl, fluorocyclohexyl, chlorocyclohexenyl, and the like, preferably fluoroethyl.

In the present application, the term "hydroxy aliphatic" refers to an aliphatic group, as defined above, substituted by one or more hydroxy groups. Examples of hydroxy aliphatic include, but are not limited to, 1-hydroxyethyl, 1,2-dihydroxyethyl, 3-hydroxy-cyclopentyl, 4-hydroxy-cyclohexyl, 3,4-dihydroxy-cyclohexyl, and the like, preferably 1-hydroxyethyl.

In the present application, the term "amino aliphatic" refers to an aliphatic group, as defined above, substituted by one or more amino groups.

In the present application, as an independent group or a part of other group(s), the term "aliphaticoxy" refers to a group as represented by formula —$OR_a$, wherein $R_a$ is an aliphatic group as defined above. The aliphatic moiety of the aliphaticoxy group may be optionally substituted as described above for an aliphatic group. Examples of aliphaticoxy include, but are not limited to, methoxy, ethoxy, isobutoxy, n-butoxy, isobutoxy, tert-butoxy, ethenyloxy, 1-propenyloxy, 1-propynyloxy, cyclopentyloxy, cyclohexyloxy, and the like, preferably methoxy and ethoxy.

In the present application, the term "hydroxy aliphaticoxy" refers to an aliphaticoxy group, as defined above, wherein the aliphatic moiety is substituted by one or more hydroxy groups. Examples of hydroxy aliphaticoxy include, but are not limited to, 1-hydroxyethoxy, 1-hydroxypropoxy, 3-hydroxy-cyclopentyloxy, 3,4-dihydroxy cyclohexyloxy, and the like, preferably 1-hydroxyethoxy.

In the present application, as an independent group or a part of other group(s), the term "aliphaticcarbonyl" refers to a group of the formula —$C(=O)—R_a$, wherein $R_a$ is an aliphatic group as defined above. The aliphatic moiety of the aliphaticcarbonyl group may be optionally substituted as described above for an aliphatic group. Aliphaticcarbonyl includes alkylcarbonyl, alkenylcarbonyl, alkynylcarbonyl, cycloalkylcarbonyl and cycloalkenylcarbonyl, wherein alkyl, alkenyl, alkynyl, cycloalkyl and cycloalkenyl are as defined above. In the present application, aliphaticcarbonyl preferably refers to alkylcarbonyl and/or cycloalkylcarbonyl. Examples of aliphaticcarbonyl include, but are not limited to, methylcarbonyl (also referred to as acetyl), ethylcarbonyl (also referred to as propionyl), isopropylcarbonyl, butylcarbonyl, ethenylcarbonyl, propenylcarbonyl, cyclopentylcarbonyl, cyclohexylcarbonyl, and the like, preferably methylcarbonyl.

In the present application, as an independent group or a part of other group(s), the term "aliphaticamino" refers to a group of the formula —$NHR_a$, wherein $R_a$ is an aliphatic group as defined above. An aliphaticamino group includes alkylamino, alkenylamino, alkynylamino, cycloalkylamino and cycloalkenylamino groups, wherein the alkyl, alkenyl, alkynyl, cycloalkyl and cycloalkenyl moieties are all defined as above. In the present application, an aliphaticamino group preferably refers to alkylamino and/or cycloalkylamino groups. Examples include, but are not limited to, methylamino, ethylamino, isopropylamino, ethenylamino, propenylamino, propynylamino, cyclobutylamino, cyclopentylamino, cyclohexylamino, cyclohexenylamino, and the like, preferably methylamino, ethylamino, and cyclohexylamino.

In the present application, as an independent group or a part of other group(s), the term "dialiphaticamino" refers to an amino group on which two hydrogen atoms are, respectively, replaced with an aliphatic group, and which can be represented by formula —$NR_aR_b$, wherein $R_a$ and $R_b$ are independently an aliphatic group as defined above. In the present application, a dialiphaticamino group preferably refers to a dialkylamino group. Examples of dialkylmino include, but are not limited to, dimethylamino, diethylamino, dipropylamino, methylethylamino, and the like, preferably dimethylamino.

In the present application, as an independent group or a part of other group(s), the term "aliphaticoxy aliphaticoxy" refers to an aliphaticoxy group as defined above, wherein the aliphatic moiety is substituted by an aliphaticoxy group as defined above. An aliphaticoxy aliphaticoxy group preferably refers to alkoxyalkoxy, alkoxycycloalkoxy and/or cycloalkoxyalkoxy groups. Examples of aliphaticoxy aliphaticoxy include, but are not limited to, methoxyethoxy, ethoxyethoxy, methoxycyclopentyloxy, methoxy cyclohexyloxy, cyclopentyloxy methoxy, and the like.

In the present application, as an independent group or a part of other group(s), the term "aliphaticamino aliphatic" refers to an aliphatic group, as defined above, which is substituted by an aliphaticamino group as defined above.

In the present application, as an independent group or a part of other group(s), the term "dialiphaticamino aliphatic" refers to an aliphatic group, as defined above, which is substituted by a dialiphaticamino group as defined above. Examples of dialiphaticamino aliphatic include, but are not limited to, dimethylamino ethyl, diethylamino ethyl, (methyl)(ethyl)amino ethyl, and the like, preferably dimethylamino ethyl.

In the present application, as an independent group or a part of other group(s), the term "dialiphaticamino aliphaticamino" refers to an aliphaticamino group as defined above, wherein the aliphatic moiety is substituted by a dialiphaticamino group as defined above. Examples of dialiphaticamino aliphaticamino include, but are not limited to, dimethylamino ethylamino, diethylamino ethylamino, (methyl)(ethyl)amino ethylamino, and the like, preferably dimethylamino ethylamino.

In the present application, as an independent group or a part of other group(s), the term "aliphaticaminoacyl" refers to an aminoacyl group wherein one hydrogen atom on the amino moiety is replaced with an aliphatic group as defined above, and which can be represented by formula —C(=O)—NH—$R_a$, wherein $R_a$ is an aliphatic group as defined above. Examples of aliphaticaminoacyl include, but are not limited to, —C(=O)—NH—$CH_3$, —C(=O)—NH—$C_2H_5$, cyclohexylaminoacyl, and the like, preferably —C(=O)—NH—$CH_3$.

In the present application, as an independent group or a part of other group(s), the term "heterocyclyl" refers to a stable 3- to 18-membered non-aromatic ring group comprising 1 to 6 heteroatoms selected from the group consisting of nitrogen, oxygen and sulphur. Unless indicated otherwise specifically in the specification, the heterocyclyl group may be a monocyclic, bicyclic, tricyclic or polycyclic ring system, which may include fused or bridged ring systems. For purpose of the present invention, heterocyclyl is preferably a stable 3- to 12-membered non-aromatic monocyclic or bicyclic ring group comprising 1 to 3 heteroatoms selected from the group consisting of nitrogen, oxygen and sulphur, more preferably a stable 3- to 8-membered non-aromatic monocyclic ring group comprising 1 to 3 heteroatoms selected from the group consisting of nitrogen, oxygen and sulphur. The nitrogen, carbon or sulphur atom in the heterocyclyl group may be optionally oxidized; the nitrogen atom may be optionally quaternized; and the heterocyclyl group may be partially or fully saturated. The heterocyclyl group may be attached to the rest of the molecule by a single bond via a carbon atom or a heteroatom. In a heterocyclyl group containing fused rings, one or more rings may be aryl or heteroaryl, provided that the point of attachment of the heterocyclyl group to the rest of the molecule is through an atom on the non-aromatic ring. Examples of such heterocyclyl groups include, but are not limited to, azetidinyl, pyranyl, tetrahydropyranyl, thiopyranyl, tetrahydrofuranyl, morpholinyl, thiomorpholinyl, piperazinyl, piperidinyl, oxazinyl, dioxolanyl, tetrahydroisoquinolinyl, decahydroisoquinolinyl, imidazolinyl, imidazolidinyl, quinolizinyl, thiazolidinyl, isothiazolidinyl, isoxazolidinyl, indolinyl, octahydroindolyl, octahydroisoindolyl, pyrrolidinyl, pyrazolidinyl, phthalimido, and the like, preferably piperazinyl, piperidyl, tetrahydropyranyl, and morpholinyl. A heterocyclyl group may be optionally substituted by any suitable substituents including, but not limited to, halogen, hydroxy, amino, alkyl, alkoxy, alkylcarbonyl, and the like.

In the present application, "N-heterocyclyl" refers to a heterocyclyl group, as defined above, containing at least one nitrogen atom on its ring.

In the present application, as an independent group or a part of other group(s), the term "heterocyclyloxy" refers to a group of the formula —$OR_h$, wherein $R_h$ is a heterocyclyl group as define above. The heterocyclyl moiety of the heterocyclyloxy group may be optionally substituted as described above for a heterocyclyl group.

In the present application, as an independent group or a part of other group(s), the term "heterocyclylcarbonyl" refers to a group of the formula —C(=O)—$R_h$, wherein $R_h$ is a heterocyclyl group as defined above. The heterocyclyl moiety of the heterocyclylcarbonyl group may be optionally substituted as described above for a heterocyclyl group.

In the present application, as an independent group or a part of other group(s), the term "heterocyclylamino" refers to a group of the formula $R_h$—NH—, wherein $R_h$ is a heterocyclyl group as defined above. The heterocyclyl moiety of the heterocyclylamino group may be optionally substituted as described above for a heterocyclyl group.

In the present application, as an independent group or a part of other group(s), the term "heterocyclylaminoacyl" refers to an aminoacyl group as defined above, wherein one hydrogen on the amino moiety is replaced with a heterocyclyl group as defined above, and which can be represented by formula —C(=O)—NH—R$_h$, wherein R$_h$ is a heterocyclyl group as defined above. The heterocyclyl moiety of the heterocyclylaminoacyl group may be optionally substituted as described above for a heterocyclyl group.

In the present application, as an independent group or a part of other group(s), the term "heterocyclyl aliphatic" refers to an aliphatic group, as defined above, that is substituted by a heterocyclyl group as defined above. The heterocyclyl moiety of the heterocyclyl aliphatic group may be optionally substituted as described above for a heterocyclyl group, and the aliphatic moiety of the heterocyclyl aliphatic group may be optionally substituted as described above for an aliphatic group.

In the present application, as an independent group or a part of other group(s), the term "heterocyclyl aliphaticoxy" refers to an aliphaticoxy group as defined above, wherein the aliphatic moiety is substituted by a heterocyclyl group as defined above. The heterocyclyl moiety of the heterocyclyl aliphaticoxy group may be optionally substituted as described above for heterocyclyl, and the aliphatic moiety of the heterocyclyl aliphaticoxy group may be optionally substituted as described above for an aliphatic group.

In the present application, as an independent group or a part of other group(s), the term "aryl" refers to a system group having from 6 to 18, preferably 6 to 12 carbon atoms and at least one aromatic ring. For the purpose of the present invention, the aryl group may be a monocylic, bicylic, tricylic or polycyclic ring system, which may include a fused or bridged ring system. The aryl group is attached to the rest of the molecule by a single bond via an atom on the aromatic ring. Examples of such aryl groups include, but are not limited to, phenyl, naphthyl, anthryl, phenanthryl, fluorenyl, 2-benzoxazolinone, 2H-1,4-benzoxazin-3(4H)-one-7-yl, and the like; preferably phenyl.

In the present application, as an independent group or a part of other group(s), the term "heteroaryl" refers to a 5- to 16-membered ring system group containing 1 to 4 heteroatoms selected from the group consisting of nitrogen, oxygen and sulphur on its ring, and at least one aromatic ring. Unless otherwise indicated in the present specification, the heteroaryl group may be a monocyclic, bicyclic, tricyclic or polycyclic ring system, which may include a fused or bridged ring system, provided that the point of attachment is through an atom on the aromatic ring. The nitrogen, carbon or sulphur atoms in the heteroaryl group may be optionally oxidized; and the nitrogen atom may be optionally quaternized. For the purpose of the present invention, the heteroaryl group is preferably a stable 5- to 12-membered aromatic monocyclic or bicyclic ring group containing 1 to 3 heteroatoms selected from the group consisting of nitrogen, oxygen and sulphur, more preferably a stable 5- to 8-membered aromatic monocyclic or bicyclic ring group containing 1 to 3 heteroatoms selected from the group consisting of nitrogen, oxygen and sulphur, and most preferably a stable 5- to 6-membered aromatic monocyclic ring group containing 1 to 2 heteroatoms selected from the group consisting of nitrogen, oxygen and sulphur. Examples of such heteroaryl groups include, but are not limited to, thienyl, furyl, pyrrolyl, imidazolyl, benzimidazolyl, pyrazolyl, benzopyrazolyl, triazolyl, tetrazolyl, pyridinyl, pyrazinyl, triazinyl, pyrimidinyl, pyridazinyl, indolizinyl, indolyl, isoindolyl, indazolyl, isoindazolyl, purinyl, quinolyl, isoquinolyl, naphthyridinyl, naphthyridinyl, quinoxalinyl, pteridinyl, carbazolyl, carbolinyl, phenanthridinyl, phenanthrolinyl, acridinyl, phenazinyl, thiazolyl, isothiazolyl, benzothiazolyl, benzothienyl, oxazolyl, isoxazolyl, oxadiazolyl, oxatriazolyl, cinnolinyl, quinazolinyl, phenylthio, indolizinyl, phenanthrolinyl, phenoxazinyl, phenothiazinyl, 4,5,6,7-tetrahydro-benzo[b]thienyl, naphthopyridinyl, imidazo[1,2-a]pyridinyl, and the like, preferably pyrrolyl, pyrazolyl, imidazolyl, thienyl, isoxazolyl, thiazolyl, isothiazolyl, pyridinyl, and imidazo[1,2-a]pyridinyl, and more preferably pyrazolyl, thienyl, isoxazolyl, thiazolyl, and isothiazolyl.

In the present application, "optional" or "optionally" means that the subsequently described event or circumstance may or may not occur, and that the description includes instances where said event or circumstance occurs and instances in which it does not. For example, "alkyl optionally substituted by one or more halogens" means the alkyl group is unsubstituted or substituted by one or more halogens, and that the description includes both substituted alkyl groups and unsubstituted alkyl groups.

A "stereoisomer" refers to a compound made up of the same atoms bonded by the same bonds but having different three-dimensional structures. The present invention contemplates various stereoisomers and mixtures thereof.

As the compounds of formula I of the present invention contain an olefinic double bond, and unless specified otherwise, it is intended that the compounds include both E- and Z-geometric isomers.

A "tautomer" refers to an isomer resulted from a proton shift from one atom of a molecule to another atom of the same molecule. All tautomeric forms of the compound of formula I of the present invention are included within the scope of the present invention.

In the present application, the term "pharmaceutically acceptable salt" includes both pharmaceutically acceptable acid and base addition salts.

"Pharmaceutically acceptable acid addition salt" refers to those salts which are capable of retaining the biological effectiveness of the free bases without any undesirable effects, and which are formed with inorganic acid or organic acids. The inorganic acids include, but are not limited to, hydrochloric acid, hydrobromic acid, sulfuric acid, nitric acid, phosphoric acid and the like; and the organic acids include, but are not limited to, formic acid, acetic acid, trifluoroacetic acid, propionic acid, caprylic acid, caproic acid, capric acid, undecylenic acid, glycolic acid, gluconic acid, lactic acid, oxalic acid, sebacic acid, adipic acid, glutaric acid, malonic acid, maleic acid, succinic acid, fumaric acid, tartaric acid, citric acid, palmitic acid, stearic acid, oleic acid, cinnamic acid, lauric acid, malic acid, glutamic acid, pyroglutamic acid, aspartic acid, benzoic acid, methanesulfonic acid, p-toluene sulfonic acid, alginic acid, ascorbic acid, salicylic acid, 4-amino salicylic acid, naphthalene disulfonic acid, and the like. These salts can be prepared by the methods known in the art.

"Pharmaceutically acceptable base addition salt" refers to those salts which are capable of retaining the biological effectiveness of free acids without any undesirable effects. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, dicyclohexylamine, lysine, arginine, histidine, caffeine, choline, betaine, ethylenediamine, glucosamine, methylglucamine, theobromine, tromethamine, purines, piperazine, piperidine, N-ethylpiperidine, polyamine resins, and the like.

Depending on the number of the charged function groups and the valency of cations or anions, the compound of the present invention may contain a plurality of cations or anions.

Often crystallizations produce a solvate of the compound of the present invention. In the present application, a "solvate" refers to an aggregate that comprises one or more molecules of a compound of the present invention with one or more molecules of solvent. They either react with each other in the solvent or precipitate or crystallize from the solvent. The solvent may be water, in which case the solvate is a hydrate. Alternatively, the solvent may be an organic solvent. The solvates of the compounds of the present invention are also within the scope of the present invention.

In the present application, a "pharmaceutical composition" refers to a formulation of a compound of the present invention and a medium generally accepted in the art for the delivery of the biologically active compound to mammals, e.g., humans. Said a medium includes pharmaceutically acceptable excipients. The pharmaceutical composition of the present invention may be a single formulation, or may be a combination of a plurality of formulations.

In the present application, "pharmaceutically acceptable excipient" includes without limitation any adjuvant, carrier, excipient, glidant, sweetening agent, diluent, preservative, dyes/colorant, flavoring agent, surfactant, wetting agent, dispersing agent, suspending agent, stabilizer, isotonic agent, solvent or emulsifier which has been approved by relevant state authorities as being acceptable for use in humans or domestic animals.

In the present application, "therapeutically effective amount" refers to that amount of a compound of the present invention which, when administered to a mammal, e.g., a human, is sufficient to effect treatment of a disease or disorder in the mammal, e.g., a human. The amount of a compound of the invention which constitutes a "therapeutically effective amount" will vary depending on the particular compound used, the particular disorder to be treated, cause of the disorder, targets of the drug, severity of the disease, the manner of administration, and the age, weight, physical conditions, and the like of the mammal to be treated, but can be routinely determined by one skilled in the art having regard to his own knowledge and to the disclosure of the present application.

According to one aspect of the present invention, the present invention provides a compound represented by formula I:

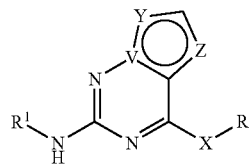

wherein:

R is selected from $C_{3-8}$ cycloalkyl substituted by $-NR^2W$; a 4- to 10-membered saturated N-heterocyclyl group, which contains only one nitrogen atom on its ring, and the nitrogen atom is substituted by W; or $C_{1-4}$ alkyl substituted by a 4- to 10-membered saturated N-heterocyclyl group which contains only one nitrogen atom on its ring and the nitrogen atom is substituted by W;

W is selected from

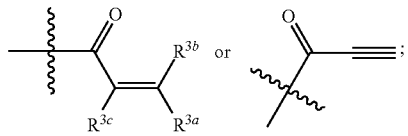

V is selected from C or N;
X is selected from O, S, or $NR^4$;
Y is selected from CH, O, or S;
Z is selected from CH, O, S, or $NR^5$;
$R^1$ is a $C_{6-12}$ aryl or a 5- to 12-membered heteroaryl group, optionally substituted by one or more $R^6$;
$R^2$ is selected from hydrogen or $C_{1-8}$ aliphatic;
$R^{3a}$, $R^{3b}$, and $R^{3c}$ are independently selected from the group consisting of hydrogen, halogen, and di($C_{1-8}$ aliphatic)aminomethyl;
$R^4$ is selected from hydrogen or $C_{1-8}$ aliphatic;
$R^5$ is selected from hydrogen or $C_{1-8}$ aliphatic;
Each $R^6$ is independently selected from the group consisting of halogen, nitro, cyano, heterocyclyl, $C_{6-12}$ aryl, 5- to 12-membered heteroaryl, $C_{1-8}$ aliphatic, $C_{1-8}$ haloaliphatic, heterocyclyl $C_{1-8}$ aliphatic, hydroxy $C_{1-8}$ aliphatic, $C_{1-8}$ aliphaticoxy $C_{1-8}$ aliphatic, $C_{1-8}$ aliphaticcarbonyloxy $C_{1-8}$ aliphatic, amino $C_{1-8}$ aliphatic, carboxyl $C_{1-8}$ aliphatic, $C_{1-8}$ aliphaticamino $C_{1-8}$ aliphatic, di($C_{1-8}$ aliphatic)amino $C_{1-8}$ aliphatic, $C_{1-8}$ aliphaticacylamino $C_{1-8}$ aliphatic, $C_{1-8}$ aliphaticcarbonyl $C_{1-8}$ aliphatic, $C_{1-8}$ aliphaticoxycarbonyl $C_{1-8}$ aliphatic, aminoacyl $C_{1-8}$ aliphatic, $C_{1-8}$ aliphaticaminoacyl $C_{1-8}$ aliphatic, di($C_{1-8}$ aliphatic)aminoacyl $C_{1-8}$ aliphatic, $C_{1-8}$ aliphaticsulfonyl $C_{1-8}$ aliphatic, $C_{1-8}$ aliphaticsulfinyl $C_{1-8}$ aliphatic, $C_{1-8}$ aliphaticsulfonylamino, $C_{1-8}$ aliphaticsulfonylamino $C_{1-8}$ aliphatic, sulfamoyl $C_{1-8}$ aliphatic, $C_{1-8}$ aliphaticaminosulfonyl $C_{1-8}$ aliphatic, di($C_{1-8}$ aliphatic)aminosulfonyl $C_{1-8}$ aliphatic, di($C_{1-8}$ aliphatic) phosphonyl $C_{1-8}$ aliphatic, hydroxy, $C_{1-8}$ aliphaticoxy, heterocyclyloxy, heterocyclyl $C_{1-8}$ aliphaticoxy, hydroxy $C_{1-8}$ aliphaticoxy, $C_{1-8}$ aliphaticoxy $C_{1-8}$ aliphaticoxy, amino $C_{1-8}$ aliphaticoxy, $C_{1-8}$ aliphaticamino $C_{1-8}$ aliphaticoxy, di($C_{1-8}$ aliphatic)amino $C_{1-8}$ aliphaticoxy, $C_{1-8}$ aliphaticacylamino $C_{1-8}$ aliphaticoxy, $C_{1-8}$ aliphaticcarbonyl $C_{1-8}$ aliphaticoxy, aminoacyl $C_{1-8}$ aliphaticoxy, $C_{1-8}$ aliphaticaminoacyl $C_{1-8}$ aliphaticoxy, di($C_{1-8}$ aliphatic)aminoacyl $C_{1-8}$ aliphaticoxy, amino, $C_{1-8}$ aliphaticamino, di($C_{1-8}$ aliphatic)amino, heterocyclyl amino, heterocyclyl $C_{1-8}$ aliphaticamino, hydroxy $C_{1-8}$ aliphaticamino, $C_{1-8}$ aliphaticoxy $C_{1-8}$ aliphaticamino, amino $C_{1-8}$ aliphaticamino, $C_{1-8}$ aliphaticamino $C_{1-8}$ aliphaticamino, di($C_{1-8}$ aliphatic)amino $C_{1-8}$ aliphaticamino, $C_{1-8}$ aliphaticacylamino $C_{1-8}$ aliphaticamino, $C_{1-8}$ aliphaticcarbonyl $C_{1-8}$ aliphaticamino, aminoacyl $C_{1-8}$ aliphaticamino, $C_{1-8}$ aliphaticaminoacyl $C_{1-8}$ aliphaticamino, di($C_{1-8}$ aliphatic)aminoacyl $C_{1-8}$ aliphaticamino, $C_{1-8}$ aliphaticacylamino, heterocyclyl $C_{1-8}$ aliphaticacylamino, heterocyclylacylamino, hydroxy $C_{1-8}$ aliphaticacylamino, $C_{1-8}$ aliphaticoxy $C_{1-8}$ aliphaticacylamino, amino $C_{1-8}$ aliphaticacylamino, $C_{1-8}$ aliphaticamino $C_{1-8}$ aliphaticacylamino, di($C_{1-8}$ aliphatic)amino $C_{1-8}$ aliphaticacylamino, $C_{1-8}$ aliphaticcarbonyl, heterocyclylcarbonyl, heterocyclyl $C_{1-8}$ aliphaticcarbonyl, $C_{1-8}$ aliphaticoxycarbonyl, heterocyclyl $C_{1-8}$ aliphaticoxycarbonyl, di($C_{1-8}$ aliphatic)amino $C_{1-8}$ aliphaticoxycarbonyl, aminoacyl, $C_{1-8}$ aliphaticaminoacyl, di($C_{1-8}$ aliphatic)aminoacyl, heterocyclyl $C_{1-8}$ aliphaticaminoacyl, heterocyclylaminoacyl, hydroxy $C_{1-8}$ aliphaticaminoacyl, $C_{1-8}$ aliphaticoxy $C_{1-8}$ aliphaticaminoacyl, amino $C_{1-8}$ aliphaticaminoacyl, $C_{1-8}$ aliphaticamino $C_{1-8}$ aliphaticaminoacyl, di($C_{1-8}$ aliphatic)amino $C_{1-8}$ aliphaticaminoacyl, $C_{1-8}$ aliphaticsulfhydryl, heterocyclylsulfhydryl, heterocyclyl $C_{1-8}$ aliphaticsulfhydryl, $C_{1-8}$ aliphaticsulfonyl, $C_{1-8}$ aliphaticsulfinyl, heterocyclylsulfonyl, heterocyclylsulfinyl, heterocyclyl $C_{1-8}$ aliphaticsulfonyl, heterocyclyl $C_{1-8}$ aliphaticsulfinyl, sulfamoyl, $C_{1-8}$ aliphaticaminosulfonyl, di($C_{1-8}$ aliphatic)aminosulfonyl, heterocyclyl $C_{1-8}$ aliphaticaminosulfonyl, heterocyclylaminosulfonyl, di($C_{1-8}$ aliphatic) amino $C_{1-8}$ aliphaticaminosulfonyl, aminosulfinyl, $C_{1-8}$ aliphaticaminosulfinyl, di($C_{1-8}$ aliphatic)aminosulfinyl, heterocyclylaminosulfinyl and di($C_{1-8}$ aliphatic)phosphonyl, wherein:

heterocyclyl, as an independent group or a part of other group(s), represents a saturated or partially unsaturated 3- to 12-membered heterocyclyl group containing one or more heteroatoms selected from the group consisting of N, O, and S; optionally, each heterocyclyl is independently substituted by one or more substituents selected from the group consisting of halogen, $C_{1-8}$ aliphatic, hydroxy $C_{1-8}$ aliphatic, $C_{1-8}$ aliphaticoxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, heterocyclyl $C_{1-8}$ aliphatic, heterocyclyl, 5- to 12-membered heteroaryl, hydroxy, $C_{1-8}$ aliphaticoxy, amino, $C_{1-8}$ aliphaticamino, di($C_{1-8}$ aliphatic)amino, $C_{1-8}$ aliphaticcarbonyl, heterocyclylcarbonyl, heterocyclyl $C_{1-8}$ aliphaticcarbonyl, hydroxy $C_{1-8}$ aliphaticcarbonyl, $C_{1-8}$ aliphaticoxy $C_{1-8}$ aliphaticcarbonyl, di($C_{1-8}$ aliphatic)amino $C_{1-8}$ aliphaticcarbonyl, $C_{1-8}$ aliphaticoxycarbonyl, aminoacyl, $C_{1-8}$ aliphaticaminoacyl, di($C_{1-8}$ aliphatic)aminoacyl, $C_{1-8}$ aliphaticsulfonyl, $C_{1-8}$ aliphaticsulfinyl, heterocyclylsulfonyl, heterocyclylsulfinyl, heterocyclyl $C_{1-8}$ aliphaticsulfonyl, heterocyclyl $C_{1-8}$ aliphaticsulfinyl, sulfamoyl, $C_{1-8}$ aliphaticaminosulfonyl, and di($C_{1-8}$ aliphatic)aminosulfonyl; and optionally, $C_{6-12}$ aryl and 5- to 12-membered heteroaryl are independently substituted by one or more substituents selected from the group consisting of halogen, $C_{1-8}$ aliphatic, hydroxy, $C_{1-8}$ aliphaticoxy, amino, $C_{1-8}$ aliphaticamino, and di($C_{1-8}$ aliphatic)amino;

wherein $C_{1-8}$ aliphatic, at each occurrence, is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl, or a stereoisomer, a tautomer, a solvate, or a pharmaceutically acceptable salt thereof.

In some embodiments of the compound of formula I, R is $C_{3-8}$ cycloalkyl substituted by —$NR^2W$, wherein $R^2$ is selected from hydrogen or $C_{1-8}$ aliphatic; and W is selected from

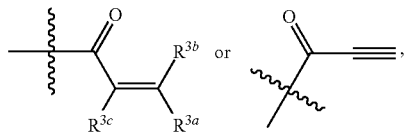

wherein $R^{3a}$, $R^{3b}$, and $R^{3c}$ are independently selected from the group consisting of hydrogen, halogen, and di($C_{1-8}$ aliphatic)aminomethyl, wherein $C_{1-8}$ aliphatic, at each occurrence, is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl.

In some embodiments of the compound of formula I, R is cyclohexyl substituted by —$NR^2W$, wherein $R^2$ is selected from hydrogen or $C_{1-8}$ aliphatic; and W is selected from

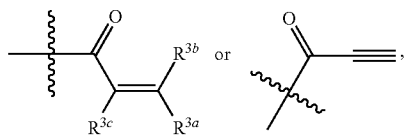

wherein $R^{3a}$, $R^{3b}$, and $R^{3c}$ are independently selected from the group consisting of hydrogen, halogen, and di($C_{1-8}$ aliphatic)aminomethyl, wherein $C_{1-8}$ aliphatic, at each occurrence, is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl.

In some embodiments of the compound of formula I, R is cyclohexyl substituted by —$NR^2W$, wherein $R^2$ is selected from hydrogen or $C_{1-8}$ alkyl; and W is selected from

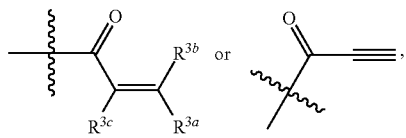

wherein $R^{3a}$, $R^{3b}$, and $R^{3c}$ are all hydrogen.

In some embodiments of the compound of formula I, R is a 4- to 10-membered saturated N-heterocyclyl group which contains only one nitrogen atom on its ring and the nitrogen atom is substituted by W, wherein W is

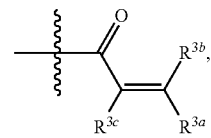

wherein $R^{3a}$, $R^{3b}$, and $R^{3c}$ are independently selected from the group consisting of hydrogen, halogen, and di($C_{1-8}$ aliphatic)aminomethyl, wherein $C_{1-8}$ aliphatic is selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl.

In some embodiments, R is a 4- to 10-membered saturated N-heterocyclyl group, which contains only one nitrogen atom on its ring, and the nitrogen atom is substituted by W, wherein W is

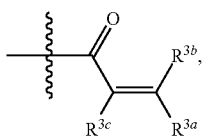

wherein $R^{3a}$, $R^{3b}$, and $R^{3c}$ are all hydrogen.

In some embodiments of the compound of formula I, R is a 4- to 10-membered saturated N-heterocyclyl group which contains only one nitrogen atom on its ring, and the nitrogen atom is substituted by W, wherein W is

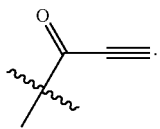

In some embodiments of the compound of formula I, R is $C_{1-4}$ alkyl substituted by a 4- to 10-membered saturated N-heterocyclyl group which contains only one nitrogen atom on its ring, and the nitrogen atom is substituted by W, wherein W is

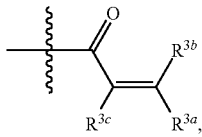

wherein $R^{3a}$, $R^{3b}$, and $R^{3c}$ are independently selected from the group consisting of hydrogen, halogen, and di($C_{1-8}$ aliphatic)aminomethyl, wherein $C_{1-8}$ aliphatic is selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl.

In some embodiments of the compound of formula I, R is $C_{1-4}$ alkyl substituted by a 4- to 10-membered saturated N-heterocyclyl group which contains only one nitrogen atom on its ring, and the nitrogen atom is substituted by W, wherein W is

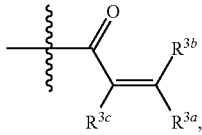

wherein $R^{3a}$, $R^{3b}$, and $R^{3c}$ are all hydrogen.

In some embodiments of the compound of formula I, R is $C_{1-4}$ alkyl substituted by a 4- to 10-membered saturated N-heterocyclyl group which contains only one nitrogen atom on its ring, and the nitrogen atom is substituted by W, wherein W is

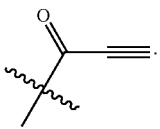

In some embodiments of the compound of formula I, X is O. In some other embodiments of the compound of formula I, X is S. In yet some other embodiments of the compound of formula I, X is $NR^4$, $R^4$ is selected from hydrogen or $C_{1-8}$ aliphatic, wherein $C_{1-8}$ aliphatic is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl. In some embodiments, X is $NR^4$, $R^4$ is selected from hydrogen or $C_{1-8}$ alkyl, and is more preferably selected from hydrogen or methyl.

In some embodiments of the compound of formula I, V is C. In some other embodiments of the compound of formula I, V is N.

In some embodiments of the compound of formula I, Y is CH. In some other embodiments of the compound of formula I, Y is O. In yet some other embodiments of the compound of formula I, Y is S.

In some embodiments of the compound of formula I, Z is CH. In some other embodiments of the compound of formula I, Z is O. In yet some other embodiments of the compound of formula I, Z is S. In some other embodiments of the compound of formula I, Z is $NR^5$, $R^5$ is selected from hydrogen or $C_{1-8}$ aliphatic, wherein $C_{1-8}$ aliphatic is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl. In some embodiments, $R^5$ is selected from hydrogen or $C_{1-8}$ alkyl, and is more preferably selected from hydrogen or methyl.

In some embodiments of the compound of formula I, at least one of V, Y and Z is a heteroatom.

In some embodiments of the compound of formula I, $R^1$ is $C_{6-12}$ aryl or 5- to 12-membered heteroaryl, optionally substituted by one or more $R^6$, wherein each $R^6$ is independently selected from the group consisting of halogen, heterocyclyl, $C_{1-8}$ aliphatic, $C_{1-8}$ halo aliphatic, heterocyclyl $C_{1-8}$ aliphatic, hydroxy $C_{1-8}$ aliphatic, $C_{1-8}$ aliphaticoxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, $C_{1-8}$ aliphaticoxy, heterocyclyloxy, heterocyclyl $C_{1-8}$ aliphaticoxy, hydroxy $C_{1-8}$ aliphaticoxy, $C_{1-8}$ aliphaticoxy $C_{1-8}$ aliphaticoxy, $C_{1-8}$ aliphaticamino, di($C_{1-8}$ aliphatic)amino, heterocyclylamino, amino $C_{1-8}$ aliphaticamino, $C_{1-8}$ aliphaticamino $C_{1-8}$ aliphaticamino, di($C_{1-8}$ aliphatic)amino $C_{1-8}$ aliphaticamino, $C_{1-8}$ aliphaticcarbonyl, heterocyclylcarbonyl, aminoacyl, $C_{1-8}$ aliphaticaminoacyl, di($C_{1-8}$ aliphatic)aminoacyl, heterocyclylaminoacyl, sulfamoyl, $C_{1-8}$ aliphaticaminosulfonyl, di($C_{1-8}$ aliphatic)aminosulfonyl, heterocyclylaminosulfonyl, aminosulfinyl, $C_{1-8}$ aliphaticamino sulfinyl, di($C_{1-8}$ aliphatic)aminosulfinyl, and heterocyclylaminosulfinyl, wherein:

heterocyclyl, as an independent group or a part of other group(s), represents a saturated or partially unsaturated 3- to 8-membered heterocyclyl group containing one or more heteroatoms selected from the group consisting of N, O, and S; optionally, each heterocyclyl is independently substituted by one or more substituents selected from the group consisting of hydroxy, $C_{1-8}$ aliphatic, $C_{1-8}$ aliphaticoxy, amino, and $C_{1-8}$ aliphaticcarbonyl;

wherein $C_{1-8}$ aliphatic, at each occurrence, is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl.

In some embodiments of the compound of formula I, $R^1$ is $C_{6-12}$ aryl or 5- to 12-membered heteroaryl, optionally substituted by one or more $R^6$; each $R^6$ is independently selected from the group consisting of halogen, heterocyclyl, $C_{1-8}$ aliphatic, $C_{1-8}$ halo aliphatic, heterocyclyl $C_{1-8}$ aliphatic, hydroxy $C_{1-8}$ aliphatic, $C_{1-8}$ aliphaticoxy $C_{1-8}$ aliphatic, C$_{1-8}$ aliphaticamino C$_{1-8}$ aliphatic, di(C$_{1-8}$ aliphatic) amino C$_{1-8}$ aliphatic, heterocyclyloxy, heterocyclyl C$_{1-8}$ aliphaticoxy, heterocyclylamino, C$_{1-8}$ aliphaticcarbonyl, heterocyclylcarbonyl, and heterocyclylaminoacyl, wherein:

heterocyclyl, as an independent group or a part of other group(s), represents a saturated or partially unsaturated 3- to 8-membered heterocyclyl group containing one or more heteroatoms selected from the group consisting of N, O, and S; optionally, each heterocyclyl is independently substituted by one or more C$_{1-8}$ aliphatic substituents.

In some embodiments of the compound of formula I, R$^1$ is C$_{6-12}$ aryl, optionally substituted by one or more R$^6$; each R$^6$ is independently selected from the group consisting of halogen, heterocyclyl, C$_{1-8}$ aliphatic, C$_{1-8}$ halo aliphatic, C$_{1-8}$ aliphaticoxy, heterocyclyloxy, heterocyclyl C$_{1-8}$ aliphaticoxy, hydroxy C$_{1-8}$ aliphaticoxy, C$_{1-8}$ aliphaticoxy C$_{1-8}$ aliphaticoxy, C$_{1-8}$ aliphaticamino, di(C$_{1-8}$ aliphatic)amino, heterocyclylamino, amino C$_{1-8}$ aliphaticamino, C$_{1-8}$ aliphaticamino C$_{1-8}$ aliphaticamino, di(C$_{1-8}$ aliphatic)amino C$_{1-8}$ aliphaticamino, C$_{1-8}$ aliphaticcarbonyl, heterocyclylcarbonyl, aminoacyl, C$_{1-8}$ aliphaticaminoacyl, di(C$_{1-8}$ aliphatic)aminoacyl, heterocyclylaminoacyl, sulfamoyl, C$_{1-8}$ aliphaticaminosulfonyl, di(C$_{1-8}$ aliphatic)aminosulfonyl, heterocyclylaminosulfonyl, aminosulfinyl, C$_{1-8}$ aliphaticaminosulfinyl, di(C$_{1-8}$ aliphatic)aminosulfinyl, and heterocyclylaminosulfinyl, wherein:

heterocyclyl, as an independent group or a part of other group(s), represents a saturated or partially unsaturated 3- to 8-membered heterocyclyl group containing one or more heteroatoms selected from the group consisting of N, O, and S; optionally, each heterocyclyl is independently substituted by one or more substituents selected from the group consisting of hydroxy, C$_{1-8}$ aliphatic, C$_{1-8}$ aliphaticoxy, amino, and C$_{1-8}$ aliphaticcarbonyl;

wherein C$_{1-8}$ aliphatic, at each occurrence, is independently selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl.

In some embodiments of the compound of formula I, R$^1$ is phenyl, optionally substituted by one or more R$^6$; each R$^6$ is independently selected from the group consisting of halogen, heterocyclyl, C$_{1-8}$ aliphatic, C$_{1-8}$ aliphaticoxy, heterocyclyloxy, heterocyclyl C$_{1-8}$ aliphaticoxy, hydroxy C$_{1-8}$ aliphaticoxy, C$_{1-8}$ aliphaticoxy C$_{1-8}$ aliphaticoxy, C$_{1-8}$ aliphaticamino, di(C$_{1-8}$ aliphatic)amino, heterocyclylamino, C$_{1-8}$ aliphaticamino C$_{1-8}$ aliphaticamino, di(C$_{1-8}$ aliphatic) amino C$_{1-8}$ aliphaticamino, C$_{1-8}$ aliphaticcarbonyl, heterocyclylcarbonyl, C$_{1-8}$ aliphaticaminoacyl, di(C$_{1-8}$ aliphatic) aminoacyl, and heterocyclylaminoacyl, wherein:

heterocyclyl, as an independent group or a part of other group(s), represents a saturated or partially unsaturated 3- to 8-membered heterocyclyl group containing one or more, preferably one or two, heteroatoms selected from the group consisting of N, O, and S, preferably selected from the group consisting of piperidinyl, piperazinyl, morpholinyl, and tetrahydropyranyl; optionally, each heterocyclyl is independently substituted by one or more, preferably one or two, substituents selected from the group consisting of hydroxy, C$_{1-8}$ aliphatic, C$_{1-8}$ aliphaticoxy, and C$_{1-8}$ aliphaticcarbonyl;

wherein C$_{1-8}$ aliphatic, at each occurrence, is independently selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl.

In some embodiments of the compound of formula I, R$^1$ is phenyl, optionally substituted by one or more R$^6$; each R$^6$ is independently selected from the group consisting of halogen, heterocyclyl, C$_{1-8}$ aliphatic, heterocyclyl C$_{1-8}$ aliphaticoxy, heterocyclylamino, heterocyclylcarbonyl, and heterocyclylaminoacyl, wherein heterocyclyl, as an independent group or a part of other group(s), represents a saturated or partially unsaturated 5- to 6-membered heterocyclyl group containing one or two heteroatoms selected from the group consisting of N, O, and S, preferably selected from the group consisting of piperidinyl, piperazinyl, and morpholinyl; optionally, each heterocyclyl is independently substituted by one or two C$_{1-8}$ aliphatic substituents, wherein C$_{1-8}$ aliphatic, at each occurrence, is independently selected from the group consisting of C$_{1-8}$ alkyl and C$_{3-8}$ cycloalkyl.

In some embodiments of the compound of formula I, R$^1$ is a 5- to 12-membered heteroaryl group, optionally substituted by one or more R$^6$, wherein each R$^6$ is independently selected from the group consisting of halogen, heterocyclyl, C$_{1-8}$ aliphatic, C$_{1-8}$ halo aliphatic, heterocyclyl C$_{1-8}$ aliphatic, hydroxy C$_{1-8}$ aliphatic, C$_{1-8}$ aliphaticoxy C$_{1-8}$ aliphatic, amino C$_{1-8}$ aliphatic, C$_{1-8}$ aliphaticamino C$_{1-8}$ aliphatic, di(C$_{1-8}$ aliphatic)amino C$_{1-8}$ aliphatic, C$_{1-8}$ aliphaticoxy, C$_{1-8}$ aliphaticcarbonyl, heterocyclylcarbonyl, and heterocyclyloxy, wherein:

heterocyclyl, as an independent group or a part of other group(s), represents a saturated or partially unsaturated 3- to 8-membered heterocyclyl group containing one or more heteroatoms selected from the group consisting of N, O, and S; optionally, each heterocyclyl is independently substituted by one or more substituents selected from the group consisting of hydroxy, C$_{1-8}$ aliphatic, C$_{1-8}$ aliphaticoxy, amino, and C$_{1-8}$ aliphaticcarbonyl;

wherein C$_{1-8}$ aliphatic, at each occurrence, is independently selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl.

In some embodiments of the compound of formula I, R$^1$ is a 5- to 10-membered heteroaryl group, optionally substituted by one or more R$^6$, wherein each R$^6$ is independently selected from the group consisting of heterocyclyl, C$_{1-8}$ aliphatic, C$_{1-8}$ halo aliphatic, heterocyclyl C$_{1-8}$ aliphatic, hydroxy C$_{1-8}$ aliphatic, C$_{1-8}$ aliphaticoxy C$_{1-8}$ aliphatic, amino C$_{1-8}$ aliphatic, C$_{1-8}$ aliphaticamino C$_{1-8}$ aliphatic, di(C$_{1-8}$ aliphatic)amino C$_{1-8}$ aliphatic, C$_{1-8}$ aliphaticoxy, and C$_{1-8}$ aliphaticcarbonyl, wherein:

heterocyclyl, as an independent group or a part of other group(s), represents a saturated or partially unsaturated 3- to 8-membered heterocyclyl group containing one or more, preferably one or two, heteroatoms selected from the group consisting of N, O, and S; optionally, each heterocyclyl is independently substituted by one or more, preferably one or two, C$_{1-8}$ aliphatic substituents;

wherein C$_{1-8}$ aliphatic, at each occurrence, is independently selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl.

In some embodiments of the compound of formula I, the compound of formula I is represented by formula Ia:

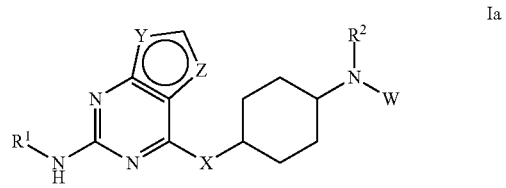

Ia wherein, X, Y, Z, W, R$^1$, and R$^2$ are all defined as in formula I.

In some embodiments of the compound of formula Ia, each group in the formula Ia is defined as follows:

W is selected from

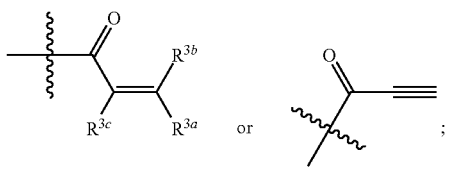

X is selected from S, O, or NR$^4$;
Y is selected from CH, O, or S;
Z is selected from CH, O, S, or NR$^5$;
R$^1$ is C$_{6-12}$ aryl or 5- to 12-membered heteroaryl, optionally substituted by one or more R$^6$;
R$^2$ is selected from hydrogen or C$_{1-8}$ aliphatic;
R$^{3a}$, R$^{3b}$ and R$^{3c}$ are independently selected from the group consisting of hydrogen, halogen, and di(C$_{1-8}$ aliphatic)aminomethyl;
R$^4$ is selected from hydrogen or C$_{1-8}$ aliphatic;
R$^5$ is selected from hydrogen or C$_{1-8}$ aliphatic;
each R$^6$ is independently selected from the group consisting of halogen, nitro, cyano, heterocyclyl, C$_{6-12}$ aryl, 5- to 12-membered heteroaryl, C$_{1-8}$ aliphatic, C$_{1-8}$ halo aliphatic, heterocyclyl C$_{1-8}$ aliphatic, hydroxy C$_{1-8}$ aliphatic, C$_{1-8}$ aliphaticoxy C$_{1-8}$ aliphatic, C$_{1-8}$ aliphaticcarbonyloxy C$_{1-8}$ aliphatic, amino C$_{1-8}$ aliphatic, C$_{1-8}$ aliphaticamino C$_{1-8}$ aliphatic, di(C$_{1-8}$ aliphatic)amino C$_{1-8}$ aliphatic, C$_{1-8}$ aliphaticacylamino C$_{1-8}$ aliphatic, C$_{1-8}$ aliphaticcarbonyl C$_{1-8}$ aliphatic, C$_{1-8}$ aliphaticoxycarbonyl C$_{1-8}$ aliphatic, aminoacyl C$_{1-8}$ aliphatic, C$_{1-8}$ aliphaticaminoacyl C$_{1-8}$ aliphatic, di(C$_{1-8}$ aliphatic)aminoacyl C$_{1-8}$ aliphatic, C$_{1-8}$ aliphaticsulfonyl C$_{1-8}$ aliphatic, C$_{1-8}$ aliphaticsulfinyl C$_{1-8}$ aliphatic, C$_{1-8}$ aliphaticsulfonylamino C$_{1-8}$ aliphatic, sulfamoyl C$_{1-8}$ aliphatic, C$_{1-8}$ aliphaticaminosulfonyl C$_{1-8}$ aliphatic, di(C$_{1-8}$ aliphatic)aminosulfonyl C$_{1-8}$ aliphatic, di(C$_{1-8}$ aliphatic)phosphonyl C$_{1-8}$ aliphatic, hydroxy, C$_{1-8}$ aliphaticoxy, heterocyclyloxy, heterocyclyl C$_{1-8}$ aliphaticoxy, hydroxy C$_{1-8}$ aliphaticoxy, C$_{1-8}$ aliphaticoxy C$_{1-8}$ aliphaticoxy, amino C$_{1-8}$ aliphaticoxy, C$_{1-8}$ aliphaticamino C$_{1-8}$ aliphaticoxy, di(C$_{1-8}$ aliphatic)amino C$_{1-8}$ aliphaticoxy, C$_{1-8}$ aliphaticacylamino C$_{1-8}$ aliphaticoxy, C$_{1-8}$ aliphaticcarbonyl C$_{1-8}$ aliphaticoxy, aminoacyl C$_{1-8}$ aliphaticoxy, C$_{1-8}$ aliphaticaminoacyl C$_{1-8}$ aliphaticoxy, di(C$_{1-8}$ aliphatic)aminoacyl C$_{1-8}$ aliphaticoxy, amino, C$_{1-8}$ aliphaticamino, di(C$_{1-8}$ aliphatic)amino, heterocyclylamino, heterocyclyl C$_{1-8}$ aliphaticamino, hydroxy C$_{1-8}$ aliphaticamino, C$_{1-8}$ aliphaticoxy C$_{1-8}$ aliphaticamino, amino C$_{1-8}$ aliphaticamino, C$_{1-8}$ aliphaticamino C$_{1-8}$ aliphaticamino, di(C$_{1-8}$ aliphatic)amino C$_{1-8}$ aliphaticamino, C$_{1-8}$ aliphaticacylamino C$_{1-8}$ aliphaticamino, C$_{1-8}$ aliphaticcarbonyl C$_{1-8}$ aliphaticamino, aminoacyl C$_{1-8}$ aliphaticamino, C$_{1-8}$ aliphaticaminoacyl C$_{1-8}$ aliphaticamino, di(C$_{1-8}$ aliphatic)aminoacyl C$_{1-8}$ aliphaticamino, C$_{1-8}$ aliphaticacylamino, heterocyclyl C$_{1-8}$ aliphaticacylamino, heterocyclylacylamino, hydroxy C$_{1-8}$ aliphaticacylamino, C$_{1-8}$ aliphaticoxy C$_{1-8}$ aliphaticacylamino, amino C$_{1-8}$ aliphaticacylamino, C$_{1-8}$ aliphaticamino C$_{1-8}$ aliphaticacylamino, di(C$_{1-8}$ aliphatic)amino C$_{1-8}$ aliphaticacylamino, C$_{1-8}$ aliphaticcarbonyl, heterocyclylcarbonyl, heterocyclyl C$_{1-8}$ aliphaticcarbonyl, C$_{1-8}$ aliphaticoxycarbonyl, heterocyclyl C$_{1-8}$ aliphaticoxycarbonyl, di(C$_{1-8}$ aliphatic)amino C$_{1-8}$ aliphaticoxycarbonyl, aminoacyl, C$_{1-8}$ aliphaticaminoacyl, di(C$_{1-8}$ aliphatic)aminoacyl, heterocyclyl C$_{1-8}$ aliphaticaminoacyl, heterocyclylaminoacyl, hydroxy C$_{1-8}$ aliphaticaminoacyl, C$_{1-8}$ aliphaticoxy C$_{1-8}$ aliphaticaminoacyl, amino C$_{1-8}$ aliphaticaminoacyl, C$_{1-8}$ aliphaticamino C$_{1-8}$ aliphaticaminoacyl, di(C$_{1-8}$ aliphatic)amino C$_{1-8}$ aliphaticaminoacyl, C$_{1-8}$ aliphaticsulfhydryl, heterocyclylsulfhydryl, heterocyclyl C$_{1-8}$ aliphaticsulfhydryl, C$_{1-8}$ aliphaticsulfonyl, C$_{1-8}$ aliphaticsulfinyl, heterocyclylsulfonyl, heterocyclylsulfinyl, heterocyclyl C$_{1-8}$ aliphaticsulfonyl, heterocyclyl C$_{1-8}$ aliphaticsulfinyl, sulfamoyl, C$_{1-8}$ aliphaticaminosulfonyl, di(C$_{1-8}$ aliphatic)aminosulfonyl, heterocyclyl C$_{1-8}$ aliphaticaminosulfonyl, heterocyclylaminosulfonyl, di(C$_{1-8}$ aliphatic)amino C$_{1-8}$ aliphaticaminosulfonyl, aminosulfinyl, C$_{1-8}$ aliphaticaminosulfinyl, di(C$_{1-8}$ aliphatic)aminosulfinyl, heterocyclylaminosulfinyl, and di(C$_{1-8}$ aliphatic)phosphonyl, wherein:

heterocyclyl, as an independent group or a part of other group(s), represents a saturated or partially unsaturated 3- to 12-membered heterocyclyl group containing one or more heteroatoms selected from the group consisting of N, O, and S; optionally, each heterocyclyl is independently substituted by one or more substituents selected from the group consisting of halogen, C$_{1-8}$ aliphatic, hydroxy C$_{1-8}$ aliphatic, C$_{1-8}$ aliphaticoxy C$_{1-8}$ aliphatic, amino C$_{1-8}$ aliphatic, C$_{1-8}$ aliphaticamino C$_{1-8}$ aliphatic, di(C$_{1-8}$ aliphatic)amino C$_{1-8}$ aliphatic, heterocyclyl C$_{1-8}$ aliphatic, heterocyclyl, 5- to 12-membered heteroaryl, hydroxy, C$_{1-8}$ aliphaticoxy, amino, C$_{1-8}$ aliphaticamino, di(C$_{1-8}$ aliphatic)amino, C$_{1-8}$ aliphaticcarbonyl, heterocyclylcarbonyl, heterocyclyl C$_{1-8}$ aliphaticcarbonyl, hydroxy C$_{1-8}$ aliphaticcarbonyl, C$_{1-8}$ aliphaticoxy C$_{1-8}$ aliphaticcarbonyl, di(C$_{1-8}$ aliphatic)amino C$_{1-8}$ aliphaticcarbonyl, C$_{1-8}$ aliphaticoxycarbonyl, aminoacyl, C$_{1-8}$ aliphaticaminoacyl, di(C$_{1-8}$ aliphatic)aminoacyl, C$_{1-8}$ aliphaticsulfonyl, C$_{1-8}$ aliphaticsulfinyl, heterocyclylsulfonyl, heterocyclylsulfinyl, heterocyclyl C$_{1-8}$ aliphaticsulfonyl, heterocyclyl C$_{1-8}$ aliphaticsulfinyl, sulfamoyl, C$_{1-8}$ aliphaticaminosulfonyl, and di(C$_{1-8}$ aliphatic)aminosulfonyl; and optionally, C$_{6-12}$ aryl and 5- to 12-membered heteroaryl are independently substituted by one or more substituents selected from the group consisting of halogen, C$_{1-8}$ aliphatic, hydroxy, C$_{1-8}$ aliphaticoxy, amino, C$_{1-8}$ aliphaticamino, and di(C$_{1-8}$ aliphatic)amino;

wherein C$_{1-8}$ aliphatic, at each occurrence, is independently selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl.

In some embodiments of the compound of formula Ia, W is

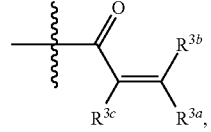

wherein R$^{3a}$, R$^{3b}$, and R$^{3c}$ are independently selected from the group consisting of hydrogen, halogen, and di(C$_{1-8}$ aliphatic)aminomethyl, wherein C$_{1-8}$ aliphatic is independently selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl.

In some embodiments, W is

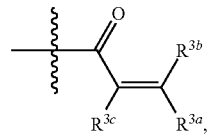

wherein R$^{3a}$, R$^{3b}$ and R$^{3c}$ are all hydrogen.

In some embodiments of the compound of formula Ia, W is

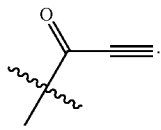

In some embodiments of the compound of formula Ia, X is S. In other some embodiments of the compound of formula Ia, X is O. In yet other some embodiments of the compound of formula Ia, X is $NR^4$, wherein $R^4$ is selected from hydrogen or $C_{1-8}$ aliphatic, wherein $C_{1-8}$ aliphatic is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl. In some embodiments, X is $NR^4$, wherein $R^4$ is selected from hydrogen or $C_{1-8}$ alkyl, more preferably selected from hydrogen or methyl, and most preferably hydrogen.

In some embodiments of the compound of formula Ia, Y is CH. In some other embodiments of the compound of formula Ia, Y is O. In yet other some embodiments of the compound of formula Ia, Y is S.

In one embodiment of the compound of formula Ia, Z is CH. In other some embodiments of the compound of formula Ia, Z is O. In yet other some embodiments of the compound of formula Ia, Z is S. In yet some other embodiments of the compound of formula Ia, Z is $NR^5$, wherein $R^5$ is selected from hydrogen or $C_{1-8}$ aliphatic, wherein $C_{1-8}$ aliphatic is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl. In yet some other embodiments, Z is $NR^5$, wherein $R^5$ is preferably selected from hydrogen or $C_{1-8}$ alkyl, more preferably selected from hydrogen or methyl, and most preferably hydrogen.

In some embodiments of the compound of formula Ia, at least one of Y and Z is a heteroatom.

In some embodiments of the compound of formula Ia, Y is S, and Z is CH.

In some embodiments of the compound of formula Ia, Y is O, and Z is CH.

In some embodiments of the compound of formula Ia, Y is CH, and Z is S. In some other embodiments of the compound of formula Ia, Y is CH, and Z is O.

In some embodiments of the compound of formula Ia, Y is CH, Z is $NR^5$, wherein $R^5$ is selected from hydrogen or $C_{1-8}$ aliphatic, wherein $C_{1-8}$ aliphatic is selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl. In some embodiments, Y is CH, and Z is $NR^5$, wherein $R^5$ is hydrogen.

In some embodiments of the compound of formula Ia, $R^1$ is a $C_{6-12}$ aryl or 5- to 12-membered heteroaryl group, optionally substituted by one or more $R^6$, wherein each $R^6$ is independently selected from the group consisting of halogen, heterocyclyl, $C_{1-8}$ aliphatic, $C_{1-8}$ halo aliphatic, heterocyclyl $C_{1-8}$ aliphatic, hydroxy $C_{1-8}$ aliphatic, $C_{1-8}$ aliphaticoxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, $C_{1-8}$ aliphaticoxy, heterocyclyloxy, heterocyclyl $C_{1-8}$ aliphaticoxy, hydroxy $C_{1-8}$ aliphaticoxy, $C_{1-8}$ aliphaticoxy $C_{1-8}$ aliphaticoxy, amino, $C_{1-8}$ aliphaticamino, di($C_{1-8}$ aliphatic)amino, heterocyclylamino, amino $C_{1-8}$ aliphaticamino, $C_{1-8}$ aliphaticamino $C_{1-8}$ aliphaticamino, di($C_{1-8}$ aliphatic)amino $C_{1-8}$ aliphaticamino, heterocyclylcarbonyl, aminoacyl, $C_{1-8}$ aliphaticaminoacyl, di($C_{1-8}$ aliphatic)aminoacyl, heterocyclylaminoacyl, sulfamoyl, $C_{1-8}$ aliphaticaminosulfonyl, di($C_{1-8}$ aliphatic)aminosulfonyl, heterocyclylaminosulfonyl, aminosulfinyl, $C_{1-8}$ aliphaticaminosulfinyl, di($C_{1-8}$ aliphatic)aminosulfinyl, and heterocyclylaminosulfinyl, wherein:

heterocyclyl, as an independent group or a part of other group(s), represents a saturated or partially unsaturated 3- to 8-membered heterocyclyl group containing one or more, preferably one or two, heteroatoms selected from the group consisting of O, N and S; optionally, which is independently substituted by one or more, optionally by one or two, substituents selected from the group consisting of $C_{1-8}$ aliphatic, hydroxy, $C_{1-8}$ aliphaticoxy and $C_{1-8}$ aliphaticcarbonyl, wherein $C_{1-8}$ aliphatic, at each occurrence, is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl.

In some embodiments of the compound of formula Ia, $R^1$ is $C_{6-12}$ aryl, optionally substituted by one or more $R^6$, wherein each $R^6$ is independently selected from the group consisting of halogen, heterocyclyl, $C_{1-8}$ aliphatic, $C_{1-8}$ aliphaticoxy, heterocyclyloxy, heterocyclyl $C_{1-8}$ aliphaticoxy, hydroxy $C_{1-8}$ aliphaticoxy, $C_{1-8}$ aliphaticoxy $C_{1-8}$ aliphaticoxy, amino, $C_{1-8}$ aliphaticamino, di($C_{1-8}$ aliphatic)amino, heterocyclylamino, amino $C_{1-8}$ aliphaticamino, $C_{1-8}$ aliphaticamino $C_{1-8}$ aliphaticamino, di($C_{1-8}$ aliphatic)amino $C_{1-8}$ aliphaticamino, $C_{1-8}$ aliphaticcarbonyl, heterocyclylcarbonyl, aminoacyl, $C_{1-8}$ aliphaticaminoacyl di($C_{1-8}$ aliphatic)aminoacyl, heterocyclylaminoacyl, sulfamoyl, $C_{1-8}$ aliphaticaminosulfonyl, di($C_{1-8}$ aliphatic)aminosulfonyl, heterocyclylaminosulfonyl, aminosulfinyl, $C_{1-8}$ aliphaticaminosulfinyl, di($C_{1-8}$ aliphatic)aminosulfinyl and heterocyclylaminosulfinyl, wherein heterocyclyl, as an independent group or a part of other group(s), represents a saturated or partially unsaturated 3- to 8-membered heterocyclyl group containing one or two heteroatoms selected from the group consisting of O, N and S; optionally, heterocyclyl is independently substituted by one or two substituents selected from the group consisting of $C_{1-8}$ aliphatic, hydroxy, $C_{1-8}$ aliphaticoxy and $C_{1-8}$ aliphaticcarbonyl, and wherein $C_{1-8}$ aliphatic, at each occurrence, is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl.

In some embodiments of the compound of formula Ia, $R^1$ is phenyl, optionally substituted by one or more $R^6$, wherein each $R^6$ is independently selected from the group consisting of halogen, heterocyclyl, $C_{1-8}$ aliphatic, $C_{1-8}$ aliphaticoxy, heterocyclyloxy, heterocyclyl $C_{1-8}$ aliphaticoxy, hydroxy $C_{1-8}$ aliphaticoxy, $C_{1-8}$ aliphaticoxy $C_{1-8}$ aliphaticoxy, di($C_{1-8}$ aliphatic)amino, $C_{1-8}$ aliphaticamino, heterocyclylamino, di($C_{1-8}$ aliphatic)amino $C_{1-8}$ aliphaticamino, $C_{1-8}$ aliphaticcarbonyl, heterocyclylcarbonyl, $C_{1-8}$ aliphaticaminoacyl and heterocyclylaminoacyl, wherein heterocyclyl, as an independent group or a part of other group(s), represents a saturated or partially unsaturated 5- to 6-membered heterocyclyl group containing one or two heteroatoms selected from the group consisting of O, N and S, preferably selected from the group consisting of piperidinyl, piperazinyl, morpholinyl and tetrahydropyranyl; optionally, each heterocyclyl is independently substituted by one or more substituents selected from the group consisting of $C_{1-8}$ aliphatic, hydroxy, $C_{1-8}$ aliphaticoxy and $C_{1-8}$ aliphaticcarbonyl, and wherein $C_{1-8}$ aliphatic, at each occurrence, is independently selected from the group consisting of $C_{1-8}$ alkyl and $C_{3-8}$ cycloalkyl.

In some embodiments of the compound of formula Ia, $R^1$ is phenyl, optionally substituted by one or more $R^6$, wherein each $R^6$ is independently selected from the group consisting of halogen, heterocyclyl, $C_{1-8}$ aliphatic, heterocyclyloxy, heterocyclyl $C_{1-8}$ aliphaticoxy, heterocyclylamino, heterocyclylcarbonyl and heterocyclylaminoacyl, wherein heterocyclyl, as an independent group or a part of other group(s), represents a saturated or partially unsaturated 5- to 6-membered heterocyclyl group containing one or two heteroatoms selected from the group consisting of O, N and S, preferably selected from the group consisting of piperidinyl, piperazinyl and morpholinyl; optionally, each heterocyclyl is independently substituted by one or two $C_{1-8}$ aliphatic substituents, and wherein $C_{1-8}$ aliphatic, at each occurrence, is independently selected from the group consisting of $C_{1-8}$ alkyl and $C_{3-8}$ cycloalkyl.

In some embodiments of the compound of formula Ia, $R^1$ is phenyl, optionally substituted by one or more $R^6$, wherein each $R^6$ is independently selected from the group consisting of fluorine, chlorine, methyl, methoxy, dimethylamino, methylaminoacyl, hydroxyethyloxy, methoxyethyloxy, dimethylaminoethylamino, heterocyclylethyloxy, heterocyclyl, cyclohexylamino, heterocyclylamino, heterocyclyloxy, heterocyclylcarbonyl and heterocyclylaminoacyl, wherein heterocyclyl, as an independent group or a part of other group(s), represents a saturated or partially unsaturated 5- to 6-membered heterocyclyl group containing one or two heteroatoms selected from the group consisting of O, N and S, preferably selected from the group consisting of piperidinyl, piperazinyl, morpholinyl and tetrahydropyranyl; optionally, each heterocyclyl is independently substituted by one or more substituents selected from the group consisting of methyl, methylcarbonyl, hydroxy, methoxy and isopropyl.

In some embodiments of the compound of formula Ia, $R^1$ is phenyl, optionally substituted by one or more $R^6$, wherein each $R^6$ is independently selected from the group consisting of fluorine, chlorine, methyl, heterocyclyl, heterocyclylethyloxy, heterocyclylamino, heterocyclyloxy, heterocyclylcarbonyl and heterocyclylaminoacyl, wherein heterocyclyl, as an independent group or a part of other group(s), represents a saturated or partially unsaturated 5- to 6-membered heterocyclyl group containing one or two heteroatoms selected from the group consisting of O, N and S, preferably selected from the group consisting of piperidinyl, piperazinyl and morpholinyl; optionally, each heterocyclyl is independently substituted by methyl or isopropyl.

In some embodiments of the compound of formula Ia, $R^1$ is a 5- to 12-membered heteroaryl group, optionally substituted by one or more $R^6$, wherein each $R^6$ is independently selected from the group consisting of heterocyclyl, $C_{1-8}$ aliphatic, $C_{1-8}$ halo aliphatic, heterocyclyl $C_{1-8}$ aliphatic, hydroxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, $C_{1-8}$ aliphaticoxy and $C_{1-8}$ aliphaticoxy $C_{1-8}$ aliphatic, wherein heterocyclyl, as an independent group or a part of other group(s), represents a saturated or partially unsaturated 3- to 8-membered heterocyclyl group containing one or two heteroatoms selected from the group consisting of O, N and S; optionally, each heterocyclyl is independently substituted by one or more $C_{1-8}$ aliphatic groups, and wherein $C_{1-8}$ aliphatic, at each occurrence, is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl.

In some embodiments of the compound of formula Ia, $R^1$ is a 5- to 10-membered heteroaryl group, optionally substituted by one or more $R^6$, wherein each $R^6$ is independently selected from the group consisting of heterocyclyl, $C_{1-8}$ aliphatic, $C_{1-8}$ halo aliphatic, heterocyclyl $C_{1-8}$ aliphatic, hydroxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, $C_{1-8}$ aliphaticoxy and $C_{1-8}$ aliphaticoxy $C_{1-8}$ aliphatic, wherein heterocyclyl, as an independent group or a part of other group(s), represents a saturated or partially unsaturated 5- to 6-membered heterocyclyl group containing one or two heteroatoms selected from the group consisting of O, N and S, preferably selected from the group consisting of morpholinyl, piperidinyl, piperazinyl and tetrahydropyranyl; optionally, each heterocyclyl is independently substituted by one or more $C_{1-8}$ aliphatic groups, and wherein $C_{1-8}$ aliphatic, at each occurrence, is independently selected from the group consisting of $C_{1-8}$ alkyl and $C_{3-8}$ cycloalkyl.

In some embodiments of the compound of formula Ia, $R^1$ is a 5- to 10-membered heteroaryl group, preferably selected from the group consisting of pyrrolyl, pyrazolyl, imidazolyl, thienyl, thiazolyl, isothiazolyl, isoxazolyl, pyridinyl, and imidazo[1,2-a] pyridinyl, which is optionally substituted by one or more $R^6$, wherein each $R^6$ is independently selected from the group consisting of methyl, cyclobutyl, cyclopentyl, hydroxyethyl, methoxy, methoxyethyl, fluoroethyl, dimethylaminoethyl, 1-methyl-piperazin-4-yl and morpholin-4-yl-ethyl.

In some embodiments of the compound of formula Ia, $R^1$ is a 5-membered heteroaryl group, preferably selected from the group consisting of pyrazolyl, thienyl, thiazolyl, isothiazolyl and isoxazolyl, which is optionally substituted by one or more $R^6$, wherein each $R^6$ is independently selected from the group consisting of $C_{1-8}$ aliphatic, $C_{1-8}$ halo aliphatic, heterocyclyl $C_{1-8}$ aliphatic, hydroxy $C_{1-8}$ aliphatic, $C_{1-8}$ aliphaticamino $C_{1-8}$ aliphatic, di($C_{1-8}$ aliphatic)amino $C_{1-8}$ aliphatic and $C_{1-8}$ aliphaticoxy $C_{1-8}$ aliphatic, wherein heterocyclyl, as an independent group or a part of other group(s), represents a saturated or partially unsaturated 5- to 6-membered heterocyclyl group containing one or two heteroatoms selected from the group consisting of O, N and S; optionally, each heterocyclyl is independently substituted by one or more $C_{1-8}$ aliphatic groups, and wherein $C_{1-8}$ aliphatic is independently selected from the group consisting of $C_{1-8}$ alkyl and $C_{3-8}$ cycloalkyl.

In some embodiments of the compound of formula Ia, $R^1$ is a 5-membered heteroaryl group, preferably selected from the group consisting of pyrazolyl, thienyl, thiazolyl, isothiazolyl and isoxazolyl, which is optionally substituted by one or more $R^6$, wherein each $R^6$ is independently selected from the group consisting of methyl, cyclobutyl, cyclopentyl, hydroxy ethyl, methoxy ethyl, fluoroethyl, dimethylaminoethyl and morpholin-4-yl-ethyl.

In some embodiments of the compound of formula Ia, $R^1$ is selected from the group consisting of:

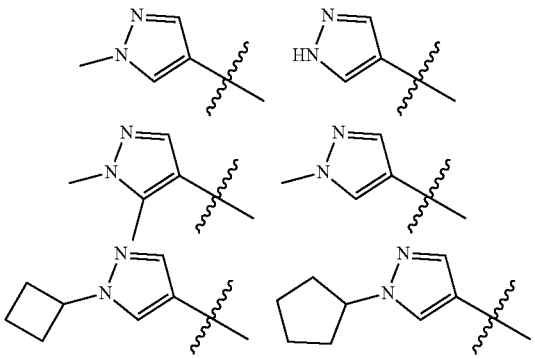

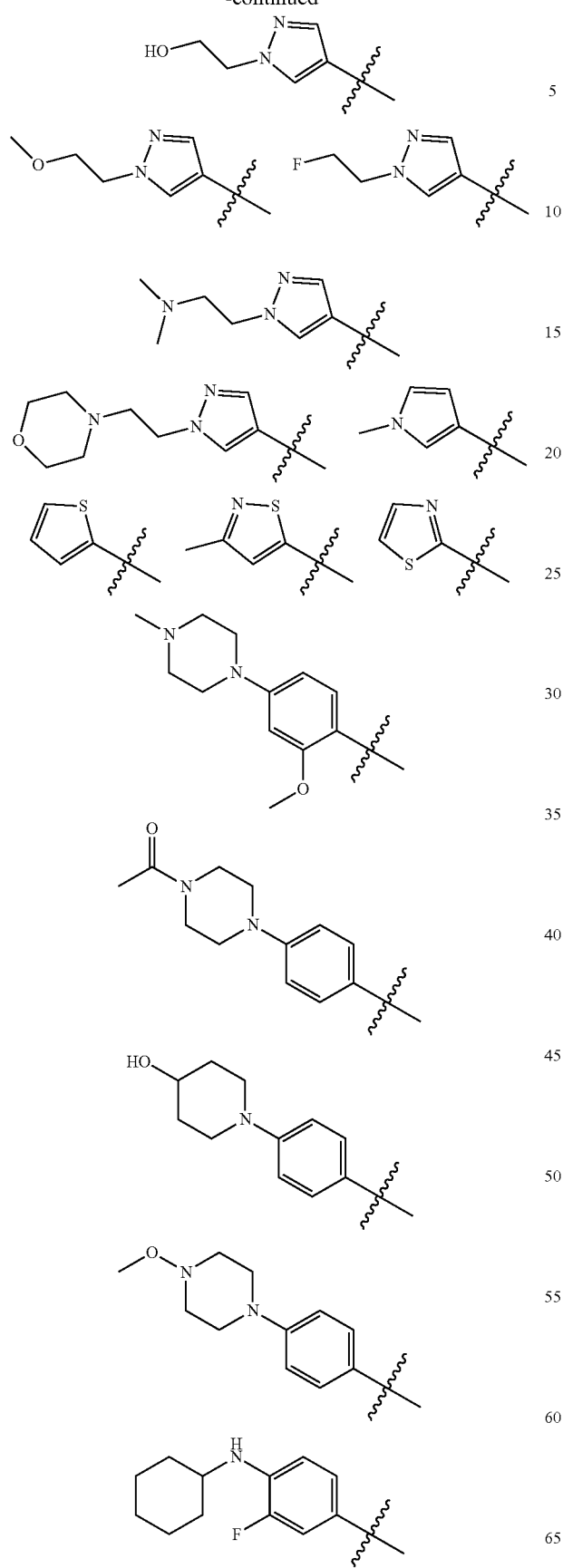
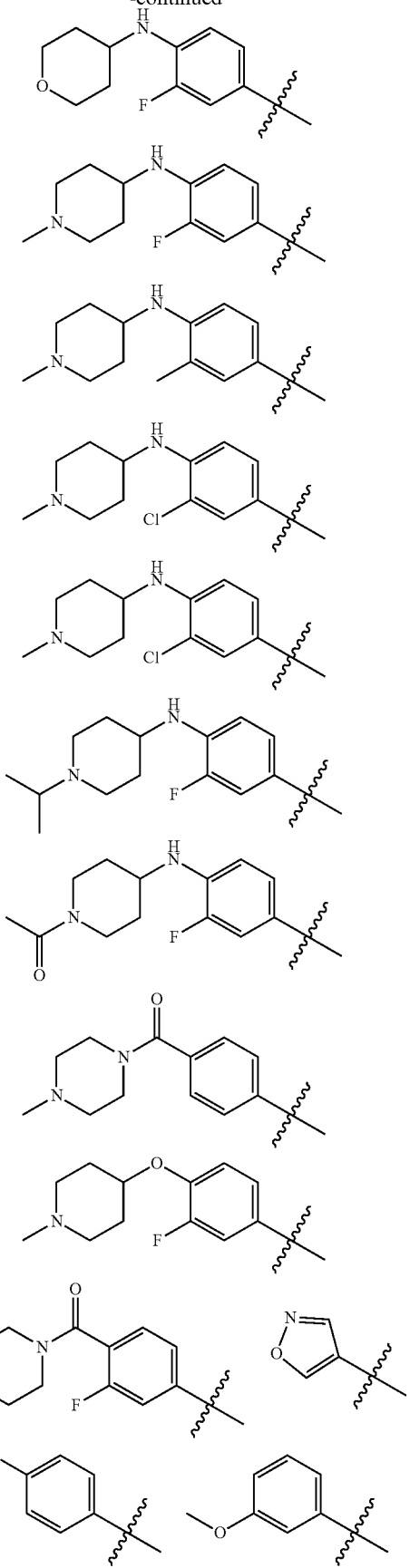

-continued

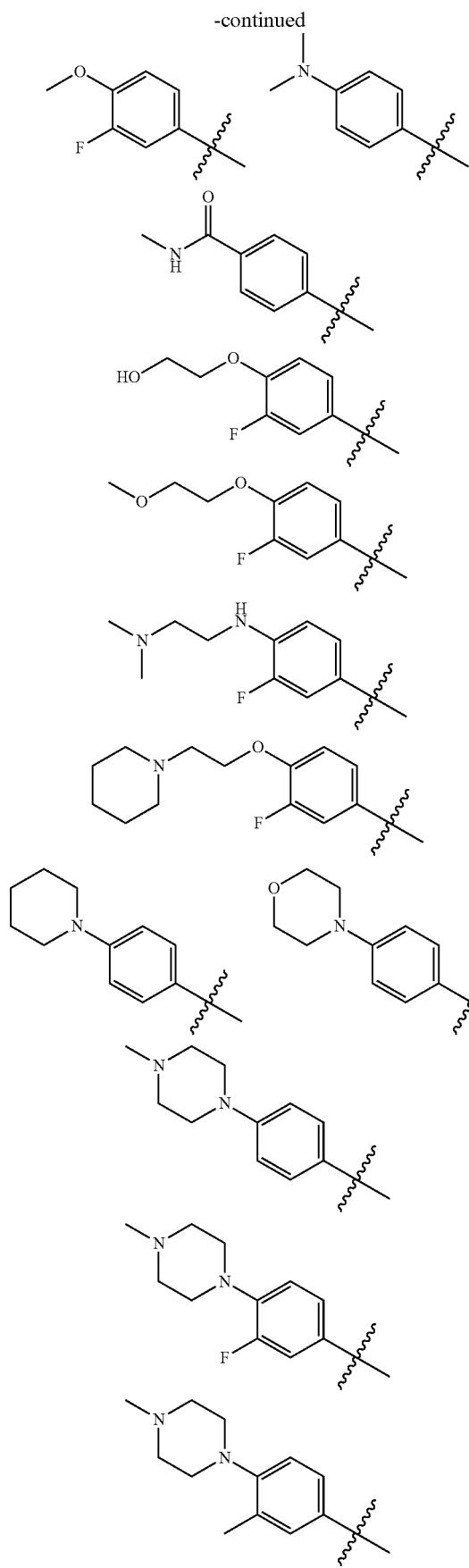

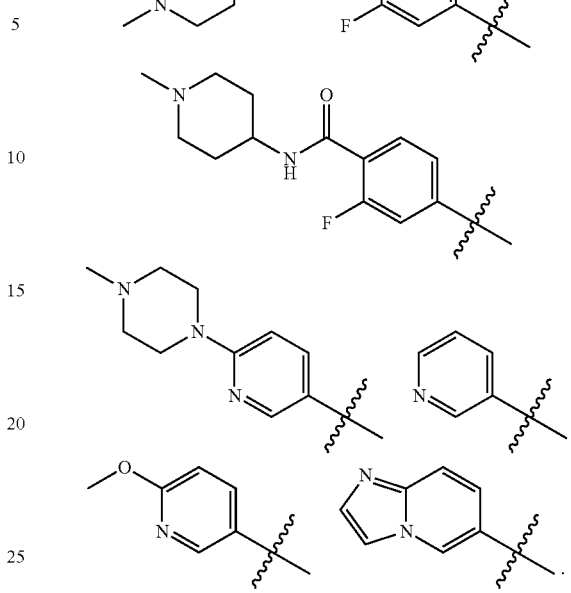

In some embodiments of the compound of formula Ia, $R^2$ is selected from hydrogen or $C_{1-8}$ aliphatic, wherein $C_{1-8}$ aliphatic is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl. In some embodiments, $R^2$ is selected from hydrogen or $C_{1-8}$ alkyl. In some embodiments, $R^2$ is selected from hydrogen or methyl. In some embodiments, $R^2$ is hydrogen.

In some embodiments of the compound of formula Ia, each group in the formula Ia is defined as follows:

W is selected from

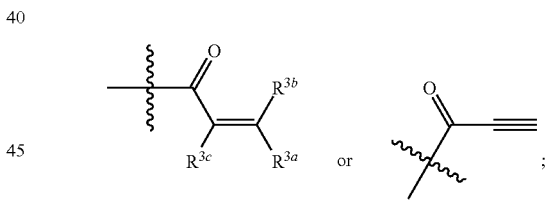

X is selected from O, S, or $NR^4$;
Y is selected from CH, O, or S;
Z is selected from CH, O, S, or $NR^5$;
$R^1$ is $C_{6-12}$ aryl or 5- to 12-membered heteroaryl, optionally substituted by one or more $R^6$;
$R^2$ is hydrogen;
$R^{3a}$, $R^{3b}$, and $R^{3c}$ are all hydrogen;
$R^4$ is selected from hydrogen or $C_{1-8}$ aliphatic;
$R^5$ is hydrogen;
each $R^6$ is independently selected from the group consisting of halogen, heterocyclyl, $C_{1-8}$ aliphatic, $C_{1-8}$ halo aliphatic, heterocyclyl $C_{1-8}$ aliphatic, hydroxy $C_{1-8}$ aliphatic, $C_{1-8}$ aliphaticoxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, $C_{1-8}$ aliphaticoxy, heterocyclyloxy, heterocyclyl $C_{1-8}$ aliphaticoxy, hydroxy $C_{1-8}$ aliphaticoxy, $C_{1-8}$ aliphaticoxy $C_{1-8}$ aliphaticoxy, $C_{1-8}$ aliphaticamino, di($C_{1-8}$ aliphatic)amino, heterocyclylamino, amino $C_{1-8}$ aliphaticamino, $C_{1-8}$ aliphaticamino $C_{1-8}$ aliphaticamino, di($C_{1-8}$ aliphatic)

amino C$_{1-8}$ aliphaticamino, C$_{1-8}$ aliphaticcarbonyl, heterocyclylcarbonyl, aminoacyl, C$_{1-8}$ aliphaticaminoacyl, di(C$_{1-8}$ aliphatic)aminoacyl, heterocyclylaminoacyl, sulfamoyl, C$_{1-8}$ aliphaticaminosulfonyl, di(C$_{1-8}$ aliphatic)aminosulfonyl, heterocyclylaminosulfonyl, aminosulfinyl, C$_{1-8}$ aliphaticaminosulfinyl, di(C$_{1-8}$ aliphatic)aminosulfinyl and heterocyclylaminosulfinyl, wherein:

heterocyclyl, as an independent group or a part of other group(s), represents a saturated or partially unsaturated 3- to 12-membered heterocyclyl group containing one or more heteroatoms selected from the group consisting of N, O, and S; optionally, each heterocyclyl is independently substituted by one or more substituents selected from the group consisting of hydroxy, C$_{1-8}$ aliphatic, C$_{1-8}$ aliphaticoxy and C$_{1-8}$ aliphaticcarbonyl;

wherein C$_{1-8}$ aliphatic, at each occurrence, is independently selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl.

In some embodiments of the compound of formula Ia, each group in the formula Ia is defined as follows:

W is selected from

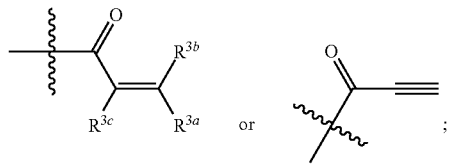

X is NR$^4$;
Y is CH;
Z is O or S;
R$^1$ is a C$_{6-12}$ aryl or 5- to 12-membered heteroaryl group, optionally substituted by one or more R$^6$;
R$^2$ is hydrogen;
R$^{3a}$, R$^{3b}$, and R$^{3c}$ are all hydrogen;
R$^4$ is hydrogen;
each R$^6$ is independently selected from the group consisting of halogen, heterocyclyl, C$_{1-8}$ aliphatic, C$_{1-8}$ halo aliphatic, heterocyclyl C$_{1-8}$ aliphatic, hydroxy C$_{1-8}$ aliphatic, C$_{1-8}$ aliphaticoxy C$_{1-8}$ aliphatic, amino C$_{1-8}$ aliphatic, C$_{1-8}$ aliphaticamino C$_{1-8}$ aliphatic, di(C$_{1-8}$ aliphatic)amino C$_{1-8}$ aliphatic, heterocyclyloxy, heterocyclyl C$_{1-8}$ aliphaticoxy, heterocyclylamino, heterocyclylcarbonyl and heterocyclylaminoacyl, wherein:

heterocyclyl, as an independent group or a part of other group(s), represents a saturated or partially unsaturated 3- to 8-membered heterocyclyl group containing one or more heteroatoms selected from the group consisting of N, O, and S; optionally, each heterocyclyl is independently substituted by one or more C$_{1-8}$ aliphatic substituents, wherein C$_{1-8}$ aliphatic, at each occurrence, is independently selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl.

In some embodiments of the compound of formula Ia, the compound of formula Ia is selected from the group consisting of:

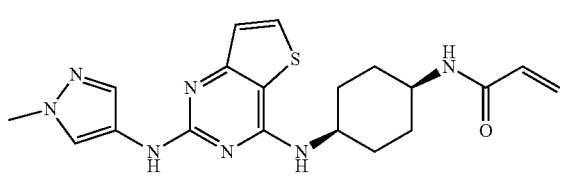

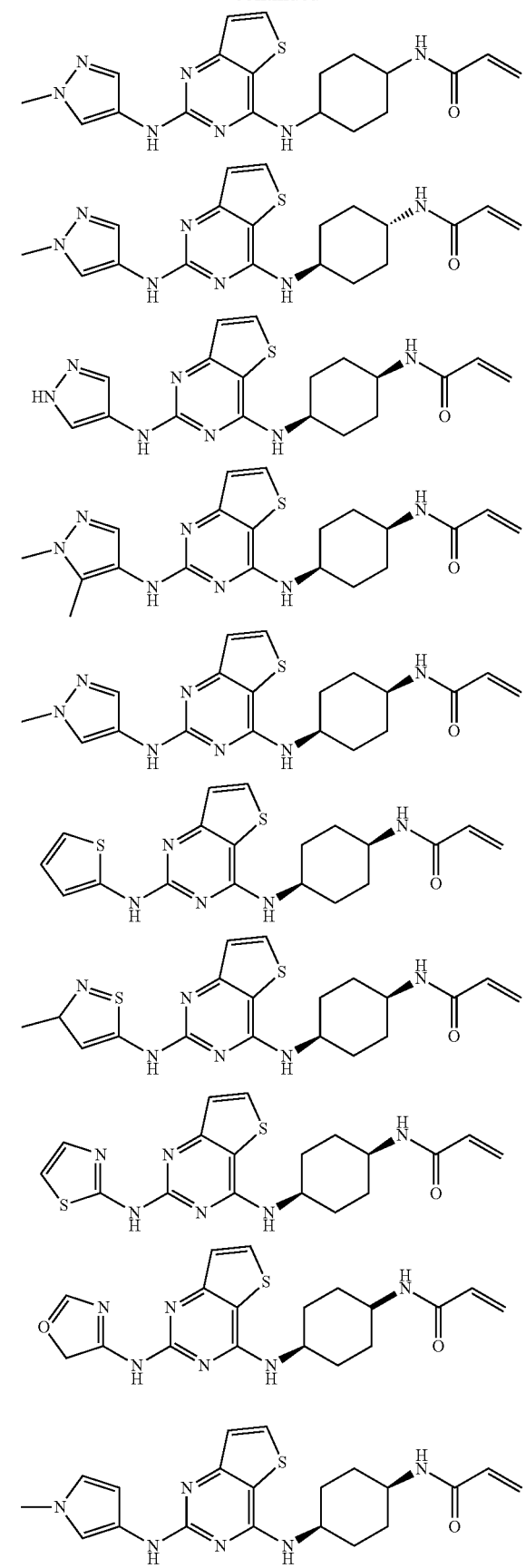

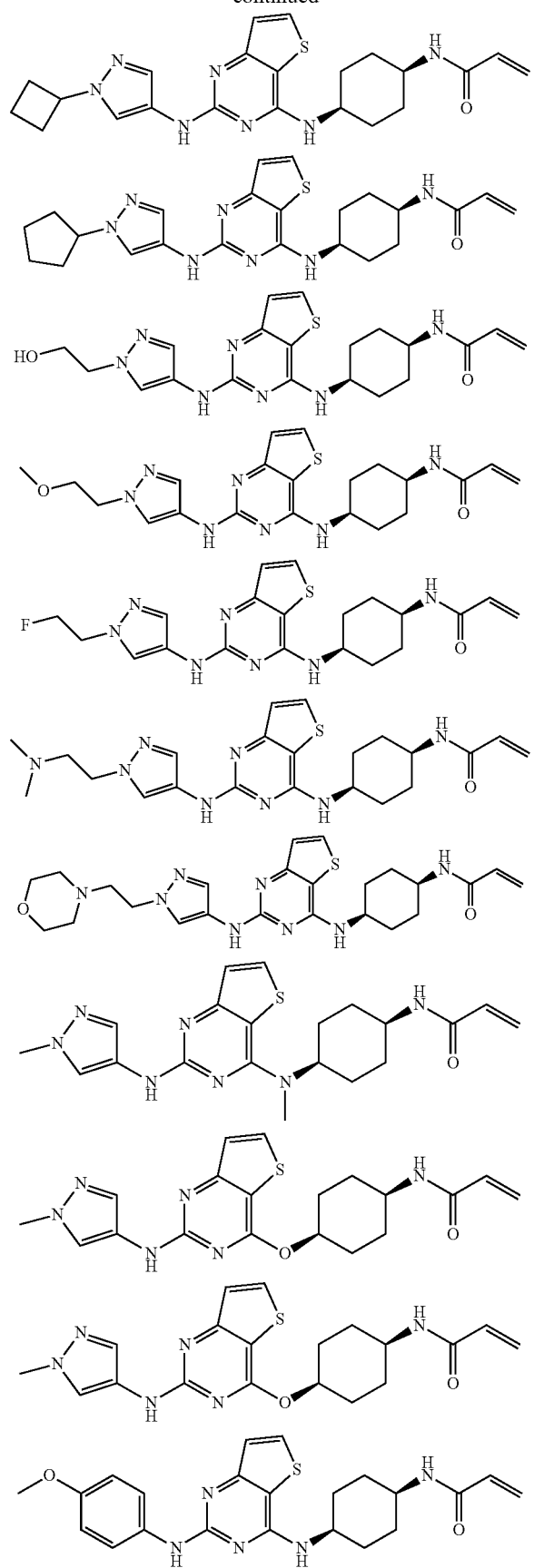
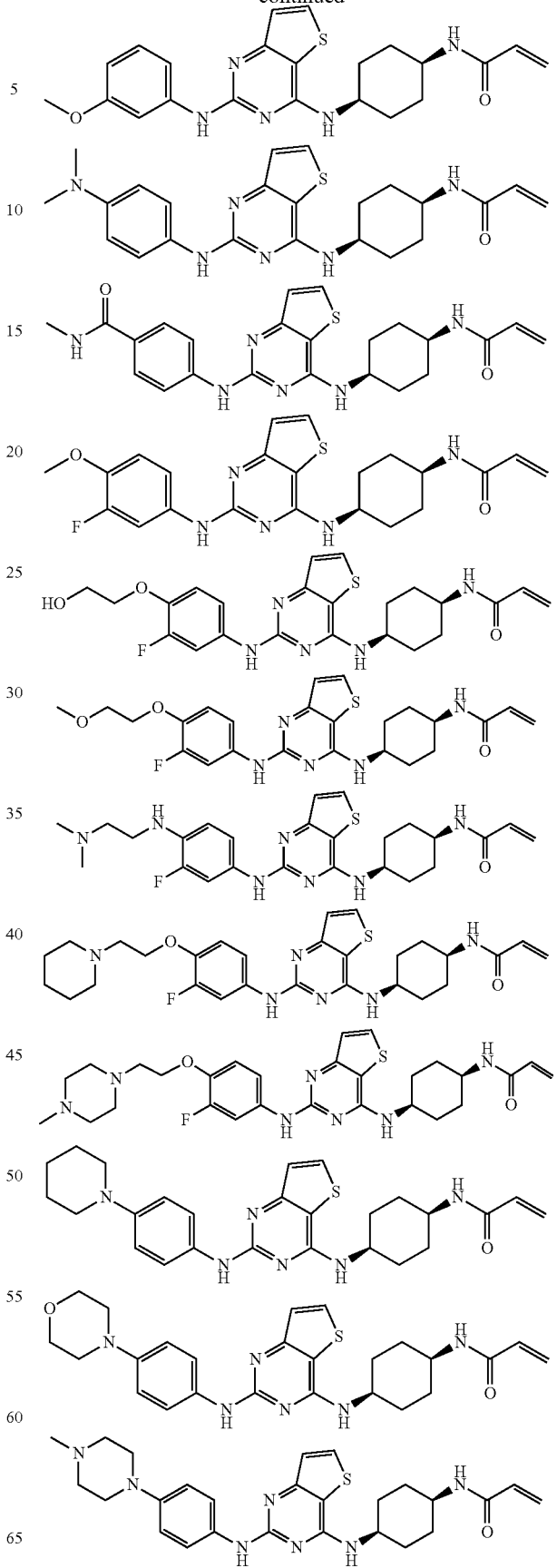

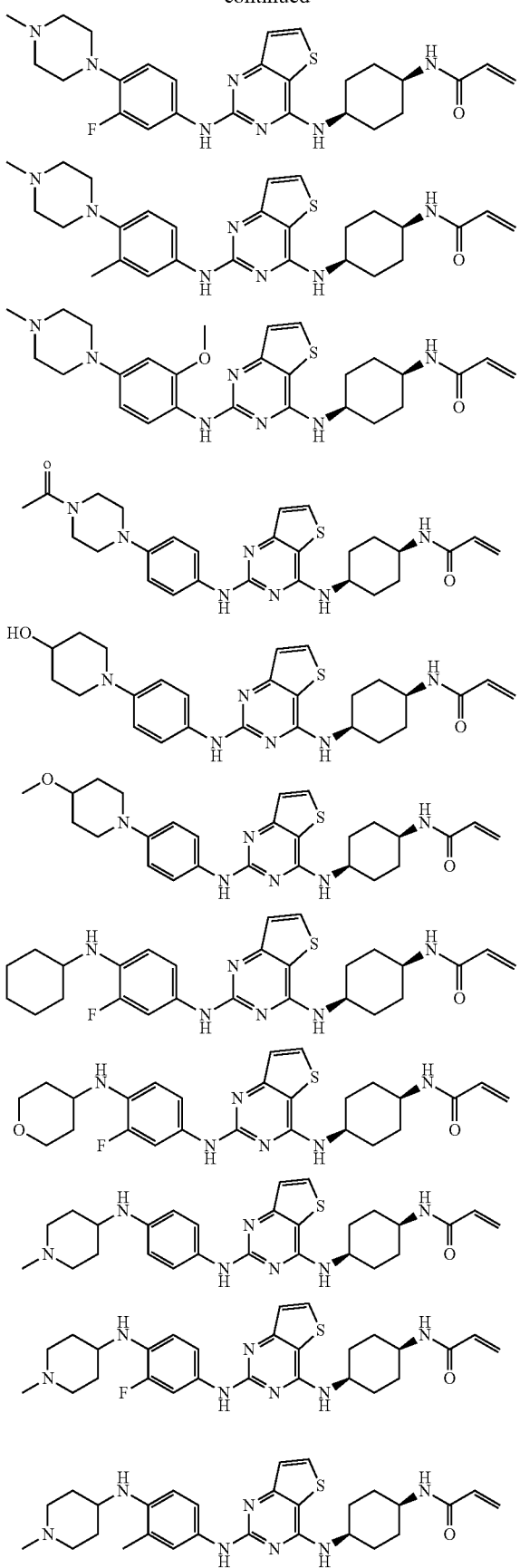
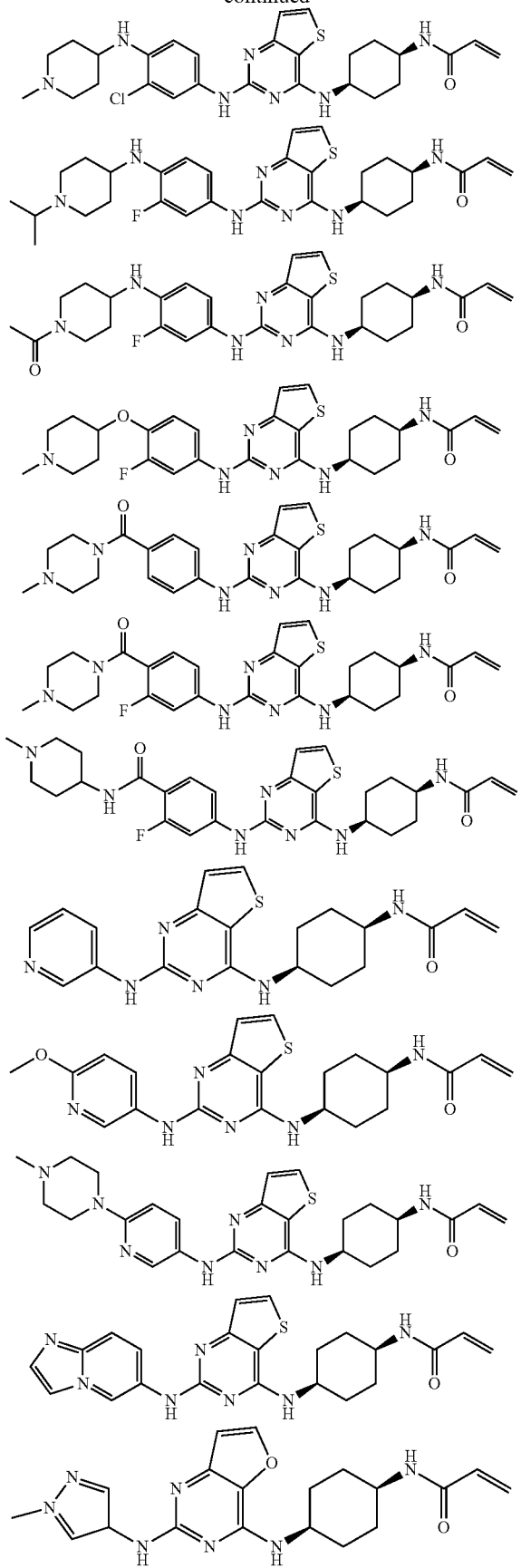

-continued

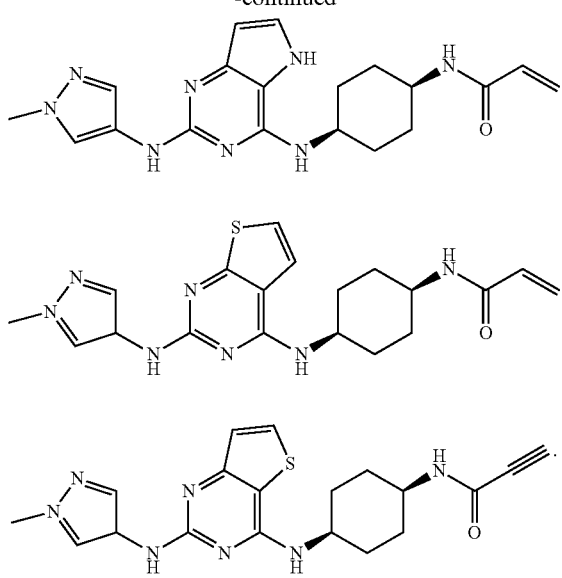

In some embodiments of the compound of formula I, the compound of formula I is represented by formula Ib:

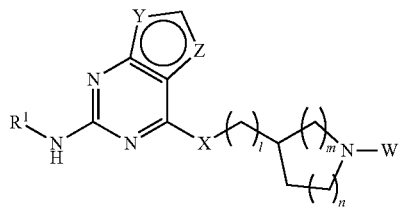

Ib wherein:
X, Y, Z, W, and $R^1$ are all defined as in formula I;
l is selected from 0, 1, 2, 3, or 4, wherein when l is 0,

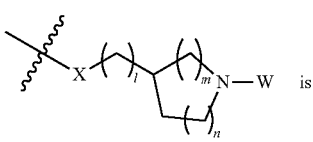

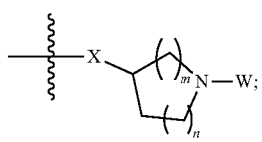

m is selected from 0, 1, 2, 3, or 4; wherein when m is 0,

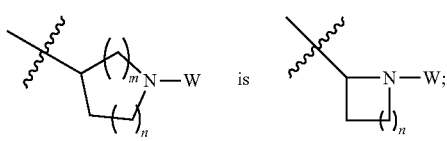

and
n is selected from 0, 1, 2 or 3; wherein when n is 0,

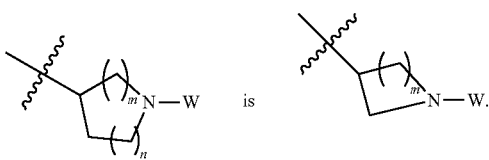

In some embodiments of the compound of formula Ib, each group in the formula Ib is defined as follows:
W is selected from

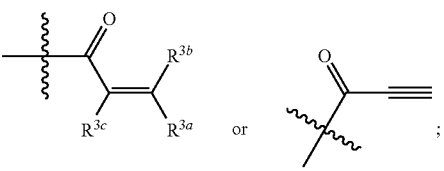

X is selected from O, S, or $NR^4$;
Y is selected from CH, O, or S;
Z is selected from CH, O, S, or $NR^5$;
l is selected from 0, 1, 2, 3, or 4, wherein when l is 0,

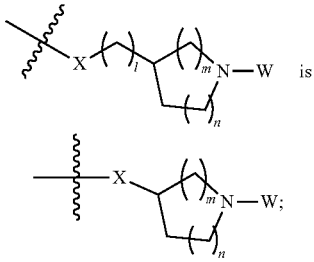

m is selected from 0, 1, 2, 3, or 4; wherein when m is 0,

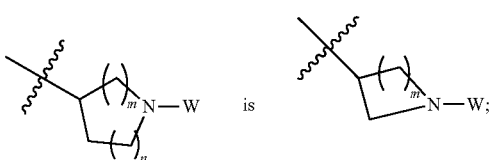

n is selected from 0, 1, 2, or 3; wherein when n is 0,

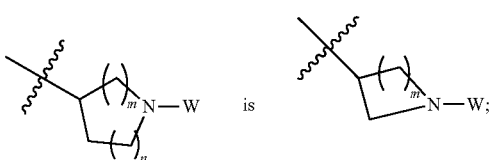

$R^1$ is a 5- to 6-membered heteroaryl group, optionally substituted by one or more $R^6$;
$R^{3a}$, $R^{3b}$, and $R^{3c}$ are independently selected from the group consisting of hydrogen, halogen, and di($C_{1-8}$ aliphatic)aminomethyl;

R$^4$ is selected from hydrogen or C$_{1-8}$ aliphatic;

R$^5$ is selected from hydrogen or C$_{1-8}$ aliphatic;

each R$^6$ is independently selected from the group consisting of halogen, nitro, cyano, C$_{1-8}$ aliphatic, C$_{1-8}$ halo aliphatic, hydroxy C$_{1-8}$ aliphatic, C$_{1-8}$ aliphaticoxy C$_{1-8}$ aliphatic, amino C$_{1-8}$ aliphatic, C$_{1-8}$ aliphaticamino C$_{1-8}$ aliphatic, di(C$_{1-8}$ aliphatic)amino C$_{1-8}$ aliphatic, heterocyclyl C$_{1-8}$ aliphatic, C$_{1-8}$ aliphaticcarbonyl C$_{1-8}$ aliphatic, C$_{1-8}$ aliphaticoxycarbonyl C$_{1-8}$ aliphatic, C$_{1-8}$ aliphaticcarbonyloxy C$_{1-8}$ aliphatic, aminoacyl C$_{1-8}$ aliphatic, C$_{1-8}$ aliphaticaminoacyl C$_{1-8}$ aliphatic, di(C$_{1-8}$ aliphatic)aminoacyl C$_{1-8}$ aliphatic, C$_{1-8}$ aliphaticacylamino C$_{1-8}$ aliphatic, C$_{1-8}$ aliphatic sulfonyl C$_{1-8}$ aliphatic, C$_{1-8}$ aliphaticsulfinyl C$_{1-8}$ aliphatic, C$_{1-8}$ aliphaticsulfonylamino C$_{1-8}$ aliphatic, sulfamoyl C$_{1-8}$ aliphatic, C$_{1-8}$ aliphaticaminosulfonyl C$_{1-8}$ aliphatic, di(C$_{1-8}$ aliphatic)aminosulfonyl C$_{1-8}$ aliphatic, C$_{1-8}$ aliphaticcarbonyl, C$_{1-8}$ aliphaticoxycarbonyl, aminoacyl, C$_{1-8}$ aliphaticaminoacyl, di(C$_{1-8}$ aliphatic)aminoacyl, C$_{1-8}$ aliphaticoxy, C$_{1-8}$ aliphaticsulfonyl, C$_{1-8}$ alkylsulfinyl, C$_{1-8}$ aliphaticsulfonylamino, sulfamoyl, C$_{1-8}$ aliphaticaminosulfonyl, di(C$_{1-8}$ aliphatic)aminosulfonyl, heterocyclyl, C$_{6-12}$ aryl and 5- to 12-membered heteroaryl, wherein heterocyclyl, as an independent group or a part of other group(s), represents a saturated or partially unsaturated 3- to 8-membered heterocyclyl group containing one or more heteroatoms selected from the group consisting of N, O, and S; each heterocyclyl is optionally substituted by one or more substituents selected from the group consisting of halogen, hydroxy, C$_{1-8}$ aliphatic, C$_{1-8}$ aliphaticoxy and C$_{1-8}$ aliphaticcarbonyl; and optionally, C$_{6-12}$ aryl and 5- to 12-membered heteroaryl are independently substituted by one or more substituents selected from the group consisting of halogen and C$_{1-8}$ aliphatic, wherein C$_{1-8}$ aliphatic, at each occurrence, is independently selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl.

In some embodiments of the compound of formula Ib, W is

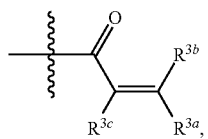

wherein R$^{3a}$, R$^{3b}$, and R$^{3c}$ are independently selected from the group consisting of hydrogen, halogen, and di(C$_{1-8}$ aliphatic)aminomethyl, wherein C$_{1-8}$ aliphatic is independently selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl. In some embodiments, W is

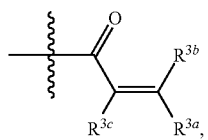

wherein R$^{3a}$, R$^{3b}$, and R$^{3c}$ are all hydrogen.

In some embodiments of the compound of formula Ib, W is

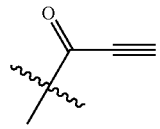

In some embodiments of the compound of formula Ib, X is O.

In some embodiments of the compound of formula Ib, X is NR$^4$, wherein R$^4$ is selected from hydrogen or C$_{1-8}$ aliphatic, wherein C$_{1-8}$ aliphatic is independently selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl. In some embodiments, X is NR$^4$, wherein R$^4$ is selected from hydrogen or C$_{1-8}$ alkyl. In some embodiments, X is NR$^4$, wherein R$^4$ is selected from hydrogen or methyl.

In some embodiments of the compound of formula Ib, Y is CH. In some other embodiments of the compound of formula Ib, Y is S. In some other embodiments of the compound of formula Ib, Y is O.

In some embodiments of the compound of formula Ib, Z is CH. In some other embodiments of the compound of formula Ib, Z is S. In yet some other embodiments of the compound of formula Ib, Z is O. In yet some other embodiments of the compound of formula Ib, Z is NR$^5$, wherein R$^5$ is selected from hydrogen or C$_{1-8}$ aliphatic, wherein C$_{1-8}$ aliphatic is independently selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl. In some embodiments, Z is NR$^5$, wherein R$^5$ is selected from hydrogen or C$_{1-8}$ alkyl. In some embodiments, Z is NR$^5$, wherein R$^5$ is selected from hydrogen or methyl.

In some embodiments of the compound of formula Ib, at least one of Y and Z is a heteroatom.

In some embodiments of the compound of formula Ib, Y is S, and Z is CH. In some other embodiments, Y is O, and Z is CH.

In some embodiments of the compound of formula Ib, Y is CH, and Z is S. In some other embodiments, Y is CH, and Z is O. In yet some other embodiments, Y is CH, and Z is NR$^5$, wherein R$^5$ is selected from hydrogen or C$_{1-8}$ aliphatic, wherein C$_{1-8}$ aliphatic is independently selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl. In yet some other embodiments, Y is CH, and Z is NR$^5$, wherein R$^5$ is selected from hydrogen or C$_{1-8}$ alkyl, and preferably selected from hydrogen or methyl.

In some embodiments of the compound of formula Ib, R$^1$ is a 5- to 6-membered heterocyclyl group, optionally substituted by one or more R$^6$, wherein each R$^6$ is independently selected from the group consisting of halogen, heterocyclyl, C$_{1-8}$ aliphatic, C$_{1-8}$ halo aliphatic, heterocyclyl C$_{1-8}$ aliphatic, hydroxy C$_{1-8}$ aliphatic, C$_{1-8}$ aliphaticoxy C$_{1-8}$ aliphatic, amino C$_{1-8}$ aliphatic, C$_{1-8}$ aliphaticamino C$_{1-8}$ aliphatic, di(C$_{1-8}$ aliphatic)amino C$_{1-8}$ aliphatic, C$_{1-8}$ aliphaticoxy, C$_{1-8}$ aliphaticcarbonyl, heterocyclylcarbonyl, and heterocyclyloxy, wherein:

heterocyclyl, as an independent group or a part of other group(s), represents a saturated or partially unsaturated 3- to 8-membered heterocyclyl group containing one or more heteroatoms selected from the group consisting of N, O, and S; optionally, each heterocyclyl is independently substituted by one or more substituents selected from the group consisting of hydroxy, C$_{1-8}$ aliphatic, C$_{1-8}$ aliphaticoxy, amino, and C$_{1-8}$ aliphaticcarbonyl, wherein $C_{1-8}$ aliphatic, at each occurrence, is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl.

In some embodiments of the compound of formula Ib, $R^1$ is a 5-membered heterocyclyl group, preferably selected from the group consisting of pyrrolyl, pyrazolyl, imidazolyl, thienyl, isoxazolyl, thiazolyl and isothiazolyl, and $R^1$ is optionally substituted by one or two $R^6$; wherein each $R^6$ is independently selected from the group consisting of halogen, $C_{1-8}$ aliphatic, hydroxy $C_{1-8}$ aliphatic, $C_{1-8}$ aliphaticoxy, $C_{1-8}$ aliphaticoxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, heterocyclyl $C_{1-8}$ aliphatic, $C_{1-8}$ aliphaticcarbonyl and heterocyclyl, wherein heterocyclyl, as an independent group or a part of other group(s), represents a saturated or partially unsaturated 3- to 8-membered heterocyclyl group containing one or two heteroatoms selected from the group consisting of N, O, and S, preferably selected from the group consisting of morpholinyl, piperidinyl, piperazinyl and tetrahydropyranyl; each heterocyclyl is optionally substituted by one or more $C_{1-8}$ aliphatic substituents, and wherein $C_{1-8}$ aliphatic, at each occurrence, is independently selected from the group consisting of $C_{1-8}$ alkyl and $C_{3-8}$ cycloalkyl.

In some embodiments of the compound of formula Ib, $R^1$ is a 5-membered heterocyclyl group, preferably selected from the group consisting of pyrazolyl, thienyl, isoxazolyl, thiazolyl and isothiazolyl, and $R^1$ is optionally substituted by one or two $R^6$; wherein each $R^6$ is independently selected from the group consisting of $C_{1-8}$ aliphatic, $C_{1-8}$ aliphaticoxy $C_{1-8}$ aliphatic, $C_{1-8}$ aliphaticamino $C_{1-8}$ aliphatic, di($C_{1-8}$ aliphatic)amino $C_{1-8}$ aliphatic, $C_{1-8}$ aliphaticcarbonyl, heterocyclyl and heterocyclyl $C_{1-8}$ aliphatic, wherein heterocyclyl, as an independent group or a part of other group(s), represents a saturated or partially unsaturated 5- to 6-membered heterocyclyl group containing one or two heteroatoms selected from the group consisting of N, O, and S, preferably selected from the group consisting of morpholinyl and tetrahydropyranyl, wherein $C_{1-8}$ aliphatic, at each occurrence, is independently selected from the group consisting of $C_{1-8}$ alkyl and $C_{3-8}$ cycloalkyl.

In some embodiments of the compound of formula Ib, $R^1$ is a 5-membered heterocyclyl group, preferably selected from the group consisting of pyrrolyl, pyrazolyl, imidazolyl, thienyl, isoxazolyl, thiazolyl and isothiazolyl, and $R^1$ is optionally substituted by one or two $R^6$, wherein each $R^6$ is independently selected from the group consisting of methyl, ethyl, isopropyl, n-butyl, hydroxyethyl, methoxymethyl, methoxyethyl, methoxypropyl, cyclobutyl, cyclopentyl, dimethylaminoethyl, morpholin-4-yl-ethyl, tetrahydropyran-4-yl and methylcarbonyl.

In some embodiments of the compound of formula Ib, $R^1$ is a 5-membered heterocyclyl group, preferably selected from the group consisting of pyrazolyl, thienyl, isoxazolyl, thiazolyl and isothiazolyl, and $R^1$ is optionally substituted by one or two $R^6$, wherein each $R^6$ is independently selected from the group consisting of methyl, ethyl, isopropyl, cyclobutyl, cyclopentyl, methoxymethyl, methoxyethyl, methoxypropyl, dimethylaminoethyl, morpholin-4-yl-ethyl, tetrahydropyran-4-yl and methylcarbonyl.

In some embodiments of the compound of formula Ib, $R^1$ is selected from the group consisting of:

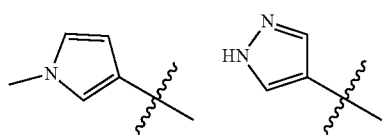

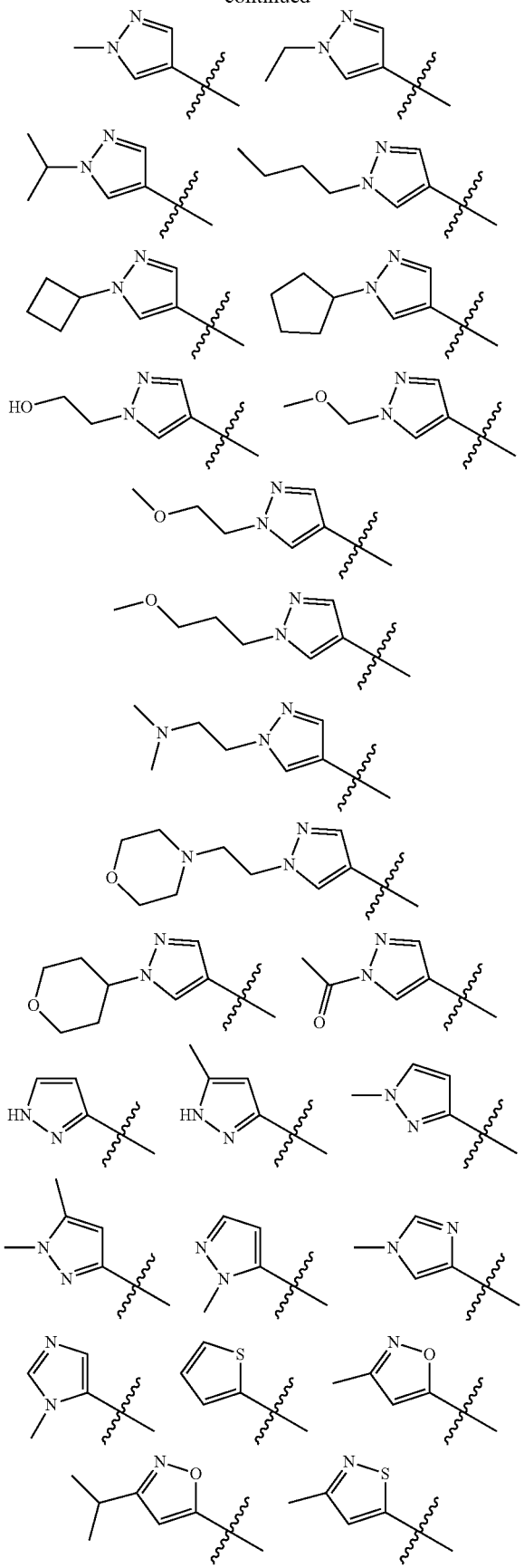

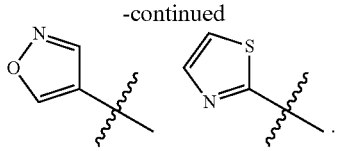

In some embodiments of the compound of formula Ib, l is selected from 0, 1 or 2.

In some embodiments of the compound of formula Ib, m is selected from 0, 1, 2 or 3.

In some embodiments of the compound of formula Ib, n is selected from 0, 1 or 2.

In some embodiments of the compound of formula Ib, m and n are not 0 simultaneously.

In some embodiments of the compound of formula Ib, each group in the formula Ib is defined as follows:
W is selected from

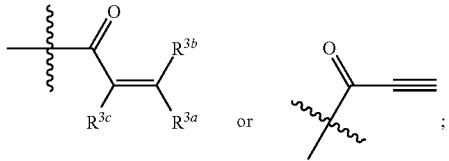

X is selected from O, S, or $NR^4$;
Y is selected from CH, O, or S;
Z is selected from CH, O, S, or $NR^5$;
l is selected from 0, 1 or 2;
m is selected from 0, 1, 2 or 3;
n is selected from 0, 1 or 2;
$R^1$ is a 5- to 6-membered heteroaryl group, optionally substituted by one or more $R^6$;
$R^{3a}$, $R^{3b}$, and $R^{3c}$ are all hydrogen;
$R^4$ is selected from hydrogen or $C_{1-8}$ aliphatic;
$R^5$ is selected from hydrogen or $C_{1-8}$ aliphatic;
each $R^6$ is independently selected from the group consisting of halogen, $C_{1-8}$ aliphatic, hydroxy $C_{1-8}$ aliphatic, $C_{1-8}$ aliphaticoxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, heterocyclyl $C_{1-8}$ aliphatic, $C_{1-8}$ aliphaticcarbonyl and heterocyclyl, wherein:

heterocyclyl, as an independent group or a part of other group(s), represents a saturated or partially unsaturated 3- to 8-membered heterocyclyl group containing one or more heteroatoms selected from the group consisting of N, O, and S; each heterocyclyl is optionally substituted by one or more $C_{1-8}$ aliphatic substituents;

wherein $C_{1-8}$ aliphatic, at each occurrence, is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl.

In some embodiments of the compound of formula Ib, each group in the formula Ib is defined as follows:
W is selected from

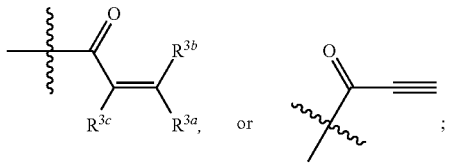

X is selected from O, or $NR^4$;
Y is selected from CH, or S;
Z is selected from CH, O, or S;
l is selected from 0, 1 or 2;
m is selected from 0, 1, 2 or 3;
n is selected from 0, 1 or 2;
$R^1$ is a 5-membered heteroaryl group, optionally substituted by one or more $R^6$;
$R^{3a}$, $R^{3b}$, and $R^{3c}$ are all hydrogen;
$R^4$ is selected from hydrogen or $C_{1-8}$ aliphatic;
each $R^6$ is independently selected from the group consisting of halogen, $C_{1-8}$ aliphatic, $C_{1-8}$ aliphaticoxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, heterocyclyl $C_{1-8}$ aliphatic, $C_{1-8}$ aliphaticcarbonyl and heterocyclyl, wherein:

heterocyclyl, as an independent group or a part of other group(s), represents a saturated or partially unsaturated 5- to 6-membered heterocyclyl group containing one or more heteroatoms selected from the group consisting of N, O, and S; each heterocyclyl is optionally substituted by one or more $C_{1-8}$ aliphatic substituents;

wherein $C_{1-8}$ aliphatic, at each occurrence, is independently selected from the group consisting of $C_{1-8}$ alkyl and $C_{3-8}$ cycloalkyl.

In some embodiments of the compound of formula Ib, the compound of formula Ib is selected from the group consisting of:

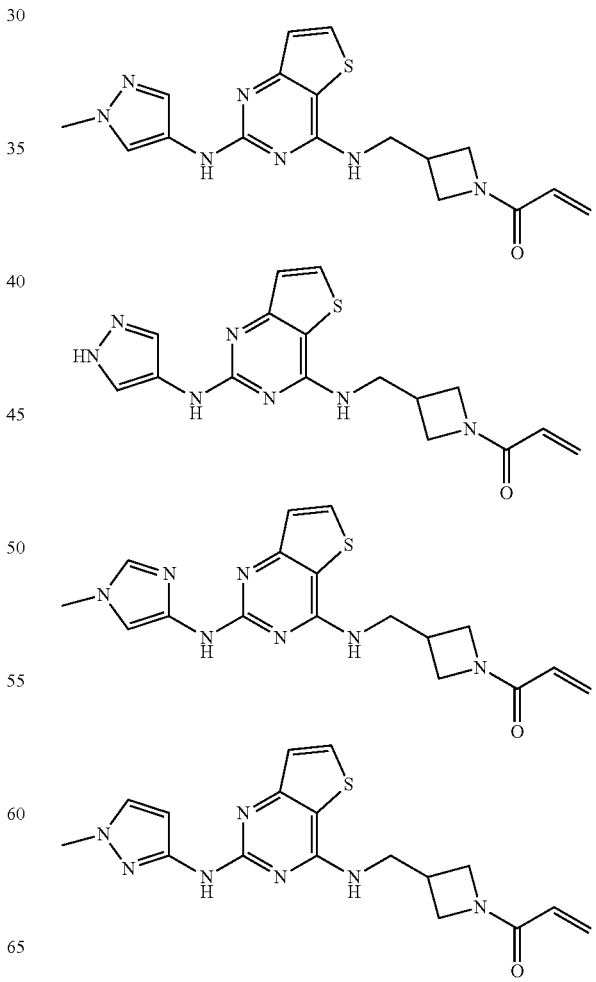

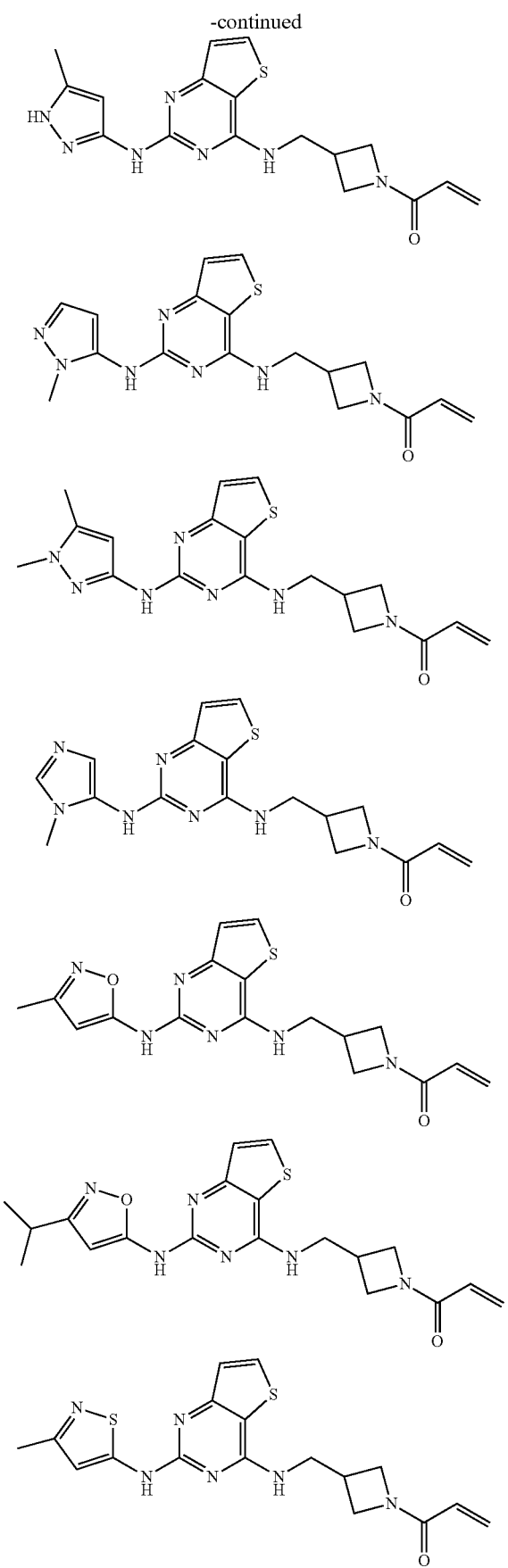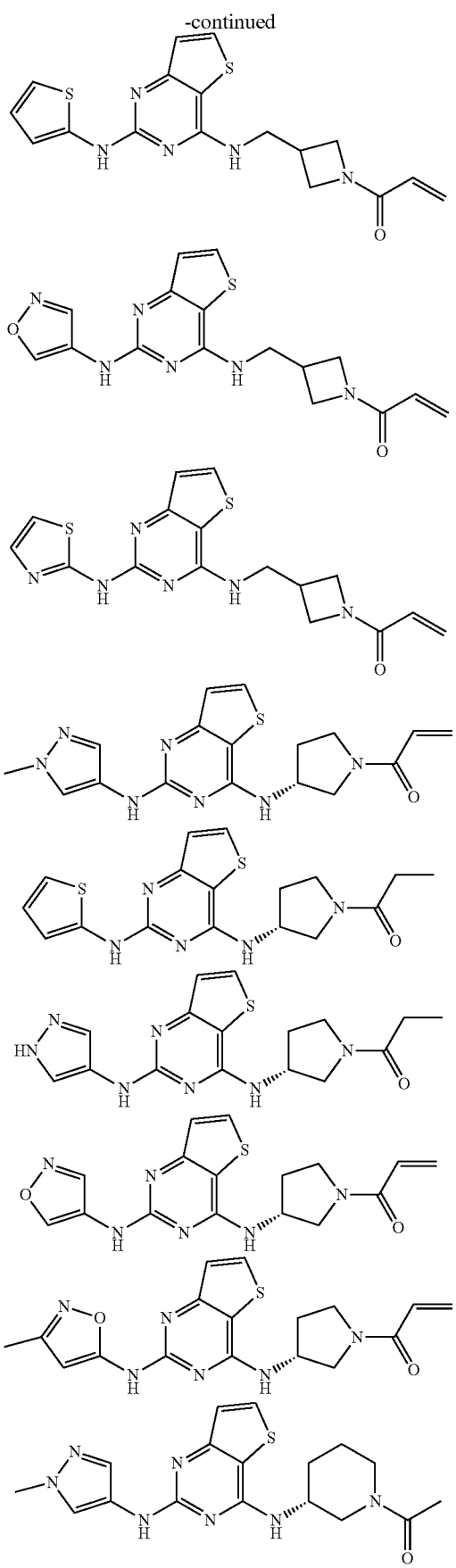

-continued
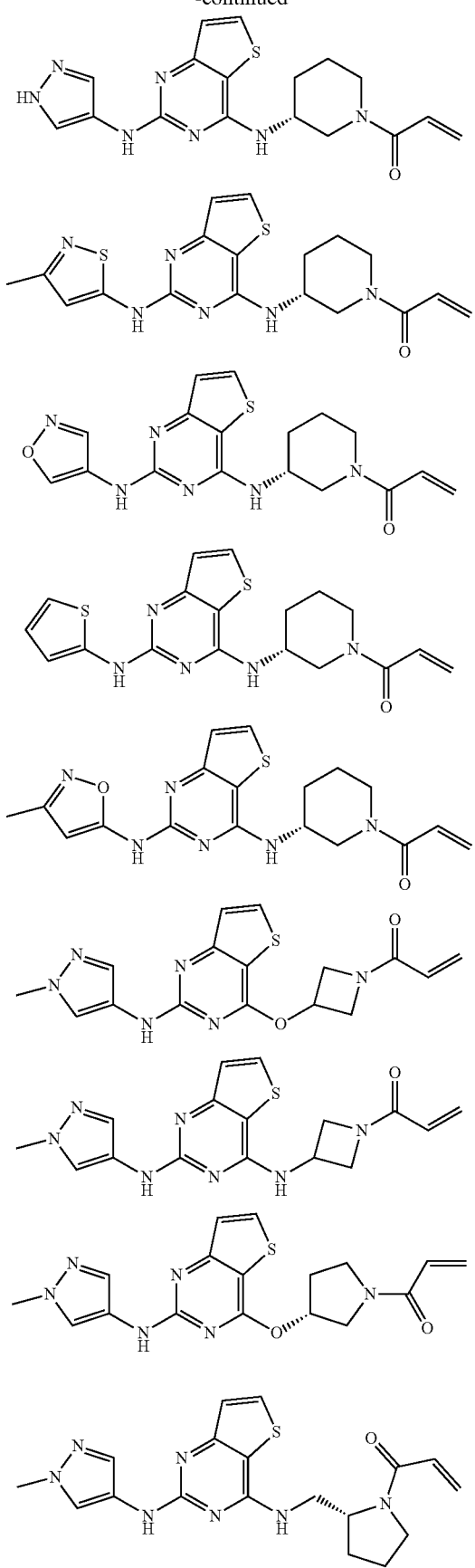
-continued
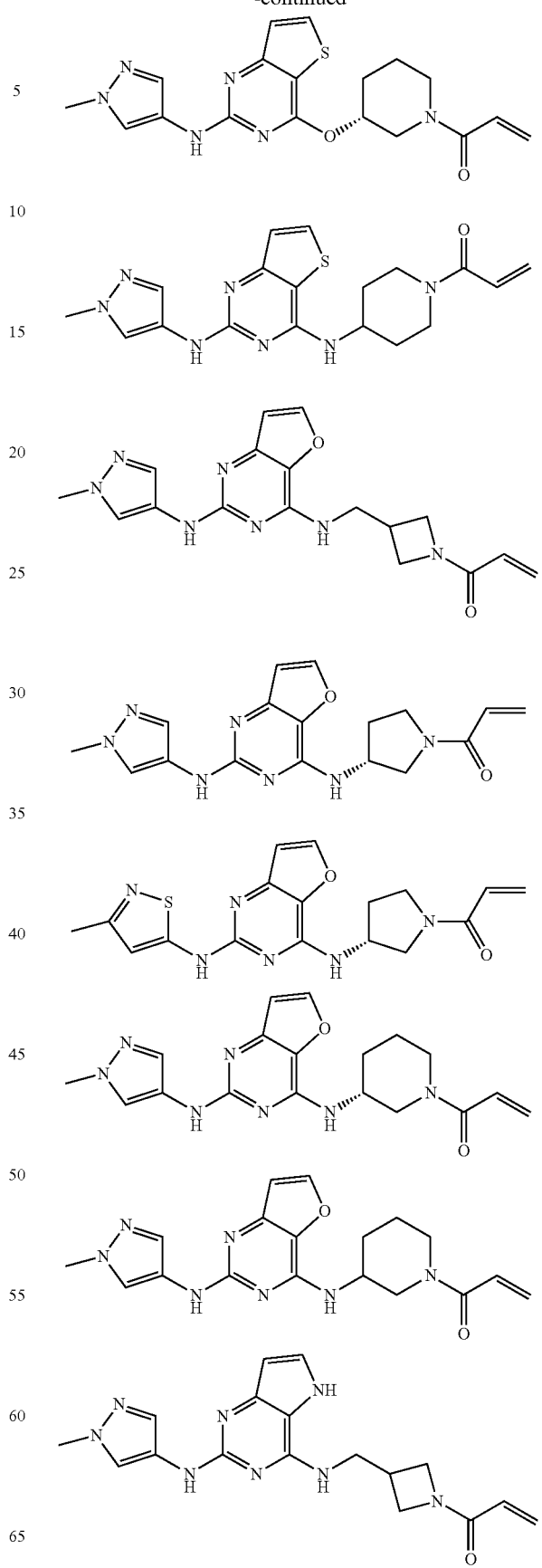

51
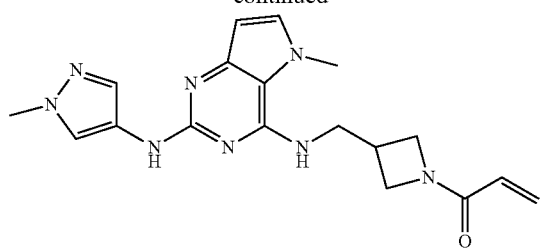
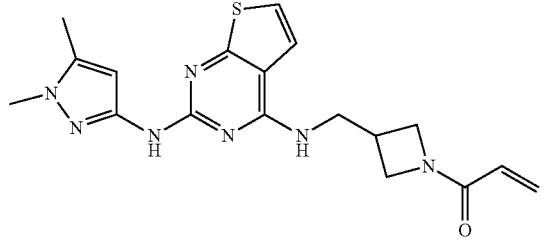
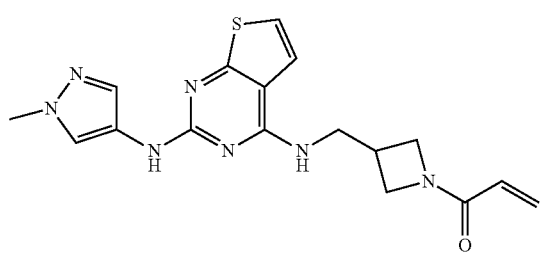
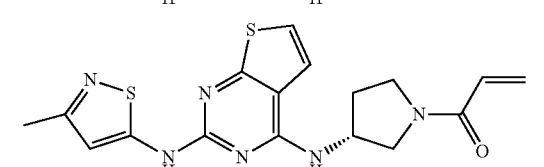
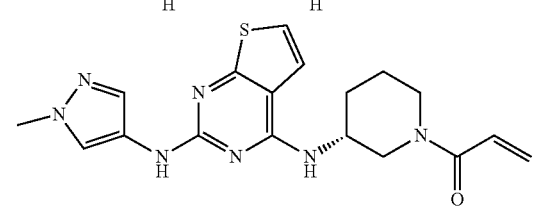
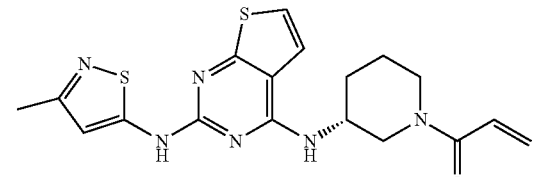
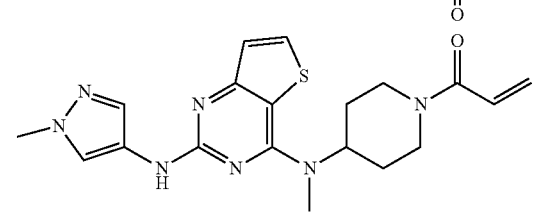
52
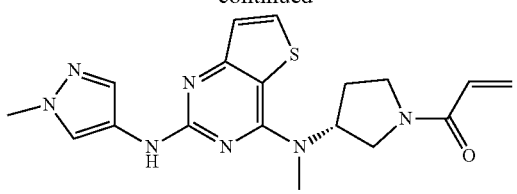
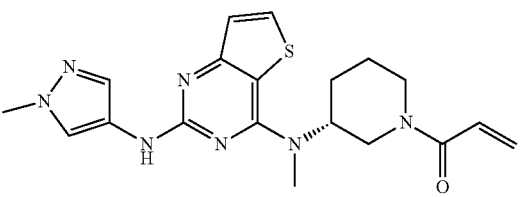
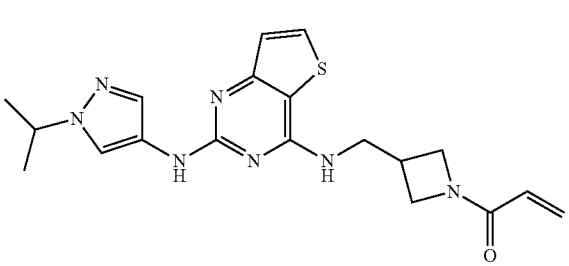
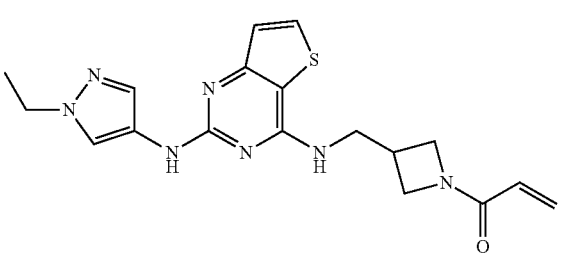
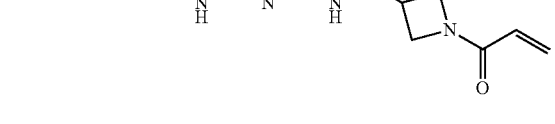
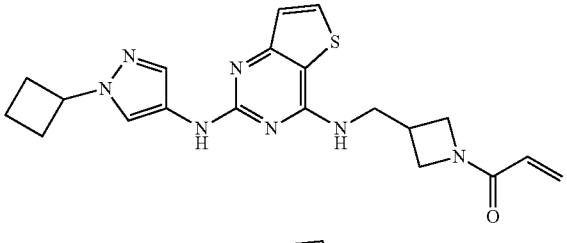
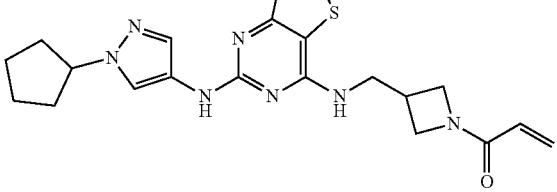

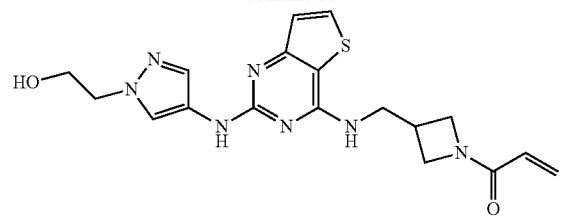
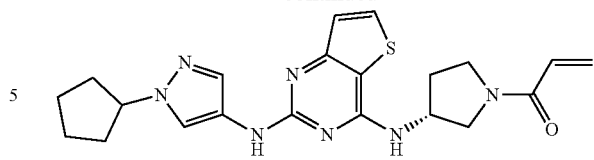
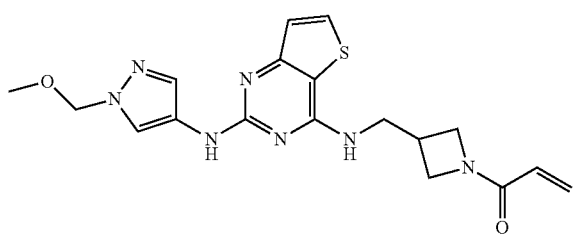
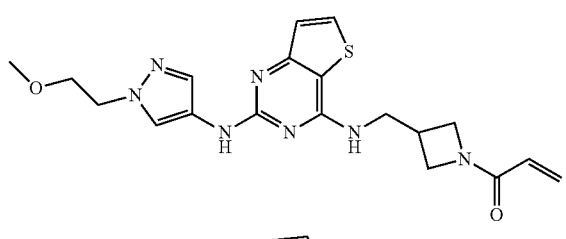
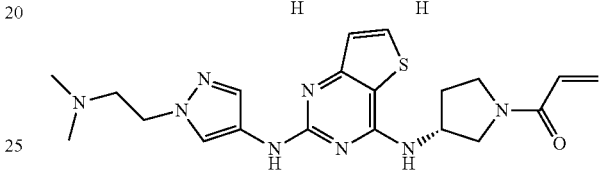
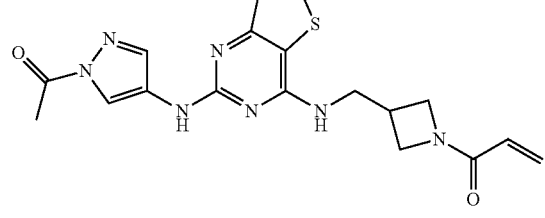
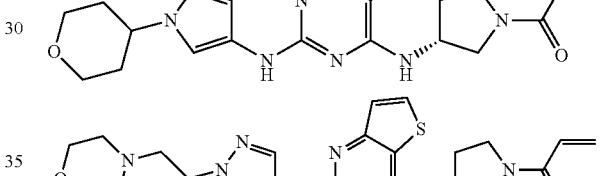
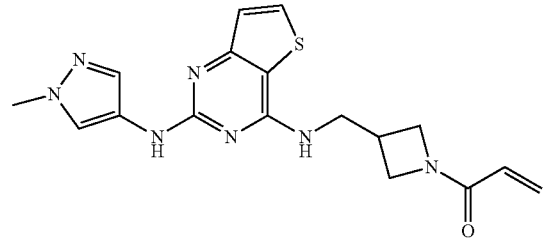
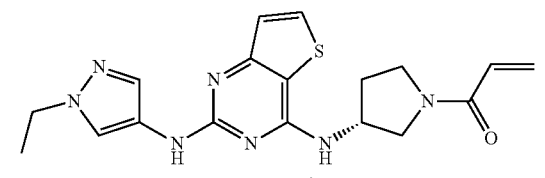
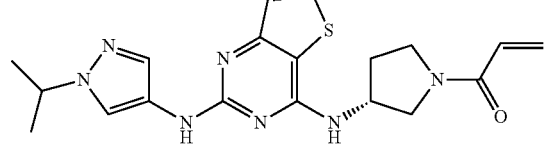
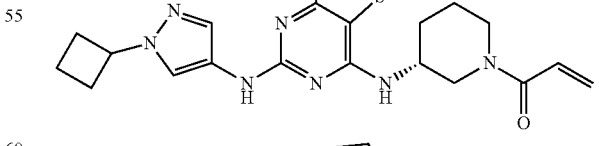
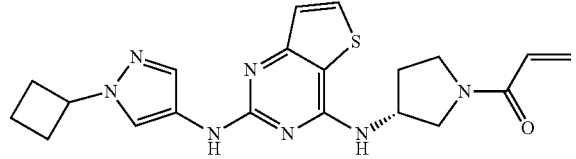
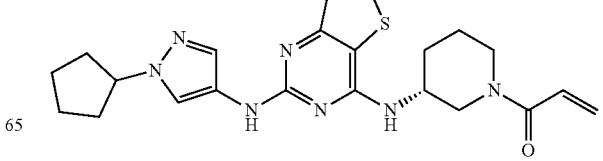

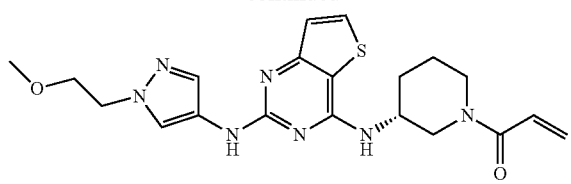

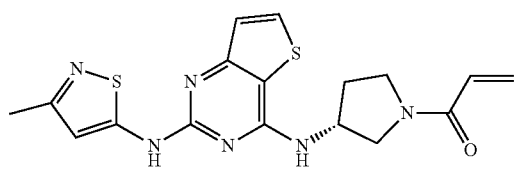

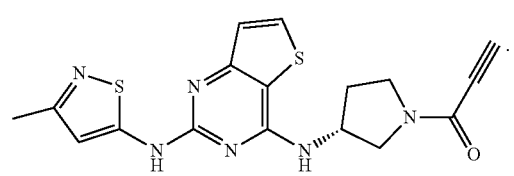

In yet some other embodiments of the compound of formula I, the compound of formula I is represented by formula Ic:

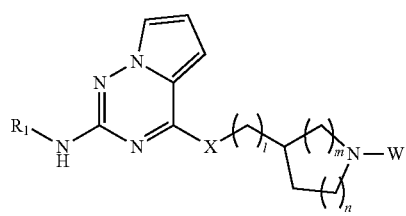

Ic wherein:
X, W, and $R^1$ are all defined as in formula I;
l is selected from 0, 1, 2, 3 or 4; wherein when l is 0,

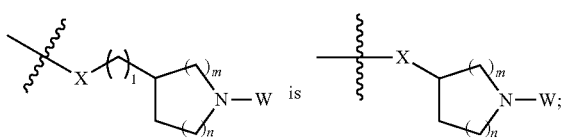

m is selected from 0, 1, 2, 3 or 4; wherein when m is 0,

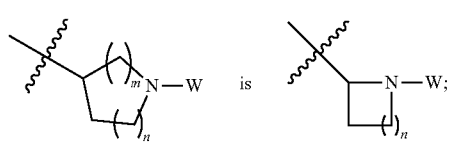

and
n is selected from 0, 1, 2 or 3; wherein when n is 0,

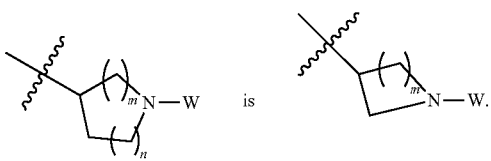

In some embodiments of the compound of formula Ic, each group in the formula Ic is defined as follows:
W is selected from

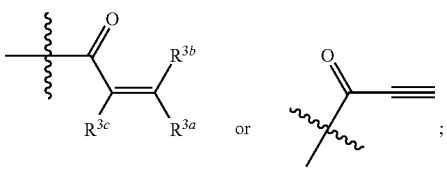

X is selected from O, S, or $NR^4$;
l is selected from 0, 1, 2, 3 or 4; wherein when l is 0,

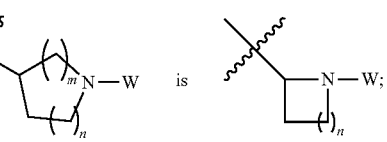

m is selected from 0, 1, 2, 3 or 4; wherein when m is 0,

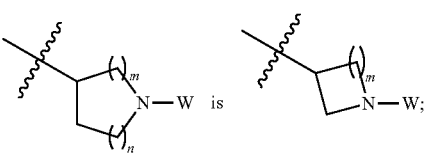

n is selected from 0, 1, 2 or 3; wherein when n is 0,

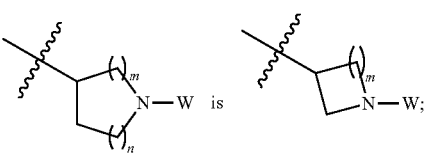

$R^1$ is a 5- to 6-membered heteroaryl group, optionally substituted by one or more $R^6$;
$R^{3a}$, $R^{3b}$, and $R^{3c}$ are independently selected from the group consisting of hydrogen, halogen, and di($C_{1-8}$ aliphatic)aminomethyl;
$R^4$ is selected from hydrogen or $C_{1-8}$ aliphatic;
each $R^6$ is independently selected from the group consisting of halogen, nitro, cyano, $C_{1-8}$ aliphatic, $C_{1-8}$ halo aliphatic, hydroxy $C_{1-8}$ aliphatic, $C_{1-8}$ aliphaticoxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, heterocyclyl $C_{1-8}$ aliphatic, $C_{1-8}$ aliphaticcarbonyl $C_{1-8}$ aliphatic, $C_{1-8}$ aliphaticoxycarbonyl $C_{1-8}$ aliphatic, $C_{1-8}$ aliphaticcarbonyloxy $C_{1-8}$ aliphatic, aminoacyl $C_{1-8}$ aliphatic, $C_{1-8}$ aliphaticaminoacyl $C_{1-8}$ aliphatic, di($C_{1-8}$ aliphatic)aminoacyl $C_{1-8}$ aliphatic, $C_{1-8}$ aliphaticacylamino $C_{1-8}$ aliphatic, $C_{1-8}$ aliphaticsulfonyl $C_{1-8}$ aliphatic, $C_{1-8}$ aliphaticsulfinyl $C_{1-8}$ aliphatic, $C_{1-8}$ aliphaticsulfonylamino $C_{1-8}$ aliphatic, sulfamoyl $C_{1-8}$ aliphatic, $C_{1-8}$ aliphaticaminosulfonyl $C_{1-8}$ aliphatic, di($C_{1-8}$ aliphatic)aminosulfonyl $C_{1-8}$ aliphatic, $C_{1-8}$ aliphaticcarbonyl, $C_{1-8}$ aliphaticoxycarbonyl, aminoacyl, $C_{1-8}$ aliphaticaminoacyl, di($C_{1-8}$ aliphatic)aminoacyl, $C_{1-8}$ aliphaticoxy, $C_{1-8}$ aliphaticsulfonyl, $C_{1-8}$ aliphaticsulfinyl, $C_{1-8}$ aliphaticsulfonylamino, sulfamoyl, $C_{1-8}$ aliphaticaminosulfonyl, di($C_{1-8}$ aliphatic)aminosulfonyl, heterocyclyl, $C_{6-12}$ aryl and 5- to 12-membered heteroaryl, wherein:

heterocyclyl, as an independent group or a part of other group(s), represents a saturated or partially unsaturated 3- to 8-membered heterocyclyl group containing one or more heteroatoms selected from the group consisting of N, O, and S; each heterocyclyl is optionally substituted by one or more substituents selected from the group consisting of halogen, hydroxy, $C_{1-8}$ aliphatic, $C_{1-8}$ aliphaticoxy and $C_{1-8}$ aliphaticcarbonyl; and optionally, $C_{6-12}$ aryl and 5- to 12-membered heteroaryl are independently substituted by one or more substituents selected from the group consisting of halogen and $C_{1-8}$ aliphatic, wherein $C_{1-8}$ aliphatic, at each occurrence, is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl.

In some embodiments of the compound of formula Ic, W is

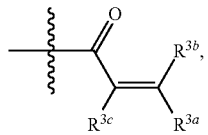

wherein $R^{3a}$, $R^{3b}$, and $R^{3c}$ are independently selected from the group consisting of hydrogen, halogen, and di($C_{1-8}$ aliphatic)aminomethyl, wherein $C_{1-8}$ aliphatic is selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl. In some embodiments of the compound of formula Ic, W is

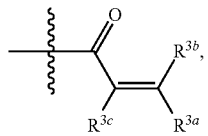

wherein $R^{3a}$, $R^{3b}$, and $R^{3c}$ are all hydrogen.

In some embodiments of the compound of formula Ic, W is

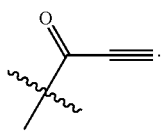

In some embodiments of the compound of formula Ic, X is O. In some other embodiments of the compound of formula Ic, X is S. In yet some other embodiments of the compound of formula Ic, X is $NR^4$, wherein $R^4$ is selected from hydrogen or $C_{1-8}$ aliphatic, wherein $C_{1-8}$ aliphatic is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl. In yet some other embodiments, X is $NR^4$, wherein $R^4$ is selected from hydrogen or $C_{1-8}$ alkyl. In yet some other embodiments, X is $NR^4$, wherein $R^4$ is hydrogen or methyl. In yet some other embodiments, X is $NR^4$, wherein $R^4$ is hydrogen.

In some embodiments of the compound of formula Ic, $R^1$ is a 5- to 6-membered heteroaryl group, preferably selected from the group consisting of pyridinyl, pyrrolyl, pyrazolyl, imidazolyl, thienyl, isoxazolyl, thiazolyl and isothiazolyl, which is optionally substituted by one or more $R^6$, wherein each $R^6$ is independently selected from the group consisting of halogen, nitro, cyano, $C_{1-8}$ aliphatic, $C_{1-8}$ halo aliphatic, hydroxy $C_{1-8}$ aliphatic, $C_{1-8}$ aliphaticoxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, heterocyclyl $C_{1-8}$ aliphatic, $C_{1-8}$ aliphaticcarbonyl $C_{1-8}$ aliphatic, $C_{1-8}$ aliphaticoxycarbonyl $C_{1-8}$ aliphatic, $C_{1-8}$ aliphaticcarbonyloxy $C_{1-8}$ aliphatic, aminoacyl $C_{1-8}$ aliphatic, $C_{1-8}$ aliphaticaminoacyl $C_{1-8}$ aliphatic, di($C_{1-8}$ aliphatic)aminoacyl $C_{1-8}$ aliphatic, $C_{1-8}$ aliphaticacylamino $C_{1-8}$ aliphatic, $C_{1-8}$ aliphaticsulfonyl $C_{1-8}$ aliphatic, $C_{1-8}$ aliphaticsulfinyl $C_{1-8}$ aliphatic, $C_{1-8}$ aliphaticsulfonylamino $C_{1-8}$ aliphatic, sulfamoyl $C_{1-8}$ aliphatic, $C_{1-8}$ aliphaticaminosulfonyl $C_{1-8}$ aliphatic, di($C_{1-8}$ aliphatic)aminosulfonyl $C_{1-8}$ aliphatic, $C_{1-8}$ aliphaticcarbonyl, $C_{1-8}$ aliphaticoxycarbonyl, aminoacyl, $C_{1-8}$ aliphaticaminoacyl, di($C_{1-8}$ aliphatic)aminoacyl, $C_{1-8}$ aliphaticoxy, $C_{1-8}$ aliphaticsulfonyl, $C_{1-8}$ aliphaticsulfinyl, $C_{1-8}$ aliphaticsulfonylamino, sulfamoyl, $C_{1-8}$ aliphaticaminosulfonyl, di($C_{1-8}$ aliphatic)aminosulfonyl, heterocyclyl, $C_{6-12}$ aryl and 5- to 12-membered heteroaryl, wherein:

heterocyclyl, as an independent group or a part of other group(s), represents a saturated or partially unsaturated 3- to 8-membered heterocyclyl group containing one or more heteroatoms selected from the group consisting of N, O, and S; each heterocyclyl is optionally substituted by one or more substituents selected from the group consisting of halogen, hydroxy, $C_{1-8}$ aliphatic, $C_{1-8}$ aliphaticoxy and $C_{1-8}$ aliphaticcarbonyl; and optionally, $C_{6-12}$ aryl and 5- to 12-membered heteroaryl are independently substituted by one or more substituents selected from the group consisting of halogen and $C_{1-8}$ aliphatic, wherein $C_{1-8}$ aliphatic, at each occurrence, is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl.

In some embodiments of the compound of formula Ic, $R^1$ is a 5-membered heteroaryl group, preferably selected from the group consisting of pyrrolyl, pyrazolyl, imidazolyl, thienyl, isoxazolyl, thiazolyl and isothiazolyl, which is optionally substituted by one or more $R^6$, wherein each $R^6$ is independently selected from the group consisting of halogen, $C_{1-8}$ aliphatic, hydroxy $C_{1-8}$ aliphatic, $C_{1-8}$ aliphaticoxy $C_{1-8}$ aliphatic, di($C_{1-8}$ aliphatic)amino $C_{1-8}$ aliphatic, heterocyclyl $C_{1-8}$ aliphatic, $C_{1-8}$ aliphaticcarbonyl and heterocyclyl, wherein heterocyclyl, as an independent group or a part of other group(s), represents a saturated or partially unsaturated 5- to 6-membered heterocyclyl group containing one or two heteroatoms selected from the group consisting of N, O, and S, and preferably selected from the group consisting of piperidinyl, piperazinyl, morpholinyl and tetrahydropyranyl; each heterocyclyl is optionally substituted by one or more $C_{1-8}$ aliphatic substituents; and wherein $C_{1-8}$ aliphatic, at each occurrence, is independently selected from the group consisting of $C_{1-8}$ alkyl and $C_{3-8}$ cycloalkyl.

In some embodiments of the compound of formula Ic, $R^1$ is a 5-membered heteroaryl group, preferably selected from the group consisting of pyrazolyl and isothiazolyl, which is optionally substituted by one or more $R^6$, wherein each $R^6$ is independently selected from the group consisting of halogen and $C_{1-8}$ aliphatic.

In some embodiments of the compound of formula Ic, $R^1$ is a 5-membered heteroaryl group, preferably selected from the group consisting of pyrrolyl, pyrazolyl, imidazolyl, thienyl, isoxazolyl, thiazolyl and isothiazolyl, which is optionally substituted by one or more $R^6$, wherein each $R^6$ is independently selected from the group consisting of methyl, ethyl, isopropyl, n-butyl, hydroxyethyl, methoxymethyl, methoxyethyl, methoxypropyl, dimethylaminoethyl, morpholin-4-yl-ethyl, tetrahydropyran-4-yl, cyclobutyl, cyclopentyl, methylcarbonyl, and more preferably is methyl.

In some embodiments of the compound of formula Ic, $R^1$ is selected from the group consisting of:

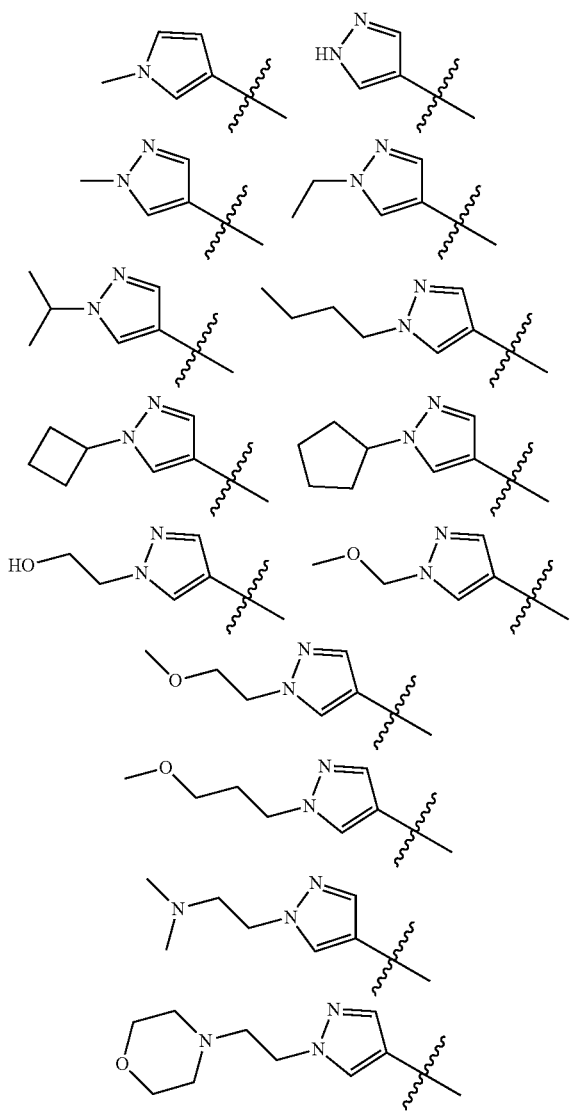

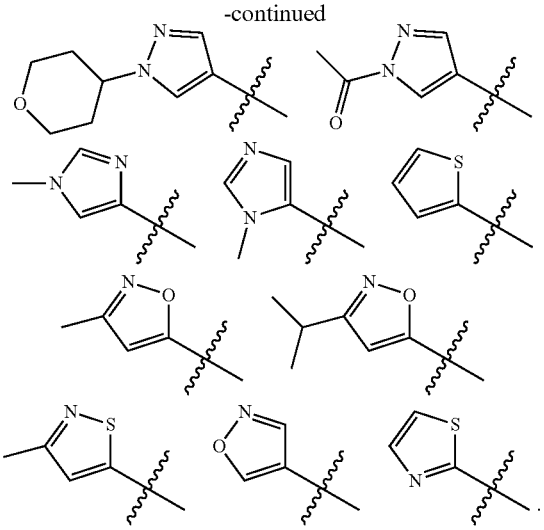

In some embodiments of the compound of formula Ic, l is selected from 0, 1 or 2, more preferably selected from 0 or 1.

In some embodiments of the compound of formula Ic, m is selected from 0, 1, 2 or 3, preferably selected from 1, 2 or 3.

In some embodiments of the compound of formula Ic, n is selected from 0, 1 or 2, and more preferably is 0.

In some embodiments of the compound of formula Ic, m and n are not 0 simultaneously.

In some embodiments of the compound of formula Ic, each group in the formula Ic is defined as follows:

W is selected from

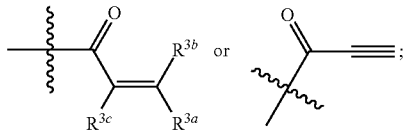

X is $NR^4$;
l is selected from 0, 1 or 2;
m is selected from 0, 1, 2 or 3;
n is selected from 0, 1 or 2;
$R^1$ is a 5- to 6-membered heteroaryl group, optionally substituted by one or more $R^6$;
$R^{3a}$, $R^{3b}$, and $R^{3c}$ are all hydrogen;
$R^4$ is hydrogen;
each $R^6$ is independently selected from the group consisting of halogen, heterocyclyl, $C_{1-8}$ aliphatic, $C_{1-8}$ halo aliphatic, hydroxy $C_{1-8}$ aliphatic, $C_{1-8}$ aliphaticoxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, heterocyclyl $C_{1-8}$ aliphatic and $C_{1-8}$ aliphaticcarbonyl, wherein heterocyclyl, as an independent group or a part of other group(s), represents a saturated or partially unsaturated 3- to 8-membered heterocyclyl group containing one or two heteroatoms selected from the group consisting of N, O, and S; each heterocyclyl is optionally substituted by one or more substituents selected from the group consisting of halogen and $C_{1-8}$ aliphatic, wherein $C_{1-8}$ aliphatic, at each occurrence, is independently selected from the group consisting of $C_{1-8}$ alkyl, $C_{2-8}$ alkenyl, $C_{2-8}$ alkynyl, $C_{3-8}$ cycloalkyl and $C_{4-8}$ cycloalkenyl.

In some embodiments of the compound of formula Ic, each group in the formula Ic is defined as follows:

W is

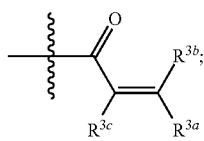

X is NR$^4$;
l is selected from 0, 1 or 2;
m is selected from 0, 1, 2 or 3;
n is selected from 0, 1 or 2;
R$^1$ is a 5-membered heteroaryl group, optionally substituted by one or more R$^6$;
R$^{3a}$, R$^{3b}$, and R$^{3c}$ are all hydrogen;
R$^4$ is hydrogen;
each R$^6$ is independently C$_{1-8}$ aliphatic,
wherein C$_{1-8}$ aliphatic is selected from the group consisting of C$_{1-8}$ alkyl, C$_{2-8}$ alkenyl, C$_{2-8}$ alkynyl, C$_{3-8}$ cycloalkyl and C$_{4-8}$ cycloalkenyl.

In some embodiments of the compound of formula Ic, the compound of formula Ic is selected from the group consisting of:

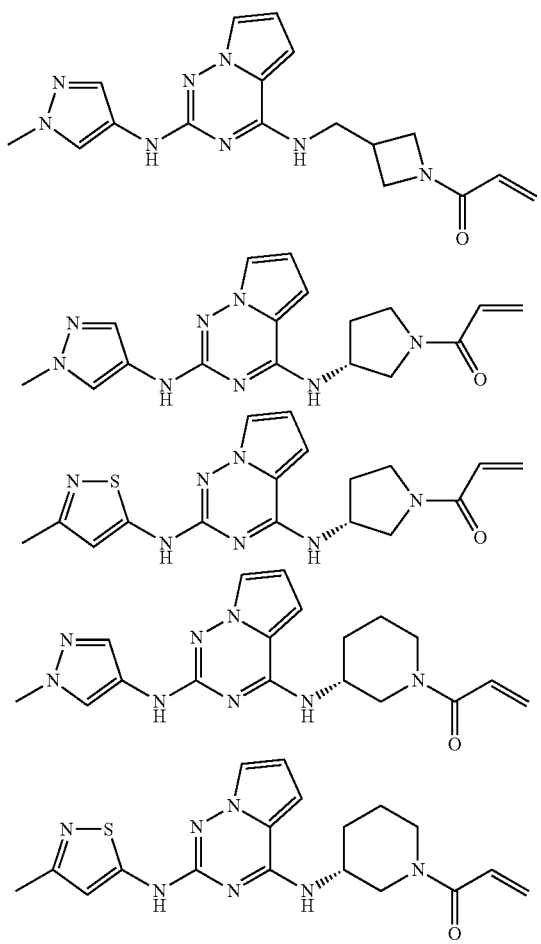

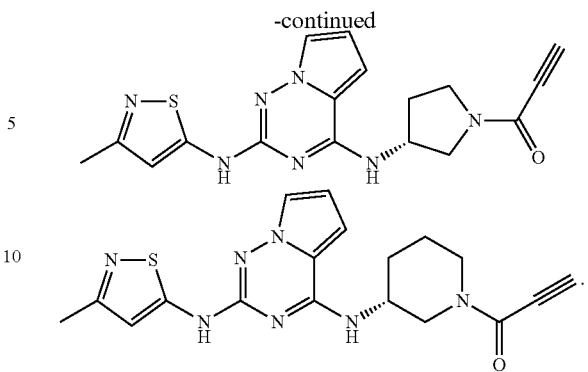

The compound of formula I, especially the compounds of formulae Ia, Ib and Ic, of the present invention, or a pharmaceutically acceptable salt thereof may contain one or more chiral carbon atoms, and each of the asymmetric carbon atom may form a R- or S-configuration, both configurations are within the scope of the present invention. Accordingly, the compounds may exist in the form of enantiomers, diastereomers or mixtures thereof. The above compounds may be prepared from racemates, diastereomers or enantiomers as starting materials or intermediates. Optically active isomers may be prepared using chiral synthons or chiral reagents, or resolved using conventional techniques, for example, chiral chromatography or fractional crystallization.

Conventional techniques for the preparation/isolation of individual isomers include chiral synthesis from a suitable optically pure precursor or resolution of the racemate (or the racemate of a salt or derivative) using, for example, chiral high pressure liquid chromatography, see, for example, Gerald Gübitz and Martin G. Schmid (Eds.), Chiral Separations, Methods and Protocols, *Methods in Molecular Biology*, Vol. 243, 2004; A. M. Stalcup, Chiral Separations, *Annu. Rev. Anal. Chem.* 3:341-63, 2010; Fumiss et al. (eds.), VOGEL'S ENCYCLOPEDIA OF PRACTICAL ORGANIC CHEMISTRY 5. sup. TH Ed., Longman Scientific and Technical Ltd., Essex, 1991, 809-816; and Heller, *Acc. Chem. Res.* 1990, 23, 128.

Another aspect of the present invention relates to a pharmaceutical composition comprising one or more compounds of formula I, especially compounds of formulae Ia, Ib and Ic, of the present invention, or a stereoisomer, a tautomer, a solvate, or a pharmaceutically acceptable salt thereof, and pharmaceutically acceptable excipients.

The pharmaceutical composition of the present invention may be formulated into preparations in solid, semi-solid, liquid or gaseous forms, such as tablets, capsules, powders, granules, ointments, solutions, suppositories, injections, inhalants, gels, microspheres, and aerosols.

The pharmaceutical composition of the present invention may be prepared by methodology well known in the pharmaceutical art. For example, a pharmaceutical composition intended to be administered by injection may be prepared by combining a compound of formula I, especially compounds of formulae Ia, Ib and Ic, of the present invention, or a pharmaceutically acceptable salt or prodrug thereof with sterile, distilled water, so as to form a solution. A surfactant may be added to facilitate the formation of a homogeneous solution or suspension. Actual methods of preparing a pharmaceutical composition are known to those skilled in the art;

for example, see *The Science and Practice of Pharmacy*, 20th Edition (Philadelphia College of Pharmacy and Science, 2000).

The routes of administration of the pharmaceutical composition of the present invention include, but are not limited to, oral, topical, transdermal, intramuscular, intravenous, inhalation, parenteral, sublingual, rectal, vaginal and intranasal. For example, dosage forms suitable for oral administration include capsules, tablets, granules, syrups, and the like. The compound of formula I, especially the compounds of formulae Ia, Ib and Ic, of the present invention, included in these dosage forms may be solid powders or granules; solutions or suspensions in aqueous or non-aqueous liquids; emulsions of water-in-oil type or oil-in-water type; and the like. The above-mentioned dosage forms may be prepared from active compounds together with one or more carriers or excipients by conventional pharmaceutical methods. The above-mentioned carriers are required to be compatible with the active compounds or the other excipients. For solid formulations, commonly used non-toxic carriers include, but are not limited to, mannitol, lactose, starch, magnesium stearate, cellulose, glucose, sucrose, and the like. Carriers for liquid formulations include, but are not limited to, water, physiological saline, aqueous solution of glucose, ethylene glycol, polyethylene glycol, and the like. The active compound may form a solution or a suspension with the above carriers. The specific route of administration and dosage form depend on the physical and chemical properties of the compounds per se and the severity of the diseases to be treated, etc. The specific route of administration can be determined by one skilled in the art based on the above-mentioned factors in combination with his own knowledge. See, for example, Li jun, "Clinical pharmacology", People's Medical Publishing House, 2008.06; Ding Yufeng, Discussion on Clinical Dosage Form factors and Drug Rational use in Hospital, *Herald of Medicine*, 26(5), 2007; Howard C. Ansel, Loyd V. Allen, Jr., Nicholas G. Popovich ed., Jiang Zhigiang translated, "Pharmaceutical Dosage Forms and Drug Delivery System", China Medical Science Press, 2003.05.

The compound of formula I, especially the compounds of formulae Ia, Ib and Ic, of the present invention, or a pharmaceutical composition comprising the compound of formula I, especially the compounds of formulae Ia, Ib and Ic, of the present invention, may be used in association or combination with one or more other drugs. Drugs to be used in combination with the compound of formula I, especially the compounds of formulae Ia, Ib and Ic, of the present invention, or the pharmaceutical composition comprising the compound of formula I, especially the compounds of formulae Ia, Ib and Ic, of the present invention, include, but are not limited to:

1) Immunosuppressants such as methotrexate, cyclophosphamide, and the like;

2) Corticosteroids such as dexamethasone, betamethasone, and the like;

3) Nonsteroidal anti-inflammatory drugs such as salicylates, aryl alkanoic acid, and the like;

4) Cox-2 specific inhibitors such as rofecoxib, celecoxib, and the like;

5) TNF-α binding proteins such as infliximab, adalimumab, and the like;

6) Interferons such as interferon-β and interferon-γ; interleukins such as interleukin-2; and the like.

Another aspect of the present invention relates to a compound of formula I, especially the compounds of formulae Ia, Ib and Ic, of the present invention, or a stereoisomer, a tautomer, a solvate, or a pharmaceutically acceptable salt thereof, for inhibiting the activities of BTK and/or JAK3.

Another aspect of the present invention relates to a compound of formula I, especially the compounds of formulae Ia, Ib and Ic, of the present invention, or a stereoisomer, a tautomer, a solvate, or a pharmaceutically acceptable salt thereof, for the prevention and/or treatment of BTK- and/or JAK3-mediated diseases.

Another aspect of the present invention relates to a pharmaceutical composition comprising the compound of formula I, especially the compounds of formulae Ia, Ib and Ic, of the present invention, or a stereoisomer, a tautomer, a solvate, or a pharmaceutically acceptable salt thereof, for inhibiting the activities of BTK and/or JAK3.

Another aspect of the present invention relates to a pharmaceutical composition comprising the compound of formula I, especially the compounds of formulae Ia, Ib and Ic, of the present invention, or a stereoisomer, a tautomer, a solvate, or a pharmaceutically acceptable salt thereof, for the prevention and/or treatment of BTK- and/or JAK3-mediated diseases.

Another aspect of the present invention relates to use of the compound of formula I, especially the compounds of formulae Ia, Ib and Ic, of the present invention, or a stereoisomer, a tautomer, a solvate, or the pharmaceutically acceptable salt thereof or of the pharmaceutical composition comprising the compound of formula I, especially the compounds of formulae Ia, Ib and Ic, of the present invention, or a stereoisomer, a tautomer, a solvate, or a pharmaceutically acceptable salt thereof in the manufacture of a medicament for inhibiting the activities of BTK and/or JAK3.

Another aspect of the present invention relates to use of the compound of formula I, especially the compounds of formulae Ia, Ib and Ic, of the present invention, or a stereoisomer, a tautomer, a solvate, or a pharmaceutically acceptable salt thereof, or of the pharmaceutical composition comprising the compound of formula I, especially the compounds of formulae Ia, Ib and Ic, of the present invention, or a stereoisomer, a tautomer, a solvate, or a pharmaceutically acceptable salt thereof in the manufacture of a medicament for the treatment and/or prevention of BTK- and/or JAK3-mediated diseases.

Another aspect of the present invention relates to use of the compound of formula I, especially the compounds of formulae Ia, Ib and Ic, of the present invention, or a stereoisomer, a tautomer, a solvate, or a pharmaceutically acceptable salt thereof, or of the pharmaceutical composition comprising the compound of formula I, especially the compounds of formulae Ia, Ib and Ic, of the present invention, or a stereoisomer, a tautomer, a solvate, or a pharmaceutically acceptable salt thereof in the manufacture of a medicament for the treatment and/or prevention BTK- and/or JAK3-mediated diseases.

Another aspect of the present invention relates to a method of inhibiting the activities of BTK and/or JAK3 in a biological system comprising bringing the biological system into contact with the compound of formula I, especially the compounds of formulae Ia, Ib and Ic, of the present invention, or a stereoisomer, a tautomer, a solvate, or a pharmaceutically acceptable salt thereof, or with the pharmaceutical composition comprising said compound. In some embodiments, the biological system is an enzyme, a cell, or a mammal. Examples of mammals include, but are not limited to, humans; non-human primates such as chimpanzee, and other apes and monkey species; farm animals such as cattle, horses, sheep, goats, swine; domestic animals such as rabbits, dogs, and cats; laboratory animals including rodents, such as rats, mice and guinea pigs, and the like.

Another aspect of the present invention relates to a method of inhibiting BTK and/or JAK3 in a mammal, especially in a human, comprising administering to the mammal, especially the human, in need thereof a therapeutically effective amount of the compound of formula I, especially the compounds of formulae Ia, Ib and Ic, of the present invention, a stereoisomer, a tautomer, a solvate, or a pharmaceutically acceptable salt thereof, or of the pharmaceutical composition comprising said compound.

Another aspect of the present invention relates to a method of treating and/or preventing BTK- and/or JAK3-mediated diseases comprising administering to a mammal, especially a human, in need thereof a therapeutically effective amount of the compound of formula I, especially the compounds of formulae Ia, Ib and Ic, of the present invention, a stereoisomer, a tautomer, a solvate, or a pharmaceutically acceptable salt thereof, or of the pharmaceutical composition comprising said compound.

In the present application, the BTK- and/or JAK3-mediated diseases are selected from the group consisting of autoimmune diseases, inflammatory diseases, heteroimmune conditions or diseases, thromboembolic diseases and cancers. The autoimmune diseases and inflammatory diseases are selected from the group consisting of rheumatoid arthritis, osteoarthritis, juvenile arthritis, chronic obstructive pulmonary diseases, multiple sclerosis, systemic lupus erythematosus, psoriasis, psoriatic arthritis, Crohn's disease, ulcerative colitis, irritable bowel syndrome, and the like. The cancers are selected from the group consisting of B-cell chronic lymphocytic leukemia, acute lymphocytic leukemia, non-Hodgkin's lymphoma, Hodgkin's lymphoma, acute myelogenous leukemia, diffuse large B-cell lymphoma, multiple myeloma, mantle cell lymphoma, small lymphocytic lymphoma, and the like.

The composition of the present invention is formulated, quantified and administered in a manner conforming to the guidelines of medical practices. The "therapeutically effective amount" of the compound of the present invention is determined depending on the specific disorders to be treated, individuals being treated, causes of the disorders, targets of the drug, and the modes of administration. Typically, the dose for parenteral administration may be from 1 to 200 mg/kg, and the dose for oral administration may be from 1 to 1000 mg/kg.

The ranges of the effective doses provided herein are not intended to limit the scope of the invention, but represent preferred dose ranges. However, the most preferred dosage will be tailored to the individual subject, as is understood and determinable by one skilled in the art (see, for example, Berkow et. al. eds., The Merck Manual, 16th edition, Merck Company, Rahway, N. J., 1992).

Preparation of the Compound of the Invention

The following Reaction Schemes, taking the compounds of formulas Ia, Ib and Ic as examples, illustrate methods to make the compounds of formula I of the present invention.

It is understood by those skilled in the art that in the following description, combinations of substituents are permissible only if such combinations result in stable compounds.

It will also be appreciated by those skilled in the art that in the process described below the functional groups of immediate compounds may need to be protected by suitable protecting groups "PGs". Said functional groups include hydroxyl, amino, mercapto and carboxylic acid. Suitable protecting groups for hydroxyl include trialkylsilyl or diarylalkylsilyl (e.g. tert-butyldimethylsilyl, tert-butyldiphenylsilyl or trimethylsilyl), tetrahydropyranyl, benzyl, and the like. Suitable protecting groups for amino, amidino and guanidino include tert-butoxycarbonyl, benzyloxycarbonyl, and the like. Suitable protecting groups for mercapto include —C(O)—R" (wherein R" is alkyl, aryl or arylalkyl), p-methoxybenzyl, trityl, and the like. Suitable protecting groups for carboxyl include alkyl, aryl or arylalkyl esters.

Protecting groups may be introduced and removed in accordance with standard techniques, which are known to those skilled in the art and as described herein.

The use of protecting groups is described in detail in Greene, T. W. and P. G. M. Wuts, Protective Groups in Organic Synthesis, (1999), 4th Ed., Wiley. The Protecting group may also be a polymer resin.

The compounds of formula Ia, Ib and Ic of the present invention may be prepared following the procedures illustrated in the following reaction scheme I.

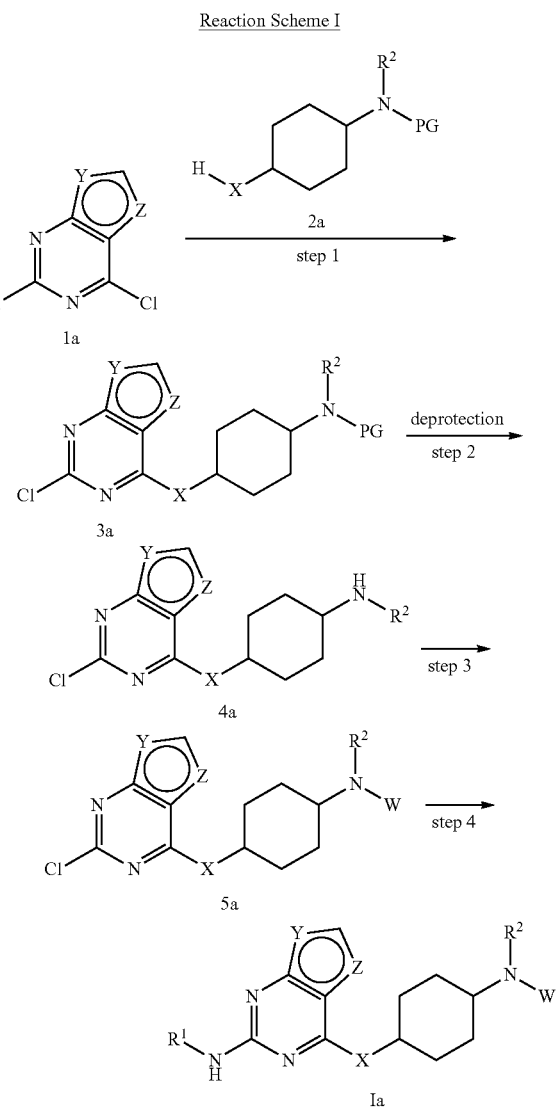

wherein, X, Y, Z, W, $R^1$, and $R^2$ in their respective formulas are all defined as in formula Ia above;

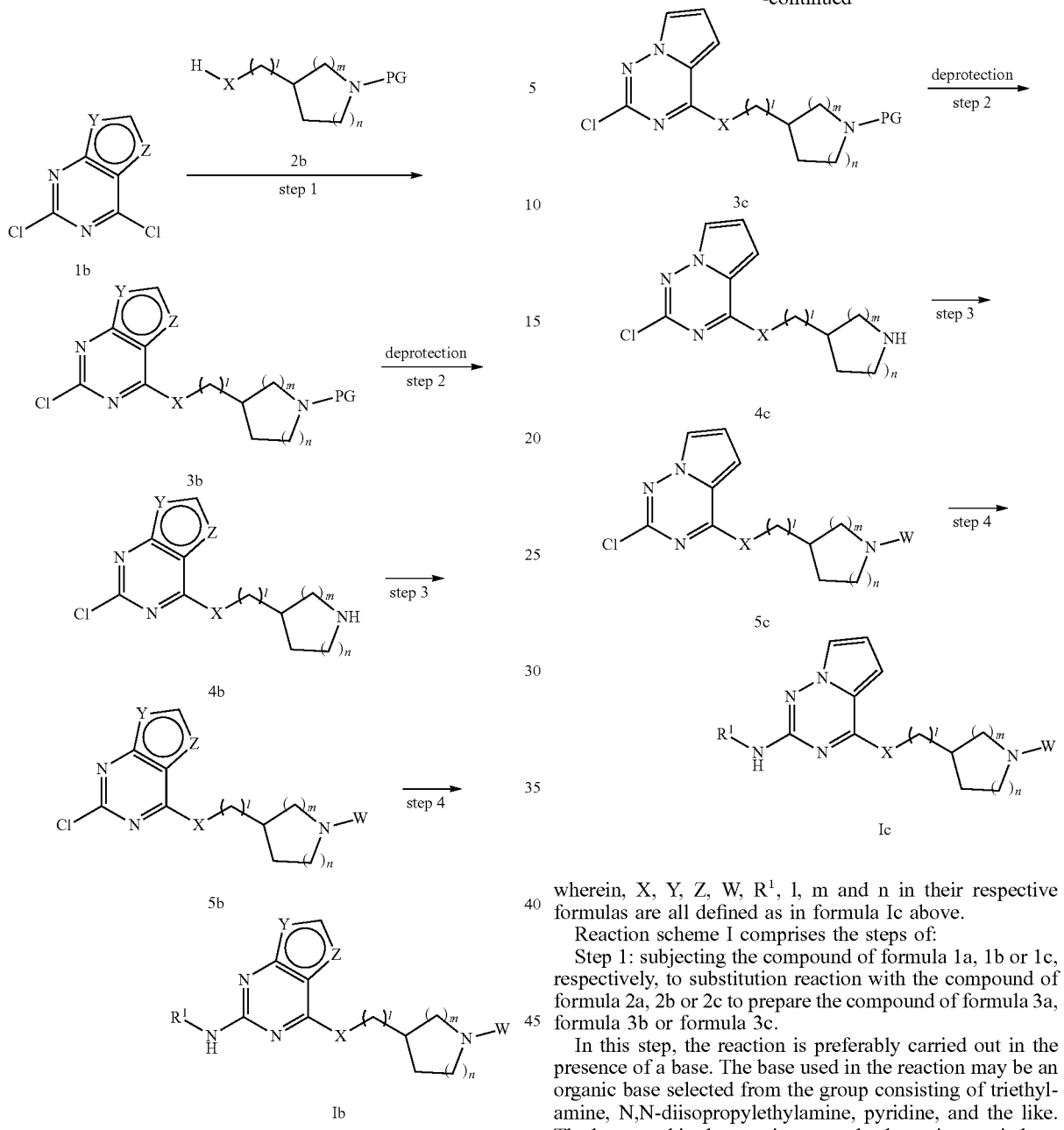

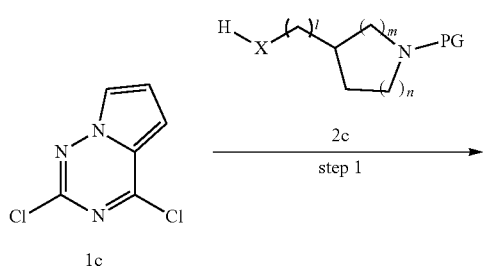

wherein, X, Y, Z, W, R¹, l, m and n in their respective formulas are all defined as in formula Ib above;

or wherein, X, Y, Z, W, $R^1$, l, m and n in their respective formulas are all defined as in formula Ic above.

Reaction scheme I comprises the steps of:

Step 1: subjecting the compound of formula 1a, 1b or 1c, respectively, to substitution reaction with the compound of formula 2a, 2b or 2c to prepare the compound of formula 3a, formula 3b or formula 3c.

In this step, the reaction is preferably carried out in the presence of a base. The base used in the reaction may be an organic base selected from the group consisting of triethylamine, N,N-diisopropylethylamine, pyridine, and the like. The base used in the reaction may also be an inorganic base selected from the group consisting of sodium carbonate, potassium carbonate, sodium hydroxide, and the like. The reaction may also be carried out in the presence of an acid or under a neutral condition. The acid used in the reaction may be selected from the group consisting of hydrochloric acid, trifluoroacetic acid, a solution of hydrogen chloride in 1,4-dioxane, acetic acid, sulfuric acid, and the like. The reaction temperature is in a range from −80° C. to 120° C. The solvent used in the reaction may be selected from the group consisting of 1,4-dioxane, tetrahydrofuran, dichloromethane, toluene, methanol, ethanol, isopropanol, butanol, and the like.

Step 2: removing the protecting group PG from the compound of formula 3a, 3b or 3c to prepare the compound of formula 4a, 4b or 4c.

The protecting group (PG) of the compound of formula 3a, 3b or 3c may be tert-butoxycarbonyl, benzyloxycarbonyl, benzyl, or the like. The deprotecting reaction may be carried out under an acid catalysis condition. The acid used in the reaction may be selected from the group consisting of hydrochloric acid, trifluoroacetic acid, a solution of hydrogen chloride in 1,4-dioxane, acetic acid, sulfuric acid, and the like. The reaction may also be carried out by catalytic hydrogenation using a palladium catalyst under an acidic or a neutral condition. The palladium catalyst used in the present invention may be selected from the group consisting of palladium on carbon and palladium hydroxide. The acid used in the reaction may be selected from the group consisting of hydrochloric acid, trifluoroacetic acid, a solution of hydrogen chloride in 1,4-dioxane, sulfuric acid, and the like. The reaction temperature is in a range from −80° C. to 120° C. The solvent used in the reaction may be selected from the group consisting of 1,4-dioxane, tetrahydrofuran, dichloromethane, toluene, ethanol, and the like.

Step 3: Subjecting the compound of formula 4a, 4b or 4c to condensation reaction to obtain the compound of formula 5a, 5b or 5c.

In this step, the condensation reagent may be selected from the group consisting of carbonyldiimidazole (CDI), O-benzotriazol-1-yl-N,N,N',N'-tetramethyluronium tetrafluoroborate (TBTU), dicyclohexylcarbodiimide (DCC), 1-(3-dimethyl)aminopropyl)-3-ethyl-carbodiimide (EDCI), and the like. The base used in the reaction may be selected from the group consisting of triethylamine, N,N-diisopropyl ethylamine, pyridine, sodium hydride, and the like. The reaction temperature is in a range from 0° C. to 80° C. The solvent used in the reaction may be selected from the group consisting of 1,4-dioxane, tetrahydrofuran, dichloromethane, toluene, and the like.

Step 4: subjecting the compound of formula 5a, 5b or 5c to substitution reaction to obtain the corresponding compound of formula Ia, Ib or Ic.

In this step, the reaction may be carried out in the presence of an acid or under a neutral condition. The acid used in the reaction may be selected from the group consisting of hydrochloric acid, trifluoroacetic acid, a solution of hydrogen chloride in 1,4-dioxane, acetic acid, sulfuric acid, and the like. The reaction may also be carried out in the presence of a base. The base used in the reaction may be a strong base selected from the group consisting of sodium hydroxide, cesium carbonate, sodium tert-butoxide, sodium hydride, and the like. The reaction may also be carried out in the presence of a palladium catalyst. The palladium catalyst which may be used in the present invention is selected from the group consisting of bis(triphenylphosphine)palladium dichloride ($Pd(PPh_3)_2Cl_2$), tris(dibenzylidenepropanone)dipalladium ($Pd_2(dba)_3$), tetra(triphenylphosphine)palladium ($Pd(PPh_3)_4$), palladium acetate ($Pd(OAc)_2$), [1,1'-bis(diphenylphosphino)ferrocene] dichloropalladium ($Pd(dppf)Cl_2$) and palladium chloride ($PdCl_2$). The base which may be useful under this condition is preferably an inorganic base, such as sodium carbonate, potassium carbonate, potassium phosphate, cesium carbonate, and the like. The reaction temperature is in a range from 80° C. to 160° C. The solvent used in the reaction may be selected from the group consisting of 1,4-dioxane, toluene, ethanol, isopropanol, butanol, 2-butanol, water, and mixtures thereof.

The compounds of formulas Ia, Ib, and Ic of the present invention may be prepared following the procedures illustrated in the following reaction scheme II.

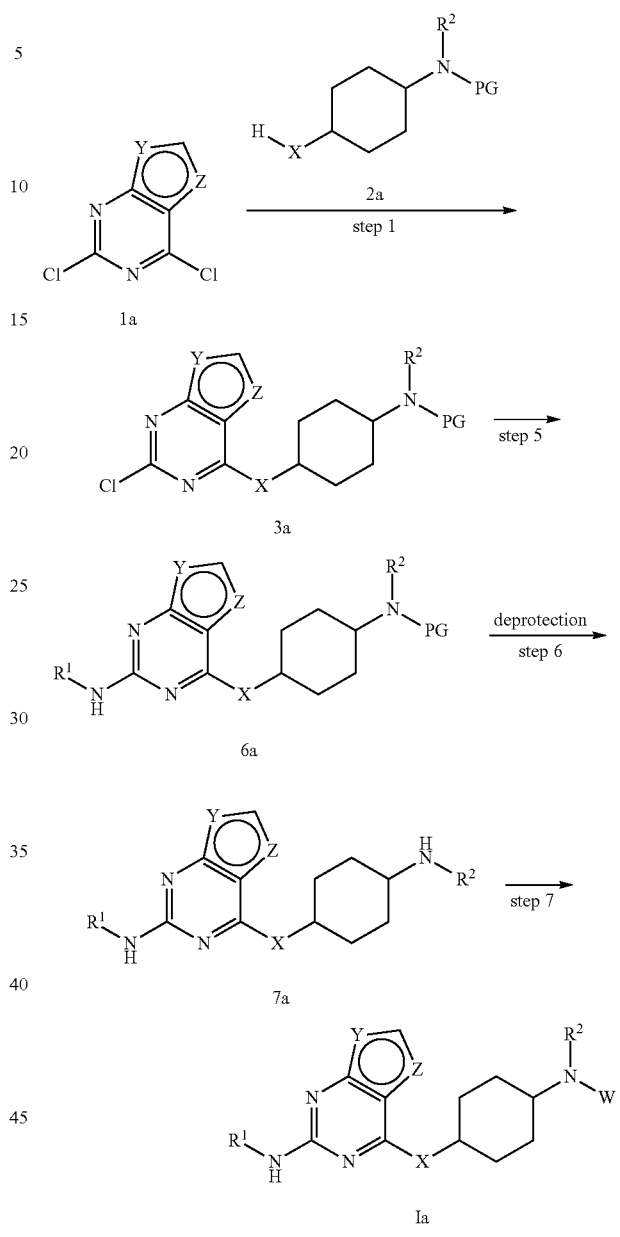

wherein, X, Y, Z, W, $R^1$ and $R^2$ in their respective formulas are all defined as above in formula Ia;

or

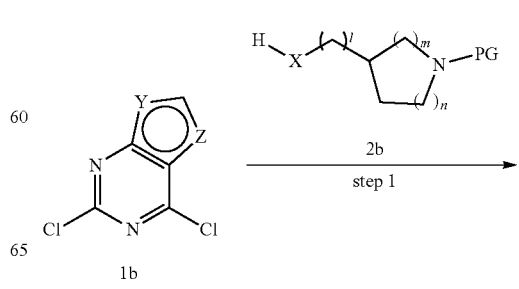

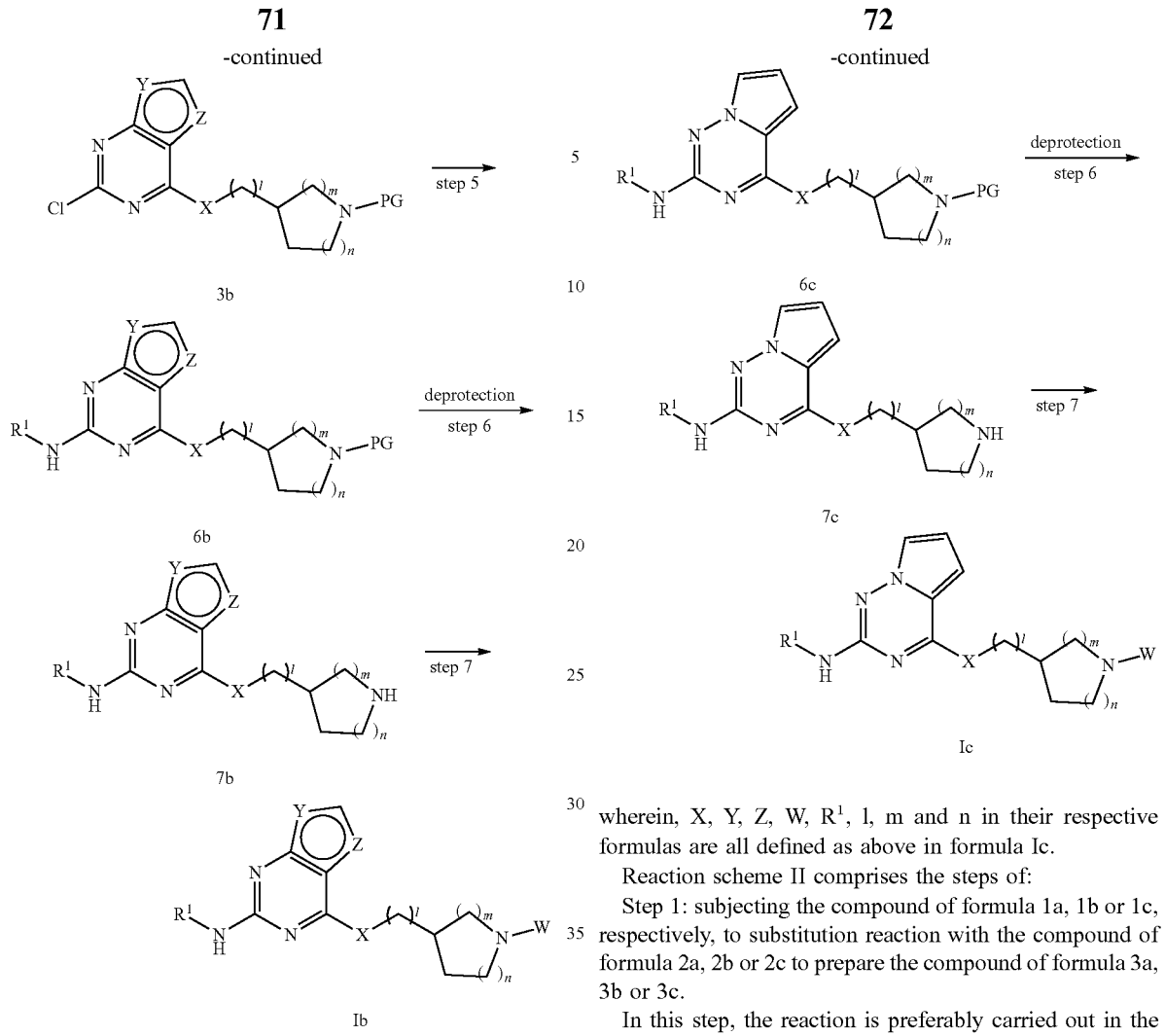

wherein, X, Y, Z, W, R¹, l, m and n in their respective formulas are all defined as above in formula Ib;

or

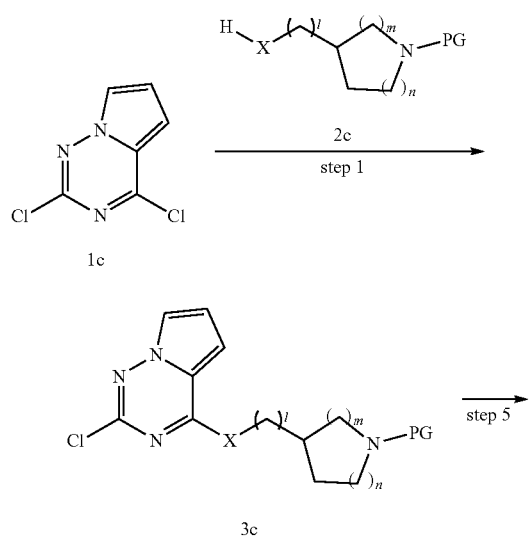

wherein, X, Y, Z, W, R¹, l, m and n in their respective formulas are all defined as above in formula Ic.

Reaction scheme II comprises the steps of:

Step 1: subjecting the compound of formula 1a, 1b or 1c, respectively, to substitution reaction with the compound of formula 2a, 2b or 2c to prepare the compound of formula 3a, 3b or 3c.

In this step, the reaction is preferably carried out in the presence of a base. The base used in the reaction may be an organic base selected from the group consisting of triethylamine, N,N-diisopropylethylamine, pyridine, and the like. The base used in the reaction may also be an inorganic base selected from the group consisting of sodium carbonate, potassium carbonate, sodium hydroxide, and the like. The reaction may also be carried out in the presence of an acid or under a neutral condition. The acid used in the reaction may be selected from the group consisting of hydrochloric acid, trifluoroacetic acid, a solution of hydrogen chloride in 1,4-dioxane, acetic acid, sulfuric acid, and the like. The reaction temperature is in a range from −80° C. to 120° C. The solvent used in the reaction may be selected from the group consisting of 1,4-dioxane, tetrahydrofuran, dichloromethane, toluene, methanol, ethanol, isopropanol, butanol, and the like.

Step 5: subjecting the compound of formula 3a, 3b or 3c to substitution reaction to obtain the compound of formula 6a, 6b or 6c.

In this step, the reaction may be carried out in the presence of an acid or under a neutral condition. The acid used in the reaction may be selected from the group consisting of hydrochloric acid, trifluoroacetic acid, a solution of hydrogen chloride in 1,4-dioxane, acetic acid, sulfuric acid, and the like. The reaction may also be carried out in the presence of a base. The base used in the reaction may be a strong base selected from the group consisting of sodium hydroxide, sodium tert-butoxide, sodium hydride, and the like. The reaction may also be carried out in the presence of a palladium catalyst. The palladium catalyst that may be used in the present invention is selected from the group consisting of bis(triphenylphosphine)palladium dichloride (Pd(PPh$_3$)$_2$Cl$_2$), tris(dibenzylidenepropanone)dipalladium (Pd$_2$(dba)$_3$), tetra(triphenylphosphine)palladium (Pd(PPh$_3$)$_4$), palladium acetate (Pd(OAc)$_2$), [1,1'-bis(diphenylphosphino)ferrocene] dichloropalladium (Pd(dppf)Cl$_2$), and palladium chloride (PdCl$_2$). The base which may be useful under this condition is preferably an inorganic base, such as sodium carbonate, potassium carbonate, potassium phosphate, cesium carbonate, and the like. The reaction temperature is in a range from 80° C. to 160° C. The solvent used in the reaction may be selected from the group consisting of 1,4-dioxane, toluene, ethanol, isopropanol, butanol, 2-butanol, water, and mixtures thereof.

Step 6: removing the protecting group PG of the compound of formula 6a, 6b or 6c to prepare the compound of formula 7a, 7b or 7c.

The protecting group (PG) of the compound of formula 6a, 6b or 6c may be tert-butoxycarbonyl, benzyloxycarbonyl, benzyl, or the like. The deprotecting reaction may be carried out under an acid catalysis condition. The acid used in the reaction may be selected from the group consisting of hydrochloric acid, trifluoroacetic acid, a solution of hydrogen chloride in 1,4-dioxane, acetic acid, sulfuric acid, and the like. The reaction may also be carried out by catalytic hydrogenation using a palladium catalyst under an acidic or a neutral condition. The palladium catalyst used in the present invention is selected from the group consisting of palladium on carbon and palladium hydroxide, and the acid used in the reaction may be selected from the group consisting of hydrochloric acid, a solution of hydrogen chloride in 1,4-dioxane, sulfuric acid, and the like. The reaction temperature is in a range from −80° C. to 120° C. The solvent used in the reaction may be selected from the group consisting of 1,4-dioxane, tetrahydrofuran, dichloromethane, toluene, methanol, ethanol, and the like.

Step 7: subjecting the compound of formula 7a, 7b or 7c to condensation reaction to obtain the corresponding compound of formula Ia, Ib or Ic.

In this step, the condensation reagent may be selected from the group consisting of carbonyldiimidazole (CDI), O-benzotriazol-1-yl-N,N,N',N'-tetramethyluronium tetrafluoroborate (TBTU), dicyclohexylcarbodiimide (DCC), 1-(3-dimethyl)aminopropyl)-3-ethyl-carbodiimide (EDCI), and the like. The base used in the reaction may be selected from the group consisting of triethylamine, N,N-diisopropylethylamine, pyridine, and the like. The reaction temperature is in a range from 0° C. to 80° C. The solvent used in the reaction may be selected from the group consisting of 1,4-dioxane, tetrahydrofuran, dichloromethane, toluene, and the like.

The compound of formula Ia of the present invention may be prepared following the procedures illustrated in the following reaction scheme III.

Reaction Scheme III

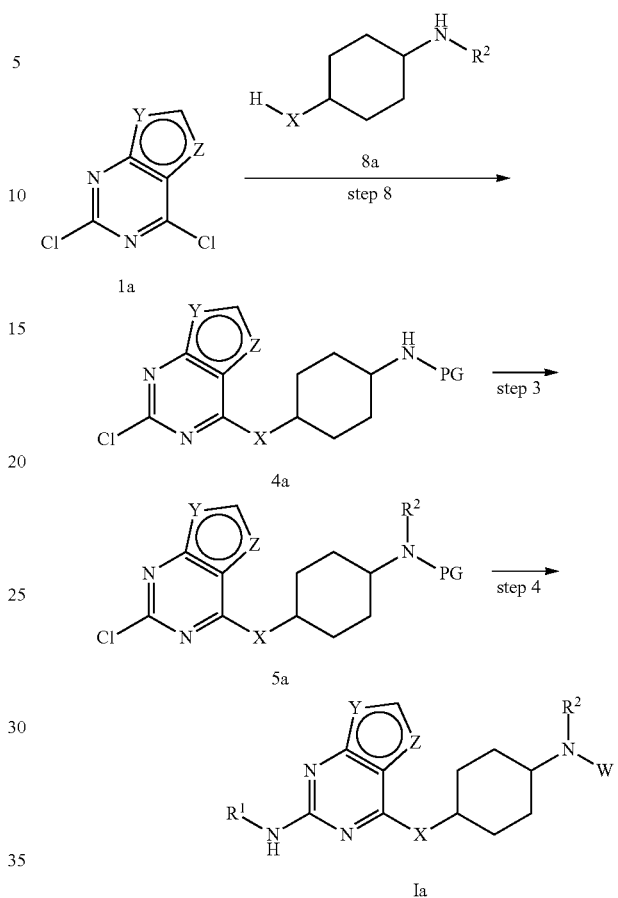

wherein, X, Y, Z, W, R$^1$ and R$^2$ in their respective formulas are all defined as above in formula Ia.

Reaction scheme III comprises the steps of:

Step 8: subjecting the compound of formula 1a to substitution reaction with the compound of formula 8a to prepare the compound of formula 4a.

In this step, the reaction is preferably carried out in the presence of a base. The base used in the reaction may be an organic base selected from the group consisting of triethylamine, N,N-diisopropylethylamine, pyridine, and the like, and the base used in the reaction may also be an inorganic base selected from the group consisting of sodium carbonate, potassium carbonate, sodium hydroxide, and the like. The reaction may also be carried out in the presence of an acid or in the neutral condition. The acid used in the reaction may be selected from the group consisting of hydrochloric acid, trifluoroacetic acid, a solution of hydrogen chloride in 1,4-dioxane, acetic acid, sulfuric acid, and the like. The reaction temperature is in a range from −80° C. to 120° C. The solvent used in the reaction may be selected from the group consisting of 1,4-dioxane, tetrahydrofuran, dichloromethane, toluene, methanol, ethanol, isopropanol, butanol, and the like.

Step 3: subjecting the compound of formula 4a to condensation reaction to obtain the compound of formula 5a.

In this step, the condensation reagent may be selected from the group consisting of carbonyldiimidazole (CDI), O-benzotriazol-1-yl-N,N,N',N'-tetramethyluronium tetrafluoroborate (TBTU), dicyclohexylcarbodiimide (DCC), 1-(3-dimethyl)aminopropyl)-3-ethyl-carbodiimide (EDCI), and the like. The base used in the reaction may be selected from the group consisting of triethylamine, N,N-diisopropyl ethylamine, pyridine, and the like. The reaction temperature is in a range from 0° C. to 80° C. The solvent used in the reaction may be selected from the group consisting of 1,4-dioxane, tetrahydrofuran, dichloromethane, toluene, and the like.

Step 4: subjecting the compound of formula 5a to substitution reaction to obtain the corresponding compound of formula Ia.

In this step, the reaction may be carried out in the presence of an acid or in the neutral condition, and the acid used in the reaction may be selected from the group consisting of hydrochloric acid, trifluoroacetic acid, a solution of hydrogen chloride in 1,4-dioxane, acetic acid, sulfuric acid, and the like. The reaction may be carried out in the presence of a base, and the base used in the reaction may be a strong base selected from the group consisting of sodium hydroxide, sodium tert-butoxide, sodium hydride, and the like. The reaction may also be carried out in the presence of a palladium catalyst. The palladium catalyst that may be used in the present invention is selected from the group consisting of bis(triphenylphosphine)palladium dichloride (Pd(PPh$_3$)$_2$Cl$_2$), tris(dibenzylidenepropanone)dipalladium (Pd$_2$(dba)$_3$), tetra(triphenylphosphine)palladium (Pd(PPh$_3$)$_4$), palladium acetate (Pd(OAc)$_2$), [1,1'-bis(diphenylphosphino)ferrocene] dichloropalladium (Pd(dppf)Cl$_2$), and palladium chloride (PdCl$_2$). The base that may be useful under this condition is preferably an inorganic base, such as sodium carbonate, potassium carbonate, potassium phosphate, cesium carbonate, and the like. The reaction temperature is in a range from 80° C. to 160° C. The solvent used in the reaction may be selected from the group consisting of 1,4-dioxane, toluene, ethanol, isopropanol, butanol, 2-butanol, water, and mixtures thereof.

It will be appreciated by those skilled in the art that the above reaction schemes and preparation methods are only for a simple and clear illustration purpose, and are not intended to be limiting, and that the compound of formula I of the present invention may also be obtained by similar methods as described above by selecting appropriate starting materials, which may be commercially available, or obtainable by using methods well known in the art.

EXAMPLES

The following experiments, synthetic methods and intermediates involved are provided as an illustration of the present invention, and are not intended to limit the scope of the present invention.

The starting materials used in the present invention are purchased from reagent suppliers or prepared from known materials by methods as known in the art. Unless otherwise specifically indicated, the following conditions are applied in the examples:

Temperature is expressed in degrees Celsius (° C.); and room temperature is defined as 18-25° C.;

The organic solvent was dried over anhydrous magnesium sulfate or anhydrous sodium sulfate, and concentrated to dryness using a rotary evaporator under reduced pressure at elevated temperature (e.g. 15 mmHg, 30° C.);

200-300 Mesh silica gel was used as a carrier in the separation and purification by column chromatography, and TLC refers to thin layer chromatography;

Typically, the progress of a reaction was monitored by TLC or LC-MS;

Identification of the final product was performed by NMR (Bruker AVANCE 300, 300 MHz) and LC-MS (Bruker esquine 6000, Agilent 1200 series) spectrometry.

Example 1

Preparation of N-(cis-4-((2-((1-methyl-1H-pyrazol-4-yl)amino)thieno[3,2-d] pyrimidin-4-yl)amino)cyclohexyl)acrylamide

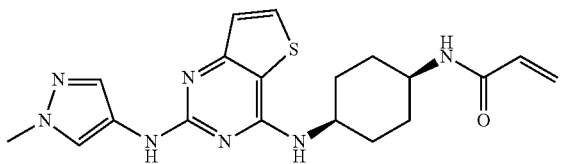 [SMILES: C=CC(=O)N[C@H]1CC[C@@H](Nc2nc(Nc3cnn(C)c3)nc3ccsc23)CC1]

Step 1: Preparation of Tert-Butyl cis-4-((2-chloro-thieno[3,2-d]pyrimidin-4-yl)amino)cyclohexyl carbamate

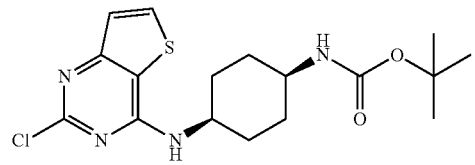 [SMILES: CC(C)(C)OC(=O)N[C@H]1CC[C@@H](Nc2nc(Cl)nc3ccsc23)CC1]

2,4-Dichloro-thieno[3,2-d]pyrimidine (678 mg, 3.31 mmol) and tert-butyl cis-4-aminocyclohexyl carbamate (849 mg, 3.97 mmol) were dissolved in tetrahydrofuran (10 mL), followed by the addition of N,N-diisopropylethylamine (0.9 mL, 4.97 mmol). The reaction solution was reacted at 70° C. overnight, and then concentrated. The residue was added with water (20 mL), and extracted with ethyl acetate (20 mL×3). The organic phase was dried over anhydrous sodium sulfate, and concentrated under reduced pressure, and purified by silica gel column chromatography (eluent:n-hexane: ethyl acetate=1:5) to give a white solid (1.07 g). Yield: 84.7%. MS (ESI, m/z): [M+H]$^+$: 383.4; $^1$H-NMR (300 MHz, CDCl$_3$) δ: 7.74 (d, 1H, J=5.4 Hz), 7.35 (d, 1H, J=5.4 Hz), 5.00 (s, 1H), 4.59 (s, 1H), 4.31-4.38 (m, 1H), 3.72-3.74 (m, 1H), 1.62-2.04 (m, 8H), 1.45 (s, 9H).

Step 2: Preparation of cis-N$^1$-(2-chloro-thieno[3,2-d]pyrimidin-4-yl)cyclohexyl-1,4-diamine

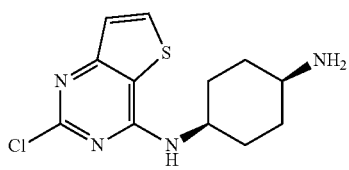 [SMILES: N[C@H]1CC[C@@H](Nc2nc(Cl)nc3ccsc23)CC1]

The product obtained in step 1 (840 mg, 2.2 mmol) was dissolved in dichloromethane (10 mL), followed by the slow addition of trifluoroacetic acid (2 mL, 30.8 mmol). The reaction solution was reacted at room temperature for 2 hours. The reaction solution was concentrated, and the crude product thus obtained was used directly in the next step without further purification. MS (ESI, m/z): [M+H]⁺: 282.9.

Step 3: Preparation of N-(cis-4-((2-chloro-thieno[3,2-d]pyrimidin-4-yl)amino) cyclohexyl)acrylamide

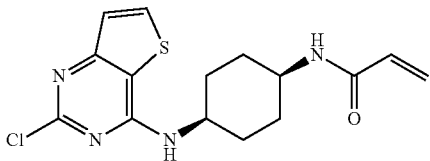

The product obtained in step 2 (620 mg, 2.20 mmol) was dissolved in dichloromethane (10 mL), followed by the addition of triethylamine (440 mg, 4.4 mmol). A solution of acryloyl chloride (0.2 mL, 2.42 mmol) dissolved in dichloromethane (5 mL) was added dropwise to the above solution at 0° C. The reaction solution was reacted at room temperature overnight. The reaction solution was washed with water (20 mL), and the organic phase was dried over anhydrous sodium sulfate, concentrated under reduced pressure, and purified by silica gel column chromatography (eluent:dichloromethane/methanol=70:1), to give a white solid (0.56 g). Yield: 75.8%. MS (ESI, m/z): [M+H]⁺: 337.2; ¹H-NMR (300 MHz, DMSO-d₆) δ: 7.76 (d, 1H, J=5.4 Hz), 7.36 (d, 1H, J=5.4 Hz), 6.07-6.35 (m, 2H), 5.65-5.69 (m, 2H), 5.23 (bs, 1H), 4.34-4.38 (m, 1H), 4.09-4.13 (m, 1H), 1.68-2.02 (m, 8H).

Step 4: Preparation of N-(cis-4-((2-((1-methyl-1H-pyrazol-4-yl)amino)thieno[3,2-d] pyrimidin-4-yl) amino)cyclohexyl)acrylamide The product obtained in step 3 (54 mg, 0.162 mmol) and 1-methyl-1H-pyrazole-4-amine (23 mg, 0.244 mmol) was dissolved in 1,4-dioxane (2 mL). The pH of the reaction solution was adjusted to 5 with trifluoroacetic acid, and the reaction mixture was reacted at 90° C. under microwave irradiation for 0.5 hours. The reaction solution was cooled to room temperature, and adjusted to pH 8 with 1N solution of sodium hydroxide. The resulting mixture was extracted with ethyl acetate (10 mL×3), and the organic phase was dried over anhydrous sodium sulfate, concentrated under reduced pressure, and purified by silica gel column chromatography (eluent: dichloromethane/methanol=10:1) to give a pale yellow solid (32 mg). Yield: 49.8%. MS (ESI, m/z): [M+H]⁺: 398.3; ¹H-NMR (300 MHz, CDCl₃) δ: 7.66-7.69 (m, 3H), 6.99-7.19 (m, 2H), 6.32 (dd, 1H, J=1.5 Hz, J=16.8 Hz), 6.15 (dd, 1H, J=10.2 Hz, J=16.8 Hz), 5.89-5.91 (m, 2H), 5.66 (dd, 1H, J=1.5 Hz, J=10.2 Hz), 4.23-4.38 (m, 1H), 4.08-4.16 (m, 1H), 3.88 (s, 3H), 1.75-2.05 (m, 8H).

The following compounds (in Table 1) were prepared from similar starting materials by similar synthetic methods to those as described in Example 1.

TABLE 1

| Example | Structure | Characterization data |
| --- | --- | --- |
| 2 | 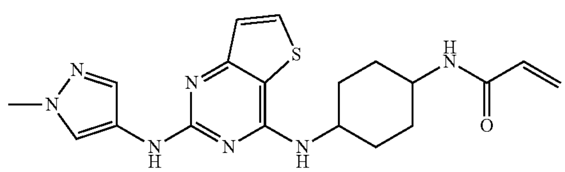 [SMILES: C=CC(=O)NC1CCC(Nc2nc(Nc3cnn(C)c3)nc3ccsc23)CC1] | ¹H-NMR (300 MHz, CD₃OD) δ: 7.96 (d, 1H, J = 5.4 Hz), 7.86 (s, 1H), 7.63 (s, 1H), 7.17 (d, 1H, J = 5.4 Hz), 6.22-8.43 (m, 2H), 5.67 (dd, 1H, J = 2.1 Hz, J = 17.1 Hz), 4.27-4.28 (m, 1H), 4.27-4.28 (m, 1H), 4.01-4.04 (m, 1H), 2.03 (s, 3H), 1.78-1.97 (m, 8H); LC-MS (ESI, m/z): [M + H]⁺ = 398.3 |
| 3 | 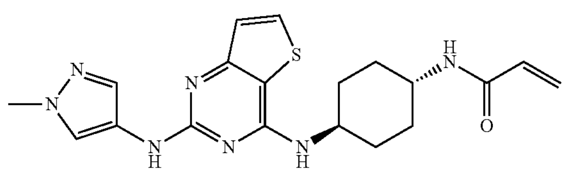 [SMILES: C=CC(=O)N[C@H]1CC[C@H](Nc2nc(Nc3cnn(C)c3)nc3ccsc23)CC1] | ¹H-NMR (300 MHz, CD₃OD) δ: 8.06 (d, 1H, J = 5.4 Hz), 7.87 (s, 1H), 7.67 (s, 1H), 7.22 (d, 1H, J = 5.4 Hz), 6.25-6.27 (m, 2H), 5.66-5.70 (m, 1H), 4.20-4.24 (m, 1H), 3.96 (s, 3H), 3.75-3.89 (m, 1H), 2.07-2.20 (m, 4H), 1.42-1.68 (m, 4H); LC-MS (ESI, m/z): [M + H]⁺ = 398.3 |
| 4 | 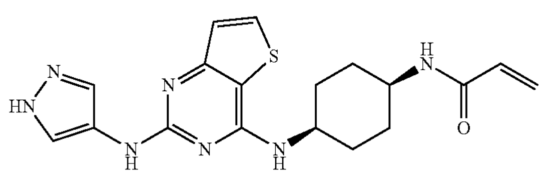 [SMILES: C=CC(=O)N[C@H]1CC[C@@H](Nc2nc(Nc3cn[nH]c3)nc3ccsc23)CC1] | ¹H-NMR (300 MHz, CD₃OD) δ: 7.91 (d, 1H, J = 5.4 Hz), 7.83 (s, 2H), 7.14 (d, 1H, J = 5.4 Hz), 6.43 (q, 1H, J = 6.9 Hz), 6.25 (dd, 1H, J = 2.1 Hz, J = 17.1 Hz), 5.66 (dd, 1H, J = 2.1 Hz, J = 10.2 Hz), 4.26 (m, 1H), 4.05 (m, 1H), 1.72-2.02 (m, 8H); LC-MS (ESI, m/z): [M + H]⁺ = 384.2 |
| 5 | 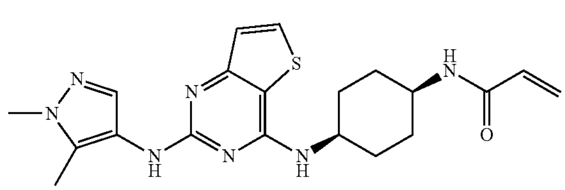 [SMILES: C=CC(=O)N[C@H]1CC[C@@H](Nc2nc(Nc3cnn(C)c3C)nc3ccsc23)CC1] | ¹H-NMR (300 MHz, CD₃OD) δ: 7.90 (d, 1H, J = 2.4 Hz), 7.51 (s, 1H), 7.63 (s, 1H), 7.99 (d, 1H, J = 5.4 Hz), 6.19-6.39 (m, 2H), 5.65 (dd, 1H, J = 2.1 Hz, J = 9.9 Hz), 4.23 (s, 1H), 3.99 (s, 1H), 3.81 (s, 3H), 2.22 (s, 3H), 1.73-1.91 (m, 8H); LC-MS (ESI, m/z): [M + H]⁺ = 412.3 |

TABLE 1-continued

| Example | Structure | Characterization data |
|---|---|---|
| 6 | 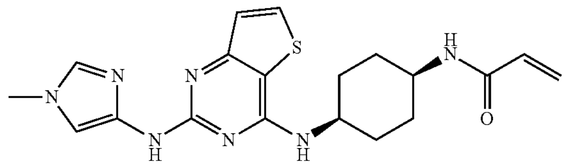 [SMILES: C=CC(=O)N[C@H]1CC[C@@H](Nc2nc(Nc3cn(C)cn3)nc3ccsc23)CC1] | ¹H-NMR (300 MHz, DMSO-d₆) δ: 8.05-8.16 (m, 2H), 7.97 (d, 1H, J = 6.3 Hz), 7.35 (d, 1H, J = 5.4 Hz), 6.32-8.41 (m, 1H), 6.08 (dd, 1H, J = 2.4 Hz, J = 17.1 Hz), 5.57 (dd, 1H, J = 2.4 Hz, J = 10.2 Hz), 4.27-4.28 (m, 1H), 4.01-4.04 (m, 1H), 2.03 (s, 3H), 1.78-1.80 (m, 8H); LC-MS (ESI, m/z): [M + H]⁺ = 398.3 |
| 7 | 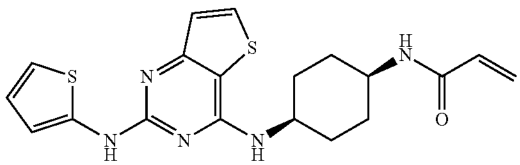 [SMILES: C=CC(=O)N[C@H]1CC[C@@H](Nc2nc(Nc3cccs3)nc3ccsc23)CC1] | ¹H-NMR (300 MHz, CD₃OD) δ: 7.90 (d, 1H, J = 5.4 Hz), 7.16 (d, 1H, J = 5.4 Hz), 6.85-6.91 (m, 2H), 6.70-6.72 (m, 1H), 6.22-8.43 (m, 2H), 5.68 (dd, 1H, J = 2.1 Hz, J = 9.9 Hz), 4.45-4.55 (m, 1H), 4.00-4.10 (m, 1H), 1.79-2.05 (m, 8H); LC-MS (ESI, m/z): [M + H]⁺ = 400.3 |
| 8 | 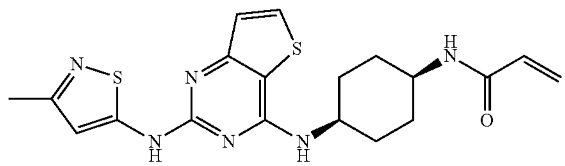 [SMILES: C=CC(=O)N[C@H]1CC[C@@H](Nc2nc(Nc3cc(C)ns3)nc3ccsc23)CC1] | ¹H-NMR (300 MHz, CD₃OD) δ: 7.89 (d, 1H, J = 5.4 Hz), 7.20 (d, 1H, J = 5.4 Hz), 6.63 (s, 1H), 6.22-8.43 (m, 2H), 5.67 (dd, 1H, J = 2.4 Hz, J = 9.9 Hz), 4.40-4.54 (m, 1H), 4.05-4.13 (m, 1H), 1.79-2.03 (m, 8H); LC-MS (ESI, m/z): [M + H]⁺ = 415.3 |
| 9 | 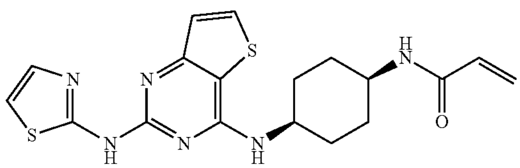 [SMILES: C=CC(=O)N[C@H]1CC[C@@H](Nc2nc(Nc3nccs3)nc3ccsc23)CC1] | ¹H-NMR (300 MHz, DMSO-d₆) δ: 8.05 (d, 1H, J = 5.4 Hz), 7.97 (d, 1H, J = 6.3 Hz), 7.37 (d, 1H, J = 5.4 Hz), 7.06 (d, 1H, J = 3.9 Hz), 7.18 (d, 1H, J = 5.4 Hz), 7.06 (d, 1H, J = 3.6 Hz), 6.33-6.42 (m, 1H), 6.09 (dd, 1H, J = 2.4 Hz, J = 17.1 Hz), 5.68 (dd, 1H, J = 2.4 Hz, J = 10.2 Hz), 4.31 (s, 1H), 3.87 (s, 1H), 1.63-1.90 (m, 8H); LC-MS (ESI, m/z): [M + H]⁺ = 401.2 |
| 10 | 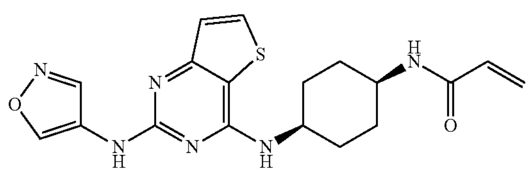 [SMILES: C=CC(=O)N[C@H]1CC[C@@H](Nc2nc(Nc3cnoc3)nc3ccsc23)CC1] | ¹H-NMR (300 MHz, CD₃OD) δ: 9.03 (s, 1H), 8.57 (s, 1H), 7.84 (d, 1H, J = 5.4 Hz), 7.16 (d, 1H, J = 5.4 Hz), 6.22-8.41 (m, 2H), 5.67 (dd, 1H, J = 2.1 Hz, J = 9.9 Hz), 4.20-4.32 (m, 1H), 4.00-4.10 (m, 1H), 1.70-2.02 (m, 8H); LC-MS (ESI, m/z): [M + H]⁺ = 385.4 |
| 11 | 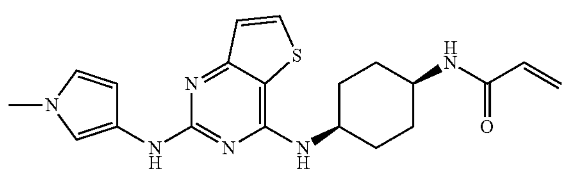 [SMILES: C=CC(=O)N[C@H]1CC[C@@H](Nc2nc(Nc3ccn(C)c3)nc3ccsc23)CC1] | ¹H-NMR (300 MHz, DMSO-d₆) δ: 9.11 (s, 1H), 7.98-8.20 (m, 3H), 7.15 (d, 1H, J = 5.4 Hz), 7.03 (s, 1H), 6.58 (s, 1H), 6.33-6.42 (m, 1H), 6.00-6.12 (m, 2H), 5.55-5.59 (m, 1H), 4.34 (m, 1H), 4.13-4.15 (m, 1H), 3.60 (s, 3H), 1.54-1.91 (m, 8H); LC-MS (ESI, m/z): [M + H]⁺ = 397.2 |
| 12 | 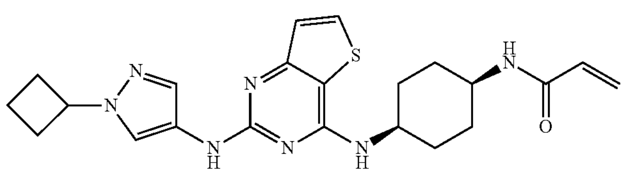 [SMILES: C=CC(=O)N[C@H]1CC[C@@H](Nc2nc(Nc3cnn(C4CCC4)c3)nc3ccsc23)CC1] | ¹H-NMR (300 MHz, CD₃OD) δ: 7.93 (s, 1H), 7.85 (d, 1H, J = 5.4 Hz), 7.63 (s, 1H), 7.11 (d, 1H, J = 5.4 Hz), 6.35 (m, 1H), 6.23 (m, 1H), 5.65 (dd, 1H, J = 2.4 Hz, J = 9.9 Hz), 4.78 (m, 1H), 4.28 (m, 1H), 4.00 (m, 1H), 2.50 (m, 4H), 1.90 (m, 10H); LC-MS (ESI, m/z): [M + H]⁺ = 438.3 |
| 13 | 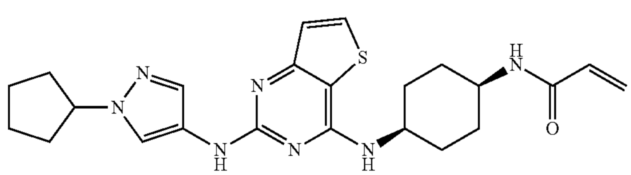 [SMILES: C=CC(=O)N[C@H]1CC[C@@H](Nc2nc(Nc3cnn(C4CCCC4)c3)nc3ccsc23)CC1] | ¹H-NMR (300 MHz, CD₃OD) δ: 8.00 (m, 1H), 7.90 (d, 1H, J = 3.0 Hz), 7.64 (d, 1H, J = 3.0 Hz), 7.20 (m, 1H), 6.20-6.41 (m, 2H), 5.66 (m, 1H), 4.72 (m, 1H), 4.28 (s, 1H), 4.00 (s, 1H), 3.21 (m, 1H), 2.19 (s, 2H), 1.75-2.03 (m, 13H); LC-MS (ESI, m/z): [M + H]⁺ = 452.4 |
| 14 | 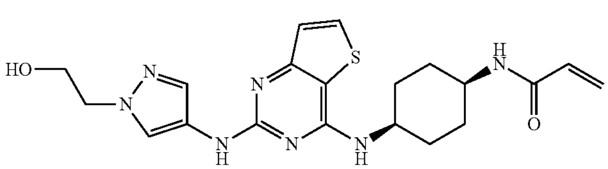 [SMILES: C=CC(=O)N[C@H]1CC[C@@H](Nc2nc(Nc3cnn(CCO)c3)nc3ccsc23)CC1] | ¹H-NMR (300 MHz, CD₃OD) δ: 7.91-8.05 (m, 2H), 7.66 (s, 1H), 7.14-7.28 (m, 1H), 6.22-8.44 (m, 2H), 5.64-5.68 (m, 1H), 3.91-3.14 (m, 3H), 3.32-3.36 (m, 3H), 1.85-2.04 (m, 8H); LC-MS (ESI, m/z): [M + H]⁺ = 428.4 |

TABLE 1-continued

| Example | Structure | Characterization data |
|---|---|---|
| 15 | 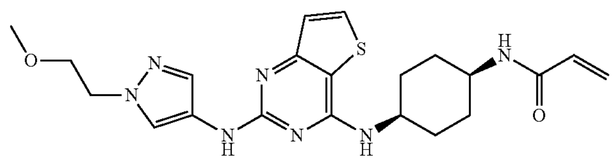 [SMILES: C=CC(=O)N[C@H]1CC[C@@H](Nc2nc(Nc3cnn(CCOC)c3)nc3ccsc23)CC1] | ¹H-NMR (300 MHz, CD₃OD) δ: 8.02 (d, 1H, J = 5.4 Hz), 7.95 (s, 1H), 7.67 (s, 1H), 7.20 (d, 1H, J = 5.4 Hz), 6.22-8.42 (m, 2H), 5.68 (dd, 1H, J = 2.1 Hz, J = 9.9 Hz), 4.31-4.35 (m, 3H), 4.00-4.08 (m, 1H), 3.79 (t, 2H, J = 4.8 Hz), 3.40 (s, 3H), 1.79-2.01 (m, 8H); LC-MS (ESI, m/z): [M + H]⁺ = 442.4 |
| 16 | 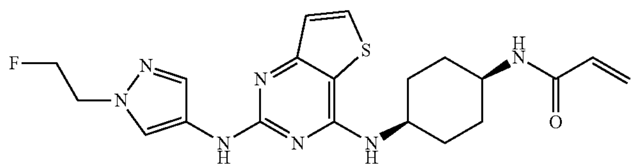 [SMILES: C=CC(=O)N[C@H]1CC[C@@H](Nc2nc(Nc3cnn(CCF)c3)nc3ccsc23)CC1] | ¹H-NMR (300 MHz, CD₃OD) δ: 7.96 (s, 1H), 7.84 (d, 1H, J = 5.4 Hz), 7.65 (s, 1H), 7.11 (d, 1H, J = 5.4 Hz), 6.36 (m, 1H), 6.22 (dd, 1H, J = 2.1 Hz, J = 16.8 Hz), 5.65 (dd, 1H, J = 2.1 Hz, J = 9.9 Hz), 4.83 (m, 1H), 4.67 (m, 1H), 4.48 (m, 1H), 4.39 (m, 1H), 4.26 (s, 1H), 4.00 (s, 1H), 1.82 (m, 8H); LC-MS (ESI, m/z): [M + H]⁺ = 430.3 |
| 17 | 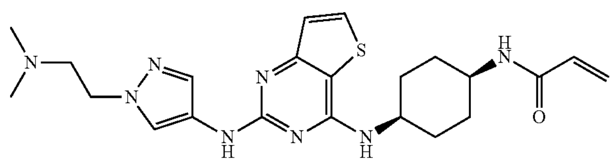 [SMILES: C=CC(=O)N[C@H]1CC[C@@H](Nc2nc(Nc3cnn(CCN(C)C)c3)nc3ccsc23)CC1] | ¹H-NMR (300 MHz, CD₃OD) δ: 8.02 (m, 2H), 7.80 (s, 1H), 7.44 (m, 1H), 7.23 (d, 1H, J = 5.4 Hz), 6.30 (m, 2H), 5.65 (dd, 1H, J = 1.8 Hz, J = 8.1 Hz), 4.59 (m, 1H), 4.29 (m, 1H), 4.02 (m, 1H), 3.63 (m, 2H), 3.02 (s, 6H), 1.78-1.99 (m, 8H); LC-MS (ESI, m/z): [M + H]⁺ = 455.3 |
| 18 | 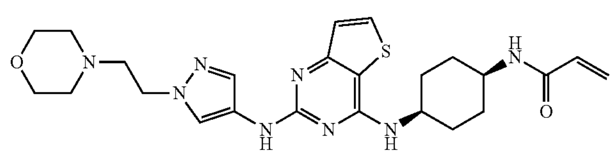 [SMILES: C=CC(=O)N[C@H]1CC[C@@H](Nc2nc(Nc3cnn(CCN4CCOCC4)c3)nc3ccsc23)CC1] | ¹H-NMR (300 MHz, CD₃OD) δ: 8.00 (m, 2H), 7.70 (s, 1H), 7.21 (d, 1H, J = 5.4 Hz), 6.40 (m, 1H), 6.24 (m, 1H), 5.67 (m, 1H), 4.38 (t, 2H, J = 6.3 Hz), 4.30 (m, 1H), 4.04 (m, 1H), 3.75 (m, 4H), 3.02 (t, 2H, J = 6.3 Hz), 2.69 (m, 4H), 1.79-2.01 (m, 8H); LC-MS (ESI, m/z): [M + H]⁺ = 497.4 |
| 19 | 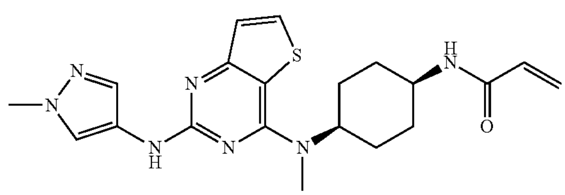 [SMILES: C=CC(=O)N[C@H]1CC[C@@H](N(C)c2nc(Nc3cnn(C)c3)nc3ccsc23)CC1] | ¹H-NMR (300 MHz, CD₃OD) δ: 8.02 (d, 1H, J = 5.7 Hz), 7.80 (s, 1H), 7.60 (s, 1H), 7.19 (d, 1H, J = 5.7 Hz), 6.41-6.50 (m, 1H), 6.25 (dd, 1H, J = 1.8 Hz, J = 17.1 Hz), 5.67 (dd, 1H, J = 1.8 Hz, J = 10.2 Hz), 4.18 (s, 1H), 3.90 (s, 3H), 3.42 (s, 1H), 1.74-2.05 (m, 8H); LC-MS (ESI, m/z): [M + H]⁺ = 412.3 |
| 20 | 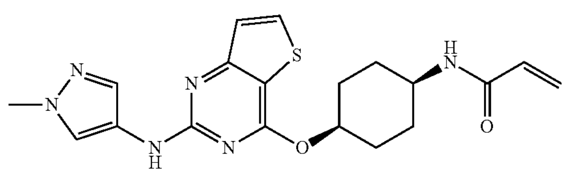 [SMILES: C=CC(=O)N[C@H]1CC[C@@H](Oc2nc(Nc3cnn(C)c3)nc3ccsc23)CC1] | ¹H-NMR (300 MHz, CD₃OD) δ: 7.85 (s, 1H), 7.73 (d, 1H, J = 5.4 Hz), 7.52 (s, 1H), 7.23 (d, 1H, J = 5.4 Hz), 6.91 (bs, 1H), 6.31 (dd, 1H, J = 1.5 Hz, J = 16.8 Hz), 6.10 (dd, 1H, J = 10.2 Hz, J = 16.8 Hz), 5.66 (dd, 1H, J = 1.5 Hz, J = 10.2 Hz), 5.58-5.61 (m, 1H), 5.47 (bs, 1H), 3.98-4.09 (m, 1H), 3.91 (s, 3H), 2.10-2.17 (m, 2H), 1.67-2.05 (m, 8H); LC-MS (ESI, m/z): [M + H]⁺ = 399.2 |
| 21 | 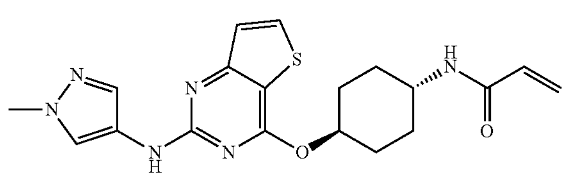 [SMILES: C=CC(=O)N[C@H]1CC[C@H](Oc2nc(Nc3cnn(C)c3)nc3ccsc23)CC1] | ¹H-NMR (300 MHz, CDCl₃) δ: CDCl₃) δ: 7.79 (s, 1H), 7.73 (d, 1H, J = 5.4 Hz), 7.60 (s, 1H), 7.20 (d, 1H, J = 5.4 Hz), 7.07 (bs, 1H), 6.31 (dd, 1H, J = 0.9 Hz, J = 16.8 Hz), 6.10 (dd, 1H, J = 10.2 Hz, J = 16.8 Hz), 5.66 (dd, 1H, J = 1.2 Hz, J = 10.2 Hz), 5.56-5.58 (m, 1H), 5.16-5.23 (m, 1H), 3.95-3.99 (m, 1H), 3.91 (s, 3H), 2.16-2.28 (m, 4H), 1.67-1.76 (m, 2H), 1.33-1.45 (m, 2H); LC-MS (ESI, m/z): [M + H]⁺ = 399.2 |
| 22 | 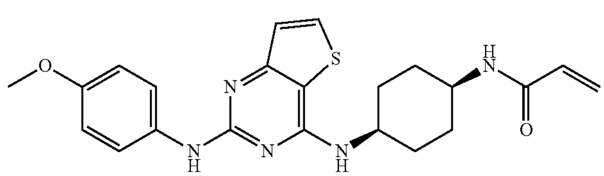 [SMILES: C=CC(=O)N[C@H]1CC[C@@H](Nc2nc(Nc3ccc(OC)cc3)nc3ccsc23)CC1] | ¹H-NMR (300 MHz, DMSO-d₆) δ: 9.23 (s, 1H), 7.98-8.03 (s, 3H), 7.62 (d, 2H, J = 8.7 Hz), 7.15 (d, 1H, J = 5.4 Hz), 7.89 (d, 2H, J = 8.7 Hz), 6.33-6.42 (m, 1H), 6.06-6.12 (m, 1H), 5.55-5.59 (m, 1H), 4.08-4.10 (m, 1H), 3.86 (m, 1H), 3.73 (s, 3H), 1.77-1.85 (m, 6H), 1.59-1.62 (m, 2H); LC-MS (ESI, m/z): [M + H]⁺ = 424.3 |

TABLE 1-continued

| Example | Structure | Characterization data |
|---|---|---|
| 23 | 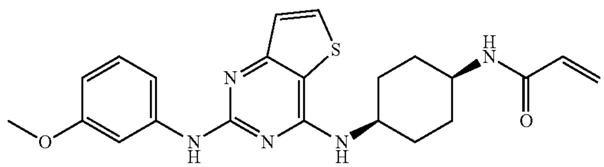 [SMILES: C=CC(=O)N[C@H]1CC[C@@H](Nc2nc(Nc3cccc(OC)c3)nc3ccsc23)CC1] | $^1$H-NMR (300 MHz, CDCl$_3$) δ: 8.12 (bs, 1H), 7.60 (d, 1H, J = 5.4 Hz), 7.43-7.45 (m, 1H), 7.09-7.23 (m, 3H), 6.57-6.60 (m, 1H), 6.12-8.35 (m, 2H), 5.95 (bs, 1H), 5.65 (dd, 1H, J = 1.8 Hz, J = 9.9 Hz), 5.49 (bs, 1H), 4.30 (bs, 1H), 4.15 (bs, 1H), 3.81 (s, 3H), 1.70-2.08 (m, 8H); LC-MS (ESI, m/z): [M + H]$^+$ = 424.3 |
| 24 | 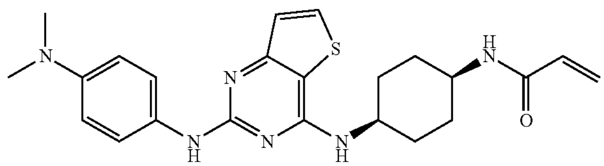 [SMILES: C=CC(=O)N[C@H]1CC[C@@H](Nc2nc(Nc3ccc(N(C)C)cc3)nc3ccsc23)CC1] | $^1$H-NMR (300 MHz, DMSO-d$_6$) δ: 9.58 (s, 1H), 8.52 (s, 1H), 8.10 (d, 1H, J = 5.4 Hz), 8.00 (d, 1H, J = 6.3 Hz), 7.42 (d, 2H, J = 8.4 Hz), 7.20 (d, 1H, J = 5.4 Hz), 6.78 (d, 2H, J = 8.7 Hz), 6.33-6.42 (m, 1H), 6.06-6.12 (m, 1H), 5.55-5.59 (m, 1H), 4.02-4.09 (m, 1H), 3.86 (m, 1H), 2.90 (s, 6H), 1.77-1.99 (m, 6H), 1.56-1.62 (m, 2H); LC-MS (ESI, m/z): [M + H]$^+$ = 437.3 |
| 25 | 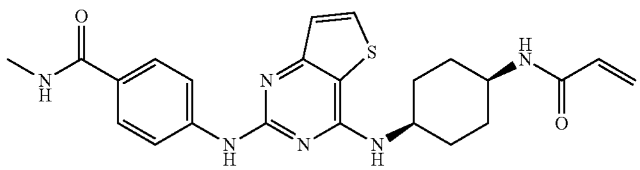 [SMILES: C=CC(=O)N[C@H]1CC[C@@H](Nc2nc(Nc3ccc(C(=O)NC)cc3)nc3ccsc23)CC1] | $^1$H-NMR (300 MHz, CD$_3$OD) δ: 8.13 (d, 1H, J = 5.1 Hz), 7.86-7.90 (m, 2H), 7.71-7.75 (m, 2H), 7.28 (d, 1H, J = 5.7 Hz), 6.36 (dd, 1H, J = 9.9 Hz, J = 17.1 Hz), 6.24 (dd, 1H, J = 2.1 Hz, J = 17.1 Hz), 5.66 (dd, 1H, J = 2.4 Hz, J = 9.9 Hz), 4.26 (bs, 1H), 4.03 (bs, 1H), 2.94 (s, 3H), 1.72-2.02 (m, 8H); LC-MS (ESI, m/z): [M + H]$^+$ = 451.4 |
| 26 | 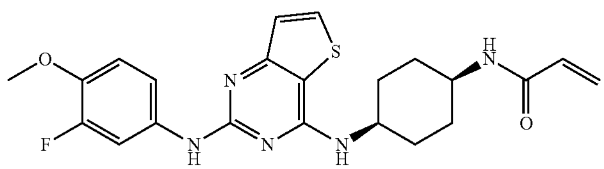 | $^1$H-NMR (300 MHz, DMSO-d$_6$) δ: 10.09 (s, 1H), 8.77 (s, 2H), 8.15 (d, 1H, J = 5.4 Hz), 8.02 (d, 1H, J = 6.3 Hz), 7.70 (dd, 1H, J = 2.4 Hz, J = 13.8 Hz), 7.13-7.30 (m, 3H), 6.34-6.43 (m, 1H), 6.10 (dd, 1H, J = 2.4 Hz, J = 17.4 Hz), 5.58 (dd, 1H, J = 2.4 Hz, J = 10.2 Hz), 4.07 (d, 1H, J = 3.3 Hz), 3.84 (s, 3H), 1.58-1.91 (m, 8H); LC-MS (ESI, m/z): [M + H]$^+$ = 472.3 |
| 27 | 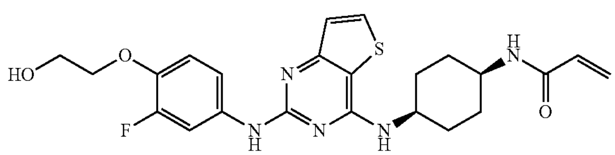 [SMILES: C=CC(=O)N[C@H]1CC[C@@H](Nc2nc(Nc3ccc(OCCO)c(F)c3)nc3ccsc23)CC1] | $^1$H-NMR (300 MHz, DMSO-d$_6$) δ: 9.12 (s, 1H), 7.97 (m, 2H), 7.87-7.93 (m, 1H), 7.61 (s, 1H), 7.03 (d, 1H, J = 8.7 Hz), 7.14 (d, 1H, J = 5.1 Hz), 7.07 (t, 1H, J = 9.3 Hz), 6.32-8.42 (m, 1H), 6.06-6.12 (m, 1H), 5.55-5.59 (m, 1H), 4.87 (s, 1H), 4.10-4.12 (m, 1H), 3.99-4.02 (m, 2H), 3.86 (m, 1H), 3.71-3.76 (m, 2H), 1.78-1.91 (m, 6H), 1.61-1.65 (m, 2H); LC-MS (ESI, m/z): [M + H]$^+$ = 472.3 |
| 28 | 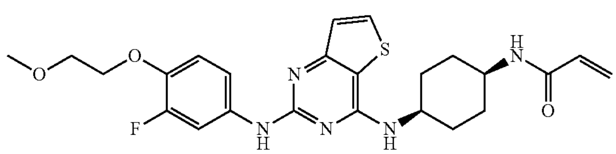 [SMILES: C=CC(=O)N[C@H]1CC[C@@H](Nc2nc(Nc3ccc(OCCOC)c(F)c3)nc3ccsc23)CC1] | $^1$H-NMR (300 MHz, DMSO-d$_6$) δ: 9.37 (s, 1H), 7.82-8.04 (m, 4H), 7.34 (d, 1H, J = 8.7 Hz), 7.07-7.18 (m, 2H), 6.33-6.42 (m, 1H), 6.07-6.13 (m, 1H), 5.56-5.60 (m, 1H), 4.11-4.14 (m, 3H), 3.87 (m, 1H), 3.64-3.68 (m, 2H), 3.32 (s, 3H), 1.79-1.87 (m, 6H), 1.61-1.64 (m, 2H); LC-MS (ESI, m/z): [M + H]$^+$ = 468.3 |
| 29 | 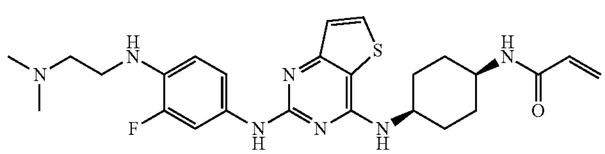 [SMILES: C=CC(=O)N[C@H]1CC[C@@H](Nc2nc(Nc3ccc(NCCN(C)C)c(F)c3)nc3ccsc23)CC1] | $^1$H-NMR (300 MHz, DMSO-d$_6$) δ: 10.14 (m, 2H), 8.86 (m, 1H), 8.17 (d, 1H, J = 5.4 Hz), 8.06 (d, 1H, J = 6.3 Hz), 7.59 (d, 1H, J = 13.8 Hz), 7.15-7.25 (m, 2H), 6.87 (t, 1H, J = 9.6 Hz), 6.35-6.44 (m, 1H), 6.06-6.13 (m, 1H), 5.56-5.60 (m, 1H), 4.02-4.08 (m, 1H), 3.87 (m, 1H), 3.17-3.61 (m, 4H), 2.83 (s, 3H), 1.78-1.99 (m, 6H), 1.58-1.61 (m, 2H); LC-MS (ESI, m/z): [M + H]$^+$ = 498.4 |
| 30 | 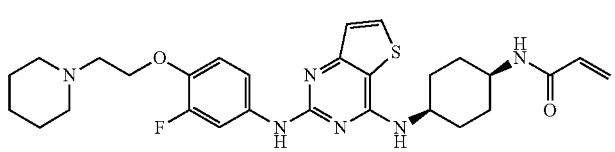 [SMILES: C=CC(=O)N[C@H]1CC[C@@H](Nc2nc(Nc3ccc(OCCN4CCCCC4)c(F)c3)nc3ccsc23)CC1] | $^1$H-NMR (300 MHz, DMSO-d$_6$) δ: 9.07 (s, 1H), 7.95-8.01 (m, 3H), 7.41-7.49 (m, 2H), 7.10-7.17 (m, 2H), 6.33-6.42 (m, 1H), 6.06-6.12 (m, 1H), 5.55-5.59 (m, 1H), 4.36 (m, 2H), 4.11-4.13 (m, 1H), 3.87 (m, 1H), 3.41 (m, 3H), 3.04 (m, 2H), 1.62-1.91 (m, 15H); LC-MS (ESI, m/z): [M + H]$^+$ = 539.4 |

TABLE 1-continued

| Example | Structure | Characterization data |
|---|---|---|
| 31 | 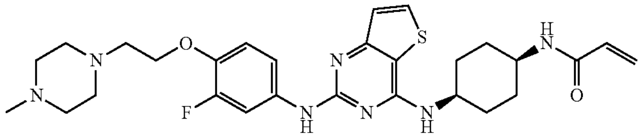 [SMILES: C=CC(=O)N[C@H]1CC[C@@H](Nc2nc(Nc3ccc(OCCN4CCN(C)CC4)c(F)c3)nc3ccsc23)CC1] | ¹H-NMR (300 MHz, DMSO-d₆) δ: 9.03 (s, 1H), 7.92-8.01 (m, 3H), 7.37-7.48 (m, 2H), 7.04-7.13 (m, 2H), 6.33-6.42 (m, 1H), 6.06-6.12 (m, 1H), 5.55-5.60 (m, 1H), 4.10-4.13 (m, 3H), 3.87 (m, 1H), 3.08 (m, 4H), 2.81 (m, 4H), 2.67 (m, 5H), 1.81-1.91 (m, 6H), 1.62-1.65 (m, 2H); LC-MS (ESI, m/z): [M + H]⁺ = 554.4 |
| 32 | 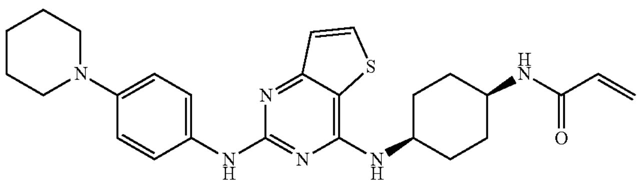 [SMILES: C=CC(=O)N[C@H]1CC[C@@H](Nc2nc(Nc3ccc(N4CCCCC4)cc3)nc3ccsc23)CC1] | ¹H-NMR (300 MHz, CD₃OD) δ: 7.88 (d, 1H, J = 5.4 Hz), 7.45 (d, 2H, J = 8.7 Hz), 7.12 (d, 1H, J = 5.4 Hz), 7.00 (d, 2H, J = 5.4 Hz), 6.38 (m, 1H), 6.23 (dd, 1H, J = 2.1 Hz, J = 17.1 Hz), 5.65 (dd, 1H, J = 2.1 Hz, J = 9.9 Hz), 4.19 (s, 1H), 4.01 (s, 1H), 3.11 (m, 4H), 1.56-1.91 (m, 14H); LC-MS (ESI, m/z): [M + H]⁺ = 477.4 |
| 33 | 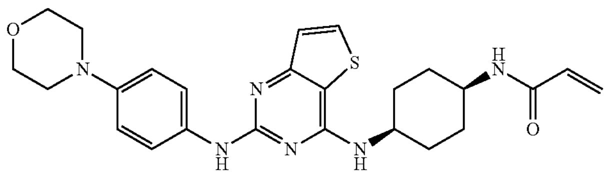 [SMILES: C=CC(=O)N[C@H]1CC[C@@H](Nc2nc(Nc3ccc(N4CCOCC4)cc3)nc3ccsc23)CC1] | ¹H-NMR (300 MHz, CD₃OD) δ: 8.13 (d, 1H, J = 5.4 Hz), 7.58 (d, 2H, J = 9.0 Hz), 7.32 (d, 1H, J = 5.4 Hz), 7.17 (d, 2H, J = 9.0 Hz), 6.35-6.55 (m, 2H), 5.81 (dd, 1H, J = 2.1 Hz, J = 9.6 Hz), 4.40 (s, 1H), 4.16 (s, 1H), 4.01 (t, 4H, J = 4.8 Hz), 2.17 (s, 5H), 1.85-2.09 (m, 7H); LC-MS (ESI, m/z): [M + H]⁺ = 479.4 |
| 34 | 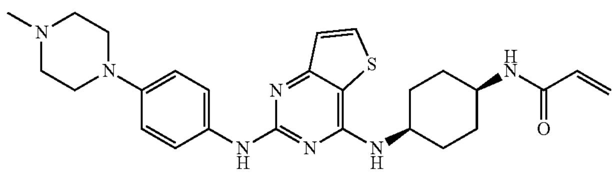 | ¹H-NMR (300 MHz, CD₃OD) δ: 7.99 (d, 1H, J = 5.4 Hz), 7.52 (d, 1H, J = 9.0 Hz), 7.21 (d, 1H, J = 5.4 Hz), 7.08 (d, 1H, J = 9.0 Hz), 6.38-6.47 (m, 1H), 6.22-8.28 (m, 1H), 5.67 (dd, 1H, J = 1.8 Hz, J = 9.9 Hz), 4.18-4.28 (m, 1H), 4.00-4.08 (m, 1H), 3.37-3.45 (m, 8H), 2.94 (s, 3H), 1.71-1.94 (m, 8H); LC-MS (ESI, m/z): [M + H]⁺ = 492.4 |
| 35 | 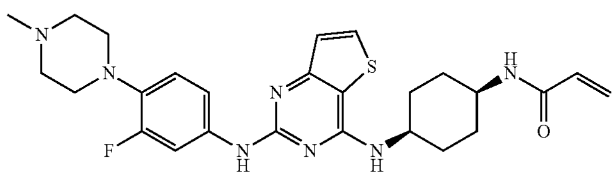 [SMILES: C=CC(=O)N[C@H]1CC[C@@H](Nc2nc(Nc3ccc(N4CCN(C)CC4)c(F)c3)nc3ccsc23)CC1] | ¹H-NMR (300 MHz, CD₃OD) δ: 7.90 (d, 1H, J = 5.4 Hz), 7.81 (dd, 1 H, J = 15 Hz, 2.1 Hz), 7.23-7.26 (m, 1H), 7.16-7.18 (m, 1H), 7.02-7.08 (m, 1H), 6.22-8.46 (m, 2H), 5.65-5.69 (m, 1H), 3.59-3.67 (m, 3H), 3.23-3.41 (m, 7H), 2.93 (s, 3H), 1.74-2.01 (m, 8H); LC-MS (ESI, m/z): [M + H]⁺ = 510.4 |
| 36 | 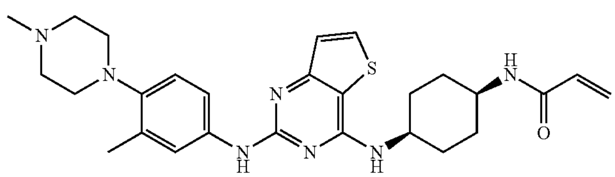 [SMILES: C=CC(=O)N[C@H]1CC[C@@H](Nc2nc(Nc3ccc(N4CCN(C)CC4)c(C)c3)nc3ccsc23)CC1] | ¹H-NMR (300 MHz, CD₃OD) δ: 8.99 (s, 1H), 7.96-8.02 (m, 2H), 7.55-7.64 (m, 3H), 7.11 (d, 1H, J = 5.1 Hz), 6.97 (d, 1H, J = 8.7 Hz), 6.33-6.42 (m, 1H), 6.05-6.12 (m, 1H), 5.55-5.59 (m, 1H), 4.14 (m, 1H), 3.86 (m, 1H), 3.08-3.18 (m, 8H), 2.82 (s, 3H), 2.26 (s, 3H), 1.80-1.91 (m, 6H), 1.60-1.65 (m, 2H); LC-MS (ESI, m/z): [M + H]⁺ = 506.4 |
| 37 | 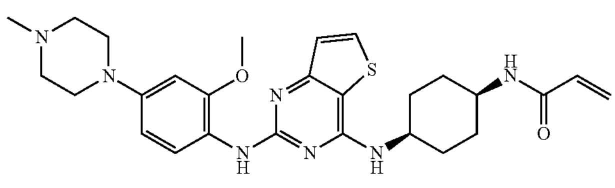 [SMILES: C=CC(=O)N[C@H]1CC[C@@H](Nc2nc(Nc3ccc(N4CCN(C)CC4)cc3OC)nc3ccsc23)CC1] | ¹H-NMR (300 MHz, CD₃OD) δ: 8.08 (d, 1H, J = 9.0 Hz), 7.85 (d, 1H, J = 5.4 Hz), 7.09 (d, 1H, J = 5.4 Hz), 6.71 (d, 1H, J = 2.4 Hz), 6.60 (dd, 1H, J = 2.4 Hz, J = 9.0 Hz), 6.36 (dd, 1H, J = 9.6 Hz, J = 16.8 Hz), 6.23 (dd, 1H, J = 2.1 Hz, J = 16.8 Hz), 5.66 (dd, 1H, J = 2.4 Hz, J = 9.9 Hz), 4.22 (bs, 1H), 4.02 (bs, 1H), 3.90 (s, 3H), 3.00-3.08 (m, 4H), 2.64 (s, 3H), 1.70-2.00 (m, 8H); LC-MS (ESI, m/z): [M + H]⁺ = 522.4 |
| 38 | 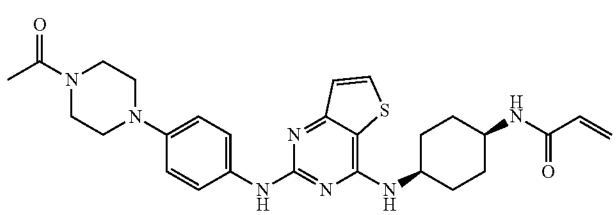 [SMILES: C=CC(=O)N[C@H]1CC[C@@H](Nc2nc(Nc3ccc(N4CCN(C(C)=O)CC4)cc3)nc3ccsc23)CC1] | ¹H-NMR (300 MHz, CD₃OD) δ: 7.89 (d, 1H, J = 5.4 Hz), 7.48 (d, 1H, J = 8.4 Hz), 7.13 (d, 1H, J = 5.4 Hz), 7.00 (d, 1H, J = 8.1 Hz), 6.19-6.41 (m, 2H), 5.63-5.67 (m, 1H), 4.01-4.21 (m, 2H), 3.67-3.75 (m, 4H), 3.05-3.21 (m, 4H), 2.15 (s, 3H), 1.70-1.92 (m, 8H); LC-MS (ESI, m/z): [M + H]⁺ = 520.5 |

TABLE 1-continued

| Example | Structure | Characterization data |
|---|---|---|
| 39 | 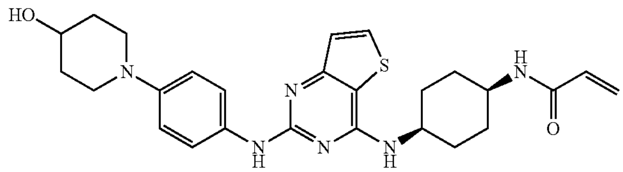 [SMILES: C=CC(=O)N[C@H]1CC[C@@H](Nc2nc(Nc3ccc(N4CCC(O)CC4)cc3)nc3ccsc23)CC1] | $^1$H-NMR (300 MHz, CD$_3$OD) δ: 8.10 (d, 1H, J = 5.4 Hz), 7.45 (d, 2H, J = 9.0 Hz), 7.18-7.25 (m, 3H), 6.36 (dd, 1H, J = 9.9 Hz, J = 17.1 Hz), 6.24 (dd, 1H, J = 2.1 Hz, J = 17.1 Hz), 5.66 (dd, 1H, J = 2.1 Hz, J = 9.9 Hz), 4.23 (bs, 1H), 4.01 (bs, 1H), 3.82-3.88 (m, 1H), 3.63-3.70 (m, 2H), 3.04-3.13 (m, 2H), 1.69-2.02 (m, 12H); LC-MS (ESI, m/z): [M + H]$^+$ = 493.4 |
| 40 | 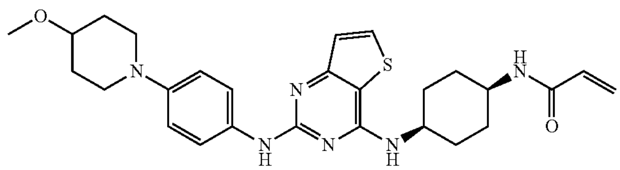 [SMILES: C=CC(=O)N[C@H]1CC[C@@H](Nc2nc(Nc3ccc(N4CCC(OC)CC4)cc3)nc3ccsc23)CC1] | $^1$H-NMR (300 MHz, CDCl$_3$) δ: 9.92 (s, 1H), 7.57 (d, 1H, J = 4.8 Hz), 7.44 (d, 1H, J = 8.4 Hz), 7.12 (s, 1H), 6.92 (d, 1H, J = 8.4 Hz), 6.29-6.48 (m, 3H), 5.59-5.63 (m, 1H), 4.10-4.28 (m, 2H), 3.39-3.55 (m, 5H), 2.87-3.02 (m, 2H), 1.68-2.05 (m, 12H); LC-MS (ESI, m/z): [M + H]$^+$ = 507.5 |
| 41 | 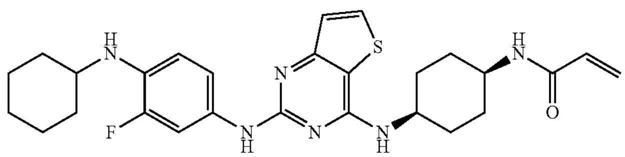 [SMILES: C=CC(=O)N[C@H]1CC[C@@H](Nc2nc(Nc3ccc(NC4CCCCC4)c(F)c3)nc3ccsc23)CC1] | $^1$H-NMR (300 MHz, CD$_3$OD) δ: 7.90 (d, 1H, J = 5.4 Hz), 7.42 (dd, 1H, J = 2.1 Hz, J = 13.5 Hz), 7.13 (d, 1H, J = 5.4 Hz), 7.04 (d, 1H, J = 7.8 Hz), 6.76 (t, 1H, J = 9.3 Hz), 6.19-6.40 (m, 2H), 5.64 (dd, 1H, J = 2.1 Hz, J = 9.9 Hz), 4.19 (s, 1H), 4.00 (s, 1H), 3.24 (s, 1H), 1.64-2.04 (m, 15H), 1.42 (m, 3H); LC-MS (ESI, m/z): [M + H]$^+$ = 509.4 |
| 42 | 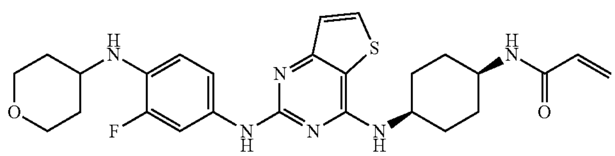 [SMILES: C=CC(=O)N[C@H]1CC[C@@H](Nc2nc(Nc3ccc(NC4CCOCC4)c(F)c3)nc3ccsc23)CC1] | $^1$H-NMR (300 MHz, CD$_3$OD) δ: 7.95 (d, 1H, J = 5.4 Hz), 7.40 (dd, 1H, J = 1.8 Hz, J = 13.2 Hz), 7.16 (d, 1H, J = 5.4 Hz), 7.05 (d, 1H, J = 8.4 Hz), 6.83 (t, 1H, J = 9.3 Hz), 6.37 (m, 1H), 6.23 (dd, 1H, J = 2.1 Hz, J = 17.1 Hz), 5.65 (dd, 1H, J = 2.1 Hz, J = 9.9 Hz), 4.20 (s, 1H), 3.97 (m, 3H), 3.55 (m, 3H), 1.68-2.01 (m, 10H), 1.55 (m, 2H); LC-MS (ESI, m/z): [M + H]$^+$ = 511.4 |
| 43 | 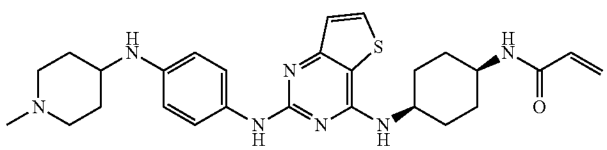 [SMILES: C=CC(=O)N[C@H]1CC[C@@H](Nc2nc(Nc3ccc(NC4CCN(C)CC4)cc3)nc3ccsc23)CC1] | $^1$H-NMR (300 MHz, CD$_3$OD) δ: 8.12-8.14 (m, 1H), 7.27-7.31 (m, 3H), 6.82-8.85 (m, 2H), 6.41-6.47 (m, 1H), 6.26-6.32 (m, 1H), 5.69-5.73 (m, 1H), 4.25 (m, 1H), 4.08 (m, 1H), 3.61-3.80 (m, 3H), 3.42-3.58 (m, 2H), 2.96 (s, 3H), 1.72-2.43 (m, 12H); LC-MS (ESI, m/z): [M + H]$^+$ = 506.4 |
| 44 | 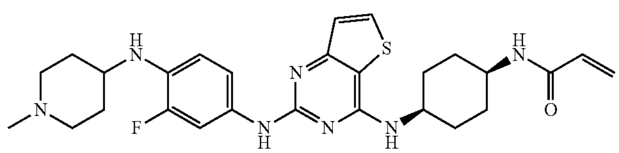 [SMILES: C=CC(=O)N[C@H]1CC[C@@H](Nc2nc(Nc3ccc(NC4CCN(C)CC4)c(F)c3)nc3ccsc23)CC1] | $^1$H-NMR (300 MHz, CD$_3$OD) δ: 10.13 (s, 1H), 9.70 (s, 1H), 8.43 (s, 1H), 8.02-8.11 (m, 2H), 7.60-7.65 (m, 1H), 7.14-7.20 (m, 2H), 6.77-6.83 (m, 1H), 6.35-6.44 (m, 1H), 6.06-6.13 (m, 1H), 5.56-5.60 (m, 1H), 5.23 (s, 1H), 4.07-4.09 (m, 1H), 3.86 (m, 1H), 3.20-3.48 (m, 2H), 3.06 (m, 2H), 2.75 (s, 3H), 1.59-2.11 (m, 12H); LC-MS (ESI, m/z): [M + H]$^+$ = 524.5 |
| 45 | 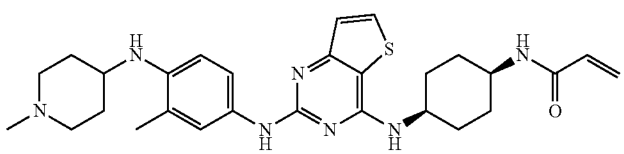 [SMILES: C=CC(=O)N[C@H]1CC[C@@H](Nc2nc(Nc3ccc(NC4CCN(C)CC4)c(C)c3)nc3ccsc23)CC1] | $^1$H-NMR (300 MHz, DMSO-d$_6$) δ: 10.32 (s, 1H), 9.97 (s, 1H), 8.92 (s, 1H), 8.17 (d, 1H, J = 5.1 Hz), 8.04 (d, 1H, J = 6.3 Hz), 7.16-7.22 (m, 3H), 6.66 (d, 1H, J = 8.4 Hz), 6.34-6.43 (m 1H), 6.06-6.12 (m, 1H), 5.55-5.60 (m, 1H), 4.02-4.04 (m, 1H), 3.85 (m, 1H), 3.09 (m, 3H), 2.75 (s, 3H), 1.99-2.21 (m, 6H), 1.76-1.86 (m, 8H), 1.55-1.58 (m, 3H); LC-MS (ESI, m/z): [M + H]$^+$ = 520.4 |
| 46 | 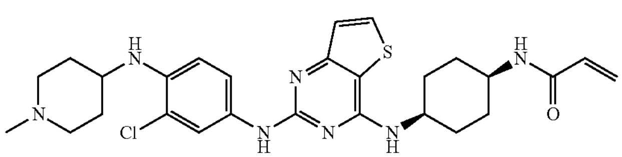 [SMILES: C=CC(=O)N[C@H]1CC[C@@H](Nc2nc(Nc3ccc(NC4CCN(C)CC4)c(Cl)c3)nc3ccsc23)CC1] | $^1$H-NMR (300 MHz, DMSO-d$_6$) δ: 10.07 (m, 1H), 8.78 (m, 1H), 8.16 (d, 1H, J = 7.2 Hz), 8.02 (d, 1H, J = 6.0 Hz), 7.75 (s, 1H), 7.28 (d, 1H, J = 8.7 Hz), 7.21 (d, 1H, J = 5.4 Hz), 6.86 (d, 1H, J = 9.0 Hz), 6.33-6.42 (m, 1H), 6.06-6.12 (m, 1H), 5.56-5.60 (m, 1H), 5.04 (m, 1H), 4.08 (m, 1H), 3.85 (m, 1H), 3.09 (m, 3H), 2.76 (s, 3H), 2.08-2.09 (m, 3H), 1.76-1.87 (m, 8H), 1.58 (m, 3H); LC-MS (ESI, m/z): [M + H]$^+$ = 540.6 |

TABLE 1-continued

| Example | Structure | Characterization data |
|---|---|---|
| 47 | 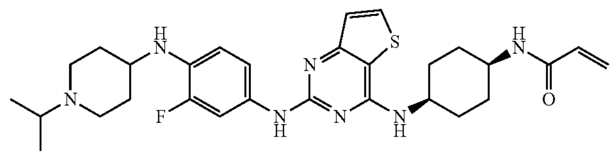 [SMILES: C=CC(=O)N[C@H]1CC[C@@H](Nc2nc(Nc3ccc(NC4CCN(C(C)C)CC4)c(F)c3)nc3ccsc23)CC1] | $^1$H-NMR (300 MHz, DMSO-d$_6$) δ: 7.87 (d, 1H, J = 5.4 Hz), 7.59 (d, 1H, J = 13.8 Hz), 7.12 (d, 2H, J = 5.4 Hz), 6.85 (t, 1H, J = 9.3 Hz), 6.33 (m, 2H), 5.66 (dd, 1H, J = 2.1 Hz, J = 9.9 Hz), 4.23 (m, 1H), 4.02 (m, 1H), 3.35 (s, 1H), 3.26 (m, 2H), 3.05-3.65 (m, 3H), 2.30 (m, 2H), 1.73-1.94 (m, 10H), 1.40 (d, 6H, J = 6.9 Hz); LC-MS (ESI, m/z): [M + H]$^+$ = 552.5 |
| 48 | 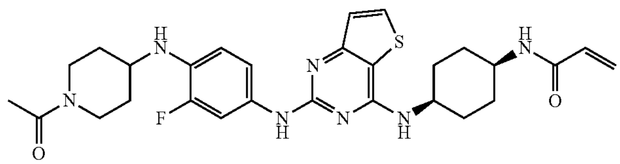 [SMILES: C=CC(=O)N[C@H]1CC[C@@H](Nc2nc(Nc3ccc(NC4CCN(C(C)=O)CC4)c(F)c3)nc3ccsc23)CC1] | $^1$H-NMR (300 MHz, CD$_3$OD) δ: 7.91 (d, 1H, J = 5.4 Hz), 7.47 (dd, 1H, J = 2.1 Hz, J = 13.5 Hz), 7.12 (m, 2H), 6.85 (t, 1H, J = 9.0 Hz), 6.31 (m, 2H), 5.65 (dd, 1H, J = 2.1 Hz, J = 9.9 Hz), 4.46 (m, 1H), 4.21 (m, 1H), 3.97 (m, 2H), 3.34 (m, 2H), 3.23 (m, 1H), 2.85 (m, 1H), 2.27 (m, 1H), 2.12 (s, 3H), 2.08 (m, 2H), 1.92 (m, 4H), 1.72 (m, 4H); LC-MS (ESI, m/z): [M + H]$^+$ = 552.5 |
| 49 | 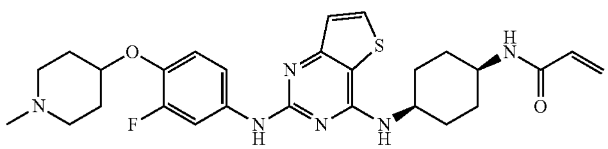 [SMILES: C=CC(=O)N[C@H]1CC[C@@H](Nc2nc(Nc3ccc(OC4CCN(C)CC4)c(F)c3)nc3ccsc23)CC1] | $^1$H-NMR (300 MHz, CD$_3$OD) δ: 8.00 (d, 1H, J = 5.4 Hz), 7.75 (dd, 1H, J = 2.4 Hz, J = 13.5 Hz), 7.21 (m, 3H), 6.20-6.41 (m, 2H), 5.66 (dd, 1H, J = 2.1 Hz, J = 9.9 Hz), 4.60 (s, 1H), 4.18 (s, 1H), 4.02 (s, 1H), 3.40 (m, 4H), 2.93 (t, 3H), 2.18 (m, 4H), 1.71-1.95 (m, 8H); LC-MS (ESI, m/z): [M + H]$^+$ = 525.4 |
| 50 | 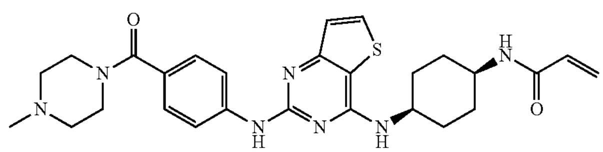 [SMILES: C=CC(=O)N[C@H]1CC[C@@H](Nc2nc(Nc3ccc(C(=O)N4CCN(C)CC4)cc3)nc3ccsc23)CC1] | $^1$H-NMR (300 MHz, DMSO-d6) δ: 9.28 (s, 1H), 7.88-7.99 (m, 3H), 7.34 (d, 2H, J = 8.4 Hz), 7.15 (d, 1H, J = 5.4 Hz), 6.37 (dd, 1H, J = 10.2 Hz, J = 17.1 Hz), 6.09 (dd, 1H, J = 2.1 Hz, J = 17.1 Hz), 5.57 (dd, 1H, J = 2.4 Hz, J = 9.9 Hz), 4.00-4.02 (m, 1H), 3.85-3.95 (m, 1H), 3.50-3.83 (m, 4H), 2.60-2.90 (m, 4H), 1.55-1.92 (m, 8H); LC-MS (ESI, m/z): [M + H]$^+$ = 520.4 |
| 51 | 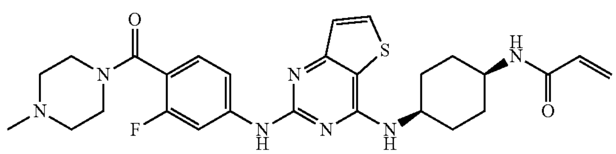 [SMILES: C=CC(=O)N[C@H]1CC[C@@H](Nc2nc(Nc3ccc(C(=O)N4CCN(C)CC4)c(F)c3)nc3ccsc23)CC1] | $^1$H-NMR (300 MHz, CD$_3$OD) δ: 8.05 (dd, 1H, J = 13.5 Hz, J = 1.8 Hz), 7.85 (d, 1H, J = 5.4 Hz), 7.42 (dd, 1H, J = 8.4, J = 2.1 Hz), 7.32 (t, 1H, J = 8.4 Hz), 7.17 (d, 1H, J = 5.4 Hz), 6.20-6.41 (m, 2H), 5.66 (dd, 1H, J = 2.1 Hz, J = 9.9 Hz), 4.28 (bs, 1H), 4.03 (bs, 1H), 3.52-3.95 (m, 4H), 2.70-2.95 (m, 4H), 2.58 (s, 3H), 1.70-2.04 (m, 8H); LC-MS (ESI, m/z): [M + H]$^+$ = 538.5 |
| 52 | 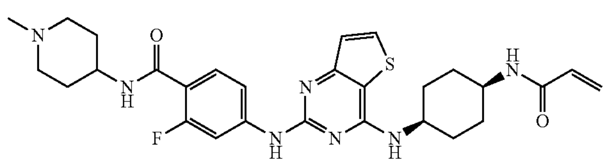 [SMILES: C=CC(=O)N[C@H]1CC[C@@H](Nc2nc(Nc3ccc(C(=O)NC4CCN(C)CC4)c(F)c3)nc3ccsc23)CC1] | $^1$H-NMR (300 MHz, DMSO-d$_6$) δ: 10.30 (s, 1H), 9.61 (s, 1H), 7.95-8.20 (m, 4H), 7.73 (s, 1H), 7.40-7.60 (m, 2H), 7.12-7.20 (m, 1H), 76.38 (dd, 1H, J = 10.2 Hz, J = 15.9 Hz), 6.09 (d, 1H, J = 17.1 Hz), 5.57 (d, 1H, J = 10.2 Hz), 4.06-4.20 (m, 1H), 3.82-4.08 (m, 2H), 2.72 (s, 3H), 2.10-2.22 (m, 2H), 1.92-2.08 (m, 2H), 1.75-1.92 (m, 8H), 1.40-1.75 (m, 4H); LC-MS (ESI, m/z): [M + H]$^+$ = 552.4 |
| 53 | 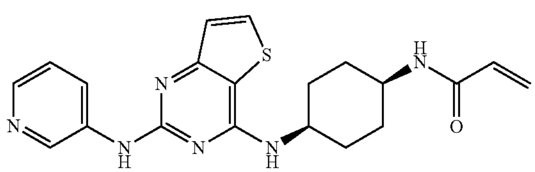 [SMILES: C=CC(=O)N[C@H]1CC[C@@H](Nc2nc(Nc3cccnc3)nc3ccsc23)CC1] | $^1$H-NMR (300 MHz, CD$_3$OD) δ: 8.96 (d, 1H, J = 2.4 Hz), 8.28-8.32 (m, 1H), 8.13-8.15 (m, 1H), 7.86 (d, 1H, J = 5.4 Hz), 7.37-7.42 (m, 1H), 7.17 (d, 1H, J = 5.4 Hz), 6.22-8.41 (m, 2H), 5.67 (dd, 1H, J = 2.1 Hz, J = 9.9 Hz), 4.14-4.35 (m, 1H), 4.00-4.09 (m, 1H), 1.75-2.01 (m, 8H); LC-MS (ESI, m/z): [M + H]$^+$ = 395.5 |
| 54 | 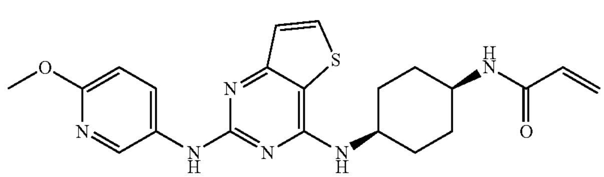 [SMILES: C=CC(=O)N[C@H]1CC[C@@H](Nc2nc(Nc3ccc(OC)nc3)nc3ccsc23)CC1] | $^1$H-NMR (300 MHz, CDCl$_3$) δ: 8.37 (d, 1H, J = 2.7 Hz), 7.90 (dd, 2H, J = 3.0 Hz, J = 9.0 Hz), 7.62 (d, 1H, J = 5.4 Hz), 7.17 (d, 1H, J = 5.4 Hz), 6.73 (d, 1H, J = 9.0 Hz), 6.31 (dd, 1H, J = 1.8 Hz, J = 16.8 Hz), 6.15 (dd, 1H, J = 10.8 Hz, J = 16.8 Hz), 5.87-5.90 (m, 1H), 5.65 (dd, 1H, J = 1.8 Hz, J = 10.8 Hz), 5.36-5.39 (m, 1H), 4.05-4.30 (m, 2H), 3.93 (s, 3H), 1.68-2.00 (m, 8H); LC-MS (ESI, m/z): [M + H]$^+$ = 425.3 |

TABLE 1-continued

| Example | Structure | Characterization data |
|---|---|---|
| 55 | 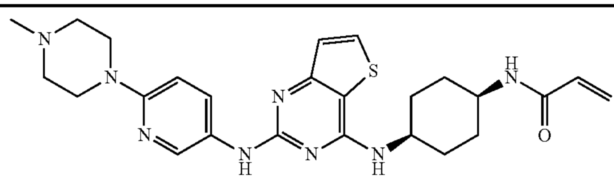 | $^1$H-NMR (300 MHz, CD$_3$OD) δ: 7.77 (d, 2H, J = 5.4 Hz), 7.31 (d, 1H, J = 5.4 Hz), 6.68 (d, 1H, J = 9.9 Hz), 6.31 (d, 1H, J = 16.8 Hz), 6.11 (dd, 1H, J = 10.2 Hz, J = 17.1 Hz), 5.59-5.74 (m, 2H), 4.23 (bs, 1H), 4.09 (bs, 1H), 3.75-3.90 (m, 4H), 3.05-3.25 (m, 4H), 2.78 (s, 3H), 1.60-2.10 (m, 8H); LC-MS (ESI, m/z): [M + H]$^+$ = 493.4 |
| 56 | 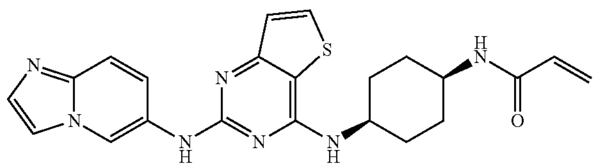 [SMILES: C=CC(=O)N[C@H]1CC[C@@H](Nc2nc(Nc3ccc4nccn4c3)nc3ccsc23)CC1] | $^1$H-NMR (300 MHz, CD$_3$OD) δ: 9.51 (s, 1H), 8.01 (s, 1H), 7.84-7.95 (m, 2H), 7.68-7.80 (m, 2H), 7.22 (d, 1H, J = 5.4 Hz), 6.30-6.43 (m, 2H), 5.67 (dd, 1H, J = 2.1 Hz, J = 9.9 Hz), 4.20-4.34 (m, 1H), 3.96-4.08 (m, 1H), 1.68-2.01 (m, 8H); LC-MS (ESI, m/z): [M + H]$^+$ = 434.3 |

Example 57

Preparation of N-(cis-4-((2-((1-methyl-1H-pyrazol-4-yl)amino)furo[3,2-d]pyrimidin-4-yl)amino)cyclohexyl)acrylamide

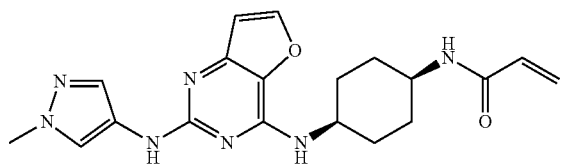 [SMILES: C=CC(=O)N[C@H]1CC[C@@H](Nc2nc(Nc3cnn(C)c3)nc3ccoc23)CC1]

Step 1: Preparation of cis-N$^1$-(2-chloro-furo[3,2-d]pyrimidin-4-yl)cyclohexyl-1,4-diamine

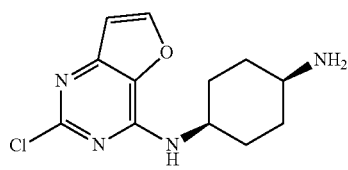 [SMILES: N[C@H]1CC[C@@H](Nc2nc(Cl)nc3ccoc23)CC1]

2,4-Dichloro-furo[3,2-d]pyrimidine (188 mg, 1 mmol) was dissolved in dichloromethane (5 mL), and dropwise added to a solution of cis-1,4-cyclohexanediamine (456 mg, 4.0 mmol) in dichloromethane (10 mL). The reaction solution was stirred at room temperature overnight, and then concentrated. The residue was added with water (20 mL), and extracted with ethyl acetate (20 mL×3). The organic phase was dried over anhydrous sodium sulfate, concentrated under reduced pressure, and was purified by silica gel column chromatography (eluent:n-hexane:ethyl acetate=1:1), to give a pale yellow solid (140 mg). Yield: 52.6%. MS (ESI, m/z): [M+H]$^+$: 267.1; $^1$H-NMR (300 MHz, CD$_3$OD): 8.01-8.00 (d, 1H, J=2.1 Hz), 6.78-6.77 (d, 1H, J=2.1 Hz), 4.24-2.22 (m, 1H), 3.07-3.03 (m, 1H), 1.91-1.66 (m, 8H).

Step 2: Preparation of N-(cis-4-((2-chloro-furo[3,2-d]pyrimidin-4-yl)amino) cyclohexyl)acrylamide

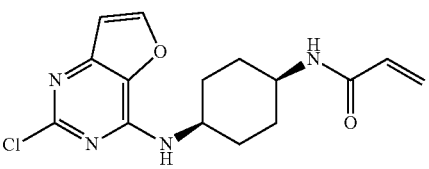

The product obtained in step 1 (120 mg, 0.45 mmol) and triethylamine (188 μL, 1.36 mmol) were dissolved in dichloromethane (20 mL), followed by the addition of acryloyl chloride (53 μL, 0.54 mmol). The reaction solution was reacted at room temperature overnight. After concentration, the residue was purified by silica gel column chromatography (eluent:dichloromethane/methanol=10:1), to give an orange solid (0.13 g). Yield: 90.3%. MS (ESI, m/z): [M+H]$^+$: 321.1; $^1$H-NMR (300 MHz, DMSO-d$_6$): 8.24-8.21 (d, 1H, J=6.3 Hz), 7.99-7.97 (d, 1H, J=6.3 Hz), 6.41-6.32 (dd, 2H, J=10.2 Hz, J=17.1 Hz), 5.68-5.64 (dd, 1H, J=2.4 Hz, J=17.1 Hz), 5.59-5.55 (dd, 1H, J=2.1 Hz, J=10.2 Hz), 4.11-4.09 (m, 1H), 3.09-3.05 (m, 1H), 1.81-1.61 (m, 8H).

Step 3: Preparation of N-(cis-4-((2-((1-methyl-1H-pyrazol-4-yl)amino) furo[3,2-d]pyrimidin-4-yl)amino)cyclohexyl)acrylamide The product obtained in step 2 (25 mg, 0.078 mmol) and 1-methyl-1H-pyrazole-4-amine (8.4 mg, 0.086 mmol) were dissolved in isopropanol (2 mL), followed by the addition of trifluoroacetic acid (250 mg, 2.2 mmol). The reaction solution was reacted at 90° C. under microwave irradiation for 1 hour. The reaction solution was cooled to room temperature, concentrated under reduced pressure, and purified by silica gel column chromatography (eluent:dichloromethane/methanol=10:1), to give a brown solid (10 mg). Yield: 33.7%. MS (ESI, m/z): [M+H]$^+$: 382.2; $^1$H-NMR (300 MHz, CD$_3$OD) δ: 7.94-7.93 (d, 1H, J=2.1 Hz), 7.86 (s, 1H), 7.60 (s, 1H), 6.76-6.75 (d, 1H, J=2.1 Hz), 6.44-6.35 (t, 1H, J=10.2 Hz, J=17.1 Hz), 6.26-6.20 (dd, 1H, J=2.1 Hz, J=17.1 Hz), 5.67-5.63 (dd, 1H, J=2.1 Hz, J=10.2 Hz), 4.23-4.21 (m, 1H), 4.02-4.01 (m, 1H), 3.90 (s, 3H), 1.90-1.74 (m, 8H).

Example 58

Preparation of N-(cis-4-((2-((1-methyl-1H-pyrazol-4-yl)amino)-5H-pyrrolo[3,2-d] pyrimidin-4-yl)amino)cyclohexyl)acrylamide

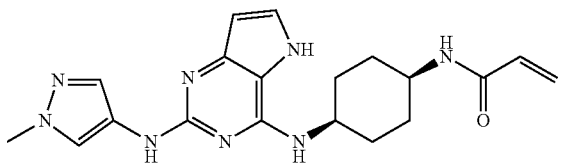 [SMILES: C=CC(=O)N[C@H]1CC[C@@H](Nc2nc(Nc3cnn(C)c3)nc3cc[nH]c23)CC1]

Step 1: Preparation of cis-N¹-(2-chloro-5H-pyrrolo[3,2-d]pyrimidin-4-yl)cyclohexyl-1,4-diamine

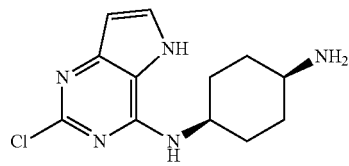 [SMILES: N[C@H]1CC[C@@H](Nc2nc(Cl)nc3cc[nH]c23)CC1]

2,4-Dichloro-pyrrolo[3,2-d]pyrimidine (187 mg, 1 mmol) was dissolved in dichloromethane (5 mL), and then added dropwise to a solution of cis-1,4-cyclohexanediamine (456 mg, 4.0 mmol) in dichloromethane (10 mL). The reaction solution was stirred at room temperature overnight, and then concentrated. The residue was added with water (20 mL), and extracted with ethyl acetate (10 mL×3). The organic phase was dried over anhydrous sodium sulfate, concentrated under reduced pressure, and purified by silica gel column chromatography (eluent:n-hexane:ethyl acetate=1:1), to give a pale yellow solid (150 mg). Yield: 56.6%. MS (ESI, m/z): [M+H]⁺: 266.1; ¹H-NMR (300 MHz, CD₃OD): 7.41-7.40 (d, 1H, J=3.0 Hz), 6.62-8.61 (d, 1H, J=3.0 Hz), 4.31 (s, 1H), 3.09 (s, 1H), 2.01-1.70 (m, 8H).

Step 2: Preparation of N-(cis-4-((2-chloro-5H-pyrrolo[3,2-d]pyridin-4-yl)amino) cyclohexyl)acrylamide

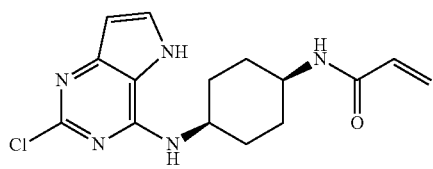 [SMILES: C=CC(=O)N[C@H]1CC[C@@H](Nc2nc(Cl)nc3cc[nH]c23)CC1]

The product obtained in step 1 (120 mg, 0.45 mmol) and triethylamine (188 µL, 1.36 mmol) were dissolved in dichloromethane (20 mL), followed by the addition of acryloyl chloride (53 µL, 0.54 mmol). The reaction solution was reacted at room temperature overnight. After concentration, the residue was purified by silica gel column chromatography (eluent:dichloromethane/methanol=10:1), to give a pale yellow solid (0.1 g). Yield: 69.7%. MS (ESI, m/z): [M+H]⁺: 320.1; ¹H-NMR (300 MHz, CDCl₃): 7.40-7.38 (d, 1H, J=7.8 Hz), 7.29-7.21 (m, 1H), 6.73-6.70 (d, 1H, J=7.8 Hz), 6.24-6.20 (m, 1H), 5.57-5.53 (m, 1H), 4.41 (s, 1H), 3.97 (s, 1H), 1.84-1.72 (m, 8H).

Step 3: Preparation of N-(cis-4-((2-((1-methyl-1H-pyrazol-4-yl)amino)-5H-pyrrolo[3,2-d]pyrimidin-4-yl)amino)cyclohexyl)acrylamide The product obtained in step 2 (25 mg, 0.078 mmol) and 1-methyl-1H-pyrazole-4-amine (8.4 mg, 0.086 mmol) were dissolved in isopropanol (2 mL), followed by the addition of trifluoroacetic acid (250 mg, 2.2 mmol). The reaction solution was reacted at 90° C. under microwave irradiation for 1 hour. The reaction solution was cooled to room temperature, concentrated under reduced pressure, and purified by silica gel column chromatography (eluent:dichloromethane/methanol=10:1), to give a brown solid (12 mg). Yield: 40.5%. MS (ESI, m/z): [M+H]⁺: 381.2; ¹H-NMR (300 MHz, CD₃OD) δ: 7.86 (s, 1H), 7.64 (s, 1H), 7.43 (s, 1H), 6.43-6.34 (m, 1H), 6.29-6.21 (m, 1H), 5.69-5.65 (m, 1H), 4.46-4.35 (m, 1H), 4.01-4.95 (m, 1H), 3.94 (s, 3H), 1.99-1.61 (m, 8H).

Example 59

Preparation of N-(cis-4-((2-((1-methyl-1H-pyrazol-4-yl)amino)-thieno[2,3-d] pyrimidin-4-yl)amino)cyclohexyl)acrylamide

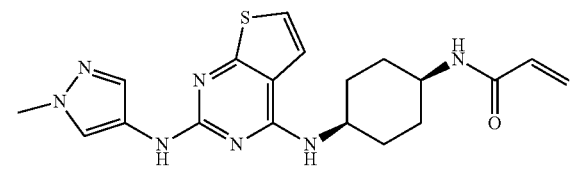 [SMILES: C=CC(=O)N[C@H]1CC[C@@H](Nc2nc(Nc3cnn(C)c3)nc3sccc23)CC1]

Step 1: Preparation of tert-butyl (cis-4-((2-chloro-thieno[2,3-d]pyrimidin-4-yl)amino) cyclohexyl) carbamate

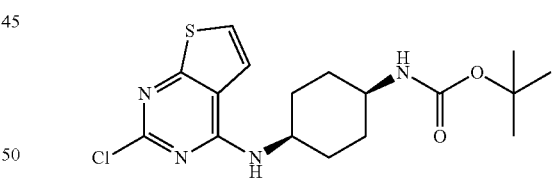

2,4-Dichloro-thieno[2,3-d]pyrimidine (204 mg, 1 mmol) and tert-butyl cis-4-amino-cyclohexyl carbamate (215 mg, 1 mmol) were dissolved in tetrahydrofuran (10 mL), followed by the addition of N,N-diisopropylethylamine (0.4 mL, 2 mmol). The reaction solution was reacted at 70° C. overnight, and then concentrated. The residue was added with water (20 mL), and extracted with ethyl acetate (20 mL×3). The organic phase was dried over anhydrous sodium sulfate, concentrated under reduced pressure, and purified by silica gel column chromatography (eluent:n-hexane:ethyl acetate=1:5) to give a pale yellow solid (150 mg). Yield: 56.6%. MS (ESI, m/z): [M+H]⁺: 383.1; ¹H-NMR (300 MHz, DMSO-d₆): 7.74-7.72 (d, 1H, J=6.0 Hz), 7.58-7.56 (d, 1H, J=6.0 Hz), 4.03 (s, 1H), 3.46 (m, 1H), 1.81-1.55 (m, 8H), 1.40 (s, 9H).

Step 2: Preparation of N-(cis-4-((2-chloro-thieno[2,3-d]pyrimidin-4-yl)amino) cyclohexyl)acrylamide

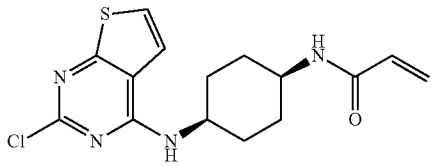 [SMILES: C=CC(=O)N[C@H]1CC[C@@H](Nc2nc(Cl)nc3sccc23)CC1]

The product obtained in step 1 (50 mg, 0.13 mmol) was dissolved in methanol (2 mL), followed by the addition of 4N solution of hydrogen chloride in 1,4-dioxane (4 mL, 1 mmol). The reaction solution was reacted at room temperature for 2 hours. The reaction solution was concentrated, and the remaining viscous liquid was dissolved in dichloromethane (5 mL) followed by the addition of triethylamine (54 μL, 0.39 mmol). To the above solution acryloyl chloride (14 μL, 0.14 mmol) was added dropwise at 0° C. The reaction solution was reacted at room temperature overnight. The reaction solution was washed with water (10 mL), and the organic phase was dried over anhydrous sodium sulfate, concentrated under reduced pressure, and purified by silica gel column chromatography (eluent:dichloromethane/methanol=8:1) to give a white solid (40 mg). Yield: 91.5%. MS (ESI, m/z): [M+H]$^+$: 337.1; $^1$H-NMR (300 MHz, DMSO-d$_6$): 7.75-7.73 (d, 1H, J=6.0 Hz), 7.57-7.55 (d, 1H, J=6.0 Hz), 6.38-6.29 (dd, 1H, J=10.2 Hz, J=17.1 Hz), 6.11-6.04 (dd, 1H, J=2.4 Hz, J=17.1 Hz), 5.57-5.53 (dd, 1H, J=2.1 Hz, J=10.2 Hz), 4.05-4.03 (m, 1H), 3.09-3.05 (m, 1H), 1.97-1.61 (m, 8H).

Step 3: Preparation of N-(cis-4-((2-((1-methyl-1H-pyrazol-4-yl)amino) thieno[2,3-d]pyrimidin-4-yl)amino)cyclohexyl)acrylamide The product obtained in step 2 (25 mg, 0.078 mmol) and 1-methyl-1H-pyrazole-4-amine (8.4 mg, 0.086 mmol) were dissolved in isopropanol (2 mL), followed by the addition of trifluoroacetic acid (250 mg, 2.2 mmol). The reaction solution was reacted at 90° C. under microwave irradiation for 1 hour. The reaction solution was cooled to room temperature, concentrated under reduced pressure, and purified by silica gel column chromatography (eluent:dichloromethane/methanol=10:1) to give a brown solid (10 mg). Yield: 33.7%. MS (ESI, m/z): [M+H]$^+$: 398.3; $^1$H-NMR (300 MHz, DMSO-d$_6$) δ: 10.51 (s, 1H), 9.08 (s, 1H), 8.20 (d, 1H, J=5.1 Hz), 8.02 (d, 1H, J=6.0 Hz), 7.87 (s, 1H), 7.57 (s, 1H), 7.21 (d, 1H, J=5.4 Hz), 6.32-8.41 (m, 1H), 6.07 (dd, 1H, J=2.1 Hz, J=17.1 Hz), 5.57 (dd, 1H, J=2.4 Hz, J=9.9 Hz), 4.14 (d, 1H, J=5.4 Hz), 3.84 (s, 3H), 1.25-1.64 (m, 8H).

Example 60

Preparation of N-(cis-4-((2-((1-methyl-1H-pyrazol-4-yl)amino)thieno[3,2-d] pyrimidin-4-yl)amino) cyclohexyl)propynamide

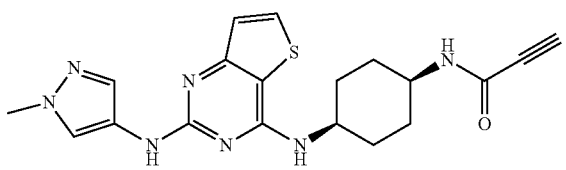 [SMILES: C#CC(=O)N[C@H]1CC[C@@H](Nc2nc(Nc3cnn(C)c3)nc3ccsc23)CC1]

Step 1: Preparation of tert-butyl (cis-4-((2-((1-methyl-1H-pyrazol-4-yl)amino) thieno[3,2-d]pyrimidin-4-yl)amino)cyclohexyl)carbamate

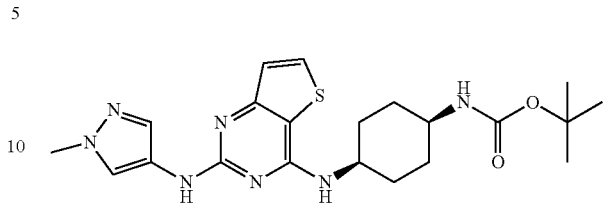

The product obtained in step 1 of Example 1 (120 mg, 0.31 mmol) and 1-methyl-1H-pyrazole-4-amine (52 mg, 0.62 mmol) were suspended in isopropanol (2 mL), followed by the addition of two drops of trifluoroacetic acid. The mixture was reacted for 25 minutes under microwave at a temperature of 90° C. To the system was added a saturated sodium carbonate solution, and the pH of the reaction solution was adjusted to about 8. The reaction mixture was concentrated, and purified by silica gel column chromatography (eluent:dichloromethane:methanol=20:1) to give a yellow solid (120 mg). Yield: 87.4%. MS (ESI, m/z): [M+H]$^+$: 444.3.

Step 2: Preparation of N$^4$-(cis-4-aminocyclohexyl)-N$^2$-(1-methyl-1H-pyrazol-4-yl)thieno[3,2-d]pyrimidine-2,4-diamine

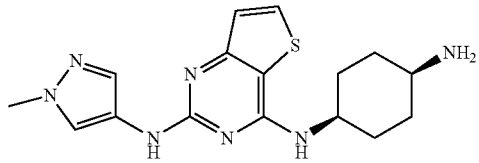 [SMILES: Cn1cc(Nc2nc(N[C@H]3CC[C@@H](N)CC3)c3sccc3n2)cn1]

The product obtained in the above step 1 (120 mg, 0.27 mmol) was dissolved in dichloromethane (10 mL), followed by the dropwise addition of 4N solution of hydrogen chloride in 1,4-dioxane (675 μL, 2.7 mmol). The reaction solution was reacted at room temperature for 2 hours. The reaction solution was concentrated, and the resulting crude product was used directly in the next step without further purification. MS (ESI, m/z): [M+H]$^+$: 344.2.

Step 3: Preparation of N-(cis-4-((2-((1-methyl-1H-pyrazol-4-yl)amino) thieno[3,2-d]pyrimidin-4-yl) amino)cyclohexyl)propynamide The product obtained in step 2 (38 mg, 0.10 mmol) and propiolic acid (8.4 mg, 0.12 mmol) were dissolved in tetrahydrofuran (10 mL), followed by the addition of N,N-diisopropylethylamine (53 μL). The mixture was stirred at room temperature for 30 minutes, followed by the addition of TBTU (4 mg). The mixture was stirred at room temperature overnight, concentrated, and purified by silica gel column chromatography (eluent:dichloromethane/methanol=10:1) to give a pale yellow solid (2.45 mg). Yield: 6.2%. MS (ESI, m/z): [M+H]$^+$: 396.2; $^1$H-NMR (300 MHz, CD$_3$OD) δ: 7.93 (d, 1H, J=5.4 Hz), 7.85 (s, 1H), 7.61 (s, 1H), 7.16 (d, 1H, J=5.4 Hz), 3.91 (s, 3H), 3.54-3.61 (m, 2H), 1.74-2.01 (m, 8H).

Example 61

Preparation of 1-(3-(((2-((1-methyl-1H-pyrazol-4-yl)amino)thieno[3,2-d]pyrimidin-4-yl)amino)methyl)azetidin-1-yl)prop-2-en-1-one

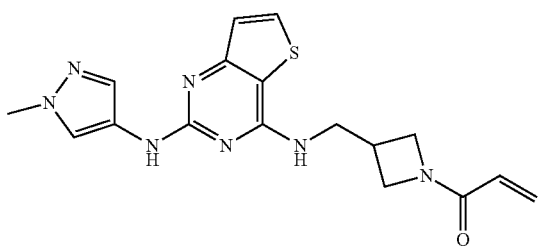 [SMILES: C=CC(=O)N1CC(CNc2nc(Nc3cnn(C)c3)nc3ccsc23)C1]

Step 1: Preparation of Tert-Butyl 3-(((2-chloro-thieno[3,2-d]pyrimidin-4-yl)amino) methyl)azetidine-1-carboxylate

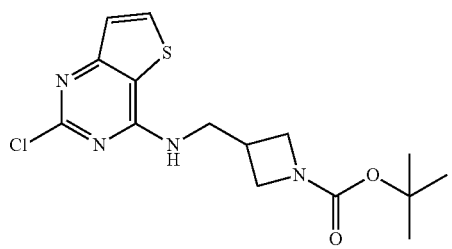

2,4-Dichloro-thieno[3,2-d]pyrimidine (205 mg, 1 mmol) and tert-butyl 3-(aminomethyl)azetidine-1-carboxylate (186 mg, 1 mmol) were dissolved in tetrahydrofuran (5 mL), followed by the addition of N,N-diisopropylethylamine (258 mg, 2 mmol). The reaction solution was reacted at 70° C. overnight, and then concentrated. The residue was added with water (20 mL), and then extracted with ethyl acetate (10 mL×3). The organic phase was dried over anhydrous sodium sulfate, concentrated under reduced pressure, and purified by silica gel column chromatography (eluent:n-hexane:ethyl acetate=5:1) to give a white solid (340 mg). Yield: 96.0%. MS (ESI, m/z): [M+H]$^+$: 355.1; $^1$H-NMR (300 MHz, CDCl$_3$): 7.76 (d, 1H, J=5.4 Hz), 7.37 (d, 1H, J=5.4 Hz), 5.49 (s, 1H), 4.05-4.09 (m, 2H), 3.87-3.91 (m, 2H), 3.71-3.75 (m, 2H), 2.94 (m, 1H), 1.44 (s, 9H).

Step 2: Preparation of N-(azetidin-3-ylmethyl)-2-chloro-thieno[3,2-d]pyrimidine-4-amine

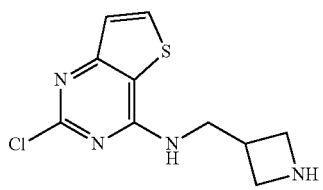

The product obtained in step 1 (340 mg, 0.96 mmol) was dissolved in dichloromethane (10 mL), followed by the addition of 4N solution of hydrogen chloride in 1,4-dioxane (2.5 mL, 10 mmol). The reaction solution was reacted at room temperature for 2 hours. The reaction solution was concentrated, and the resulting crude product was used directly in the next step without further purification. MS (ESI, m/z): [M+H]$^+$: 254.9.

Step 3: Preparation of 1-(3-(((2-chloro-thieno[3,2-d]pyrimidin-4-yl)amino)methyl) azetidin-1-yl)prop-2-en-1-one

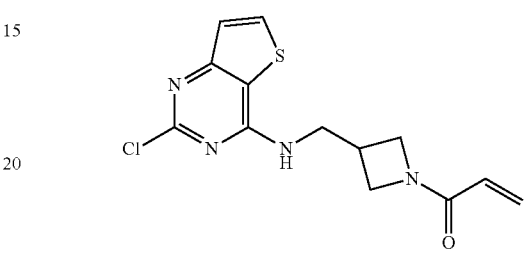

The product obtained in step 2 (1.22 g, 4.80 mmol) was dissolved in dichloromethane (10 mL), followed by the addition of triethylamine (0.969 g, 9.60 mmol). A solution of acryloyl chloride (0.434 g, 4.80 mmol) dissolved in dichloromethane (5 mL) was added dropwise to the above solution at 0° C. The reaction solution reacted at room temperature overnight. The reaction solution was washed with water (10 mL), and the organic phase was dried over anhydrous sodium sulfate, concentrated under reduced pressure, and purified by silica gel column chromatography (eluent:dichloromethane/methanol=70:1), to give a white solid (1.00 g). Yield: 67.6%. [M+H]$^+$: 309.0; $^1$H-NMR (300 MHz, DMSO-d$_6$): 8.50-8.53 (m, 1H), 8.19 (d, 1H, J=5.1 Hz), 7.35 (d, 1H, J=5.4 Hz), 6.25-6.34 (m, 1H), 6.05-6.12 (m, 1H), 5.63-5.68 (m, 1H), 4.27-4.33 (m, 1H), 3.97-4.03 (m, 2H), 3.67-3.75 (m, 3H), 2.89-2.98 (m, 1H).

Step 4: Preparation of 1-(3-(((2-((1-methyl-1H-pyrazol-4-yl)amino)thieno[3,2-d] pyrimidin-4-yl)amino)methyl)azetidin-1-yl)prop-2-en-1-one The product obtained in step 3 (50 mg, 0.162 mmol) and 1-methyl-1H-pyrazole-4-amine (23 mg, 0.244 mmol) were dissolved in 1,4-dioxane (2 mL). The pH of the reaction solution was adjusted to 5 with trifluoroacetic acid. The reaction solution was reacted at 90° C. under microwave irradiation for 0.5 hours. The reaction solution was cooled to room temperature, adjusted with 1N sodium hydroxide solution to pH 8, and extracted with ethyl acetate (10 mL×3). The organic phase was dried over anhydrous sodium sulfate, concentrated under reduced pressure, and purified by silica gel column chromatography (eluent:dichloromethane/methanol=10:1) to give a yellow solid (15 mg). Yield: 25.4%. MS (ESI, m/z): [M+H]$^+$: 370.2; $^1$H-NMR (300 MHz, DMSO-d$_6$) δ: 7.83 (s, 1H), 7.60 (d, 1H, J=5.4 Hz), 7.52 (s, 1H), 7.18 (d, 1H, J=5.4 Hz), 7.12 (s, 1H), 6.31-6.37 (m, 1H), 6.13-6.22 (m, 1H), 5.65-5.69 (m, 1H), 5.53 (s, 1H), 4.01-4.35 (m, 3H), 3.81-3.93 (m, 6H), 3.07 (m, 1H).

The following compounds (in Table 2) were prepared from similar starting materials by similar synthetic methods to those described in Example 61.

TABLE 2

| Example | Structure | Characterization data |
|---|---|---|
| 62 | 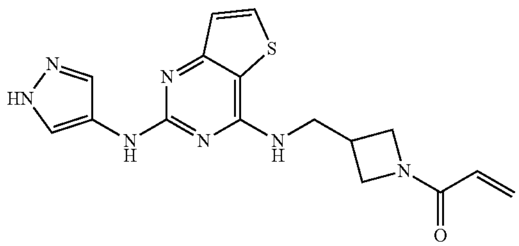 [SMILES: C=CC(=O)N1CC(CNc2nc(Nc3cn[nH]c3)nc3ccsc23)C1] | ¹H-NMR (300 MHz, CD₃OD) δ: 7.83 (m, 3H), 7.13 (d, 1H, J = 5.4 Hz), 6.27 (m, 2H), 5.73 (dd, 1H, J = 2.4 Hz, J = 9.9 Hz), 4.41 (t, 1H, J = 9.0 Hz), 4.16 (m, 2H), 3.85-3.95 (m, 3H), 3.18-3.20 (m, 1H);<br>LC-MS (ESI, m/z): [M + H]⁺ = 356.3 |
| 63 | 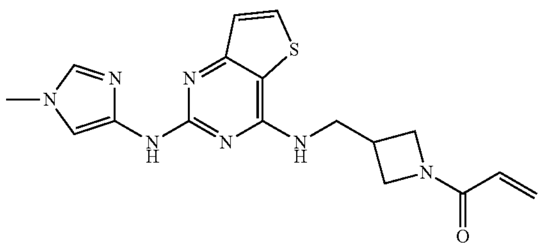 | ¹H-NMR (300 MHz, DMSO-d₆) δ: 8.54 (s, 1H), 8.11 (d, 1H, J = 5.4 Hz), 8.02 (s, 1H), 7.60 (s, 1H), 6.94 (s, 1H), 6.27-6.36 (m, 2H), 6.08 (dd, 1H, J = 2.4 Hz, J = 16.8 Hz), 5.65 (dd, 1H, J = 2.1 Hz, J = 10.2 Hz), 4.30 (t, 1H, J = 8.4 Hz), 3.99-4.06 (m, 2H), 3.63-3.83 (m, 3H), 3.05-3.14 (m, 1H), 1.99 (s, 3H);<br>LC-MS (ESI, m/z): [M + H]⁺ = 370.2 |
| 64 | 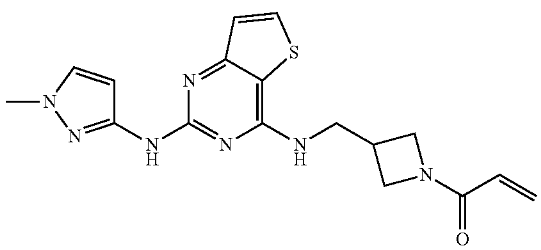 | ¹H-NMR (300 MHz, CD₃OD) δ: 8.16 (d, 1H, J = 5.4 Hz), 7.81 (d, 1H, J = 2.4 Hz), 7.44 (d, 1H, J = 5.4 Hz), 6.21-6.27 (m, 1H), 6.08-6.14 (m, 1H), 5.97 (d, 1H, J = 2.4 Hz), 5.61-5.65 (m, 1H), 4.34-4.38 (m 1H), 4.04-4.12 (m, 2H), 3.91 (s, 3H), 3.74-3.90 (m, 3H), 3.02-3.12 (m, 1H);<br>LC-MS (ESI, m/z): [M + H]⁺ = 370.2 |
| 65 | 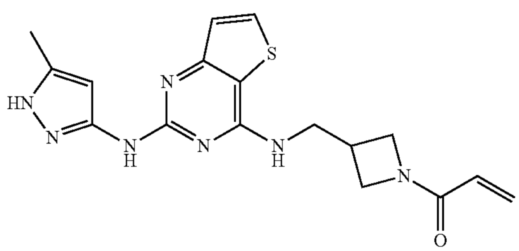 [SMILES: C=CC(=O)N1CC(CNc2nc(Nc3cc(C)[nH]n3)nc3ccsc23)C1] | ¹H-NMR (300 MHz, CD₃OD) δ: 7.87 (d, 1H, J = 5.4 Hz), 7.14 (d, 1H, J = 5.1 Hz), 6.29 (m, 2H), 6.10 (s, 1H), 5.73 (dd, 1H, J = 2.4 Hz, J = 9.6 Hz), 4.40 (t, 1H, J = 8.7 Hz), 4.16 (m, 2H), 3.88 (m, 3H), 3.13 (m, 1H), 2.27 (s, 3H);<br>LC-MS (ESI, m/z): [M + H]⁺ = 370.2 |
| 66 | 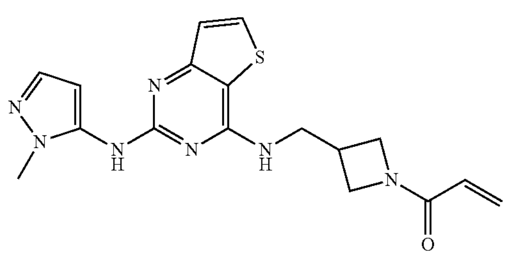 [SMILES: C=CC(=O)N1CC(CNc2nc(Nc3ccnn3C)nc3ccsc23)C1] | ¹H-NMR (300 MHz, CDCl₃) δ: 7.66 (d, 1H, J = 5.4 Hz), 7.45 (d, 1H, J = 1.8 Hz), 7.18 (d, 1H, J = 5.1 Hz), 7.11 (s, 1H), 6.29-6.38 (m, 2H), 6.13-6.22 (m, 1H), 5.66-5.70 (m, 1H), 5.54-5.55 (m, 1H), 4.13-4.31 (m, 2H), 3.68-3.97 (m, 7H), 2.98-3.03 (m, 1H);<br>LC-MS (ESI, m/z): [M + H]⁺ = 370.2 |
| 67 | 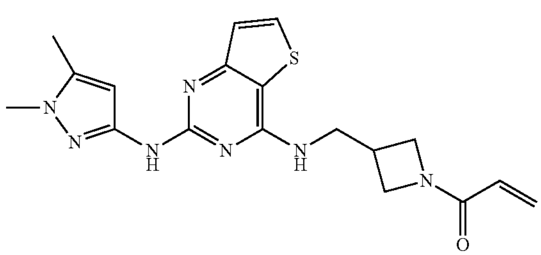 [SMILES: C=CC(=O)N1CC(CNc2nc(Nc3cc(C)n(C)n3)nc3ccsc23)C1] | ¹H-NMR (300 MHz, DMSO-d₆) δ: 8.74 (m, 1H), 7.81-8.40 (m, 2H), 7.43-7.80 (m, 1H), 7.01-7.35 (m, 1H), 6.26-6.35 (m, 1H), 6.05-6.12 (m, 1H), 5.63-5.67 (m, 1H), 4.29 (m, 1H), 4.00-4.04 (m, 2H), 3.70-3.80 (m, 6H), 2.98-3.01 (m, 1H), 2.24-2.27 (m, 3H);<br>LC-MS (ESI, m/z): [M + H]⁺ = 384.3 |

TABLE 2-continued

| Example | Structure | Characterization data |
|---|---|---|
| 68 | 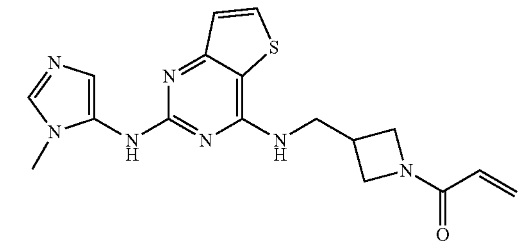 [SMILES: C=CC(=O)N1CC(CNc2nc(Nc3cncn3C)nc3ccsc23)C1] | ¹H-NMR (300 MHz, CD₃OD) δ: 8.38 (bs, 1H), 7.88 (d, 1H, J = 5.4 Hz), 7.32 (s, 1H), 7.13 (d, 1H, J = 5.4 Hz), 6.21-6.40 (m, 2H), 5.74 (dd, 1H, J = 2.4 Hz, J = 9.9 Hz), 4.37-4.42 (m, 1H), 4.07-4.16 (m, 2H), 3.77-3.90 (m, 3H), 3.74 (s, 3H), 3.06-3.10 (m, 1H);<br>LC-MS (ESI, m/z): [M + H]⁺ = 370.2 |
| 69 | 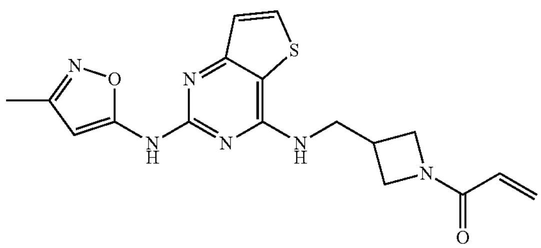 | ¹H-NMR (300 MHz, CD₃OD) δ: 7.88 (d, 1H, J = 5.4 Hz), 7.21 (d, 1H, J = 5.1 Hz), 6.20-6.38 (m, 3H), 5.72 (dd, 1H, J = 2.4 Hz, J = 9.6 Hz), 4.40 (t, 1H, J = 8.7 Hz), 4.10-4.20 (m, 2H), 3.83-3.96 (m, 2H), 3.03-3.23 (m, 1H);<br>LC-MS (ESI, m/z): [M + H]⁺ = 371.2 |
| 70 | 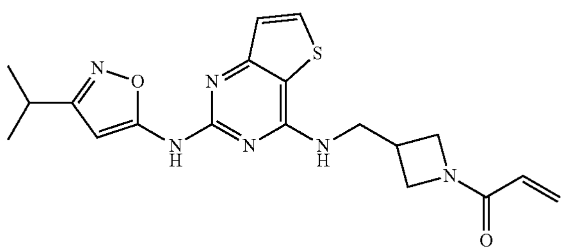 [SMILES: C=CC(=O)N1CC(CNc2nc(Nc3cc(C(C)C)no3)nc3ccsc23)C1] | ¹H-NMR (300 MHz, CD₃OD) δ: 7.89 (d, 1H, J = 5.4 Hz), 7.23 (d, 1H, J = 5.4 Hz), 6.20-6.39 (m, 3H), 5.73 (dd, 1H, J = 2.4 Hz, J = 9.9 Hz), 4.41 (t, 1H, J = 8.7 Hz), 4.08-4.15 (m, 2H), 3.86-3.95 (m, 3H), 2.97-2.01 (m, 1H), 3.13-3.15 (m, 1H), 2.03 (s, 6H);<br>LC-MS (ESI, m/z): [M + H]⁺ = 399.3 |
| 71 | 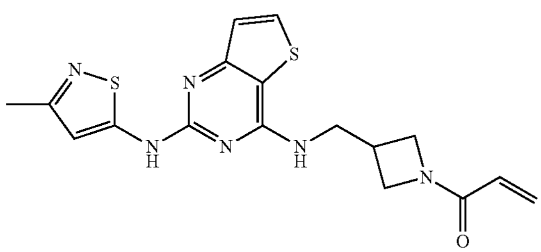 [SMILES: C=CC(=O)N1CC(CNc2nc(Nc3cc(C)ns3)nc3ccsc23)C1] | ¹H-NMR (300 MHz, CD₃OD) δ: 7.91 (d, 1H, J = 5.4 Hz), 7.23 (d, 1H, J = 5.1 Hz), 6.63 (s, 1H), 6.21-6.37 (m, 1H), 5.71-5.75 (m, 1H), 4.42-4.45 (m, 1H), 4.17-4.21 (m, 2H), 3.93-3.99 (m, 3H), 3.18-3.25 (m, 1H), 2.36 (s, 3H);<br>LC-MS (ESI, m/z): [M + H]⁺ = 387.3 |
| 72 | 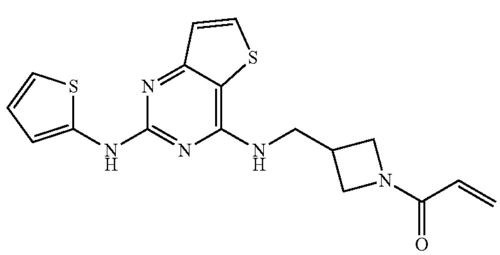 [SMILES: C=CC(=O)N1CC(CNc2nc(Nc3cccs3)nc3ccsc23)C1] | ¹H-NMR (300 MHz, CD₃OD) δ: 7.85 (d, 1H, J = 5.4 Hz), 7.13 (d, 1H, J = 5.4 Hz), 6.75-6.84 (m, 2H), 6.63-6.65 (m, 1H), 6.17-6.36 (m, 2H), 5.70 (dd, 1H, J = 2.4 Hz, J = 9.6 Hz), 4.40 (t, 1H, J = 8.7 Hz), 4.04-4.22 (m, 3H), 3.91-3.97 (m, 2H), 3.08-3.28 (m, 1H);<br>LC-MS (ESI, m/z): [M + H]⁺ = 372.2 |
| 73 | 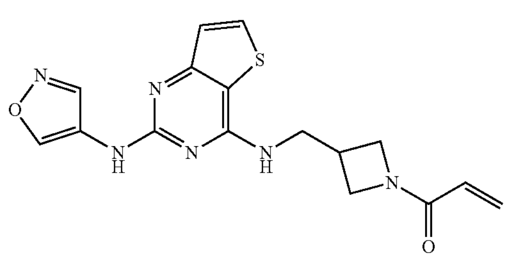 [SMILES: C=CC(=O)N1CC(CNc2nc(Nc3cnoc3)nc3ccsc23)C1] | ¹H-NMR (300 MHz, CD₃OD) δ: 9.04 (s, 1H), 8.54 (s, 1H), 7.83 (d, 1H, J = 5.4 Hz), 7.17 (d, 1H, J = 5.4 Hz), 6.20-6.38 (m, 2H), 5.73 (dd, 1H, J = 2.4 Hz, J = 9.9 Hz), 4.41 (t, 1H, J = 8.7 Hz), 4.10-4.17 (m, 2H), 3.84-3.95 (m, 3H), 3.03-3.23 (m, 1H);<br>LC-MS (ESI, m/z): [M + H]⁺ = 357.1 |

TABLE 2-continued

| Example | Structure | Characterization data |
|---|---|---|
| 74 | 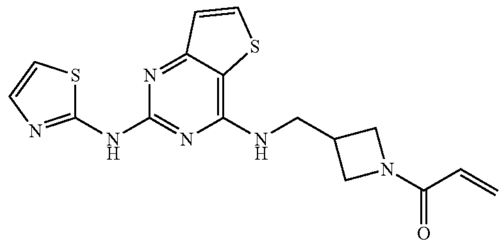 [SMILES: C=CC(=O)N1CC(CNc2nc(Nc3nccs3)nc3ccsc23)C1] | ¹H-NMR (300 MHz, CD$_3$OD) δ: 7.91 (d, 1H, J = 5.4 Hz), 7.33-7.36 (m, 2H), 6.99 (d, 1H, J = 3.6 Hz), 6.16-6.34 (m, 2H), 5.68 (dd, 1H, J = 2.4 Hz, J = 9.6 Hz), 4.38 (t, 1H, J = 8.7 Hz), 4.05-4.17 (m, 2H), 3.88-3.92 (m, 3H), 3.05-3.14 (m, 1H); LC-MS (ESI, m/z): [M + H]$^+$ = 373.2 |
| 75 | 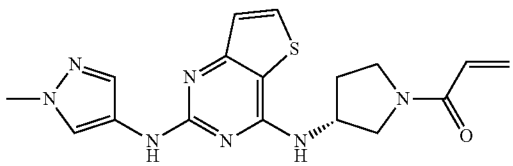 [SMILES: C=CC(=O)N1CC[C@@H](Nc2nc(Nc3cnn(C)c3)nc3ccsc23)C1] | ¹H-NMR (300 MHz, CDCl$_3$) δ: 7.61-7.81 (m, 3H), 7.21 (d, 1H, J = 5.4 Hz), 6.39-6.64 (m, 2H), 5.69-5.78 (m, 1H), 3.61-3.99 (m, 8H), 2.10-2.45 (m, 2H); LC-MS (ESI, m/z): [M + H]$^+$ = 370.2 |
| 76 | 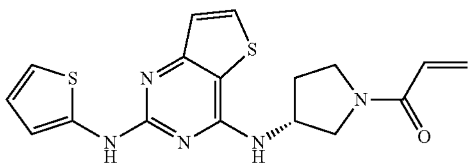 [SMILES: C=CC(=O)N1CC[C@@H](Nc2nc(Nc3cccs3)nc3ccsc23)C1] | ¹H-NMR (300 MHz, CD$_3$OD) δ: 7.84-7.86 (m, 1H), 7.12-7.15 (m, 1H), 6.83-6.86 (m, 1H), 6.77-6.80 (m, 1H), 6.55-6.73 (m, 2H), 6.26-6.35 (m, 1H), 5.72-5.81 (m, 1H), 5.07-5.11 (m, 1H), 3.99-4.23 (m, 1H), 3.62-3.92 (m, 4H), 2.16-2.53 (m, 2H); LC-MS (ESI, m/z): [M + H]$^+$ = 372.2 |
| 77 | 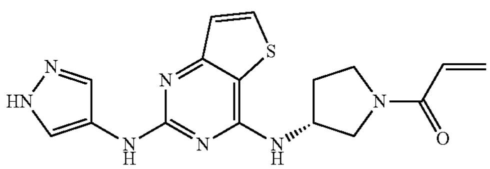 [SMILES: C=CC(=O)N1CC[C@@H](Nc2nc(Nc3cn[nH]c3)nc3ccsc23)C1] | ¹H-NMR (300 MHz, CD$_3$OD) δ: 7.98 (m, 1H), 7.85 (s, 2H), 7.18 (d, 1H, J = 12.3 Hz), 6.55-6.72 (m, 1H), 6.26-6.34 (m, 1H), 5.77 (td, 1H, J = 1.8 Hz, J = 10.2 Hz), 3.53-3.99 (m, 5H), 2.19-2.47 (m, 2H); LC-MS (ESI, m/z): [M + H]$^+$ = 356.2 |
| 78 | 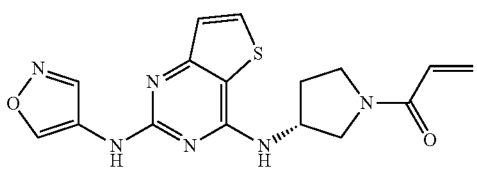 [SMILES: C=CC(=O)N1CC[C@@H](Nc2nc(Nc3cnoc3)nc3ccsc23)C1] | ¹H-NMR (300 MHz, CD$_3$OD) δ: 9.07 (s, 1H), 8.56 (s, 1H), 7.85 (dd, 1H, J = 0.9 Hz, J = 5.4 Hz), 7.18 (dd, 1H, J = 1.8 Hz, 5.4 Hz), 6.56-6.72 (m, 1H), 6.26-6.34 (m, 1H), 5.73-5.81 (m, 1H), 3.57-4.01 (m, 5H), 2.12-2.52 (m, 2H); LC-MS (ESI, m/z): [M + H]$^+$ = 357.1 |
| 79 | 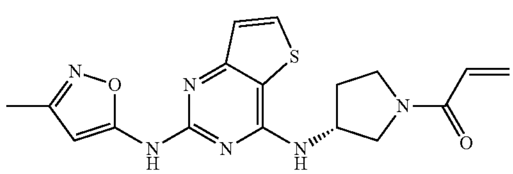 [SMILES: C=CC(=O)N1CC[C@@H](Nc2nc(Nc3cc(C)no3)nc3ccsc23)C1] | ¹H-NMR (300 MHz, CD$_3$OD) δ: 7.89 (dd, 1H, J = 1.5 Hz, J = 5.4 Hz), 7.22 (dd, 1H, J = 2.1 Hz, J = 5.1 Hz), 6.57-6.72 (m, 1H), 6.27-6.34 (m 2H), 5.73-5.81 (m, 1H), 3.61-4.15 (m, 5H), 2.16-2.47 (m, 4H), 2.26 (s, 3H); LC-MS (ESI, m/z): [M + H]$^+$ = 371.2 |
| 80 | 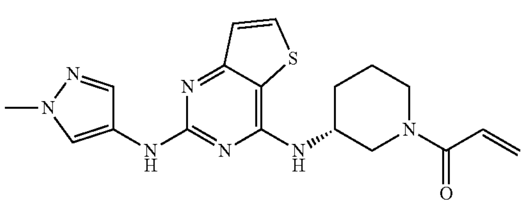 [SMILES: C=CC(=O)N1CCC[C@@H](Nc2nc(Nc3cnn(C)c3)nc3ccsc23)C1] | ¹H-NMR (300 MHz, CDCl$_3$) δ: 7.78 (s, 1H), 7.56-7.67 (m, 2H), 7.21 (d, 1H, J = 5.4 Hz), 6.28-6.69 (m, 2H), 5.55-5.82 (m, 1H), 4.34 (bs, 1H), 4.00-4.12 (m, 1H), 3.88 (s, 3H), 3.30-3.80 (m, 3H), 1.60-2.20 (m, 4H); LC-MS (ESI, m/z): [M + H]$^+$ = 384.3 |
| 81 | 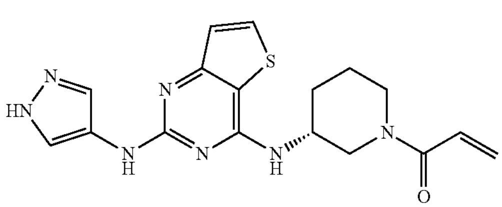 [SMILES: C=CC(=O)N1CCC[C@@H](Nc2nc(Nc3cn[nH]c3)nc3ccsc23)C1] | ¹H-NMR (300 MHz, CD$_3$OD) δ: 7.90 (s, 1H), 7.81 (s, 2H), 7.15 (m, 1H), 6.52-6.88 (m, 1H), 6.08-6.29 (m, 1H), 5.54-5.82 (m, 1H), 4.80 (m, 1H), 4.66 (m, 1H), 4.15-4.40 (m, 2H), 3.15 (m, 1H), 3.87 (m, 1H), 2.52 (m, 1H), 2.22 (m, 1H), 1.95 (m, 1H); LC-MS (ESI, m/z): [M + H]$^+$ = 370.2 |

TABLE 2-continued

| Example | Structure | Characterization data |
|---|---|---|
| 82 | 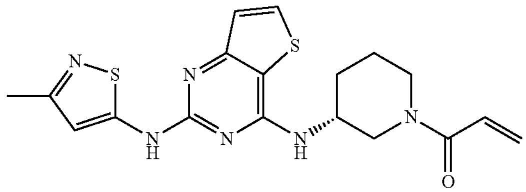 | $^1$H-NMR (300 MHz, CD$_3$OD) δ: 7.82 (d, 1H, J = 4.5 Hz), 7.15 (s, 1H), 6.54-6.80 (m, 2H), 6.06-6.27 (m, 1H), 5.53-5.76 (m, 1H), 4.77 (m, 1H), 4.05-4.46 (m, 2H), 3.10 (m 1H), 2.84 (m, 1H), 2.31 (s, 3H), 2.22 (s, 1H), 1.66-2.00 (m, 3H); LC-MS (ESI, m/z): [M + H]$^+$ = 401.3 |
| 83 | 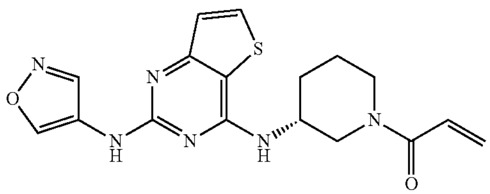 [SMILES: C=CC(=O)N1CCC[C@@H](Nc2nc(Nc3cnoc3)nc3ccsc23)C1] | $^1$H-NMR (300 MHz, CD$_3$OD) δ: 9.02 (d, 1H, J = 6.9 Hz), 8.54 (d, 1H, J = 6.6 Hz), 7.82 (d, 1H, J = 5.1 Hz), 7.15 (d, 1H, J = 5.1 Hz), 6.72 (m, 1H), 6.20 (dd, 1H, J = 15.6 Hz, J = 46.5 Hz), 5.68 (dd, 1H, J = 10.8 Hz, J = 69.3 Hz), 4.05-4.29 (m, 3H), 3.08-3.36 (m, 2H), 2.17 (m, 1H), 1.93 (d, 1H, J = 12.6 Hz), 1.79 (t, 1H, J = 12.0 Hz), 1.61 (m, 1H); LC-MS (ESI, m/z): [M + H]$^+$ = 371.2 |
| 84 | 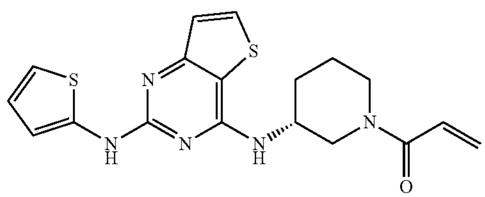 [SMILES: C=CC(=O)N1CCC[C@@H](Nc2nc(Nc3cccs3)nc3ccsc23)C1] | $^1$H-NMR (300 MHz, CDCl$_3$) δ: 7.65 (d, 1H, J = 5.4 Hz), 7.19 (d, 1H, J = 5.4 Hz), 6.84-6.87 (m, 1H), 6.75-6.77 (m, 1H), 6.59 (bs, 1H), 6.18-6.49 (m, 1H), 5.65-5.85 (m, 1H), 5.49-5.52 (m, 1H), 4.57 (bs, 1H), 3.83-4.03 (m, 2H), 3.68-3.79 (m, 1H), 3.47-3.60 (m, 2H), 2.00-2.25 (m, 2H), 1.70-1.89 (m, 2H); LC-MS (ESI, m/z): [M + H]$^+$ = 386.2 |
| 85 | 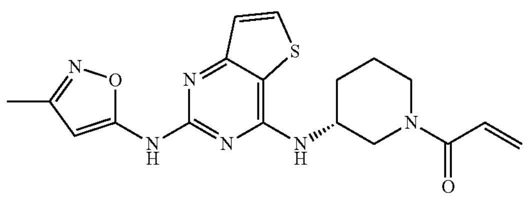 [SMILES: C=CC(=O)N1CCC[C@@H](Nc2nc(Nc3cc(C)no3)nc3ccsc23)C1] | $^1$H-NMR (300 MHz, CD$_3$OD) δ: 7.86-7.89 (m, 1H), 7.35-7.40 (m, 1H), 7.21 (d, 1H, J = 5.1 Hz), 6.63-6.90 (m, 1H), 6.11-6.30 (m, 1H), 5.56-5.82 (m, 1H), 3.61-4.15 (m, 5H), 2.16-2.47 (m, 4H), 2.23 (s, 3H); LC-MS (ESI, m/z): [M + H]$^+$ = 385.2 |
| 86 | 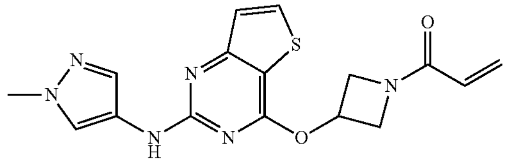 [SMILES: C=CC(=O)N1CC(Oc2nc(Nc3cnn(C)c3)nc3ccsc23)C1] | $^1$H-NMR (300 MHz, CDCl$_3$) δ: 7.72-7.74 (m, 2H), 7.48 (m, 1H), 7.17 (s, 1H), 6.31 (dd, 1H, J = 1.8 Hz, J = 16.8 Hz), 6.13 (dd, 1H, J = 10.2 Hz, J = 17.1 Hz), 5.65 (dd, 1H, J = 1.8 Hz, J = 10.2 Hz), 5.50-5.53 (m, 1H), 4.56-4.62 (m, 1H), 4.43-4.49 (m, 1H), 4.26-4.31 (m, 1H), 4.16-4.21 (m, 1H), 3.85 (S, 3H); LC-MS (ESI, m/z): [M + H]$^+$ = 357.2 |
| 87 | 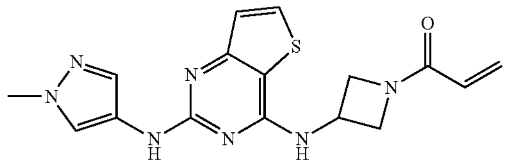 [SMILES: C=CC(=O)N1CC(Nc2nc(Nc3cnn(C)c3)nc3ccsc23)C1] | $^1$H-NMR (300 MHz, CD$_3$OD) δ: 7.86 (s, 1H), 7.78 (d, 1H, J = 5.4 Hz), 7.57 (s, 1H), 7.11 (d, 1H, J = 5.4 Hz), 6.22-6.39 (m, 2H), 5.71-5.76 (m, 1H), 4.48-4.98 (m, 1H), 4.63-4.69 (m, 1H), 4.41-4.47 (m, 1H), 4.21-4.26 (m, 1H), 4.06-4.11 (m, 1H), 3.87 (s, 3H); LC-MS (ESI, m/z): [M + H]$^+$ = 356.2 |
| 88 | 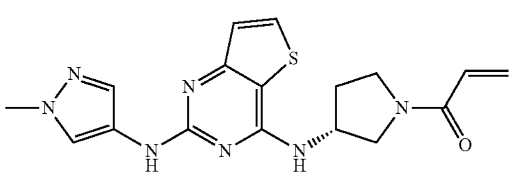 | $^1$H-NMR (300 MHz, CDCl$_3$) δ: 7.80 (bS, 1H), 7.65-7.69 (m, 1H), 7.47 (s, 1H), 7.14-7.16 (m, 1H), 6.94 (bs, 1H), 6.32-6.43 (m, 2H), 5.61-5.76 (m, 2H), 3.63-3.91 (m, 8H), 2.24-2.36 (m, 2H); LC-MS (ESI, m/z): [M + H]$^+$ = 371.2 |
| 89 | 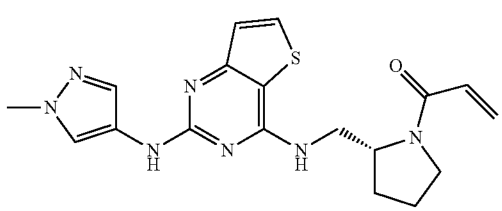 [SMILES: C=CC(=O)N1CCC[C@@H]1CNc1nc(Nc2cnn(C)c2)nc2ccsc12] | $^1$H-NMR (300 MHz, CDCl$_3$) δ: 8.09 (s, 1H), 7.76 (s, 1H), 7.64 (d, 1H, J = 5.1 Hz), 7.18 (d, 1H, J = 5.4 Hz), 6.48 (d, 2H, J = 6.3 Hz), 5.78 (d, 1H, J = 6.0 Hz), 4.63-4.69 (m, 1H), 3.89 (s, 3H), 3.54-3.83 (m, 4H), 2.02-2.14 (m, 3H), 1.86-1.90 (m, 1H); LC-MS (ESI, m/z): [M + H]$^+$ = 384.3 |

TABLE 2-continued

| Example | Structure | Characterization data |
|---|---|---|
| 90 | 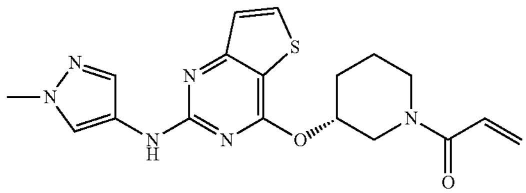 [SMILES: C=CC(=O)N1CCC[C@@H](Oc2nc(Nc3cnn(C)c3)nc3ccsc23)C1] | $^1$H-NMR (300 MHz, CD$_3$OD) δ: 7.89 (m, 2H), 7.54 (d, 1H, J = 6.0 Hz), 7.16 (m, 1H), 6.46-6.84 (m, 1H), 5.99-6.20 (m, 1H), 5.44-5.76 (m, 1H), 5.34 (m, 1H), 4.10 (m, 1H), 3.88 (m, 4H), 3.70 (m, 1H), 3.20-3.34 (m, 1H), 1.84-2.16 (m, 3H), 1.65 (m, 1H); LC-MS (ESI, m/z): [M + H]$^+$ = 385.2 |
| 91 | 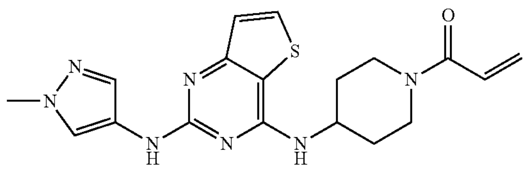 [SMILES: C=CC(=O)N1CCC(Nc2nc(Nc3cnn(C)c3)nc3ccsc23)CC1] | $^1$H-NMR (300 MHz, CDCl$_3$) δ: 7.74 (S, 1H), 7.54 (d, 1H, J = 5.4 Hz), 7.47 (s, 1H), 7.12 (d, 1H, J = 5.4 Hz), 6.54 (dd, 1H, J = 10.5 Hz, J = 16.8 Hz), 6.24 (dd, 1H, J = 1.8 Hz, J = 16.8 Hz), 5.65 (dd, 1H, J = 1.8 Hz, J = 10.5 Hz), 4.60-4.80 (m, 2H), 4.29-4.35 (m, 1H), 3.97-4.04 (m, 1H), 3.15-3.25 (m, 1H), 2.70-2.90 (m, 2H), 2.11-2.21 (m, 2H); LC-MS (ESI, m/z): [M + H]$^+$ = 384.3 |

Example 92

Preparation of 1-(3-(((2-((1-methyl-1H-pyrazol-4-yl)amino)furo[3,2-d]pyrimidin-4-yl) amino)methyl) azetidin-1-yl)prop-2-en-1-one

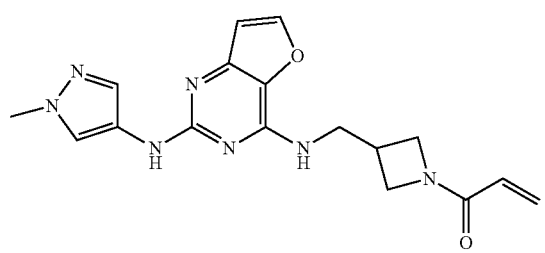 [SMILES: C=CC(=O)N1CC(CNc2nc(Nc3cnn(C)c3)nc3ccoc23)C1]

Step 1: Preparation of Tert-Butyl 3-(((2-chloro-furo[3,2-d]pyrimidin-4-yl)amino) methyl)azetidine-1-carboxylate

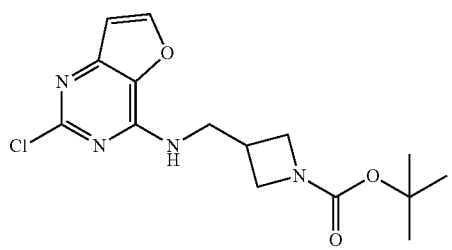 [SMILES: CC(C)(C)OC(=O)N1CC(CNc2nc(Cl)nc3ccoc23)C1]

2,4-Dichloro-furo[3,2-d]pyrimidine (189 mg, 1 mmol) and tert-butyl 3-(aminomethyl)azetidine-1-carboxylate (186 mg, 1 mmol) were dissolved in tetrahydrofuran (20 mL), followed by the addition of N,N-diisopropylethylamine (258 mg, 2 mmol). The reaction solution was reacted under reflux overnight, then cooled to room temperature, and concentrated. The residue was added with water (20 mL), and extracted with ethyl acetate (10 mL×3). The organic phase was dried over anhydrous sodium sulfate, concentrated under reduced pressure, and purified by silica gel column chromatography (eluent:n-hexane:ethyl acetate=6:1), to give a white solid (283 mg). Yield: 83.5%. MS (ESI, m/z): [M+H]+: 339.1.

Step 2: Preparation of N-(azetidin-3-ylmethyl)-2-chloro-furo[3,2-d]pyrimidine-4-amine

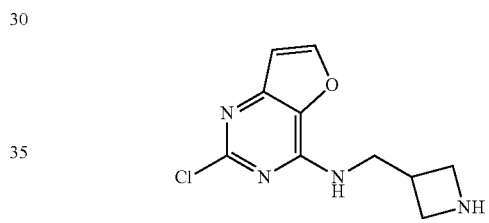

The compound obtained in step 1 (283 mg, 0.84 mmol) was dissolved in dichloromethane (2 mL), followed by the slow and dropwise addition of a solution of trifluoroacetic acid (1.43 g, 12.5 mmol) in methylene chloride (1 mL) in an ice bath. The reaction solution was reacted at room temperature for 1 hour, and then concentrated. The resulting crude product was used directly in the next step without further purification. MS (ESI, m/z): [M+H]$^+$: 238.9.

Step 3: Preparation of 1-(3-(((2-chloro-furo[3,2-d]pyrimidin-4-yl)amino)methyl) azetidin-1-yl)prop-2-en-1-one

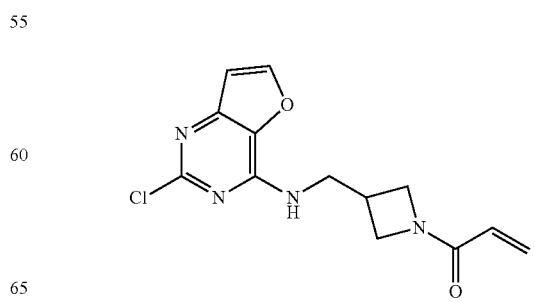

The product obtained in step 2 (0.84 mmol) was dissolved in dichloromethane (10 mL), followed by the addition of triethylamine (254 mg, 2.51 mmol). A solution of acryloyl chloride (83.1 mg, 0.92 mmol) dissolved in dichloromethane (5 mL) was dropwise added to the above solution in an ice-bath. The reaction solution was reacted at room temperature overnight. The reaction solution was washed with water (10 mL), and the organic phase was dried over anhydrous sodium sulfate, concentrated under reduced pressure, and purified by silica gel column chromatography (eluent:dichloromethane/methanol=70:1), to give a white solid (176 mg). Yield: 72.0%. MS (ESI, m/z): [M+H]$^+$: 293.0.

Step 4: Preparation of 1-(3-(((2-((1-methyl-1H-pyrazol-4-yl)amino)furo[3,2-d] pyrimidin-4-yl)amino)methyl)azetidin-1-yl)prop-2-en-1-one The compound obtained in step 3 (29.3 mg, 0.1 mmol) and 1-methyl-1H-pyrazole-4-amine (14.6 mg, 0.15 mmol) were dissolved in isopropanol (2 mL). The reaction solution was adjusted to pH 5 with trifluoroacetic acid, and reacted at 90° C. under microwave irradiation for 0.5 hours. The reaction solution was cooled to room temperature, adjusted with 1N sodium hydroxide solution to pH 8, and extracted with ethyl acetate (10 mL×3). The organic phase was dried over anhydrous sodium sulfate, concentrated under reduced pressure, and purified by silica gel column chromatography (eluent:dichloromethane/methanol=10:1) to give a yellow solid (15.5 mg). Yield: 43.9%. MS (ESI, m/z): [M+H]$^+$: 354.2; $^1$H-NMR (300 MHz, DMSO-d$_6$) δ: 7.80 (s, 1H), 7.61 (d, 1H, J=2.1 Hz), 7.49 (s, 1H), 7.04 (s, 1H), 6.66 (d, 1H, J=1.8 Hz), 6.33 (dd, 1H, J=1.8 Hz, J=17.1 Hz), 6.12-6.21 (m, 1H), 5.67 (dd, 1H, J=2.1 Hz, J=10.2 Hz), 4.00-4.35 (m, 3H), 3.87 (s, 3H), 3.79-3.92 (m, 3H), 3.01-3.06 (m, 1H).

The following compounds (in Table 3) were prepared from similar starting materials by similar synthetic methods to those described in Example 92.

TABLE 3

| Example | Structure | Characterization data |
|---|---|---|
| 93 | 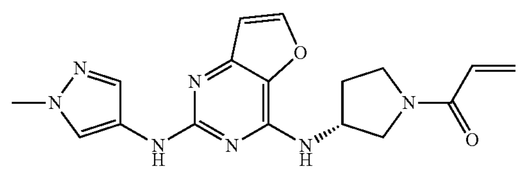 [SMILES: C=CC(=O)N1CC[C@@H](Nc2nc(Nc3cnn(C)c3)nc3ccoc23)C1] | $^1$H-NMR (300 MHz, CD$_3$OD) δ: 7.83-7.87 (m, 2H), 7.55-7.57 (m, 1H), 6.54-6.71 (m, 2H), 6.26-6.34 (m, 1H), 5.73-5.80 (m, 1H), 3.88 (s, 1H), 3.57-4.01 (m, 5H), 2.12-2.44 (m, 2H); LC-MS (ESI, m/z): [M + H]$^+$ = 354.3 |
| 94 | 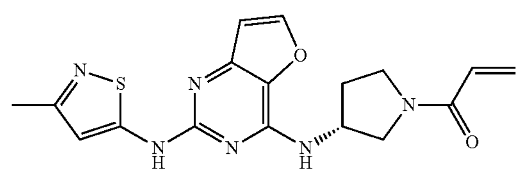 | $^1$H-NMR (300 MHz, CD$_3$OD) δ: 7.89 (s, 1H), 6.54-6.72 (m, 3H), 6.26-6.33 (m, 1H), 5.71-5.80 (m, 1H), 3.97-4.19 (m, 1H), 3.59-3.1 (m, 4H), 2.14-2.53 (m, 2H), 2.34 (s, 3H); LC-MS (ESI, m/z): [M + H]$^+$ = 371.2 |
| 95 | 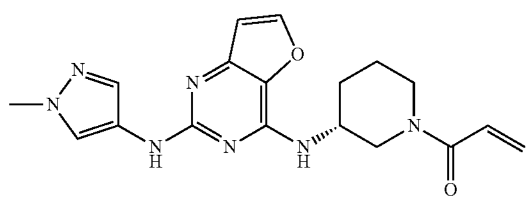 | $^1$H-NMR (300 MHz, CD$_3$OD) δ: 7.83-7.91 (m, 2H), 7.50 (d, 1H, J = 11.4 Hz), 6.50-6.89 (m, 2H), 6.08-6.29 (m, 1H), 5.52-5.81 (m, 1H), 4.05-4.21 (m, 2H), 3.78-3.89 (m, 1H), 3.84 (s, 3H), 2.77-3.36 (m, 2H), 2.14-2.20 (m, 1H), 1.90-1.97 (m, 1H), 1.59-1.82 (m, 2H); LC-MS (ESI, m/z): [M + H]$^+$ = 368.2 |
| 96 | 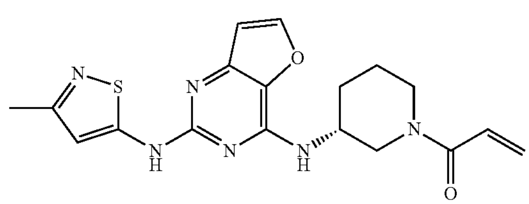 [SMILES: C=CC(=O)N1CCC[C@@H](Nc2nc(Nc3cc(C)ns3)nc3ccoc23)C1] | $^1$H-NMR (300 MHz, CD$_3$OD) δ: 7.88 (d, 1H, J = 4.2 Hz), 6.56-6.68 (m, 3H), 6.07-6.27 (m, 1H), 5.50-5.57 (m, 1H), 4.02-4.71 (m, 3H), 2.88-3.36 (m, 2H), 2.33 (s, 3H), 2.14-2.27 (m, 1H), 1.94-1.99 (m, 1H), 1.59-1.85 (m, 2H); LC-MS (ESI, m/z): [M + H]$^+$ = 385.2 |

Example 97

Preparation of 1-(3-(((2-((1-methyl-1H-pyrazol-4-yl)amino)-5H-pyrrolo[3,2-d] pyrimidin-4-yl)amino)methyl)azetidin-1-yl)prop-2-en-1-one

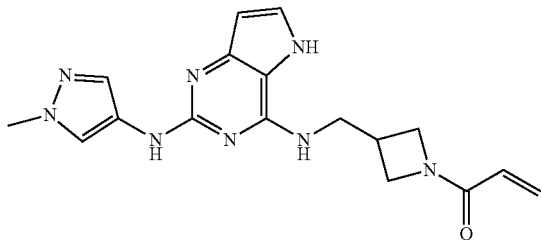 [SMILES: C=CC(=O)N1CC(CNc2nc(Nc3cnn(C)c3)nc3cc[nH]c23)C1]

Step 1: Preparation of Tert-Butyl 3-(((2-chloro-5H-pyrrolo[3,2-d]pyrimidin-4-yl)amino)methyl)azetidine-1-carboxylate

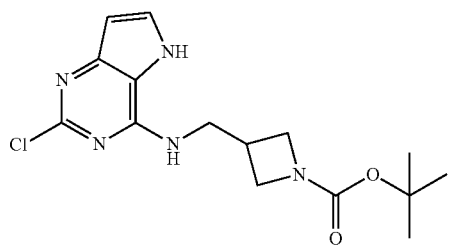 [SMILES: CC(C)(C)OC(=O)N1CC(CNc2nc(Cl)nc3cc[nH]c23)C1]

2,4-Dichloro-5H-pyrrolo[3,2-d]pyrimidine (360 mg, 1.92 mmol) and tert-butyl 3-(aminomethyl)azetidine-1-carboxylate (374 mg, 2.01 mmol) were dissolved in methanol (20 mL), followed by the addition of N,N-diisopropylethylamine (667 µL, 3.83 mmol) under stirring at room temperature. The reaction solution was refluxed for 3 hours, and then concentrated, re-dissolved in dichloromethane (50 mL), washed with water (30 mL) and concentrated to give a white solid (350 mg). Yield: 51.2%. MS (ESI, m/z): [M+H]$^+$: 338.2.

Step 2: Preparation of 1-(3-(((2-chloro-5H-pyrrolo[3,2-d]pyrimidin-4-yl)amino) methyl)azetidin-1-yl)prop-2-en-1-one

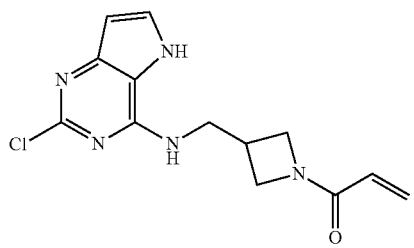 [SMILES: C=CC(=O)N1CC(CNc2nc(Cl)nc3cc[nH]c23)C1]

The product obtained in step 1 (222 mg, 0.66 mmol) was dissolved in dichloromethane (5 mL), followed by the addition of trifluoroacetic acid (2 mL) under stirring at room temperature. After stirring for 3 hours, the reaction solution was concentrated under reduced pressure to remove most of trifluoroacetic acid, and re-dissolved in dichloromethane (30 mL). N,N-diisopropylethylamine (229 µL, 1.31 mmol) was added under stirring at room temperature, and then a solution of acryloyl chloride (59 µL, 0.66 mmol) in dichloromethane (10 mL) was slowly, dropwise added in an ice bath. After 5 hours, water (50 mL) was added to the reaction system, and the organic phase was separated, dried over anhydrous sodium sulfate, and concentrated to give a pale yellow solid, which was then purified by silica gel column chromatography (eluent: dichloromethane/methanol=70:1), to give a white solid (150 mg). Yield: 77.7%. MS (ESI, m/z): [M+H]$^+$: 292.0.

Step 3: Preparation of 1-(3-(((2-((1-methyl-1H-pyrazol-4-yl)amino)-5H-pyrrolo[3,2-d]pyrimidin-4-yl)amino)methyl)azetidin-1-yl)prop-2-en-1-one The compound obtained in step 2 (40 mg, 0.14 mmol) and 1-methyl-1H-pyrazole-4-amine (15 mg, 0.15 mmol) were dissolved in isopropanol (2 mL). The reaction solution was adjusted to pH 5 with trifluoroacetic acid, and then reacted under microwave irradiation at 90° C. for 0.5 hours. The reaction solution was cooled to room temperature, adjusted with 1N sodium hydroxide solution to pH 8, and extracted with ethyl acetate (10 mL×3). The organic phase was dried over anhydrous sodium sulfate, concentrated under reduced pressure, and purified by silica gel column chromatography (eluent:dichloromethane/methanol=10:1) to give a yellow solid (2 mg). Yield: 4.1%. MS (ESI, m/z): [M+H]$^+$: 353.2; $^1$H-NMR (300 MHz, DMSO-d$_6$) δ: 7.52 (s, 2H), 7.41 (s, 1H), 6.98 (d, 1H, J=3.0 Hz), 6.13-6.19 (m, 2H), 5.98 (d, 1H, J=3.0 Hz), 5.67 (dd, 1H, J=2.4 Hz, J=9.6 Hz), 4.25-4.35 (m, 1H), 4.04-4.08 (m, 2H), 3.80-3.85 (m, 2H), 3.74 (s, 3H), 3.65-3.73 (m, 1H), 2.95-3.05 (m, 1H).

Example 98

Preparation of 1-(3-(((5-methyl-2-((1-methyl-1H-pyrazol-4-yl)amino)-5H-pyrrolo[3,2-d]pyrimidin-4-yl)amino)methyl)azetidin-1-yl)prop-2-en-1-one

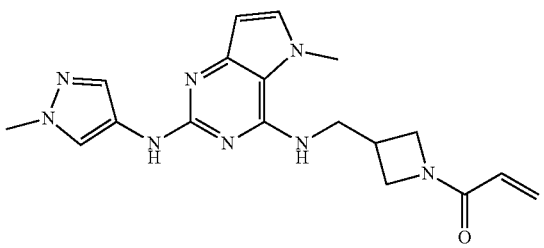 [SMILES: C=CC(=O)N1CC(CNc2nc(Nc3cnn(C)c3)nc3ccn(C)c23)C1]

Step 1: Preparation of Tert-Buty 3-(((2-chloro-5-methyl-5H-pyrrolo[3,2-d]pyrimidin-4-yl)amino)methyl)azetidine-1-carboxylate

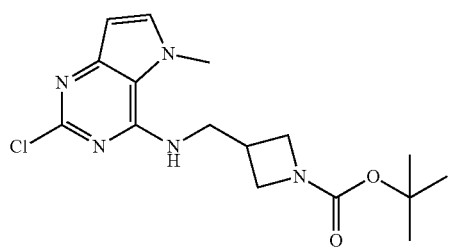 [SMILES: Cn1ccc2nc(Cl)nc(NCC3CN(C(=O)OC(C)(C)C)C3)c21]

2,4-Dichloro-5-methyl-5H-pyrrolo[3,2-d]pyrimidine (300 mg, 1.48 mmol) and tert-butyl 3-(aminomethyl)azetidine-1-carboxylate (290 mg, 1.56 mmol) were dissolved in tetrahydrofuran (10 mL), followed by the addition of N,N-diisopropylethylamine (258 mg, 2 mmol). The reaction solution was reacted under reflux overnight, and then cooled to room temperature. The reaction solution was concentrated and the residue was added with water (50 mL), and extracted with ethyl acetate (20 mL×3). The organic phase was dried over anhydrous sodium sulfate, concentrated under reduced pressure, and purified by silica gel column chromatography (eluent:n-hexane:ethyl acetate=6:1), to give a colorless liquid (300 mg). Yield: 50.7%. MS (ESI, m/z): [M+H]⁺: 352.2.

Step 2: Preparation of 1-(3-(((2-chloro-5-methyl-5H-pyrrolo[3,2-d]pyrimidin-4-yl)amino)methyl)azetidin-1-yl) prop-2-en-1-one

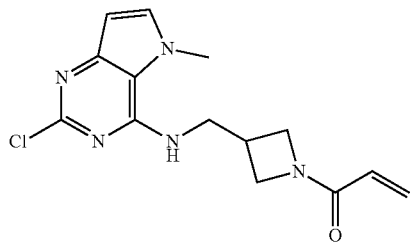 [SMILES: C=CC(=O)N1CC(CNc2nc(Cl)nc3ccn(C)c23)C1]

The product obtained in step 1 (229 mg) was dissolved in dichloromethane (4 mL), followed by the addition of trifluoroacetic acid (1.5 mL) under stirring at room temperature. After stirring for 3 hours, the reaction solution was concentrated under reduced pressure to remove most of trifluoroacetic acid, and was then re-dissolved in dichloromethane (20 mL). To the solution, N,N-diisopropylethylamine (276 μL, 1.59 mmol) was added under stirring at room temperature, and then a solution of acryloyl chloride (64 μL, 0.66 mmol) in dichloromethane (10 mL) was slowly, dropwise added in an ice bath. After 5 hours, water (50 mL) was added to the reaction system. The organic phase was separated, dried over anhydrous sodium sulfate, and concentrated to give a pale yellow solid, which was then purified by silica gel column chromatography (eluent: dichloromethane/methanol=70:1), to give a white solid (180 mg). Yield: 90.5%. MS (ESI, m/z): [M+H]⁺: 306.1.

Step 3: Preparation of 1-(3-(((5-methyl-2-((1-methyl-1H-pyrazol-4-yl)amino)-5H-pyrrolo[3,2-d]pyrimidin-4-yl)amino)methyl)azetidin-1-yl)prop-2-en-1-one The compound obtained in step 2 (50 mg, 0.16 mmol) and 1-methyl-1H-pyrazole-4-amine (18 mg, 0.18 mmol) were dissolved in isopropanol (2 mL). The reaction solution was adjusted to pH 5 with trifluoroacetic acid, and reacted under microwave irradiation at 90° C. for 0.5 hours. The reaction solution was cooled to room temperature, adjusted with 1N sodium hydroxide solution to pH 8, and extracted with ethyl acetate (10 mL×3). The organic phase was dried over anhydrous sodium sulfate, concentrated under reduced pressure, and purified by silica gel column chromatography (eluent:dichloromethane/methanol=10:1) to give a pale yellow solid (3 mg). Yield: 5%. MS (ESI, m/z): [M+H]⁺: 367.3; ¹H-NMR (300 MHz, DMSO-d₆) δ: 7.59 (d, 1H, J=3.0 Hz), 7.54 (s, 1H), 6.89 (d, 1H, J=3.0 Hz), 6.77 (bs, 1H), 6.11-6.30 (m, 3H), 5.68 (dd, 1H, J=1.8 Hz, J=10.2 Hz), 4.31-4.37 (m, 1H), 4.11-4.18 (m, 1H), 3.90-4.06 (m, 5H), 3.83 (s, 3H), 3.70-3.80 (m, 2H), 3.05-3.17 (m, 1H).

Example 99

Preparation of 1-(3-(((2-((1-methyl-1H-pyrazol-4-yl)amino)thieno[2,3-d]pyrimidin-4-yl)amino)methyl)azetidin-1-yl)prop-2-en-1-one

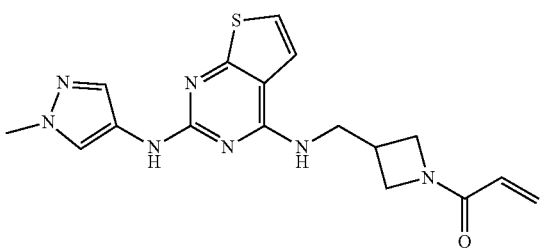 [SMILES: C=CC(=O)N1CC(CNc2nc(Nc3cnn(C)c3)nc3sccc23)C1]

Step 1: Preparation of Tert-Butyl 3-(((2-chloro-thieno[2,3-d]pyrimidin-4-yl)amino) methyl)azetidine-1-carboxylase

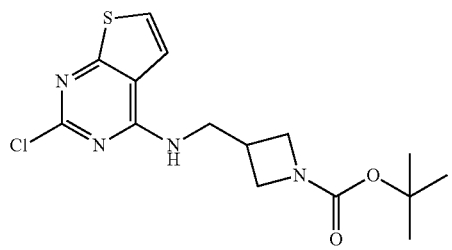 [SMILES: CC(C)(C)OC(=O)N1CC(CNc2nc(Cl)nc3sccc23)C1]

2,4-Dichloro-thieno[2,3-d]pyrimidine (300 mg, 1.46 mmol) and tert-butyl 3-(aminomethyl)azetidine-1-carboxylate (272 mg, 1.46 mmol) were dissolved in tetrahydrofuran (25 mL), followed by the addition of N,N-diisopropylethylamine (258 mg, 2 mmol). The reaction solution was reacted at 70° C. overnight, and then concentrated. The residue was added with water (50 mL), and extracted with ethyl acetate (20 mL×3). The organic phase was dried over anhydrous sodium sulfate, concentrated under reduced pressure, and purified by silica gel column chromatography (eluent:n-hexane:ethyl acetate=1:5) to give a white solid (425 mg). Yield: 81.9%. MS (ESI, m/z): [M+H]⁺: 355.2.

Step 2: Preparation of 1-(3-(((2-Chloro-Thieno[2,3-d]Pyrimidin-4-Yl)Amino)Methyl) azetidin-1-yl) prop-2-en-1-one

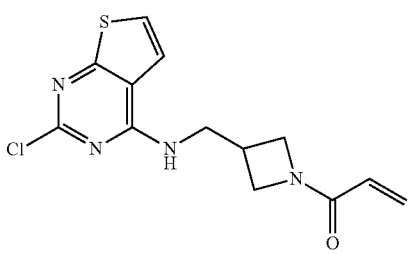 [SMILES: C=CC(=O)N1CC(CNc2nc(Cl)nc3sccc23)C1]

The product obtained in step 1 (425 mg, 1.20 mmol) was dissolved in dichloromethane (10 mL), followed by the addition of trifluoroacetic acid (3 mL) under stirring at room temperature. After stirring for 3 hours, the reaction solution was concentrated under reduced pressure to remove most of trifluoroacetic acid, and was then re-dissolved in dichloromethane (30 mL), followed by the addition of N,N-diisopropylethylamine (417 µL, 2.40 mmol) under stirring at room temperature. Then a solution of acryloyl chloride (140 µL, 1.73 mmol) in dichloromethane (20 mL) was slowly, dropwise added in an ice bath. After 5 hours, water (50 mL) was added to the reaction system, and the organic phase was separated, dried over anhydrous sodium sulfate, and concentrated to give a pale yellow solid, which was purified by silica gel column chromatography (eluent:dichloromethane/methanol=70:1), to give a white solid (300 mg). Yield: 81.1%. MS (ESI, m/z): [M+H]$^+$: 309.1.

Step 3: Preparation of 1-(3-(((2-((1-methyl-1H-pyrazol-4-yl)amino)thieno[2,3-d] pyrimidin-4-yl) amino)methyl)azetidin-1-yl)prop-2-en-1-one The product obtained in step 2 (40 mg, 0.13 mmol), 1-methyl-1H-pyrazole-4-amine (19 mg, 0.19 mmol), tris (dibenzylidenepropanone)dipalladium (12 mg, 0.013 mmol), (±)-2,2'-bis(diphenylphosphino)-1,1'-binaphthyl (12 mg, 0.019 mmol) and cesium carbonate (127 mg, 0.39 mmol) were suspended in 1,4-dioxane (1.5 mL), followed by the addition of water (300 µL). Argon air was purged to remove air, and the reaction was carried out with the assistance of microwave at 100° C. for half an hour. The reaction mixture was filtered through celite, and purified by silica gel column chromatography (eluent:dichloromethane/methanol=10:1), to give a yellow solid (9 mg). Yield: 18.8%. MS (ESI, m/z): [M+H]$^+$: 370.2; $^1$H-NMR (300 MHz, CDCl$_3$) δ: 7.79 (bs, 1H), 7.07 (s, 1H), 6.97 (d, 1H, J=6.0 Hz), 6.91 (s, 1H), 6.82 (d, 1H, J=6.0 Hz), 6.75 (bs, 1H), 6.26 (dd, 1H, J=1.8 Hz, J=16.8 Hz), 6.10 (dd, 1H, J=10.2 Hz, J=16.8 Hz), 5.60 (dd, 1H, J=1.8 Hz, J=10.2 Hz), 4.21-4.27 (m, 1H), 4.08-4.14 (m, 1H), 3.92-3.97 (m, 1H), 3.78-3.86 (m, 5H), 3.65-3.76 (m, 1H), 2.95-3.05 (m, 1H).

The following compounds (in Table 4) were prepared from similar starting materials by similar synthetic methods to those described in Example 99.

TABLE 4

| Example | Structure | Characterization Data |
|---|---|---|
| 100 | 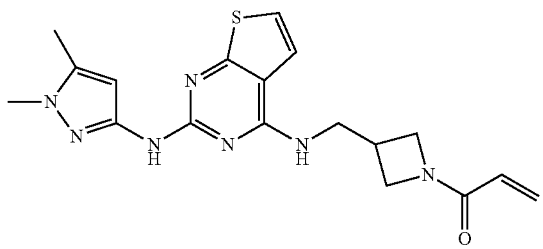 [SMILES: C=CC(=O)N1CC(CNc2nc(Nc3cc(C)n(C)n3)nc3sccc23)C1] | $^1$H-NMR (300 MHz, CDCl$_3$) δ: 7.04 (d, 1H, J = 6.0 Hz), 6.90 (d, 1H, J = 6.0 Hz), 6.53 (s, 1H), 6.32 (dd, 1H, J = 2.1 Hz, J = 16.8 Hz), 6.16 (dd, 1H, J = 10.2 Hz, J = 16.8 Hz), 5.65 (dd, 1H, J = 2.1 Hz, J = 10.2 Hz), 4.26-4.32 (m, 1H), 4.15-4.22 (m, 1H), 4.04-4.09 (m, 1H), 3.85-3.96 (m, 2H), 3.72-3.81 (m, 1H), 3.67 (s, 3H), 3.05-3.10 (m, 1H), 2.26 (s, 3H); LC-MS (ESI, m/z): [M + H]$^+$ = 384.2 |
| 101 | 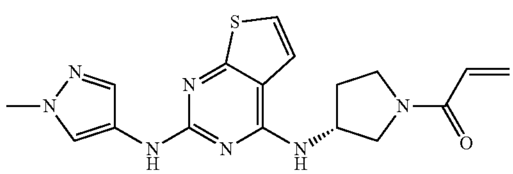 [SMILES: C=CC(=O)N1CC[C@@H](Nc2nc(Nc3cnn(C)c3)nc3sccc23)C1] | $^1$H-NMR (300 MHz, CD$_3$OD) δ: 7.90 (s, 1H), 7.58 (s, 1H), 7.35-7.37 (m, 1H), 6.96-6.98 (m, 1H), 6.56-6.72 (m, 1H), 6.27-6.34 (m, 1H), 5.73-5.81 (m, 1H), 4.80-4.88 (m, 1H), 3.96-4.14 (m, 1H), 3.88 (s, 3H), 3.58-3.86 (m, 3H), 2.14-2.47 (m, 2H); LC-MS (ESI, m/z): [M + H]$^+$ = 370.2 |
| 102 | 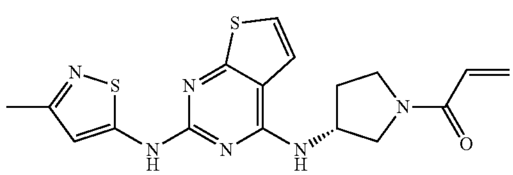 [SMILES: C=CC(=O)N1CC[C@@H](Nc2nc(Nc3cc(C)ns3)nc3sccc23)C1] | $^1$H-NMR (300 MHz, CD$_3$OD) δ: 7.37-7.46 (m, 2H), 7.12-7.15 (m, 1H), 6.56-6.73 (m, 2H), 6.27-6.35 (m, 1H), 5.73-5.81 (m, 1H), 5.00-5.10 (m, 1H), 4.00-4.24 (m, 1H), 3.62-3.91 (m, 3H), 2.13-2.55 (m, 5H); LC-MS (ESI, m/z): [M + H]$^+$ = 387.2 |
| 103 | 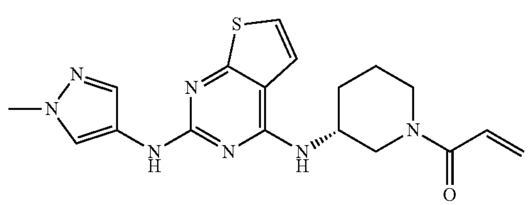 [SMILES: C=CC(=O)N1CCC[C@@H](Nc2nc(Nc3cnn(C)c3)nc3sccc23)C1] | $^1$H-NMR (300 MHz, CD$_3$OD) δ: 7.87-7.94 (m, 1H), 7.51 (d, 1H, J = 11.7 Hz), 7.32 (t, 1H, J = 6.0 Hz), 6.93-6.96 (m, 1H), 6.50-6.88 (m, 1H), 6.08-6.30 (m, 1H), 5.51-5.81 (m, 1H), 4.07-4.26 (m, 2H), 3.83 (s, 3H), 2.66-3.27 (m, 2H), 2.15-2.20 (m, 1H), 1.90-1.95 (m, 1H), 1.60-1.81 (m, 2H); LC-MS (ESI, m/z): [M + H]$^+$ = 384.2 |
| 104 | 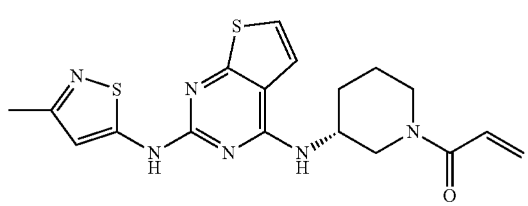 [SMILES: C=CC(=O)N1CCC[C@@H](Nc2nc(Nc3cc(C)ns3)nc3sccc23)C1] | $^1$H-NMR (300 MHz, CD$_3$OD) δ: 7.35-7.42 (m, 1H), 7.07-7.12 (m, 1H), 6.57-6.85 (m, 2H), 6.17 (dd, 1H, J = 16.8 Hz, J = 50.4 Hz), 5.50-580 (m, 1H), 4.80 (bs, 1H), 4.50 (bs, 1H), 4.06-4.22 (m, 2H), 2.70-3.43 (m, 2H), 2.34 (s, 3H), 2.21-2.27 (m, 1H), 1.58-2.05 (m, 3H); LC-MS (ESI, m/z): [M + H]$^+$ = 401.3 |

Example 105

Preparation of (R)-1-(3-(methyl(2-((1-methyl-1H-pyrazol-4-yl)amino)thieno[3,2-d] pyrimidin-4-yl)amino)pyrrolidin-1-yl)prop-2-en-1-one

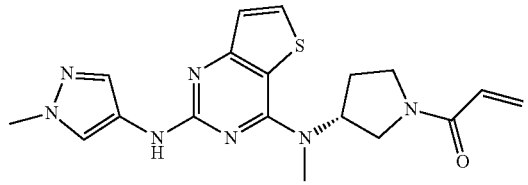 [SMILES: C=CC(=O)N1CC[C@@H](N(C)c2nc(Nc3cnn(C)c3)nc3ccsc23)C1]

Step 1: Preparation of Tert-Butyl (R)-3-((2-chloro-thieno[3,2-d]pyrimidin-4-yl) amino)pyrrolidin-1-yl carboxylate

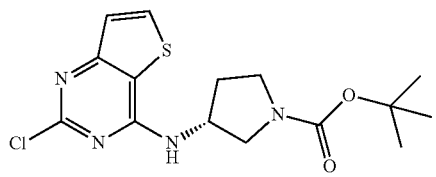 [SMILES: CC(C)(C)OC(=O)N1CC[C@@H](Nc2nc(Cl)nc3ccsc23)C1]

2,4-Dichloro-thieno[3,2-d]pyrimidine (2.26 g, 0.011 mol) and tert-butyl (R)-3-amino pyrrolidin-1-yl carboxylate (2.25 g, 0.012 mol) were dissolved in tetrahydrofuran (50 mL), followed by the addition of N,N-diisopropylethylamine (2.838 g, 0.022 mol). The reaction solution was reacted at 70° C. overnight, and then concentrated. The residue was added with water (50 mL), and extracted with ethyl acetate (50 mL×3). The organic phase was dried over anhydrous sodium sulfate, concentrated under reduced pressure, and purified by silica gel column chromatography (eluent:n-hexane:ethyl acetate=5:1), to give a white solid (3.8 g). Yield: 97.4%. MS (ESI, m/z): [M+H]$^+$: 355.1; $^1$H-NMR (300 MHz, DMSO-d$_6$): 8.05 (d, 1H, J=6.3 Hz), 8.02 (d, 1H, J=5.4 Hz), 7.35 (d, 1H, J=6.3 Hz), 4.60-4.48 (m, 1H), 3.60-3.67 (m, 1H), 3.22-3.48 (m, 3H), 2.15-2.19 (m, 1H), 1.91-2.01 (m, 1H), 1.40 (s, 9H).

Step 2: Preparation of (R)-2-chloro-N-(pyrrolidin-3-yl)thieno[3,2-d]pyrimidine-4-amine

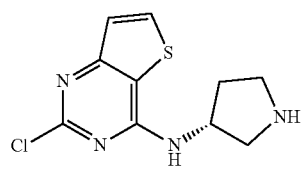 [SMILES: Clc1nc(N[C@@H]2CCNC2)c2sccc2n1]

The compound obtained in step 1 (0.3 g, 0.845 mmol) was dissolved in ethanol (10 mL), followed by the addition of 4N solution of hydrogen chloride in 1,4-dioxane (2 mL, 8 mmol). The reaction solution was reacted at 80° C. for 4 hours, and then concentrated. The resulting crude product was used directly in the next step without further purification. MS (ESI, m/z): [M+H]$^+$: 254.9.

Step 3: Preparation of (R)-1-(3-((2-chloro-thieno[3,2-d]pyrimidin-4-yl)amino) pyrrolidin-1-yl)prop-2-en-1-one

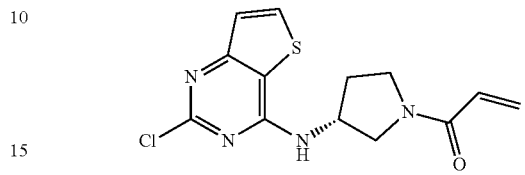

The compound obtained in step 2 (0.497 g, 1.96 mmol) was dissolved in dichloromethane (10 mL), followed by the addition of triethylamine (0.396 g, 3.92 mmol). A solution of acryloyl chloride (0.195 g, 2.15 mmol) dissolved in dichloromethane (5 mL) was added dropwise to the above solution at 0° C. The reaction solution was reacted at room temperature overnight, and then washed with water (20 mL). The organic phase was dried over anhydrous sodium sulfate, concentrated under reduced pressure, and purified by silica gel column chromatography (eluent:dichloromethane/methanol=70:1), to give a white solid (0.44 g). Yield: 72.8%. MS (ESI, m/z): [M+H]$^+$: 309.0; $^1$H-NMR (300 MHz, DMSO-d$_6$): 8.52-8.55 (m, 1H), 8.20 (m, 1H), 7.35 (m, 1H), 6.52-6.67 (m, 1H), 6.11-6.19 (m, 1H), 5.64-5.71 (m, 1H), 4.63-4.80 (m, 1H), 3.43-3.97 (m, 4H), 2.00-2.23 (m, 2H).

Step 4: Preparation of (R)-1-(3-((2-chloro-thieno[3,2-d]pyrimidin-4-yl)methyl) amino)pyrrolidin-1-yl)prop-2-en-1-cm e

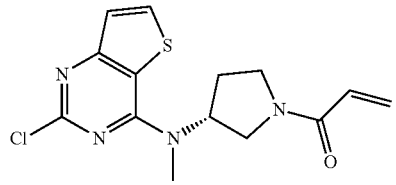 [SMILES: C=CC(=O)N1CC[C@@H](N(C)c2nc(Cl)nc3ccsc23)C1]

To a solution of the compound obtained in step 3 (100 mg, 0.32 mmol) and sodium hydride (60%, in mineral oil, 39 mg, 0.97 mmol) in tetrahydrofuran (15 mL) was added iodomethane (24 µL, 0.39 mmol), and was stirred at room temperature for 3 hours. The reaction solution was concentrated, and then purified by silica gel column chromatography (eluent:dichloromethane/methanol=30:1) to give a white solid (80 mg). Yield: 76.5%. MS (ESI, m/z): [M+H]$^+$: 323.1; $^1$H-NMR (300 MHz, CDCl$_3$): 7.79-7.82 (m, 1H), 7.36-7.38 (m, 1H), 6.40-6.54 (m, 1H), 5.58-5.77 (m, 1H), 3.81-4.03 (m, 2H), 3.48-3.70 (m, 2H), 3.40 (s, 3H), 2.12-2.40 (m, 2H).

Step 5: Preparation of (R)-1-(3-(methyl(2-((1-methyl-1H-pyrazol-4-yl)amino) thieno[3,2-d]pyrimidin-4-yl)amino)pyrrolidin-1-yl)prop-2-en-1 one The compound obtained in step 4 (40 mg, 0.12 mmol), 1-methyl-1H-pyrazole-4-amine (13 mg, 0.14 mmol) and trifluoroacetic acid (20 mg, 0.18 mmol) were dissolved in 2-butanol (1.2 mL), and reacted under microwave at 100° C. for 40 minutes, and then purified by silica gel column chromatography (eluent:dichloromethane/methanol=20:1), to give a brown solid (22 mg). Yield: 46.3%. MS (ESI, m/z): [M+H]$^+$: 384.3; $^1$H-NMR (300 MHz, CDCl$_3$): δ: 7.79 (d, 1H, J=9.9 Hz), 7.68 (d, 1H, J=5.4 Hz), 7.50 (d, 1H, J=5.7 Hz), 7.22 (d, 1H, J=5.7 Hz), 6.42-6.48 (m, 2H), 5.70-5.77 (m, 1H), 5.47-5.56 (m, 1H), 3.79-3.98 (m, 5H), 3.49-3.67 (m, 2H), 3.35 (d, 3H, J=5.4 Hz), 2.12-2.34 (m, 2H).

The following compounds (in Table 5) were prepared from similar starting materials by similar synthetic methods to those described in Example 105.

reacted at 70° C. for 2 hours, then poured into water (20 mL), and extracted with ethyl acetate (20 mL×3). The organic phase was dried over anhydrous sodium sulfate, concentrated under reduced pressure, and purified by silica gel column chromatography (eluent: n-hexane/ethyl acetate=5:1) to give a white solid (250 mg). Yield: 80.0%. MS (ESI, m/z): [M+H]$^+$: 155.8; $^1$H-NMR (300 MHz, CDCl$_3$) δ: 8.16 (s, 1H), 8.08 (s, 1H), 4.48-4.57 (m, 1H), 1.57 (s, 3H), 1.55 (s, 3H).

TABLE 5

| Example | Structure | Characterization Data |
|---|---|---|
| 106 | 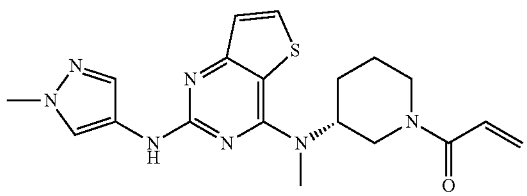 [SMILES: C=CC(=O)N1CCC[C@@H](N(C)c2nc(Nc3cnn(C)c3)nc3ccsc23)C1] | $^1$H-NMR (300 MHz, CDCl$_3$) δ: 7.75 (s, 1H), 7.69 (d, 1H, J = 5.4 Hz), 7.47-7.52 (m, 1H), 7.22 (d, 1H, J = 5.4 Hz), 6.50-6.69 (m, 1H), 6.29-6.37 (m, 1H), 5.63-5.76 (m, 1H), 4.70-4.82 (m, 2H), 4.06-4.15 (m, 1H), 3.85 (s, 3H), 3.37 (s, 3H), 2.50-3.18 (m, 2H), 1.94-2.04 (m, 2H); LC-MS (ESI, m/z): [M + H]$^+$ = 398.3 |
| 107 | 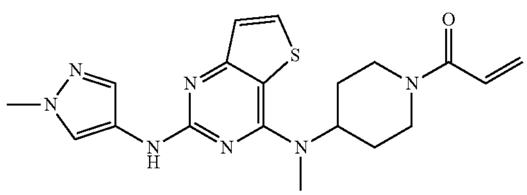 [SMILES: C=CC(=O)N1CCC(N(C)c2nc(Nc3cnn(C)c3)nc3ccsc23)CC1] | $^1$H-NMR (300 MHz, CDCl$_3$) δ: 7.76-7.78 (m, 1H), 7.64-7.65 (m, 2H), 7.29 (s, 1H), 6.62 (dd, 1H, J = 10.5 Hz, J = 16.8 Hz), 6.33 (dd, 1H, J = 1.8 Hz, J = 16.8 Hz), 5.75 (dd, 1H, J = 1.8 Hz, J = 10.5 Hz), 4.89-5.08 (m, 2H), 4.17-4.21 (m, 1H), 3.89 (s, 3H), 3.32 (s, 3H), 3.20-3.30 (m, 2H), 2.71-2.79 (m, 1H), 1.69-1.90 (m, 4H); LC-MS (ESI, m/z): [M + H]$^+$ = 398.3 |

Example 108

Preparation of 1-(3-(((2-((1-isopropyl-1H-pyrazol-4-ylamino)thieno[3,2-d]pyrimidin-4-yl)amino)methyl)azetidin-1-yl)prop-2-en-1-one

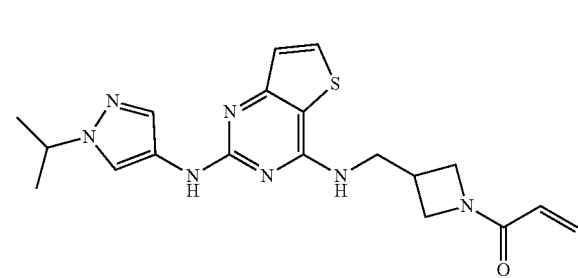 [SMILES: C=CC(=O)N1CC(CNc2nc(Nc3cnn(C(C)C)c3)nc3ccsc23)C1]

Step 1: Preparation of 1-isopropyl-4-nitro-1H-pyrazole

4-Nitro-1H-pyrazole (226 mg, 2 mmol) and 2-iodopropane (340 mg, 2 mmol) were dissolved in N,N-dimethylformamide (5 mL), followed by the addition of potassium carbonate (276 mg, 2 mmol). The reaction solution was

Step 2: Preparation of 1-isopropyl-1H-pyrazole-4-amine

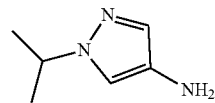

The product obtained in step 1 (250 mg, 1.61 mmol) was dissolved in ethanol (10 mL), followed by the addition of palladium on carbon (25 mg), and reacted under hydrogen atmosphere for 2 hours at room temperature. The reaction solution was filtered and concentrated, and the resulting crude product was used directly in the next step. MS (ESI, m/z): [M+H]$^+$: 125.9.

Step 3: Preparation of 1-(3-(((2-((1-isopropyl-1H-pyrazol-4-yl-amino)thieno[3,2-d] pyrimidin-4-yl)amino)methyl)azetidin-1-yl)prop-2-en-1-one The product obtained in step 3 of Example 61 (30 mg, 0.1 mmol) and 1-isopropyl-1H-pyrazole-4-amine (19 mg, 0.15 mmol) were dissolved in 1,4-dioxane (2 mL). The reaction solution was adjusted to pH 5 with trifluoroacetic acid, and reacted under microwave irradiation at 90° C. for 0.5 hours. The reaction solution was cooled to room temperature, adjusted with 1N sodium hydroxide solution to pH 8, and extracted with ethyl acetate (10 mL×3). The organic phase was dried over anhydrous sodium sulfate, concentrated under reduced pressure, and purified by silica gel column chromatography (eluent:dichloromethane/methanol=20:1) to give a yellow solid (15 mg). Yield: 37.8%. MS (ESI, m/z): [M+H]$^+$: 398.3; $^1$H-NMR (300 MHz, DMSO-d$_6$) δ: 7.81 (s, 1H), 7.64 (d, 1H, J=5.4 Hz), 7.60 (s, 1H), 7.20 (d, 1H, J=5.4

Hz), 6.31-6.37 (m, 1H), 6.13-6.22 (m, 1H), 5.66-5.70 (m, 1H), 4.31-4.37 (m, 1H), 4.18-4.24 (m, 1H), 4.00-4.05 (m, 1H), 3.81-3.95 (m, 3H), 3.09 (m, 1H), 1.53 (s, 3H), 1.51 (s, 3H).

The following compounds (in Table 6) were prepared from similar starting materials by similar synthetic methods to those described in Example 108.

TABLE 6

| Example | Structure | Characterization Data |
| --- | --- | --- |
| 109 | 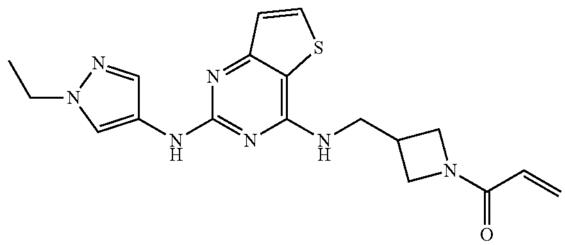 [SMILES: C=CC(=O)N1CC(CNc2nc(Nc3cnn(CC)c3)nc3ccsc23)C1] | $^1$H-NMR (300 MHz, CD$_3$OD) δ: 8.17 (m, 2H), 7.74 (s, 1H), 7.28 (d, 1H, J = 5.1 Hz), 6.28 (m, 2H), 5.73 (q, 1H, J = 3.9 Hz), 4.22 (q, 2H, J = 7.2 Hz), 4.35 (m, 1H), 3.95 (m, 1H), 3.71 (m, 1H), 3.40-3.53 (m, 3H), 2.63 (m, 1H), 1.50 (t, 3H, J = 7.2 Hz); LC-MS (ESI, m/z): [M + H]$^+$ = 384.3 |
| 110 | 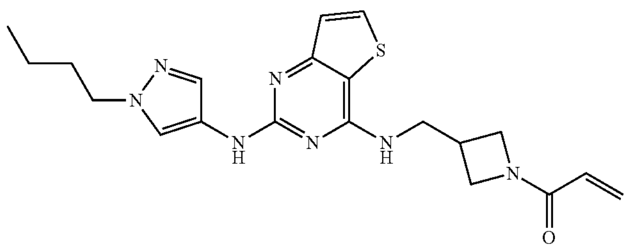 [SMILES: C=CC(=O)N1CC(CNc2nc(Nc3cnn(CCCC)c3)nc3ccsc23)C1] | $^1$H-NMR (300 MHz, CD$_3$OD) δ: 8.19 (d, 2H, J = 5.1 Hz), 8.14 (s, 1H), 7.28 (d, 1H, J = 5.4 Hz), 6.22-6.36 (m, 2H), 5.72 (dd, 1H, J = 2.4 Hz, J = 8.7 Hz), 4.31-4.37 (m, 1H), 4.18 (t, 2H, J = 7.2 Hz), 3.92-3.99 (m, 1H), 3.71-3.77 (m, 1H), 3.52 (d, 2H, J = 6.6 Hz), 3.41-3.48 (m, 1H), 2.62-2.67 (m, 1H), 1.85-1.90 (m, 2H), 1.30-1.40 (m, 3H), 8.19 (t, 3H, J = 7.5 Hz); LC-MS (ESI, m/z): [M + H]$^+$ = 412.3 |
| 111 | 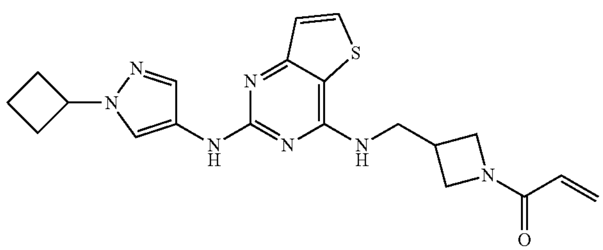 [SMILES: C=CC(=O)N1CC(CNc2nc(Nc3cnn(C4CCC4)c3)nc3ccsc23)C1] | $^1$H-NMR (300 MHz, CDCl$_3$) δ: 8.22 (s, 1H), 7.81 (s, 1H), 7.65 (m, 2H), 7.20 (d, 1H, J = 5.1 Hz), 6.32-6.38 (m, 1H), 6.14-6.23 (m, 1H), 6.11 (s, 1H), 5.68-5.71 (m, 1H), 4.71-4.76 (m, 1H), 4.33-4.38 (m, 1H), 4.19-4.25 (m, 1H), 4.03-4.07 (m, 1H), 3.83-3.97 (m, 3H), 3.12 (m, 1H), 2.36-2.59 (m, 4H), 1.84-1.92 (m, 2H); LC-MS (ESI, m/z): [M + H]$^+$ = 410.4 |
| 112 | 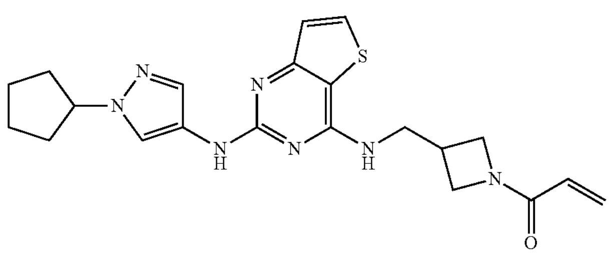 [SMILES: C=CC(=O)N1CC(CNc2nc(Nc3cnn(C4CCCC4)c3)nc3ccsc23)C1] | $^1$H-NMR (300 MHz, CDCl$_3$) δ: 9.94 (s, 1H), 8.41-8.45 (m, 1H), 8.16 (d, 1H, J = 5.4 Hz), 7.81 (d, 1H, J = 2.4 Hz), 7.44 (d, 1H, J = 5.4 Hz), 6.22-6.31 (m, 1H), 6.08-6.15 (m, 1H), 5.97 (d, 1H, J = 2.4 Hz), 5.61-5.65 (m, 1H), 4.58-4.64 (m, 1H), 3.56-4.02 (m, 5H), 1.67-2.36 (m, 10 H); LC-MS (ESI, m/z): [M + H]$^+$ = 424.5 |
| 113 | 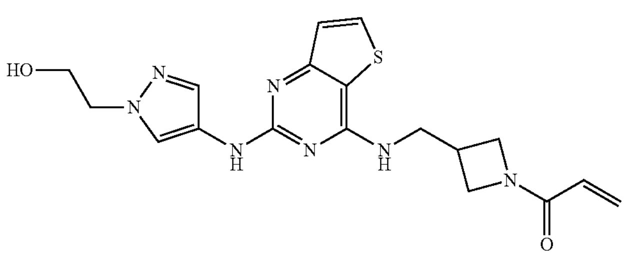 [SMILES: C=CC(=O)N1CC(CNc2nc(Nc3cnn(CCO)c3)nc3ccsc23)C1] | $^1$H-NMR (300 MHz, CD$_3$OD) δ: 8.18 (d, 2H, J = 5.4 Hz), 7.79 (s, 1H), 7.25 (d, 1H, J = 5.4 Hz), 6.28 (m, 2H), 5.72 (dd, 1H, J = 3.0 Hz, J = 9.0 Hz), 4.35 (dd, 1H, J = 4.5 Hz, J = 12.3 Hz), 4.26 (t, 2H, J = 5.1 Hz), 4.11 (m, 1H), 3.95 (m, 3H), 3.73 (m, 1H), 3.52 (d, 1H, J = 6.6 Hz), 3.43 (m, 1H), 2.65 (m, 1H); LC-MS (ESI, m/z): [M + H]$^+$ = 400.3 |

TABLE 6-continued

| Example | Structure | Characterization Data |
|---|---|---|
| 114 | 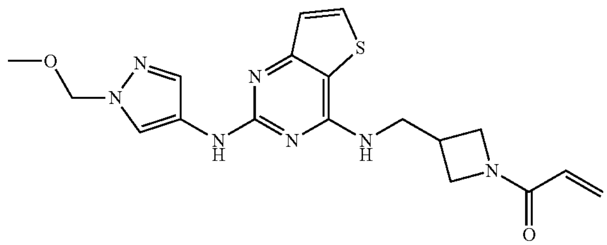 [SMILES: C=CC(=O)N1CC(CNc2nc(Nc3cnn(COC)c3)nc3ccsc23)C1] | $^1$H-NMR (300 MHz, CD$_3$OD) δ: 8.11 (s, 1H), 7.86 (d, 1H, J = 5.4 Hz), 7.69 (s, 1H), 7.15 (d, 1H, J = 5.1 Hz), 6.20-6.38 (m, 2H), 5.71-5.75 (m, 1H), 5.38 (s, 2H), 4.38-4.44 (m, 1H), 4.13-4.20 (m, 2H), 3.85-3.94 (m, 3H), 3.34 (s, 3H), 3.14 (m, 1H); LC-MS (ESI, m/z): [M + H]$^+$ = 400.3 |
| 115 | 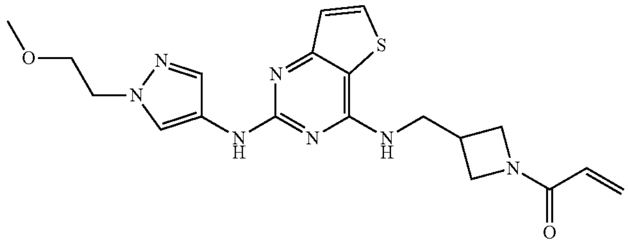 [SMILES: C=CC(=O)N1CC(CNc2nc(Nc3cnn(CCOC)c3)nc3ccsc23)C1] | $^1$H-NMR (300 MHz, CD$_3$OD) δ: 7.95 (s, 1H), 7.77 (d, 1H, J = 5.1 Hz), 7.58 (s, 1H), 7.09 (d, 1H, J = 5.4 Hz), 6.19-6.34 (m, 2H), 5.68-5.72 (m, 1H), 4.34-4.39 (m, 1H), 4.24 (t, 2H, J = 5.1 Hz), 4.10-4.18 (m, 2H), 3.87-3.93 (m, 1H), 3.81-3.85 (m, 2H), 3.72 (t, 2H, J = 5.1 Hz), 3.33 (s, 3H), 3.04-3.18 (m, 1H); LC-MS (ESI, m/z): [M + H]$^+$ = 414.3 |
| 116 | 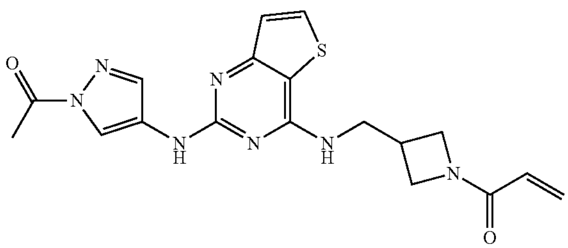 [SMILES: C=CC(=O)N1CC(CNc2nc(Nc3cnn(C(C)=O)c3)nc3ccsc23)C1] | $^1$H-NMR (300 MHz, CD$_3$OD) δ: 8.17 (m, 2H), 7.74 (s, 1H), 7.28 (d, 1H, J = 5.1 Hz), 6.28 (m, 2H), 5.73 (q, 1H, J = 3.9 Hz), 4.35 (m, 1H), 3.95 (m, 1H), 3.71 (m, 1H), 3.40-3.53 (m, 3H), 2.85 (s, 3H), 2.63 (m, 1H); LC-MS (ESI, m/z): [M + H]$^+$ = 398.3 |
| 117 | 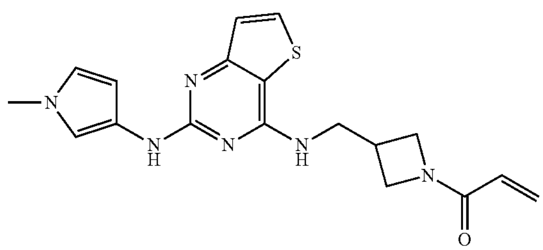 [SMILES: C=CC(=O)N1CC(CNc2nc(Nc3ccn(C)c3)nc3ccsc23)C1] | $^1$H-NMR (300 MHz, CD$_3$OD) δ: 8.01 (d, 1H, J = 5.4 Hz), 7.20 (d, 1H, J = 5.4 Hz), 6.65-6.67 (m, 1H), 6.21-6.36 (m, 2H), 6.08-6.11 (m, 1H), 5.72-5.76 (m, 1H), 4.38-4.44 (m, 1H), 4.08-4.22 (m, 2H), 3.87-3.96 (m, 3H), 3.69 (s, 3H), 3.61-3.77 (m, 1H); LC-MS (ESI, m/z): [M + H]$^+$ = 369.2 |
| 118 | 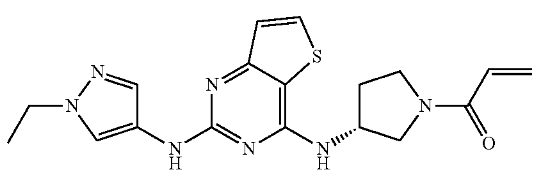 [SMILES: C=CC(=O)N1CC[C@@H](Nc2nc(Nc3cnn(CC)c3)nc3ccsc23)C1] | $^1$H-NMR (300 MHz, CD$_3$OD) δ: 7.93 (s, 1H), 7.85 (dd, 1H, J = 1.2 Hz, J = 5.4 Hz), 7.61 (s, 1H), 7.14 (d, 1H, J = 5.1 Hz), 6.55-6.71 (m, 1H), 6.26-6.34 (m, 1H), 5.73-5.80 (m, 1H), 4.09 (q, 2H, J = 6.9 Hz), 3.72-4.01 (m, 3H), 3.57-3.67 (m, 2H), 2.12-2.53 (m, 2H), 1.47 (t, 3H, J = 7.2 Hz); LC-MS (ESI, m/z): [M + H]$^+$ = 384.3 |
| 119 | 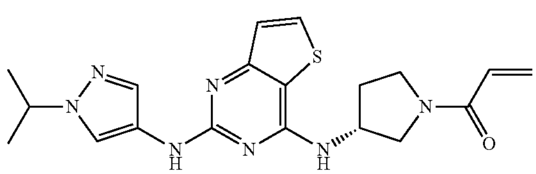 [SMILES: C=CC(=O)N1CC[C@@H](Nc2nc(Nc3cnn(C(C)C)c3)nc3ccsc23)C1] | $^1$H-NMR (300 MHz, CDCl$_3$) δ: 7.62-7.81 (m, 3H), 7.20 (d, 1H, J = 5.1 Hz), 6.44 (d, 1H, J = 6.0 Hz), 6.38 (d, 1H, J = 6.0 Hz), 5.67-5.76 (m, 1H), 4.87-4.95 (m, 1H), 4.42-4.51 (m, 1H), 3.57-3.98 (m, 4H), 2.28-2.39 (m, 1H), 1.50-1.52 (m, 6H), 1.42-1.45 (m, 1H); LC-MS (ESI, m/z): [M + H]$^+$ = 398.4 |
| 120 | 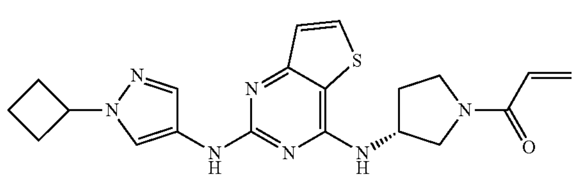 [SMILES: C=CC(=O)N1CC[C@@H](Nc2nc(Nc3cnn(C4CCC4)c3)nc3ccsc23)C1] | $^1$H-NMR (300 MHz, CDCl$_3$) δ: 7.86 (d, 1H, J = 8.4 Hz), 7.58-7.62 (m, 2H), 7.16-7.20 (m, 1H), 6.37-6.46 (m, 2H), 5.66-5.75 (m, 1H), 4.67-4.92 (m, 2H), 3.58-4.02 (m, 5H), 2.42-2.62 (m, 4H), 2.26-2.37 (m, 2H), 2.07-2.15 (m, 1H), 1.78-1.93 (m, 2H); LC-MS (ESI, m/z): [M + H]$^+$ = 410.4 |

TABLE 6-continued

| Example | Structure | Characterization Data |
|---|---|---|
| 121 | 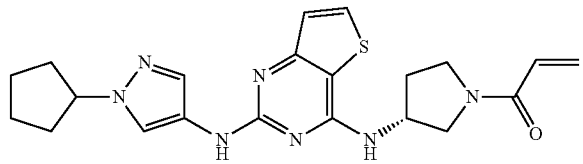 [SMILES: C=CC(=O)N1CC[C@@H](Nc2nc(Nc3cnn(C4CCCC4)c3)nc3ccsc23)C1] | $^1$H-NMR (300 MHz, CDCl$_3$) δ: 7.84 (d, 1H, J = 6.0 Hz), 7.56-7.61 (m, 2H), 7.16-7.19 (m, 1H), 6.37-6.46 (m, 2H), 5.66-5.75 (m, 1H), 4.83-4.94 (m, 1H), 4.57-4.66 (m, 1H), 3.56-4.02 (m, 5H), 1.67-2.36 (m, 10H); LC-MS (ESI, m/z): [M + H]$^+$ = 424.4 |
| 122 | 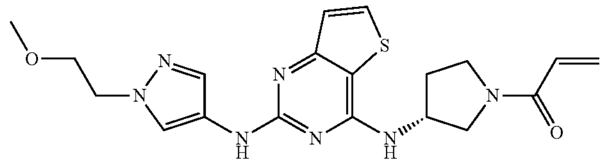 [SMILES: C=CC(=O)N1CC[C@@H](Nc2nc(Nc3cnn(CCOC)c3)nc3ccsc23)C1] | $^1$H-NMR (300 MHz, CD$_3$OD) δ: 7.97 (s, 1H), 7.87 (dd, 1H, J = 1.8 Hz, J = 5.4 Hz), 7.62 (s, 1H), 7.13 (d, 1H, J = 5.4 Hz), 6.55-6.71 (m, 1H), 6.26-6.34 (m, 1H), 5.73-5.80 (m, 1H), 4.28-4.31 (m, 2H), 4.11-4.26 (m, 1H), 3.59-3.98 (m, 6H), 3.31 (s, 3H), 2.17-2.48 (m, 2H); LC-MS (ESI, m/z): [M + H]$^+$ = 414.4 |
| 123 | 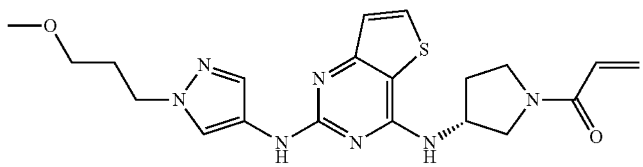 [SMILES: C=CC(=O)N1CC[C@@H](Nc2nc(Nc3cnn(CCCOC)c3)nc3ccsc23)C1] | $^1$H-NMR (300 MHz, CD$_3$OD) δ: 7.90 (m, 2H), 7.62 (s, 1H), 7.15 (d, 1H, J = 6.0 Hz), 6.61 (m, 1H), 6.31 (m, 1H), 5.77 (t, 1H, J = 10.5 Hz), 3.60-4.25 (m, 8H), 3.38 (s, 3H), 2.03-2.36 (m, 5H); LC-MS (ESI, m/z): [M + H]$^+$ = 428.3 |
| 124 | 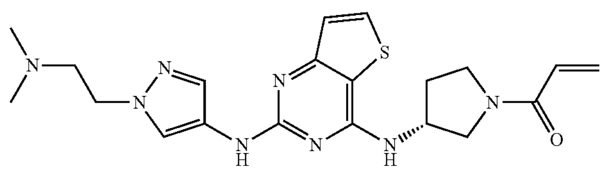 | $^1$H-NMR (300 MHz, CD$_3$OD) δ: 8.03 (m, 2H), 7.73 (s, 1H), 7.29 (d, 1H, J = 5.4 Hz), 6.64 (m, 1H), 6.31 (m, 1H), 5.78 (m, 1H), 4.63 (m, 2H), 4.13 (m, 1H), 4.04 (m, 1H), 3.85 (m, 1H), 3.60-3.80 (m, 4H), 3.47 (s, 1H), 3.36 (s, 3H), 2.20-2.50 (m, 3H), 2.02 (m, 1H); LC-MS (ESI, m/z): [M + H]$^+$ = 427.4 |
| 125 | 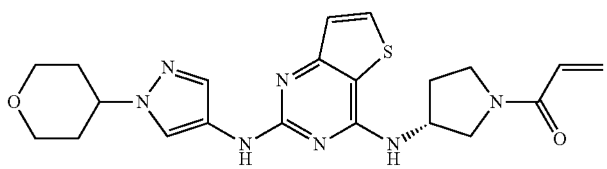 [SMILES: C=CC(=O)N1CC[C@@H](Nc2nc(Nc3cnn(C4CCOCC4)c3)nc3ccsc23)C1] | $^1$H-NMR (300 MHz, CD$_3$OD) δ: 7.93-8.00 (m, 2H), 7.64 (s, 1H), 7.18 (d, 1H, J = 5.4 Hz), 6.54-6.71 (m, 1H), 6.31 (m, 1H), 6.27-6.34 (m, 1H), 5.73-5.81 (m, 1H), 3.58-4.13 (m, 8H), 2.00-2.48 (m, 6H), 1.29-1.35 (m, 2H); LC-MS (ESI, m/z): [M + H]$^+$ = 440.4 |
| 126 | 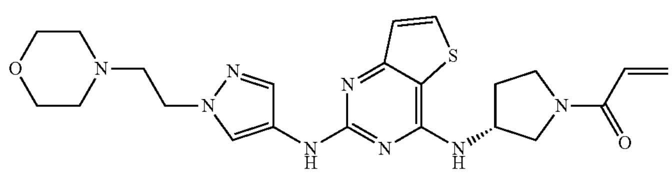 [SMILES: C=CC(=O)N1CC[C@@H](Nc2nc(Nc3cnn(CCN4CCOCC4)c3)nc3ccsc23)C1] | $^1$H-NMR (300 MHz, CD$_3$OD) δ: 7.99 (s, 1H), 7.90 (m, 1H), 7.66 (s, 1H), 7.16 (dd, 1H, J = 0.4 Hz, J = 5.4 Hz), 6.63 (m, 1H), 6.30 (m, 1H), 5.77 (m, 1H), 4.34 (m, 2H), 4.13 (m, 1H), 3.75-4.01 (m, 2H), 3.72 (m, 4H), 3.65 (m, 1H), 2.95 (m, 2H), 2.63 (m, 4H), 2.19-2.43 (m, 2H); LC-MS (ESI, m/z): [M + H]$^+$ = 469.3 |
| 127 | 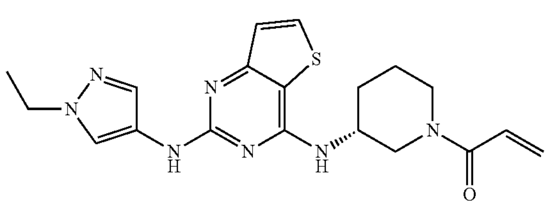 [SMILES: C=CC(=O)N1CCC[C@@H](Nc2nc(Nc3cnn(CC)c3)nc3ccsc23)C1] | $^1$H-NMR (300 MHz, CD$_3$OD) δ: 7.91 (m, 2H), 7.55 (d, 1H, J = 13.5 Hz), 7.14 (d, 1H, J = 5.1 Hz), 6.49-6.90 (m, 1H), 6.07-6.31 (m, 1H), 5.53-5.83 (m, 1H), 4.83 (m, 1H), 4.12-4.33 (m, 4H), 3.19 (q, 1H, J = 12.0 Hz), 2.74-3.01 (m, 1H), 2.17 (d, 1H, J = 12.0 Hz), 1.94 (d, 1H, J = 13.2 Hz), 1.80 (m, 1H), 1.60 (m, 1H), 1.42 (m, 3H); LC-MS (ESI, m/z): [M + H]$^+$ = 398.3 |
| 128 | 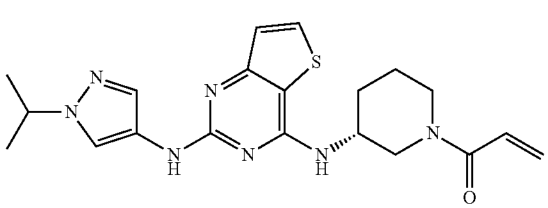 [SMILES: C=CC(=O)N1CCC[C@@H](Nc2nc(Nc3cnn(C(C)C)c3)nc3ccsc23)C1] | $^1$H-NMR (300 MHz, CD$_3$OD) δ: 7.93 (m, 2H), 7.58 (d, 1H, J = 7.8 Hz), 7.17 (t, 1H, J = 5.1 Hz), 6.52-6.92 (m, 1H), 6.07-6.30 (m, 1H), 5.55-5.83 (m, 1H), 4.80 (dd, 1H, J = 4.2 Hz, J = 12.9 Hz), 4.51 (q, 1H, J = 6.9 Hz), 4.32 (m, 1H), 4.12 (m, 1H), 3.25 (m, 1H), 2.78-3.00 (m, 1H), 2.19 (m, 1H), 1.97 (m, 1H), 1.82 (m, 1H), 1.65 (m, 1H), 1.47 (m, 6H); LC-MS (ESI, m/z): [M + H]$^+$ = 412.4 |

TABLE 6-continued

| Example | Structure | Characterization Data |
|---|---|---|
| 129 | 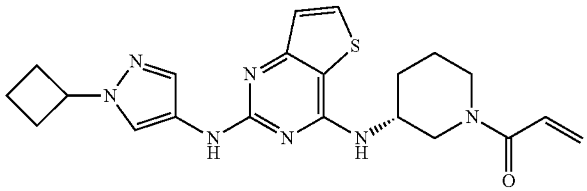 [SMILES: C=CC(=O)N1CCC[C@@H](Nc2nc(Nc3cnn(C4CCC4)c3)nc3ccsc23)C1] | $^1$H-NMR (300 MHz, CD$_3$OD) δ: 7.98 (s, 1H), 7.93 (t, 1H, J = 5.1 Hz), 7.59 (d, 1H, J = 2.1 Hz), 7.15 (d, 1H, J = 5.4 Hz), 6.47-6.92 (m, 1H), 6.01-6.33 (m, 1H), 5.51-5.85 (m, 1H), 4.80 (m, 1H), 4.10-4.37 (m, 3H), 3.19 (t, 1H, J = 10.5 Hz), 2.77-2.95 (m, 1H), 2.44-2.59 (m, 4H), 2.19 (d, 1H, J = 12.0 Hz), 1.78-1.99 (m, 4H), 1.59-1.68 (m, 1H); LC-MS (ESI, m/z): [M + H]$^+$ = 424.4 |
| 130 | 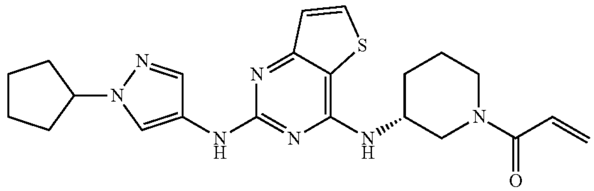 [SMILES: C=CC(=O)N1CCC[C@@H](Nc2nc(Nc3cnn(C4CCCC4)c3)nc3ccsc23)C1] | $^1$H-NMR (300 MHz, CD$_3$OD) δ: 7.95 (d, 1H, J = 9.9 Hz), 7.83 (d, 1H, J = 5.4 Hz), 7.54 (d, 1H, J = 6.9 Hz), 7.11 (d, 1H, J = 5.4 Hz), 6.51-6.91 (m, 1H), 6.06-6.31 (m, 1H), 5.52-5.83 (m, 1H), 4.85 (m, 1H), 4.62 (m, 1H), 4.31 (m, 1H), 4.14 (m, 1H), 3.21 (m, 1H), 2.74-3.01 (m, 1H), 2.16 (m, 3H), 1.65-2.03 (m, 9H); LC-MS (ESI, m/z): [M + H]$^+$ = 438.5 |
| 131 | 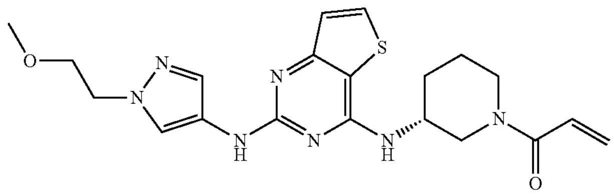 [SMILES: C=CC(=O)N1CCC[C@@H](Nc2nc(Nc3cnn(CCOC)c3)nc3ccsc23)C1] | $^1$H-NMR (300 MHz, CD$_3$OD) δ: 8.00 (d, 1H, J = 10.8 Hz), 7.86 (d, 1H, J = 1.8 Hz, J = 5.4 Hz), 7.58 (d, 1H, J = 10.8 Hz), 7.13 (d, 1H, J = 5.4 Hz), 6.52-6.90 (m, 1H), 6.08-6.32 (m, 1H), 5.53-5.84 (m, 1H), 4.10-4.27 (m, 5H), 3.67-3.76 (m, 3H), 3.32 (s, 3H), 3.07-3.27 (m, 1H), 2.17-2.23 (m, 1H), 1.93-2.02 (m, 1H), 1.62-1.86 (m, 2H); LC-MS (ESI, m/z): [M + H]$^+$ = 428.5 |

Example 132

Preparation of (R)-1-(3-((2-((3-methyl-isothiazol-5-yl)amino)thieno[3,2-d]pyrimidin-4-yl)amino)pyrrolidin-1-yl)prop-2-en-1-one

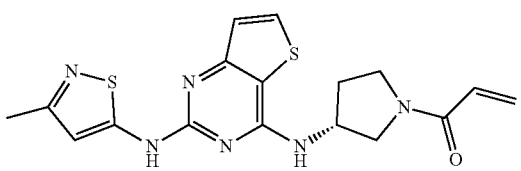 [SMILES: C=CC(=O)N1CC[C@@H](Nc2nc(Nc3cc(C)ns3)nc3ccsc23)C1]

Step 1: Preparation of Tert-Butyl (R)-3-((2-((3-methyl-isothiazol-5-yl)amino) thieno[3,2-d]pyrimidin-4-yl)amino)pyrrolidine-1-carboxylate

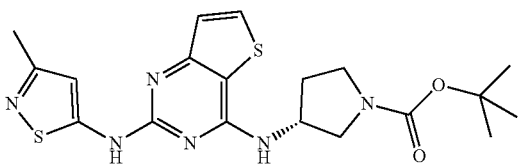 [SMILES: Cc1cc(Nc2nc(N[C@@H]3CCN(C(=O)OC(C)(C)C)C3)c3sccc3n2)sn1]

The product obtained in step 1 of Example 105 (35.6 g, 0.1 mol) and 3-methyl-isothiazole-5-amine hydrochloride (16.3 g, 0.11 mol) were dissolved in 1,4-dioxane/water (700 mL, 20:1), followed by the addition of tris (dibenzylidenepropanone)dipalladium (7.3 g, 8 mmol), (±)-2,2'-bis(diphenylphosphino)-1,1'-binaphthyl (7.5 g, 12 mmol) and cesium carbonate (130 g, 0.4 mol) under nitrogen atmosphere, and refluxed at 100° C. overnight. The reaction solution was cooled to room temperature, and filtered through celite. The filtrate was concentrated under reduced pressure, and purified by silica gel column chromatography (eluent:dichloromethane:methanol=30:1) to give a crude yellow solid (44 g). To the crude product was added a solvent mixture (n-hexane:dichloromethane:ethyl acetate=3:1:1) (500 mL). The mixture was stirred at 70° C. for 1 hour, cooled in an ice bath, and filtered to give a pale yellow solid (35 g). Yield: 80.6%. MS (ESI, m/z): [M+H]$^+$: 433.3; $^1$H-NMR (300 MHz, CDCl$_3$) δ: 7.69 (d, 1H, J=3.6 Hz), 7.22 (s, 1H), 6.46 (s, 1H), 5.00-5.30 (m, 2H), 3.46-3.87 (m, 4H), 2.37-2.40 (m, 4H), 2.12 (m, 1H), 1.84-1.86 (m, 1H), 1.49 (s, 9H).

Step 2: Preparation of (R)—N$^2$-(3-methyl-isothiazol-5-yl)-N$^4$-(pyrrolidin-3-yl) thieno[3,2-d]pyrimidine-2,4-diamine

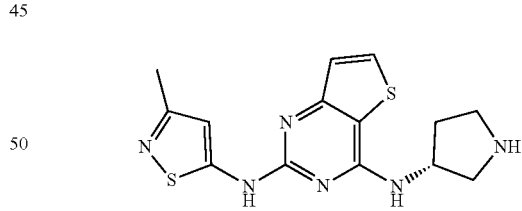

The product obtained in step 1 (35 g, 0.081 mol) was dissolved in dichloromethane (1.5 L), and to solubilize it methanol (1 L) was added, followed by the addition of 4N solution of hydrogen chloride in 1,4-dioxane (200 mL, 0.8 mol), and then reacted at room temperature for 2 hours. The reaction solution was concentrated under reduced pressure, and used directly in the next step. MS (ESI, m/z): [M+H]$^+$: 333.1.

Step 3: Preparation of (R)-1-(3-((2-((3-methyl-isothiazol-5-yl)amino)thieno[3,2-d] pyrimidin-4-yl) amino)pyrrolidin-1-yl)prop-2-en-1-one The product obtained in step 2 (26.9 g, 0.081 mol) was dissolved in dichloromethane (500 mL), followed by the addition of triethylamine (16.36 g, 0.162 mol) in an ice bath, and then the dropwise addition of a solution of acryloyl chloride (7.33 g, 0.081 mol) in dichloromethane (50 mL) in the ice bath, and reacted at room temperature overnight. The reaction solution was concentrated under reduced pressure, and purified by silica gel column chromatography (eluent: dichloromethane/methanol=30:1) to give a white solid (15 g). Yield: 47.9%. MS (ESI, m/z): [M+H]$^+$: 387.2; $^1$H-NMR (300 MHz, DMSO-d$_6$) δ: 8.06-8.14 (m, 2H), 7.23 (s, 1H), 6.53-6.70 (m, 2H), 6.12-6.20 (m, 1H), 5.64-5.72 (m, 1H), 4.88 (s, 1H), 3.51-4.09 (m, 4H), 2.05-2.66 (m, 6H).

Example 133

Preparation of (R)-1-(3-((2-((3-methyl-isothiazol-5-yl)amino)thieno[3,2-d]pyrimidin-4-yl)amino)pyrrolidin-1-yl)prop-2-yn-1-one

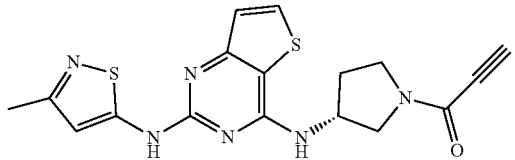 [SMILES: C#CC(=O)N1CC[C@@H](Nc2nc(Nc3cc(C)ns3)nc3ccsc23)C1]

The product obtained in step 2 of Example 132 (33 mg, 0.10 mmol) and propiolic acid (8.4 mg, 0.12 mmol) were dissolved in tetrahydrofuran (10 mL), followed by the addition of N,N-diisopropylethylamine (53 μL). The mixture was stirred at room temperature for 30 minutes, followed by the addition of TBTU (4 mg). The mixture was stirred at room temperature overnight, concentrated and purified by silica gel column chromatography (eluent:dichloromethane/methanol=10:1) to give a pale yellow solid (6.4 mg). Yield: 16.7%. MS (ESI, m/z): [M+H]$^+$: 385.2; $^1$H-NMR (300 MHz, CD$_3$OD) δ: 7.89-7.92 (m, 1H), 7.22 (d, 1H, J=5.1 Hz), 6.62 (s, 1H), 5.04 (s, 1H), 3.53-4.86 (m, 5H), 2.42-2.50 (m, 1H), 2.35 (s, 3H), 2.20-2.28 (m, 1H).

Example 134

Preparation of (R)-1-(3-((2-((3-methyl-isothiazol-5-yl)amino)pyrrolo[2,1-f][1,2,4] triazin-4-yl)amino) piperidin-1-yl)prop-2-en-1-one

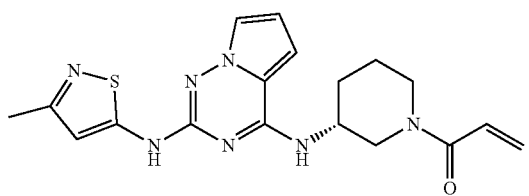 [SMILES: C=CC(=O)N1CCC[C@@H](Nc2nc(Nc3cc(C)ns3)nn3cccc23)C1]

Step 1: Preparation of tert-butyl (R)-3-((2-chloro-pyrrolo[2,1-f][1,2,4]triazin-4-yl)amino)piperidine-1-carboxylate

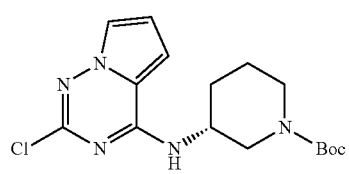 [SMILES: CC(C)(C)OC(=O)N1CCC[C@@H](Nc2nc(Cl)nn3cccc23)C1]

2,4-Dichloro-pyrrolo[2,1-f][1,2,4]triazine (325 mg, 1.73 mmol) and (R)-1-tert-butoxycarbonyl-3-amino piperidine (364 mg, 1.80 mmol) were dissolved in tetrahydrofuran (50 mL), followed by the addition of N,N-diisopropylethylamine (603 μL, 3.46 mmol) under stirring at room temperature, and refluxed for 3 hours. The reaction solution was concentrated, re-dissolved in dichloromethane (50 mL), washed with water (30 mL), concentrated, and dried over anhydrous sodium sulfate to give a crude product (640 mg). MS (ESI, m/z): [M+H]$^+$: 352.2.

Step 2: Preparation of (R)-1-(3-((2-chloro-pyrrolo[2,1-f][1,2,4]triazin-4-yl)amino) piperidin-1-yl)prop-2-en-1-one

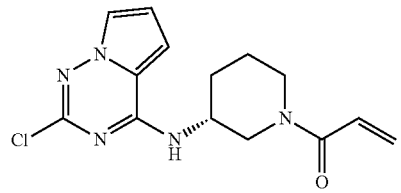 [SMILES: C=CC(=O)N1CCC[C@@H](Nc2nc(Cl)nn3cccc23)C1]

The crude product obtained in step 1 (640 mg) was dissolved in dichloromethane (3 mL), followed by the addition of trifluoroacetic acid (1.5 mL) under stirring at room temperature. After stirring for 3 hours, the reaction solution was concentrated under reduced pressure to remove most of trifluoroacetic acid. The residue was re-dissolved in dichloromethane (30 mL), followed by the addition of N,N-diisopropylethylamine (603 μL, 3.46 mmol) under stirring at room temperature. A solution of acryloyl chloride (140 μL, 1.73 mmol) in dichloromethane (20 mL) was slowly, dropwise added in an ice bath. After 5 hours, water (50 mL) was added to the reaction system. The organic phase was separated, dried over anhydrous sodium sulfate, and concentrated to give a pale yellow solid, which was purified by silica gel column chromatography (eluent:dichloromethane/methanol=70:1) to give a white solid (408 mg). Yield: 77.14%. MS (ESI, m/z): [M+H]$^+$: 306.2.

Step 3: Preparation of (R)-1-(3-((2-((3-methyl-isothiazol-5-yl)amino) pyrrolo[2,1-f][1,2,4]triazin-4-yl)amino)piperidin-1-yl)prop-2-en-1-one The product obtained in step 2 (31 mg, 0.1 mmol), 3-methyl-isothiazole-5-amine hydrochloride (15 mg, 0.1 mmol), tris(dibenzylideneacetone)dipalladium (9 mg, 0.01 mmol), 4,5-bis-diphenylphosphine-9,9-dimethylxanthene (9 mg, 0.015 mmol) and cesium carbonate (130 mg, 0.4 mmol) were suspended in 1,4-dioxane (1.5 mL), and added with water (300 μL), purged with argon, reacted at 100° C. under microwave for half an hour. The reaction mixture was filtered through celite, and the filtrate was purified by silica gel column chromatography (eluent:dichloromethane/methanol=30:1) to give a yellow solid (20 mg). Yield: 51.44%. MS (ESI, m/z): [M+H]$^+$: 384.3; $^1$H-NMR (300 MHz, CD$_3$OD) δ: 7.43 (s, 1H), 6.70-6.89 (m, 2H), 6.52-6.56 (m, 2H), 6.20 (dd, 1H, J=16.8 Hz, J=40.2 Hz), 5.71 (dd, 1H, J=10.8 Hz, J=55.5 Hz), 4.78-4.82 (m, 1H), 4.08-4.46 (m, 2H), 2.82-3.46 (m, 2H), 2.34 (s, 3H), 2.18-2.30 (m, 1H), 1.90-2.02 (m, 1H), 1.60-1.85 (m, 2H).

The following compounds (in Table 7) were prepared from similar starting materials by similar synthetic methods to those described in Example 134.

TABLE 7

| Examples | Structures | Characterization Data |
|---|---|---|
| 135 | 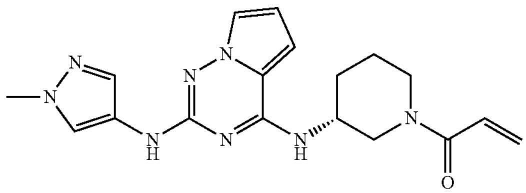 [SMILES: C=CC(=O)N1CCC[C@@H](Nc2nc(Nc3cnn(C)c3)nn3cccc23)C1] | ¹H-NMR (300 MHz, CD₃OD) δ: 7.92 (s, 1H), 7.49 (d, 1H, J = 6.3 Hz), 7.35 (s, 1H,), 6.66-6.87 (m, 2H), 6.41-6.43 (m, 1H), 6.11-6.30 (m, 1H), 5.61-5.81 (m, 1H), 4.06-4.28 (m, 3H), 3.86 (s, 3H), 3.07-3.20 (m, 1H), 2.68-2.76 (m, 1H), 2.10-2.22 (m, 1H), 1.52-1.98 (m, 3H); LC-MS (ESI, m/z): [M + H]⁺ = 367.3 |
| 136 | 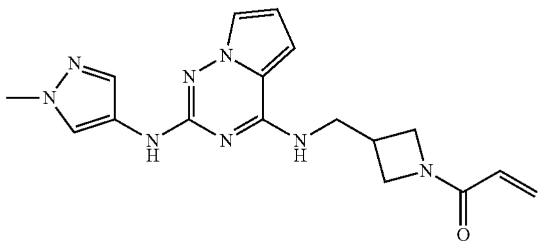 [SMILES: C=CC(=O)N1CC(CNc2nc(Nc3cnn(C)c3)nn3cccc23)C1] | ¹H-NMR (300 MHz, CDCl₃) δ: 7.87 (s, 1H), 7.47 (s, 1H), 7.41 (s, 1H), 6.55 (bs, 1H), 6.45-6.48 (m, 1H), 6.36 (dd, 1H, J = 1.8 Hz, J = 17.1 Hz), 6.20 (dd, 1H, J = 1.8 Hz, J = 10.2 Hz), 5.69 (dd, 1H, J = 1.8 Hz, J = 10.2 Hz), 4.31-4.37 (m, 1H), 4.17-4.23 (m, 1H), 4.01-4.05 (m, 1H), 3.93-3.97 (m, 1H), 3.91 (s, 3H), 3.79-3.87 (m, 2H), 3.00-3.12 (m, 1H); LC-MS (ESI, m/z): [M + H]⁺ = 353.2 |
| 137 | 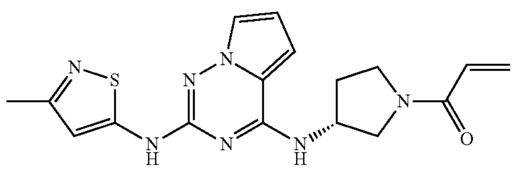 [SMILES: C=CC(=O)N1CC[C@@H](Nc2nc(Nc3cc(C)ns3)nn3cccc23)C1] | ¹H-NMR (300 MHz, CD₃OD) δ: 7.41-7.43 (m, 1H), 6.85-6.87 (m, 1H), 6.50-6.71 (m, 3H), 6.26-6.34 (m, 1H), 5.73-5.80 (m, 1H), 4.90-5.05 (m, 2H), 3.97-4.20 (m, 1H), 3.63-3.93 (m, 3H), 2.19-2.50 (m, 5H); LC-MS (ESI, m/z): [M + H]⁺ = 370.2 |
| 138 | 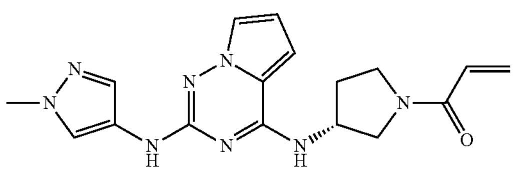 [SMILES: C=CC(=O)N1CC[C@@H](Nc2nc(Nc3cnn(C)c3)nn3cccc23)C1] | ¹H-NMR (300 MHz, CD₃OD) δ: 7.91 (d, 1H, J = 2.7 Hz), 7.52 (s, 1H), 7.35 (d, 1H, J = 1.5 Hz), 6.74 (d, 1H, J = 3.3 Hz), 6.53-6.67 (m, 1H), 6.41-6.42 (m, 1H), 6.23-6.33 (m, 1H), 5.71-5.78 (m, 1H), 4.77-4.87 (m, 1H), 3.91-4.13 (m, 1H), 3.86 (s, 3H), 3.55-3.81 (m, 3H), 2.03-2.41 (m, 2H); LC-MS (ESI, m/z): [M + H]⁺ = 353.2 |

Example 139

Preparation of (R)-1-(3-((2-((3-methyl-isothiazol-5-yl)amino)pyrrolo[2,1-f][1,2,4] triazin-4-yl)amino)piperidin-1-yl)prop-2-yn-1-one

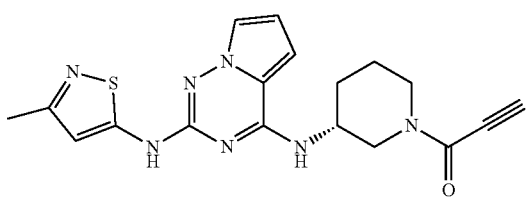 [SMILES: C#CC(=O)N1CCC[C@@H](Nc2nc(Nc3cc(C)ns3)nn3cccc23)C1]

Step 1: Preparation of Tert-Butyl (R)-3-((2-((3-methyl-isothiazol-5-yl)amino) pyrrolo[2,1-f][1,2,4] triazin-4-yl)amino)piperidine-1-carboxylate

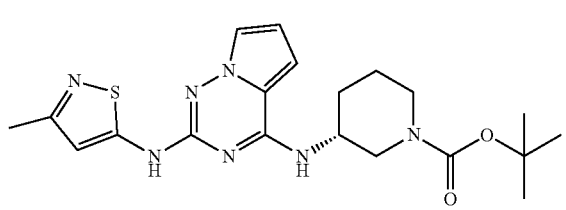 [SMILES: Cc1cc(Nc2nc(N[C@@H]3CCCN(C(=O)OC(C)(C)C)C3)c3cccn3n2)sn1]

The product obtained in step 1 of Example 134 (352 mg, 1 mmol) and 3-methyl-isothiazole-5-amine hydrochloride (163 mg, 1.1 mmol) were dissolved in 1,4-dioxane/water (21 mL, 20:1), followed by the addition of tris(dibenzylidenepropanone)dipalladium (46 mg, 0.05 mmol), (±)-2,2'-bis-(diphenylphosphino)-1,1'-binaphthyl (63 mg, 0.1 mmol) and cesium carbonate (650 mg, 2 mmol) under nitrogen atmosphere, and refluxed at 100° C. overnight. The reaction solution was cooled to room temperature, and filtered through celite. The filtrate was concentrated under reduced pressure, and purified by silica gel column chromatography (eluent:dichloromethane:methanol=30:1) to give a pale yellow solid (349 mg). Yield: 81.2%. MS (ESI, m/z): [M+H]⁺: 430.2.

Step 2: Preparation of (R)—N²-(3-methyl-isothiazol-5-yl)-N⁴-(piperidin-3-yl) pyrrolo[2,1-f][1,2,4] triazine-2,4-diamine

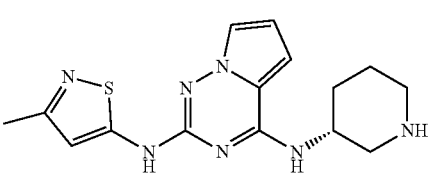 [SMILES: Cc1cc(Nc2nc(N[C@@H]3CCCNC3)c3cccn3n2)sn1]

The product obtained in step 1 (64 mg, 0.2 mmol) was dissolved in dichloromethane (15 mL), and to solubilize it methanol (10 mL) was added. Then 4N solution of hydrogen chloride in 1,4-dioxane (0.5 mL, 2 mmol) was added, and the mixture was reacted at room temperature for 2 hours. The reaction solution was concentrated under reduced pressure, and used directly into the next step. MS (ESI, m/z): [M+H]$^+$: 330.1.

Step 3: Preparation of (R)-1-(3-((2-((3-methyl-isothiazol-5-yl)amino) pyrrolo[2,1-f][1,2,4]triazin-4-yl) amino)piperidine-1-yl)prop-2-yn-1-one The product obtained in step 2 (33 mg, 0.10 mmol) and propiolic acid (8.4 mg, 0.12 mmol) were dissolved in tetrahydrofuran (10 mL), followed by the addition of N,N-diisopropylethylamine (53 µL). The mixture was stirred at room temperature for 30 minutes, added with TBTU (4 mg), and then stirred at room temperature overnight. The reaction solution was concentrated, and purified by silica gel column chromatography (eluent:dichloromethane/methanol=10:1) to give a pale yellow solid (6.1 mg). Yield: 16.1%. MS (ESI, m/z): [M+H]$^+$: 382.2.

The following compounds (in Table 8) were prepared from similar starting materials by similar synthetic methods to those described in Example 139.

TABLE 8

| Example | Structure | Characterization Data |
| --- | --- | --- |
| 140 | 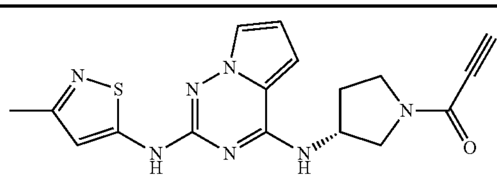 | LC-MS (ESI, m/z): [M + H]$^+$ = 368.2 |

Pharmacological Evaluation

Test Sample 1: BTK Kinase Activity Inhibition Assay

The BTK kinase (purchased from Invitrogen, No.: PV3363) was diluted with reaction buffer (40 mM Tris-HCl, pH 7.5; 20 mM MgCl$_2$, 0.1 mg/ml BSA; 1 mM DTT; 2 mM MnCl$_2$) to 2 times of the final concentration (which is 1.1 ng/µL) and added with 5 µL/well to a 96-well plate. The compounds of the present invention were serial diluted with deionized water to four times (i.e., 40 µM, 4 µM, 0.4 µM, 80 nM, 16 nM, 3.2 nM, respectively) of the final concentrations (10 µM, 1 µM, 0.1 µM, 20 nM, 4 nM, 0.8 nM, respectively), and added at 2.5 µL/well to the test wells of the 96-well plate. After incubation at 25° C. for 10 minutes, ATP (50 µM) (purchased from Promega, No.: V9102) and 0.2 µg/µL of Poly E4Y1 (purchased from Sigma, No.: P0275-25MG) were added with 2.5 µL/well and incubated at 25° C. for 120 minutes. After the reaction was completed, 10 µL of the ADP-Glo reagent (ADP-Glo™ kinase assay kit, purchased from Promega, No.: V9102) was added to each well, and reacted at 25° C. for 40 minutes. Then 20 µL of the ADP-Glo kinase detection reagent was added to each well and reacted at 25° C. for 30 minutes. The kinase activity was detected by luminescence using the ADP-Glo kinase assay kit according to the manufacture's instruction, and IC$_{50}$ values of the compounds of the present invention were calculated. The results are shown in Table 9.

TABLE 9

Results from the BTK kinase activity inhibition assay

| Compound | BTK |
| --- | --- |
| 1 | +++ |
| 2 | +++ |
| 4 | +++ |
| 8 | +++ |
| 12 | +++ |
| 13 | +++ |
| 14 | +++ |
| 15 | +++ |
| 16 | +++ |
| 17 | ++ |
| 18 | +++ |
| 30 | ++ |
| 31 | +++ |
| 33 | ++ |
| 34 | +++ |
| 35 | +++ |
| 36 | ++ |
| 43 | +++ |
| 44 | +++ |
| 45 | ++ |
| 46 | +++ |
| 47 | +++ |

TABLE 9-continued

Results from the BTK kinase activity inhibition assay

| Compound | BTK |
| --- | --- |
| 49 | +++ |
| 50 | +++ |
| 51 | +++ |
| 52 | ++ |
| 57 | +++ |
| 60 | +++ |
| 61 | +++ |
| 62 | +++ |
| 65 | +++ |
| 69 | +++ |
| 70 | ++ |
| 71 | +++ |
| 72 | +++ |
| 73 | +++ |
| 74 | ++ |
| 75 | +++ |
| 76 | +++ |
| 77 | +++ |
| 78 | ++ |
| 79 | + |
| 80 | +++ |
| 81 | +++ |
| 82 | +++ |
| 83 | +++ |
| 84 | +++ |
| 85 | ++ |
| 88 | ++ |
| 92 | +++ |
| 93 | +++ |
| 94 | +++ |

TABLE 9-continued

Results from the BTK kinase activity inhibition assay

| Compound | BTK |
|---|---|
| 95 | +++ |
| 96 | +++ |
| 99 | ++ |
| 101 | ++ |
| 102 | +++ |
| 103 | +++ |
| 104 | +++ |
| 105 | +++ |
| 108 | +++ |
| 111 | +++ |
| 112 | +++ |
| 114 | +++ |
| 115 | +++ |
| 116 | +++ |
| 118 | +++ |
| 119 | +++ |
| 120 | +++ |
| 121 | +++ |
| 122 | +++ |
| 123 | +++ |
| 124 | +++ |
| 125 | +++ |
| 126 | +++ |
| 127 | +++ |
| 128 | +++ |
| 129 | +++ |
| 130 | +++ |
| 131 | +++ |
| 132 | +++ |
| 134 | +++ |
| 135 | +++ |
| 136 | +++ |
| 137 | +++ |
| 138 | +++ |

Table 9 shows the activity of the selected compounds of the present invention in the BTK activity inhibition assay, wherein "+++" means that the compound designated by it has an $IC_{50} \leq 50$ nM; "++" means that the compound designated by it has an $IC_{50}$ of $50 < IC_{50} \leq 100$ nM; and "+" means that the compound designated by it has an $IC_{50}$ of $100 < IC_{50} < 1000$ nM.

Test Example 2: JAK3 Kinase Activity Inhibition Assay

The JAK3 kinase (purchased from SignalChem, No.: J03-11G) was diluted with reaction buffer (40 mM Tris-HCl, pH 7.5; 20 mM $MgCl_2$, 0.1 mg/ml BSA; 1 mM DTT) to 2 times of the final concentration (which is 0.5 ng/μL) and added with 5 μL/well to a 96-well plate. The compounds of the present invention were serial diluted with deionized water to four times (i.e., 40 μM, 4 μM, 0.4 μM, 80 nM, 16 nM, 3.2 nM, respectively) of the final concentrations (10 μM, 1 μM, 0.1 μM, 20 nM, 4 nM, 0.8 nM, respectively), and added with 2.5 μL/well to the test wells of the 96-well plate. After incubation at 25° C. for 10 minutes, 10 μM of ATP (purchased from Promega, No.: V9102) and 0.2 μg/μL of Poly E4Y1 (purchased from Sigma, No.: P0275-25MG) were added at 2.5 μL/well and reacted at 25° C. for 60 minutes. After the reaction was completed, 10 μL of the ADP-Glo reagent (ADP-Glo™ kinase assay kit, purchased from Promega, No.: V9102) was added to each well and reacted at 25° C. for 40 minutes. Then 20 μL of the ADP-Glo kinase detection reagent was added to each well and reacted at 25° C. for 30 minutes. The kinase activity was detected by luminescence using the ADP-Glo kinase assay kit according to the manufacture's instruction, and $IC_{50}$ values of the compounds of the present invention were calculated. The results are shown in Table 10.

TABLE 10

Results from the JAK3 kinase activity inhibition assay

| Compound | JAK3 |
|---|---|
| 61 | +++ |
| 62 | ++ |
| 65 | ++ |
| 69 | ++ |
| 70 | ++ |
| 71 | +++ |
| 72 | ++ |
| 73 | ++ |
| 74 | + |
| 75 | ++ |
| 76 | ++ |
| 77 | ++ |
| 78 | ++ |
| 79 | ++ |
| 80 | ++ |
| 81 | ++ |
| 82 | +++ |
| 83 | +++ |
| 84 | ++ |
| 85 | ++ |
| 88 | ++ |
| 92 | + |
| 93 | ++ |
| 94 | +++ |
| 95 | ++ |
| 96 | +++ |
| 99 | ++ |
| 101 | + |
| 102 | ++ |
| 103 | + |
| 104 | ++ |
| 105 | ++ |
| 108 | +++ |
| 111 | ++ |
| 112 | ++ |
| 114 | ++ |
| 115 | ++ |
| 116 | ++ |
| 118 | ++ |
| 119 | ++ |
| 120 | ++ |
| 121 | ++ |
| 122 | +++ |
| 123 | ++ |
| 124 | ++ |
| 125 | +++ |
| 126 | ++ |
| 127 | +++ |
| 128 | ++ |
| 129 | ++ |
| 130 | ++ |
| 131 | ++ |
| 132 | +++ |
| 134 | +++ |
| 135 | ++ |
| 137 | +++ |
| 138 | ++ |

Table 10 shows the activity of the selected compounds of the present invention in the JAK3 activity inhibition assay, wherein "+++" means that the compound designated by it has an $IC_{50} \leq 10$ nM; "++" means that the compound designated by it has an $IC_{50}$ of $10 < IC_{50} \leq 100$ nM; and "+" means that the compound designated by it has an $IC_{50}$ of $100 < IC_{50} < 1000$ nM.

Test Example 3: IL-2 Induced CTLL-2 Cell Proliferation Assay

The compounds of the present invention were serial diluted with RPMI-1640 complete medium (purchased from Gibco, No.: 22440) to three times (i.e., 3 µM, 0.6 µM, 120 nM, 24 nM, 4.8 nM, 0.96 nM, respectively) of the final concentrations (1 µM, 0.2 µM, 40 nM, 8 nM, 1.6 nM, 0.32 nM, respectively), and added at 50 µL/well to the test wells of a 96-well plate. Control wells with IL-2 (referred to as IL-2$^+$) (IL-2 was purchased from R & D, No.: 402-ML-020/CF) and without IL-2 (referred to as IL-2$^-$) (with addition of 50 µL of the medium). CTLL-2 cells (purchased from ATCC, No.: TIB-214) at the logarithmic growth phase were rinsed with PBS buffer (pH 7.2), then resuspended in RPMI-1640 complete medium without IL-2, and seeded at 50000 cells/50 µL/well in the 96-well plate. The plate was placed at 37° C., 5% $CO_2$ and pre-incubated for 1 hour. Then, to the test wells and the IL-2$^+$ control well RPMI-1640 complete medium containing IL-2 (50 µL/well) was added, while to the IL-2$^-$ control well RPMI-1640 complete medium without IL-2 (50 µL/well) was added. The cells were stimulated for 24 hours at 37° C., 5% $CO_2$. After this, the 96-well plate was taken out from the incubator. To each well 15 µL of CCK-8 reagent (purchased from DOJINDO, No.: DOJINDO-CK04) was added, and then the plate was placed in the incubator again and cultured for another 1-4 hours. Absorption was determined at 450 nm of wavelength, and $IC_{50}$ values of the compounds of the present invention were thereby calculated. The results are shown in Table 11.

TABLE 11

Results of the IL-2 induced CTLL-2 cell proliferation assay

| Compound | CTLL-2 |
|---|---|
| 134 | +++ |
| 137 | ++ |

Table 12 shows the activity of the selected compounds of the present invention in the CTLL-2 cell proliferation assay, wherein "+++" means that the compound designated by it has an $IC_{50} \leq 100$ nM; "++" means that the compound designated by it has an $IC_{50}$ of $100 < IC_{50} < 1000$ nM.

Test Example 4: p-BTK and p-PCL-γ2 Inhibition Assay in Ramos Cells (Western Blot Assay)

Ramos cells (purchased from the Beijing Union Medical College) with starvation culture for 1 hour were treated with the compounds of the present invention for 1 hour, and then rinsed with PBS buffer (pH 7.2) to remove the compounds. Then they were resuspended in 100 µL of serum-free culture medium containing 1 µM of anti-human IgM F(ab')2 (purchased from SBA company, No.: 2022-01) and stimulated on ice for 10 minutes. The cells were rinsed with PBS buffer (pH 7.2) to remove IgM and resuspended in 100 µL of protein lysis buffer (purchased from Sigma, No.: C2978), and then prepared and quantified the protein sample. 100 µg of the protein sample were taken and loaded on polyacrylamide gels for electrophoresis under 200V of voltage. After electrophoresis, protein blots were transferred to a PVDF membrane. The membrane was blocked with 3% BSA at room temperature for 2 hours and incubated overnight with the corresponding anti-p-BTK (pY223) (purchased from CST, No.: 5082S); anti-BTK (purchased from Abcam, No.: ab118156); anti-p-PLCγ2 (pY1217) (purchased from CST, No.: 3871S); anti-PLCγ2 (purchase from CST, No.: 3872S); and anti-β-actin (purchased from CWBIO, No.: CW0096A)) antibodies at 4° C., and then incubated with horseradish peroxidase-conjugated IgG secondary antibody (purchased from CWBIO, No.: CW0103A) for 1 hour. The protein expression was detected by coloration using ECL substrate (purchased from GE, No.: RPN2109).

By the above method, compound 132 of the present application was tested. The results showed that compound 132 can significantly inhibit the expressions of p-BTK and p-PLCγ2 in Ramos cells in a dose-dependent manner.

The result is shown in FIG. 1.

Test Example 5: Type II Collagen-Induced Arthritis (CIA) Model in DBA/1J Mice

The CIA model is a widely-used animal model in the study of drugs for the treatment of rheumatoid arthritis in human. The experimental animals used in this experiment are DBA/1J mice (male, 6 to 8 weeks of age, purchased from Shanghai Silaike Laboratroy Animal Co., Ltd., China). Mice were housed in an IVC system.

In order to induce the mice CIA model, a bovine type II collagen (CII) (purchased from Chondrex company, No.: 20022) solution was emulsified with the same volume of complete Freund's adjuvant (CFA) (purchased from Sigma-Aldrich, No.: F5881) using an electronic homogenizer to prepare an emulsion. Then, 70 µL of the prepared emulsion was intradermally injected into the base of the tail of the mice as a primary immunization. Three weeks after the primary immunization, one booster immunization was carried out. A bovine type II collagen solution was emulsified with the same volume of incompletely Freund's adjuvant (IFA) (purchased from Sigma-Aldrich, No.: F5506) to prepare an emulsion, and then 70 µL of the prepared emulsion was intradermally injected in a single point into the hind back to complete the immunization. According to the following criteria, Mice were evaluated for the severity of arthritis using an established scoring system ranging from 0 to 4 (0 score: no evidence of edema or swelling; 1 score: mild edema and redness confined to the ankle joint or tarsal; 2 scores: mild edema and redness, from the ankle joint to the tarsal; 3 scores: moderate edema and redness, from the ankle joint to the metatarsal; and 4 scores: severe edema and redness, from the ankle to the whole instep and toes, or ankylosis of the ankle or wrist joints). The scores for the four limbs of each mouse were added together and the highest score was 16 (4×4).

According to their arthritis scores, 5 to 7 mice were assigned to each group of three groups, one model control group and two administration groups. Treatment stars when the average arthritis severity scores in each group were about 1-2. Two doses of 3 mg/kg and 10 mg/kg were designed and orally administrated once a day for 14 days. At the same time, a normal control group was established. The results from the test groups were compared with the results of the normal control group and the model control group, so as to determine the therapeutic effect of the test compounds on arthritis in the model.

By comparison of the arthritis severity scores, compound 132 of the present invention was confirmed to have a good therapeutic effect on arthritis in the CIA model at the designed doses in a dose dependent manner.

Figure 2:
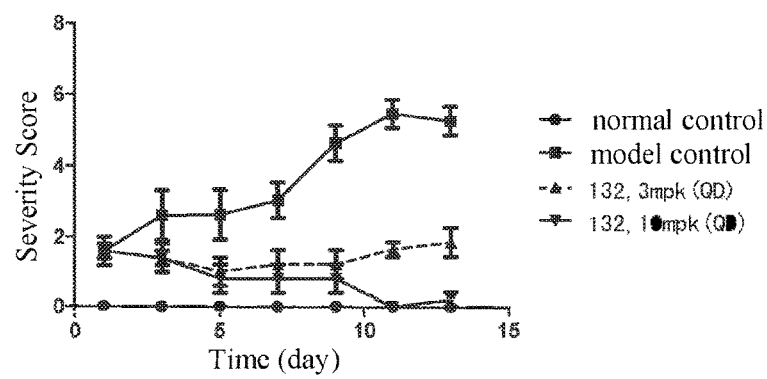
FIG. 2 shows the scores of compound 132 in mCIA model.

The results are shown in FIG. 2.

Test Example 6: Adjuvant-Induced Arthritis (AIA) Model in Rats 100 mg of inactivated *Mycobacterium tuberculosis* (purchased from BD Difco, No.: 231141) accurately weighed and dissolved in 5 mL of incomplete Freund's adjuvant (IFA) (purchased from Sigma, No.: F5506), and then with 5 mL of physiological saline added, was homogeneously emulsified into 10 mg/mL of complete Freund's adjuvant (CFA). In order to induce the AIA model in rats, 50 Lewis rats in SPF grade (purchased from BeijingVital River Laboratories (VRL), animal production license number: SCXK (Beijing) 2012-0001), male, weighing 180-200 g, and adaptively feeding for 7 days, were injected with the complete Freund's adjuvant containing the inactivated *Mycobacterium tuberculosis* (H37RA, 10 mg/ml) at a dose of 0.1 ml/rat at the dorsal base of the tail to induce arthritis in rats. At the same time, three non-immunized rats were used as a normal control group. Rats were evaluated for the severity of arthritis using an established scoring system ranging from 0 to 4 as follows: 0=no evidence of erythema or swelling; 1=slight erythema or swelling of one of the toe joints; 2=erythema or swelling of more than one toe; 3=swelling of the ankle or wrist joint; 4=swelling of all toes including the ankle joint. All four paws of the rat were scored individually, and the highest score was 16.

The paw volumes of the rats were measured by the drainage method using a plethysmometer (Plethysmometer PV-200, Chengdu Taimeng Science and Technology Co., Ltd.) to determine the volumes below the ankle joints (in mL). The rats were measured for paw volumes every other day from day 10 after primary immunization, i.e. day 1 of the administration. The volumes of the four limbs of each rat were added together, and then divided by 4 to give an average value. Two doses of 30 mg/kg and 100 mg/kg were designed and orally administrated once a day for 7 days. At the same time, a normal control group and a model control group were established, and the results from the test groups were compared with the results from the normal control group and the model control group, so as to determine the therapeutic effect of the test compounds on arthritis in the model.

By comparison of the arthritis severity scores, compound 132 of the present invention was confirmed to have a good therapeutic effect on arthritis in the AIA model at the designed doses.

Figure 3:
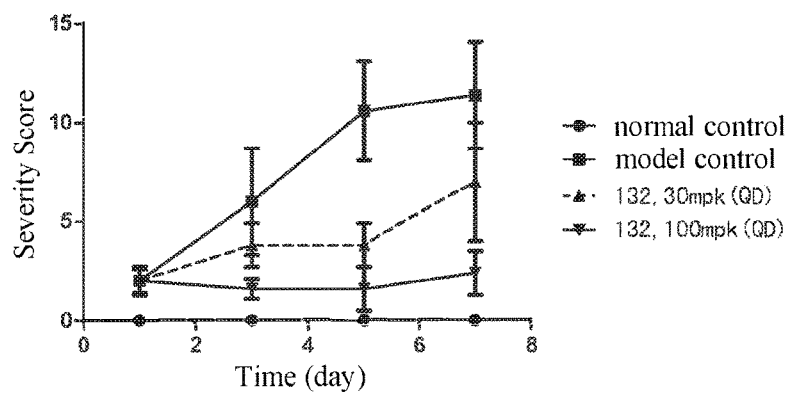
FIG. 3 shows the scores of compound 132 in rAIA model.

The results are shown in FIG. 3.

What is claimed is:
1. A compound represented by formula Ia:

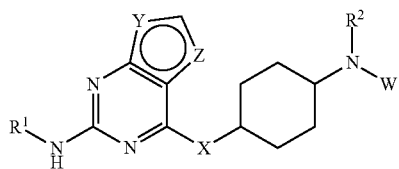

Ia wherein:
W is selected from

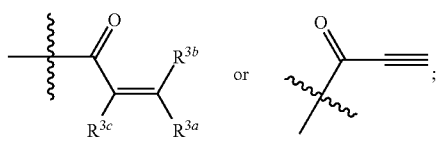

X is selected from $NR^4$, O or S;
Y is selected from CH, S or O;
Z is selected from CH, S, O or $NR^5$;

provided that either: (i) Y is S or O, and Z is CH, or (ii) Z is S, O, or $NR^5$, and Y is CH;
$R^1$ is selected from phenyl and 5- to 12-membered heteroaryl, optionally substituted by one or more $R^6$;
$R^2$ is selected from hydrogen or $C_{1-8}$ aliphatic;
$R^{3a}$, $R^{3b}$, and $R^{3c}$ are hydrogen;
$R^4$ is selected from hydrogen or $C_{1-8}$ aliphatic;
$R^5$ is selected from hydrogen or $C_{1-8}$ aliphatic;
each $R^6$ is independently selected from the group consisting of halogen, heterocyclyl, $C_{1-8}$ aliphatic, $C_{1-8}$ halo aliphatic, heterocyclyl $C_{1-8}$ aliphatic, hydroxy $C_{1-8}$ aliphatic, $C_{1-8}$ aliphaticoxy $C_{1-8}$ aliphatic, amino $C_{1-8}$ aliphatic, $C_{1-8}$ aliphaticamino $C_{1-8}$ aliphatic, di($C_{1-8}$ aliphatic)amino $C_{1-8}$ aliphatic, $C_{1-8}$ aliphaticoxy, heterocyclyloxy, heterocyclyl $C_{1-8}$ aliphaticoxy, hydroxy $C_{1-8}$ aliphaticoxy, $C_{1-8}$ aliphaticoxy $C_{1-8}$ aliphaticoxy, amino, $C_{1-8}$ aliphaticamino, di($C_{1-8}$ aliphatic)amino, heterocyclylamino, amino $C_{1-8}$ aliphaticamino, $C_{1-8}$ aliphaticamino $C_{1-8}$ aliphaticamino, di($C_{1-8}$ aliphatic)amino $C_{1-8}$ aliphaticamino, $C_{1-8}$ aliphaticcarbonyl, heterocyclylcarbonyl, aminoacyl, $C_{1-8}$ aliphaticaminoacyl, di($C_{1-8}$ aliphatic)aminoacyl, heterocyclyl $C_{1-8}$ aliphaticaminoacyl, and heterocyclylaminoacyl, wherein:
heterocyclyl, as an independent group or a part of other group(s), represents a saturated or partially unsaturated 3- to 8-membered heterocyclyl group containing one or two heteroatoms selected from the group consisting of N, O, and S; optionally, each heterocyclyl is independently substituted by one or more substituents selected from the group consisting of $C_{1-8}$ aliphatic, hydroxy, $C_{1-8}$ aliphaticoxy, and $C_{1-8}$ aliphaticcarbonyl,
wherein $C_{1-8}$ aliphatic, at each occurrence, is independently selected from the group consisting of $C_{1-8}$ alkyl and $C_{3-8}$ cycloalkyl, or
a stereoisomer, a tautomer, a solvate, or a pharmaceutically acceptable salt thereof.

2. The compound according to claim 1, wherein:
$R^1$ is selected from phenyl, optionally substituted by one or more $R^6$;
each $R^6$ is independently selected from the group consisting of halogen, heterocyclyl, $C_{1-8}$ aliphatic, $C_{1-8}$ aliphaticoxy, heterocyclyloxy, heterocyclyl $C_{1-8}$ aliphaticoxy, hydroxy $C_{1-8}$ aliphaticoxy, $C_{1-8}$ aliphaticoxy $C_{1-8}$ aliphaticoxy, $C_{1-8}$ aliphaticamino, di($C_{1-8}$ aliphatic) amino, heterocyclylamino, di($C_{1-8}$ aliphatic)amino $C_{1-8}$ aliphaticamino, $C_{1-8}$ aliphaticcarbonyl, heterocyclylcarbonyl, $C_{1-8}$ aliphaticaminoacyl, and heterocyclylaminoacyl, wherein heterocyclyl, as an independent group or a part of other group(s), represents a saturated or partially unsaturated 5- to 6-membered heterocyclyl group containing one or two heteroatoms selected from the group consisting of N, O, and S; optionally, each heterocyclyl is independently substituted by one or more substituents selected from the group consisting of $C_{1-8}$ aliphatic, hydroxy, $C_{1-8}$ aliphaticoxy, and $C_{1-8}$ aliphaticcarbonyl;
wherein $C_{1-8}$ aliphatic, at each occurrence, is independently selected from the group consisting of $C_{1-8}$ alkyl, and $C_{3-8}$ cycloalkyl or
a stereoisomer, a tautomer, a solvate, or a pharmaceutically acceptable salt thereof.

3. The compound according to claim 1, wherein $R^1$ is selected from the group consisting of:

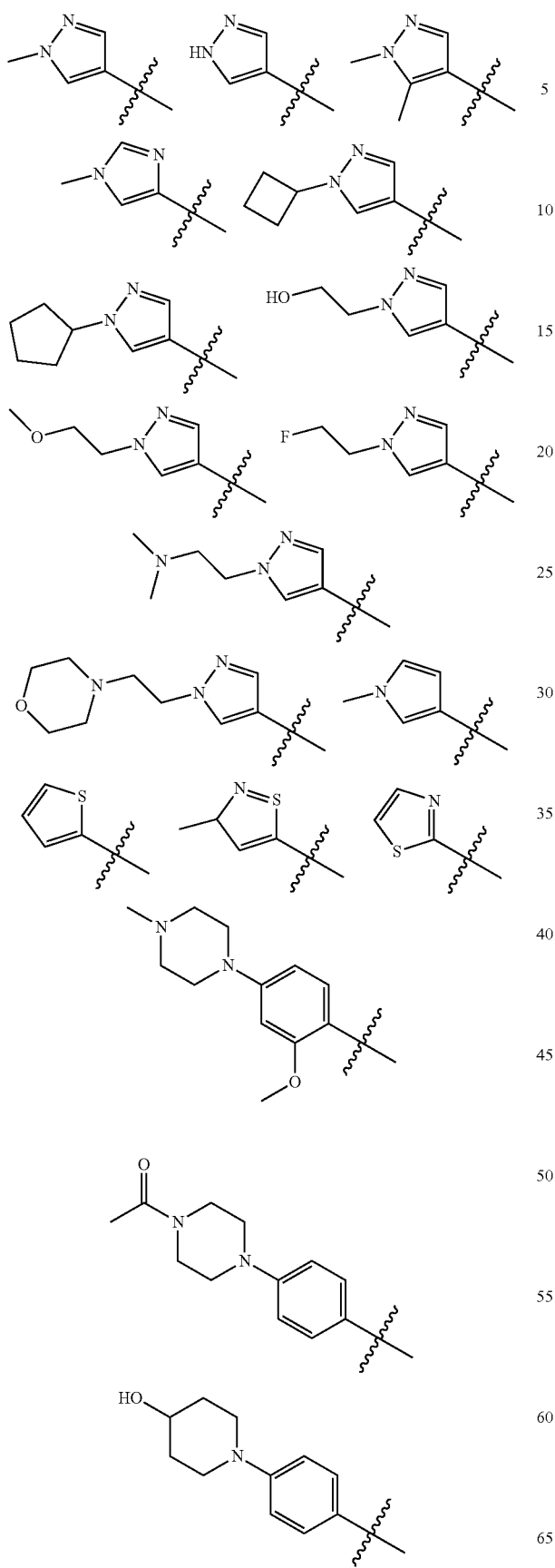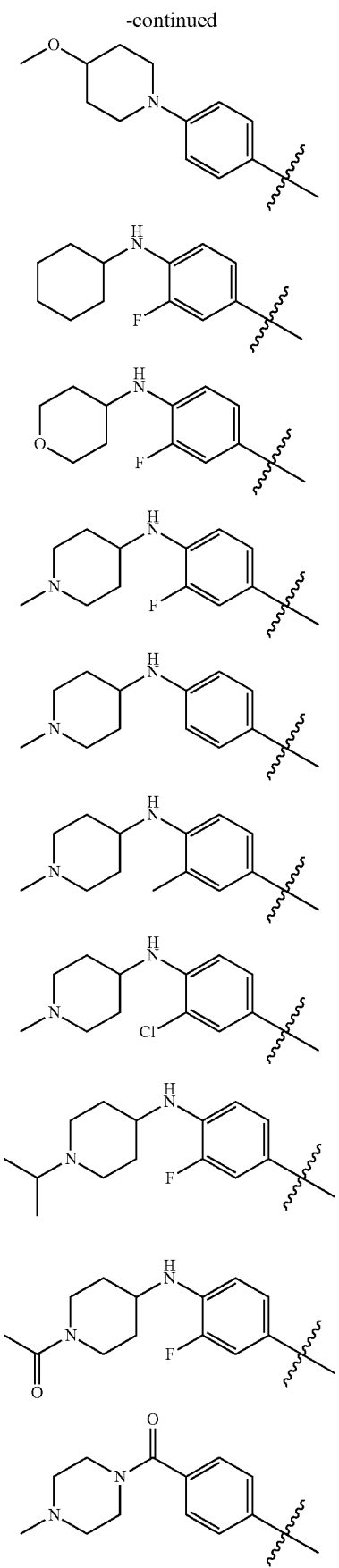

-continued

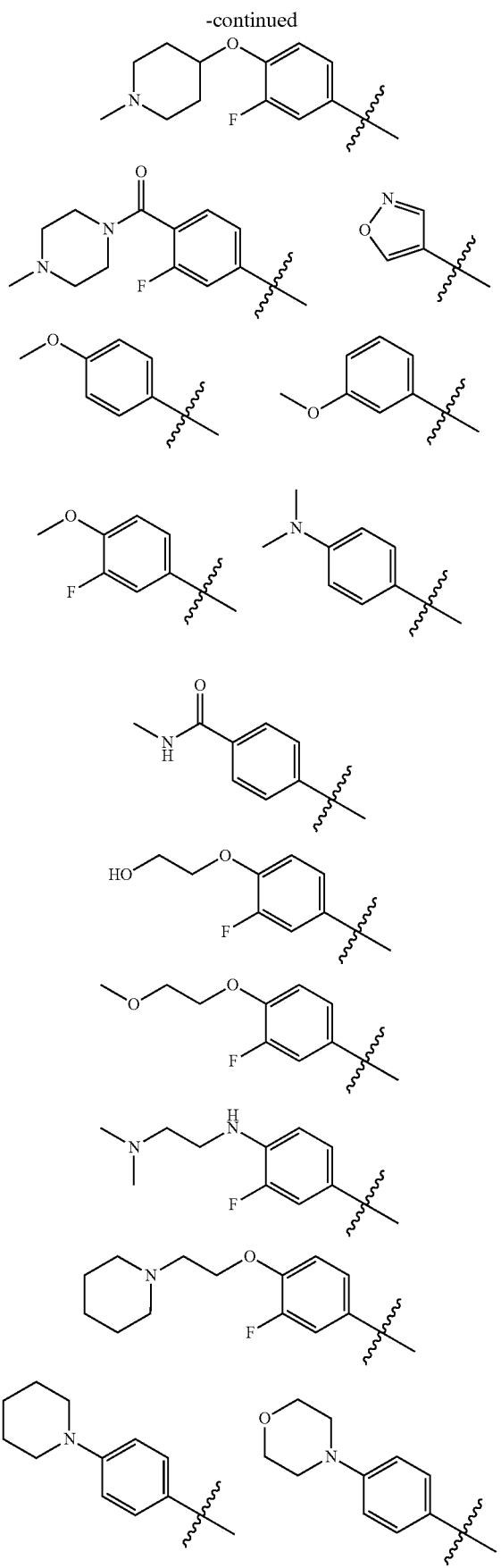

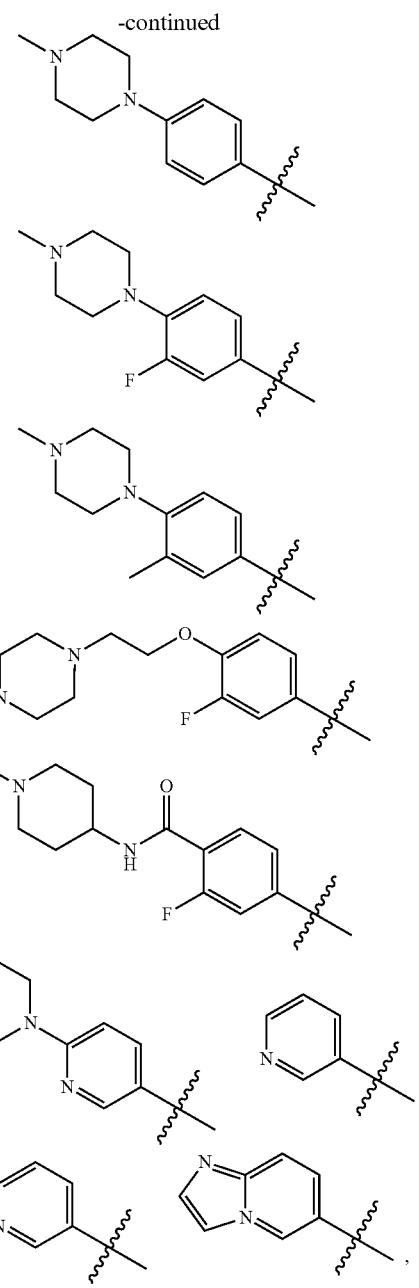

or a stereoisomer, a tautomer, a solvate, or a pharmaceutically acceptable salt thereof.

4. The compound according to claim 1, wherein:
R$^1$ is a 5- to 10-membered heteroaryl group, optionally substituted by one or more R$^6$;
each R$^6$ is independently selected from the group consisting of heterocyclyl, C$_{1-8}$ aliphatic, C$_{1-8}$ halo aliphatic, heterocyclyl C$_{1-8}$ aliphatic, hydroxy C$_{1-8}$ aliphatic, amino C$_{1-8}$ aliphatic, C$_{1-8}$ aliphaticamino C$_{1-8}$ aliphatic, di(C$_{1-8}$ aliphatic)amino C$_{1-8}$ aliphatic, C$_{1-8}$ aliphaticoxy and C$_{1-8}$ aliphaticoxy C$_{1-8}$ aliphatic, wherein heterocyclyl, as an independent group or a part of other group(s), represents a saturated or partially unsaturated 5- to 6-membered heterocyclyl group containing one or two heteroatoms selected from the group consisting of O, N and S, preferably selected from the group consisting of morpholinyl, piperidinyl, piperazinyl and tetrahydropyranyl; optionally, each heterocyclyl is independently substituted by one or more $C_{1-8}$ aliphatic groups;

wherein $C_{1-8}$ aliphatic, at each occurrence, is independently selected from the group consisting of $C_{1-8}$ alkyl and $C_{3-8}$ cycloalkyl, or a stereoisomer, a tautomer, a solvate, or a pharmaceutically acceptable salt thereof.

5. The compound according to claim 1, wherein provided that either: (i) Y is S or O, and Z is CH, or (ii) Z is S or O, and Y is CH.

6. The compound according to claim 1, wherein Z is S or O, and Y is CH.

7. The compound according to claim 1, wherein $R^1$ is a 5- to 10-membered heteroaryl, optionally substituted by one or more $R^6$.

8. The compound according to claim 1, wherein the compound is selected from the group consisting of:

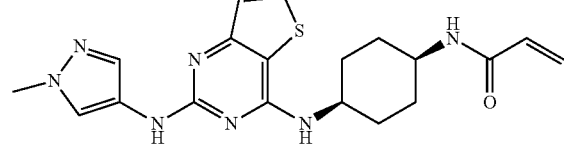

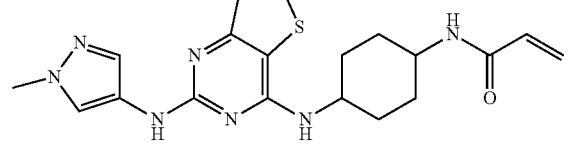

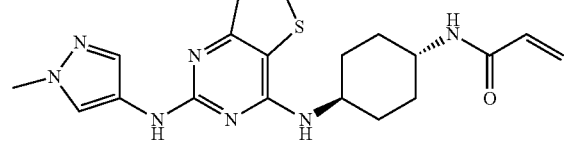

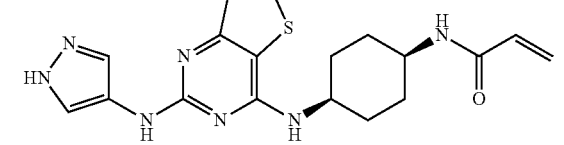

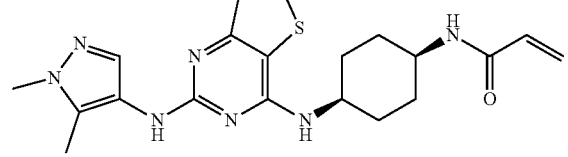

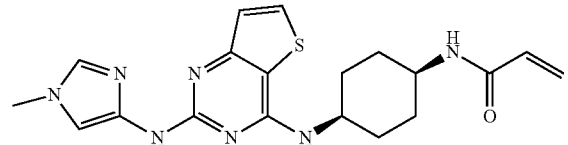

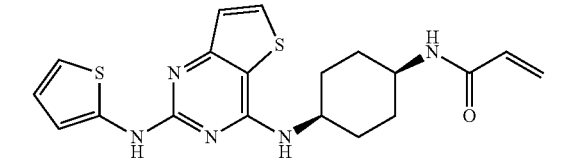

-continued

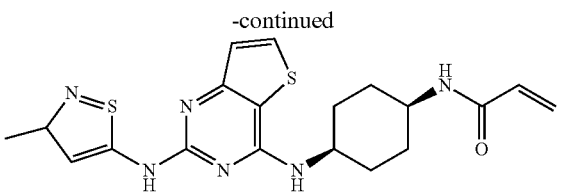

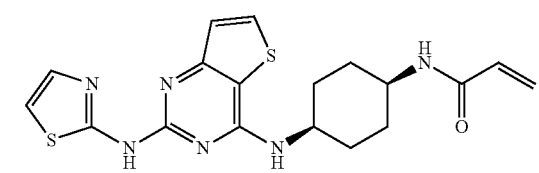

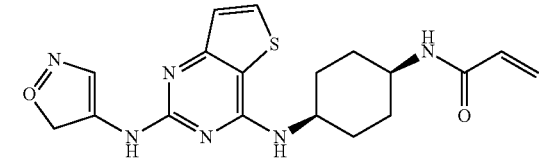

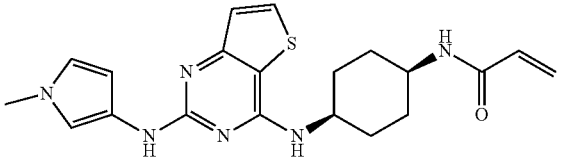

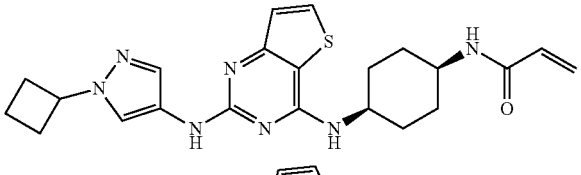

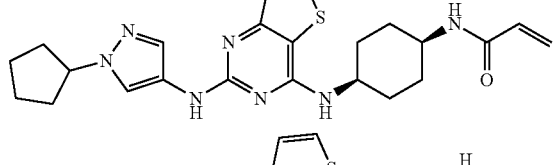

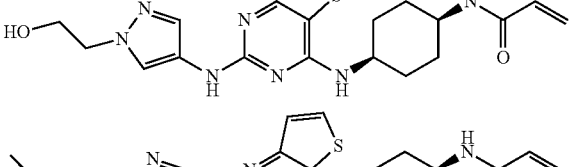

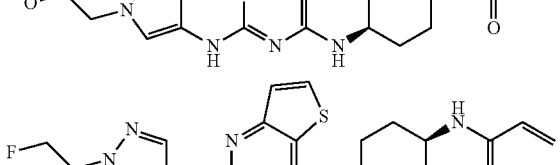

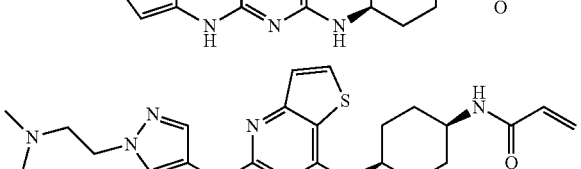

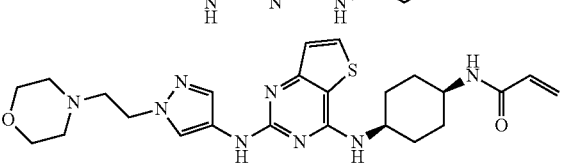

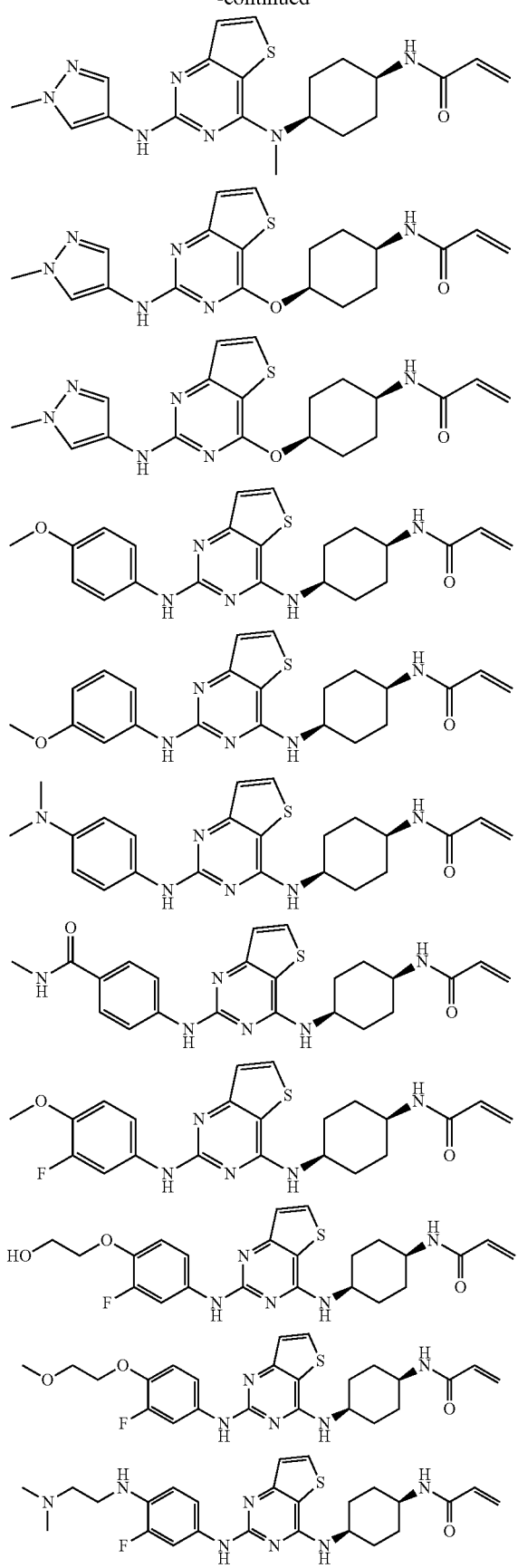
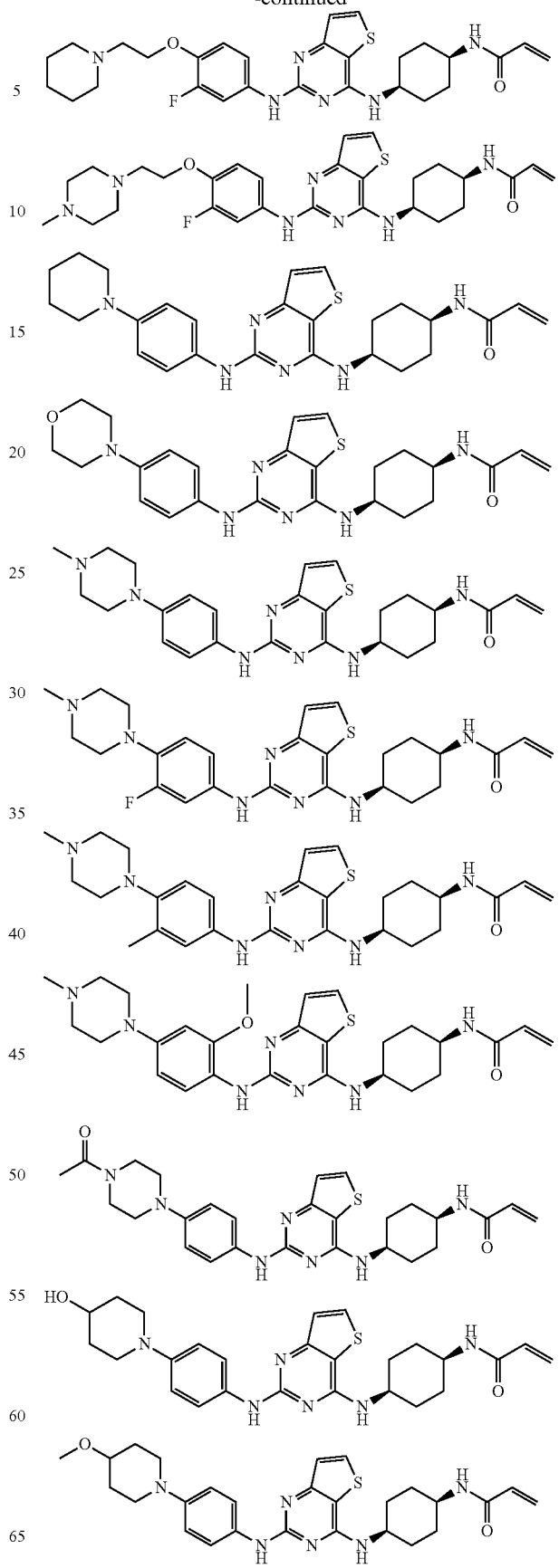

-continued
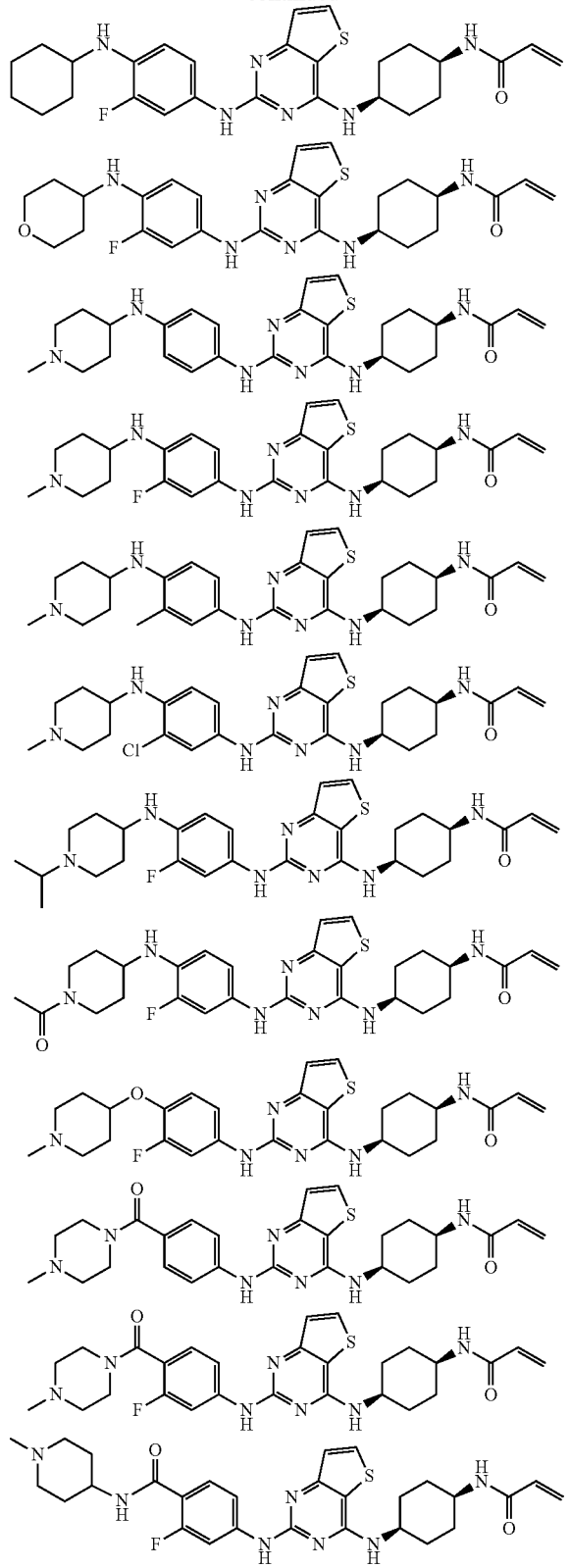
-continued
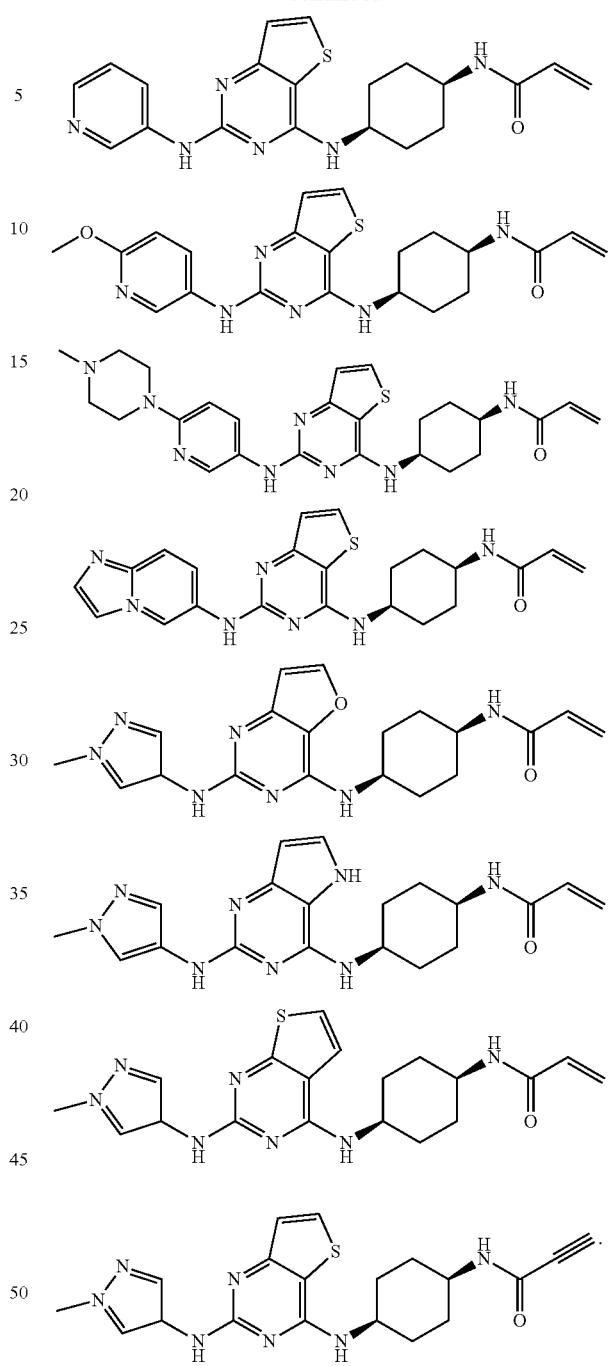
or a stereoisomer, a tautomer, a solvate, or a pharmaceutically acceptable salt thereof.
9. A pharmaceutical composition comprising the compound according to claim 1, or a stereoisomer, a tautomer, a solvate, or a pharmaceutically acceptable salt thereof, and pharmaceutically acceptable excipients.
* * * * *